(12) United States Patent
Yang et al.

(10) Patent No.: US 9,081,023 B2
(45) Date of Patent: *Jul. 14, 2015

(54) ANALYTE SENSORS, METHODS FOR PREPARING AND USING SUCH SENSORS, AND METHODS OF DETECTING ANALYTE ACTIVITY

(71) Applicant: Georgia State University Research Foundation, Inc., Atlanta, GA (US)

(72) Inventors: Jenny Jie Yang, Marietta, GA (US); Shen Tang, Atlanta, GA (US)

(73) Assignee: Georgia State University Research Foundation, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/465,070

(22) Filed: Aug. 21, 2014

(65) Prior Publication Data

US 2015/0072353 A1    Mar. 12, 2015

Related U.S. Application Data

(63) Continuation of application No. 13/879,656, filed as application No. PCT/US2011/056952 on Oct. 19, 2011, now Pat. No. 8,865,416.

(60) Provisional application No. 61/526,420, filed on Aug. 23, 2011, provisional application No. 61/394,501, filed on Oct. 19, 2010.

(51) Int. Cl.
*G01N 33/84* (2006.01)
*C07K 14/435* (2006.01)
*G01N 33/58* (2006.01)

(52) U.S. Cl.
CPC .......... *G01N 33/84* (2013.01); *C07K 14/43595* (2013.01); *G01N 33/582* (2013.01)

(58) Field of Classification Search
None
See application file for complete search history.

(56) References Cited

U.S. PATENT DOCUMENTS

2006/0030029 A1   2/2006   Yang
2010/0196918 A1   8/2010   Ellis et al.

FOREIGN PATENT DOCUMENTS

| EP | 2020418 | 4/2009 |
| WO | 03025220 | 3/2003 |
| WO | 2006020550 | 2/2006 |
| WO | 2008019123 | 2/2008 |
| WO | 2008076365 | 6/2008 |

OTHER PUBLICATIONS

The International Search Report and Written Opinion dated Nov. 1, 2012.
Yang, et al., "Rational Design of a Calcium-Binding Protein," Journal of the American Chemical Society, Apr. 24, 2003, vol. 125, No. 20, pp. 6165-6171.
The International Preliminary Report on Patentability dated May 2, 2013.
Clapham, DE. Calcium Signalling, Cell, Cell Press US, vol. 80, Jan. 27, 1995, pp. 259-268.
Holder AN, et al. Facilitating Chromophore Formation of Engineered Ca2+ Binding Green Fluorescent Proteins, Arch Biochem Biophys. Jun. 1, 2009; vol. 486(1), pp. 27-34.
Yang W et al. Rational Design of a Calcium Binding Protein, Journal of the American Chemical Society, May 2003, vol. 125(20), pp. 6165-6171.

*Primary Examiner* — Jacob Cheu
(74) *Attorney, Agent, or Firm* — Thomas|Horstemeyer, LLP

(57) ABSTRACT

Analyte sensors, methods for producing and using analyte sensors, methods of detecting and/or measuring analyte activity, detecting pH change, and/or, controlling the concentration of an analyte in a system, are disclosed. Embodiments of the analyte sensors according to the disclosure can provide an accurate and convenient method for characterizing analyte activity, detecting pH change, controlling the concentration of an analyte in a system, and the like, in both in vivo and in vitro environments, in particular in living cell imaging.

15 Claims, 45 Drawing Sheets

Ca-G1'      EGFP(1-172)-III-EGFP(173-238)
Ca-G1       EGFP(1-172)-E-III-F-EGFP(173-238)
Ca-G1-37    EGFP(1-172)-E-III-F-EGFP(173-238)
            M153T/V163A
Ca-G1-ER    kz-Crsig-EGFP(1-172)-III-EGFP(173-238)-KDEL
Ca-G2'      EGFP(1-157)-III-EGFP(158-238)
Ca-G2       EGFP(1-157) )-E-III-F-EGFP(158-238)
Ca-G3'      EGFP(1-144) )-E-III-F-EGFP(145-238)

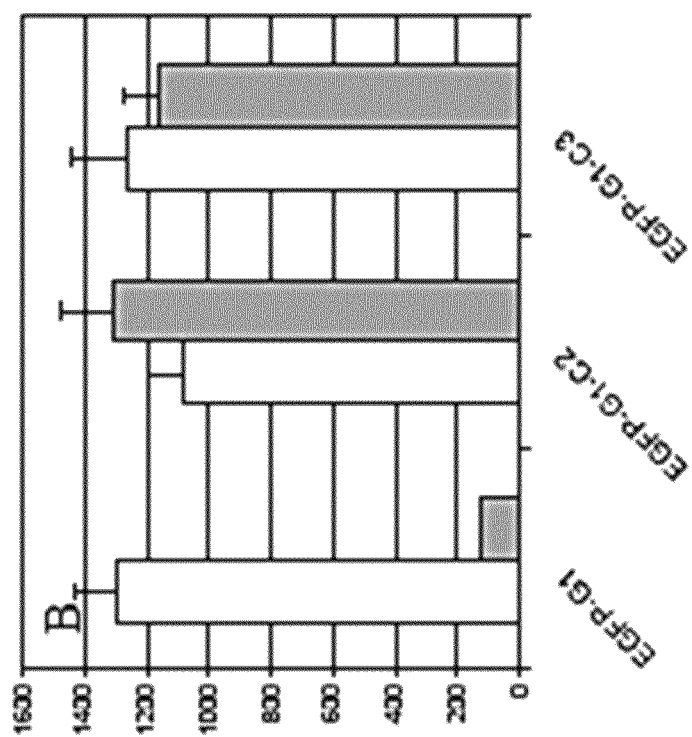
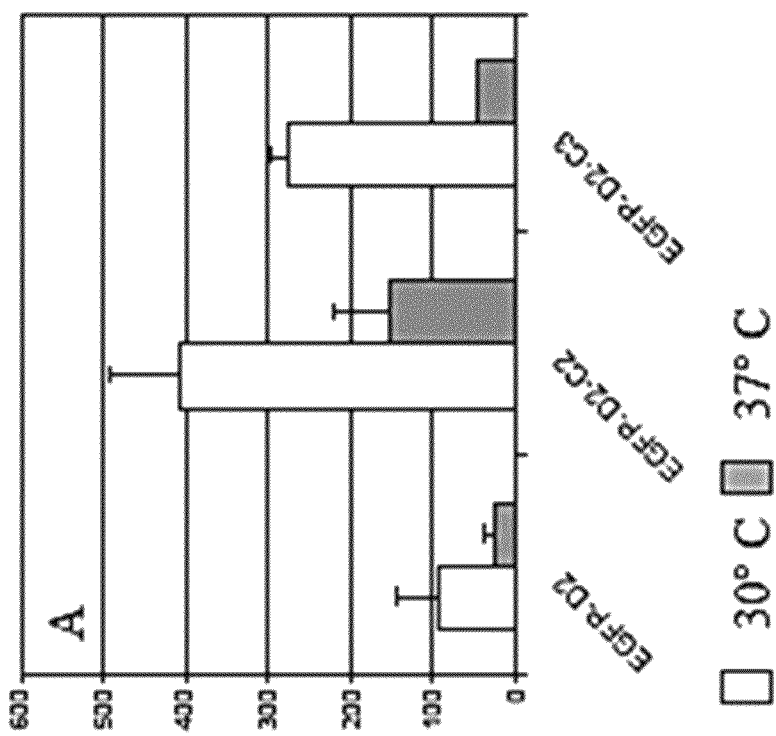
Fig. 12B
Fig. 12A

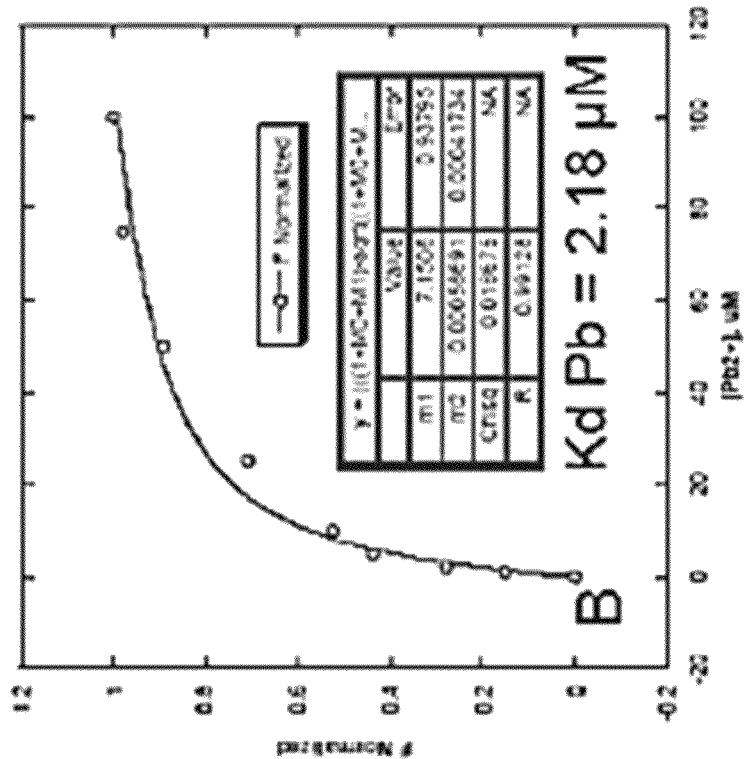
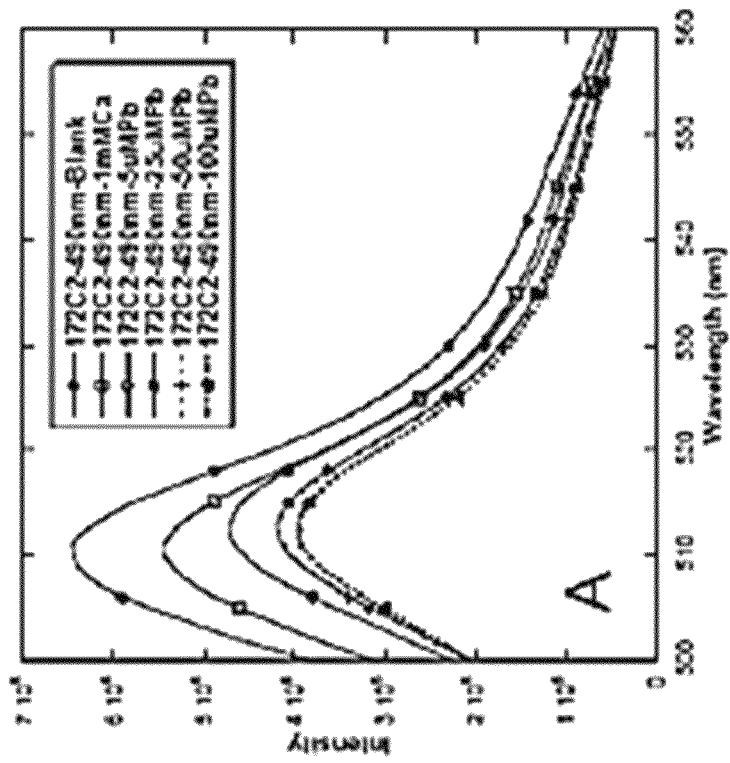
Fig. 19A
Fig. 19B

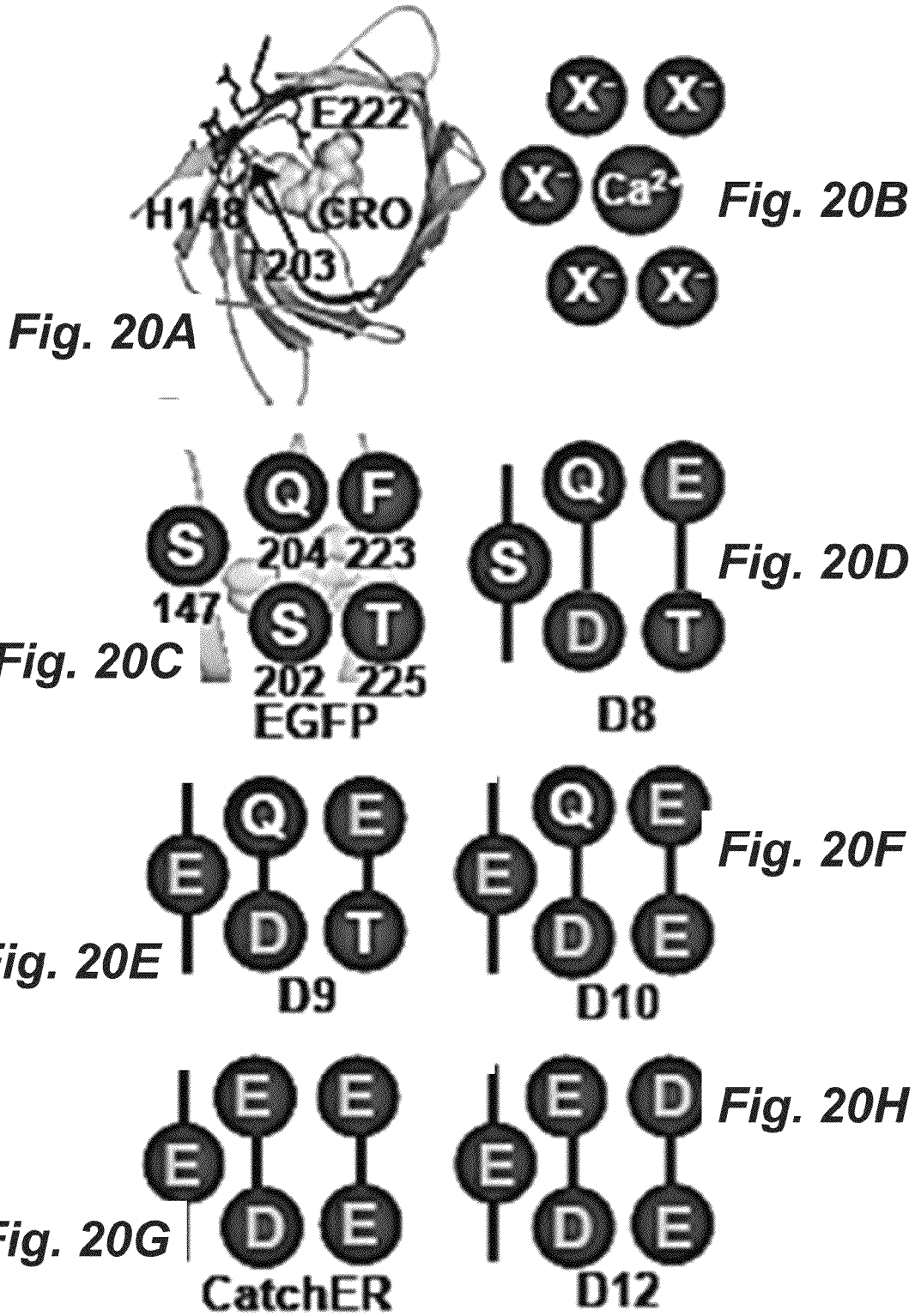

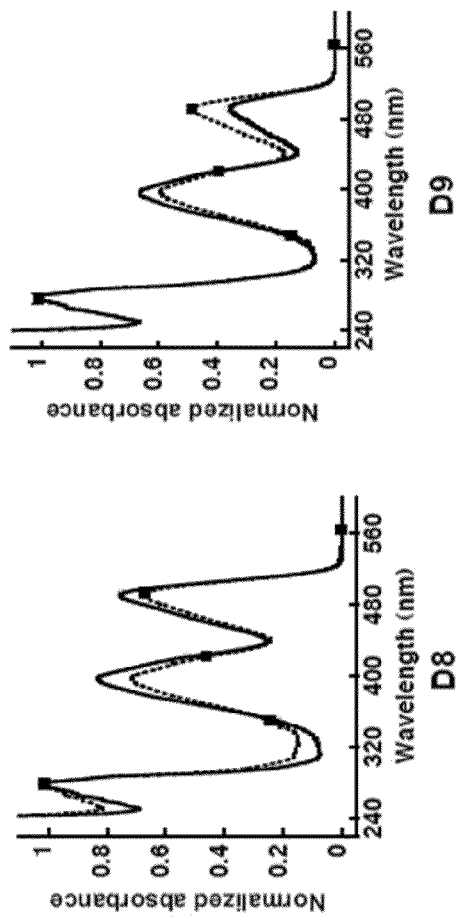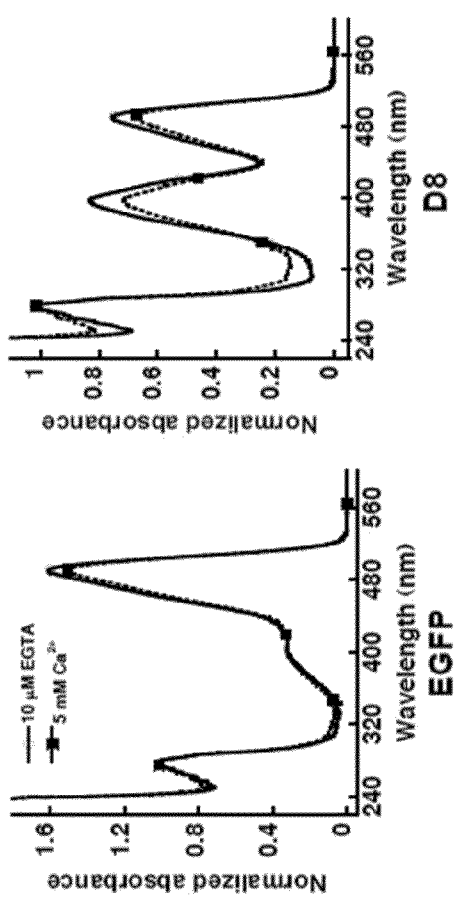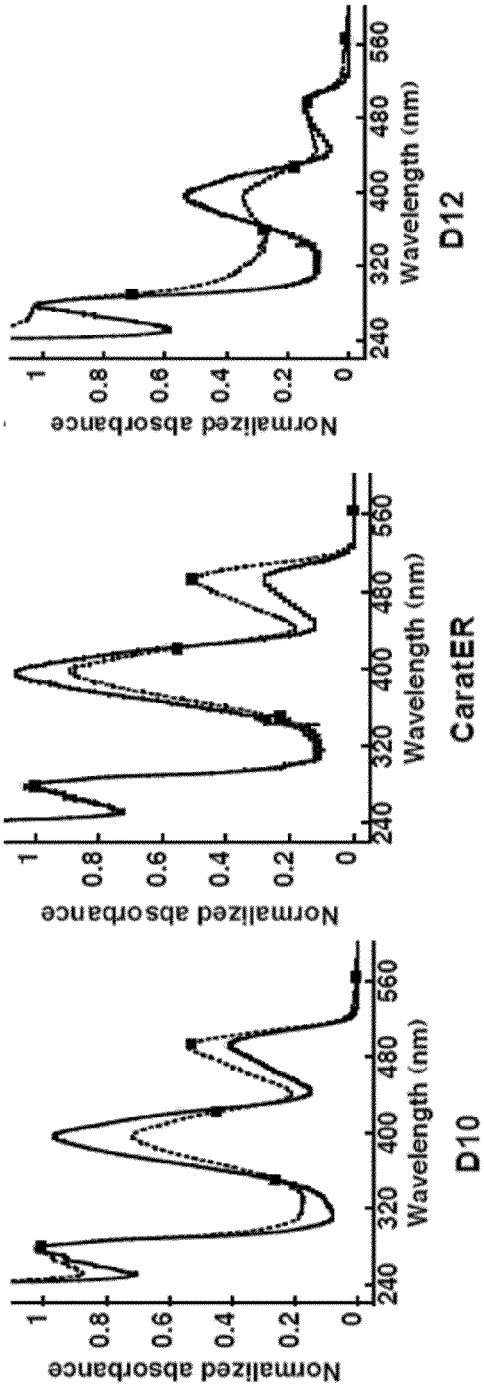
Fig. 25A  Fig. 25B  Fig. 25C  Fig. 25D  Fig. 25E  Fig. 25F

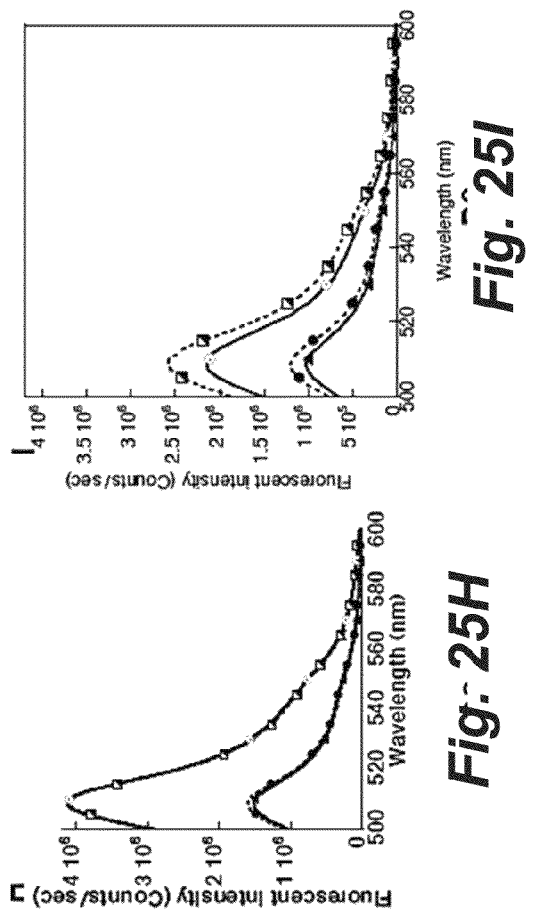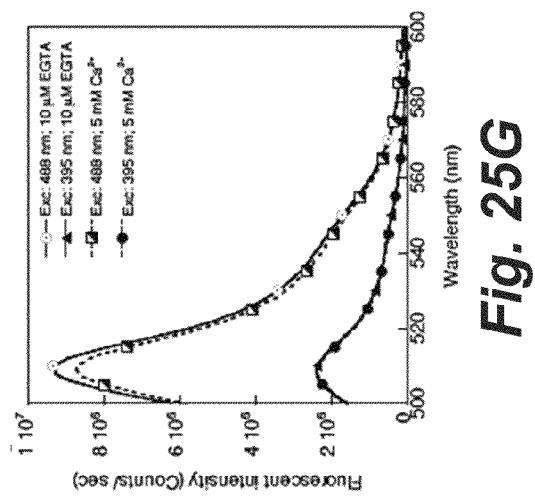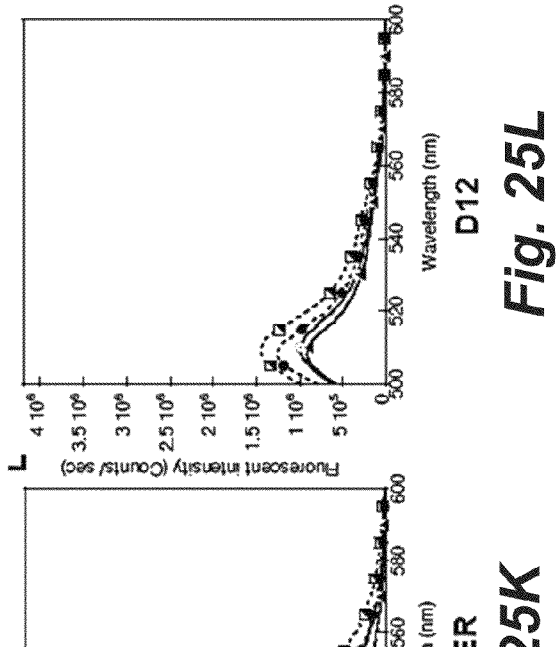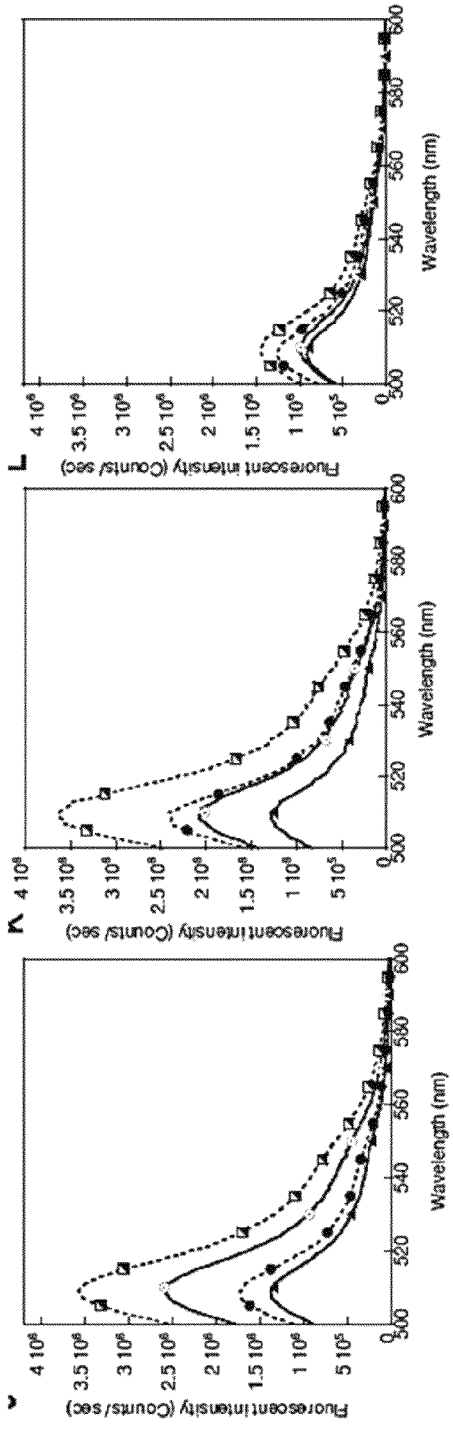
Fig. 25G  Fig. 25H  Fig. 25I
Fig. 25J  Fig. 25K  Fig. 25L

| [CatchER] µM | [Ca²⁺] µM | [Ca-CatchER] $F_{488}$ | [Ca-CatchER] $F_{395}$ | [Ca-CatchER] $A_{488}$ | [CatchER]/ [Ca²⁺] |
|---|---|---|---|---|---|
| 28.7 | 11.3 | 1.4 | 2.1 | 1.8 | 2.5 |
| 23.3 | 16.7 | 2.6 | 2.4 | 2.2 | 1.4 |
| 19.4 | 20.6 | 3.3 | 2.7 | 2.4 | 0.9 |
| 15.1 | 24.9 | 2.1 | 2.4 | 2.2 | 0.6 |
| 11.6 | 28.4 | 1.8 | 1.8 | 2.0 | 0.4 |

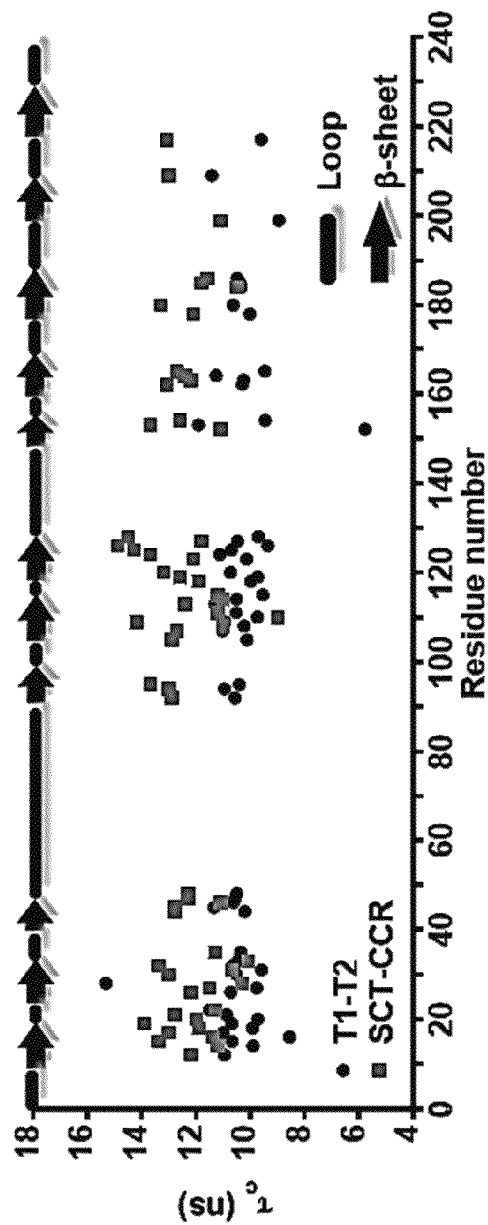
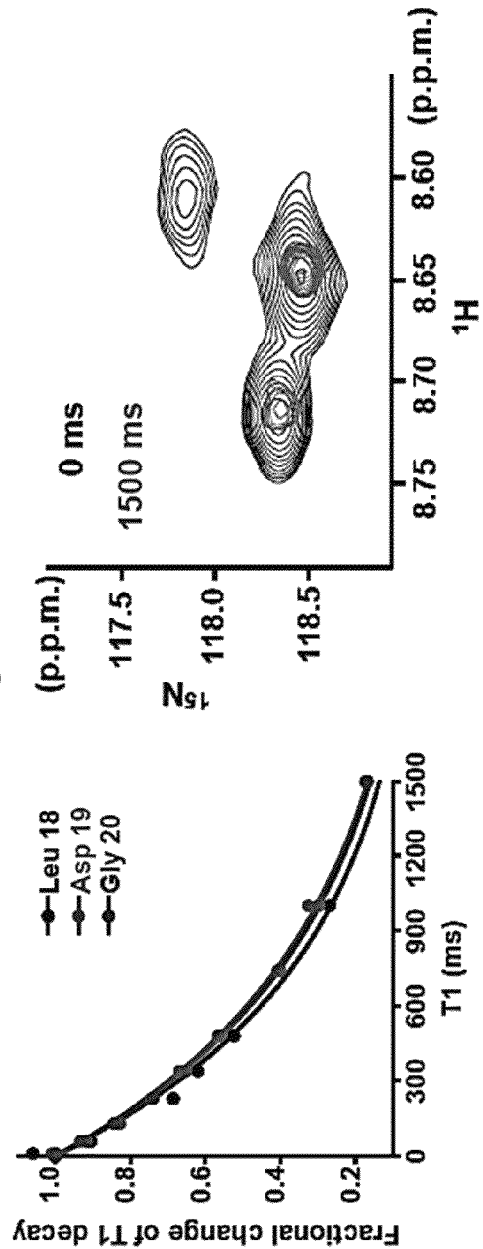
Fig. 28A
Fig. 28B
Fig. 28C

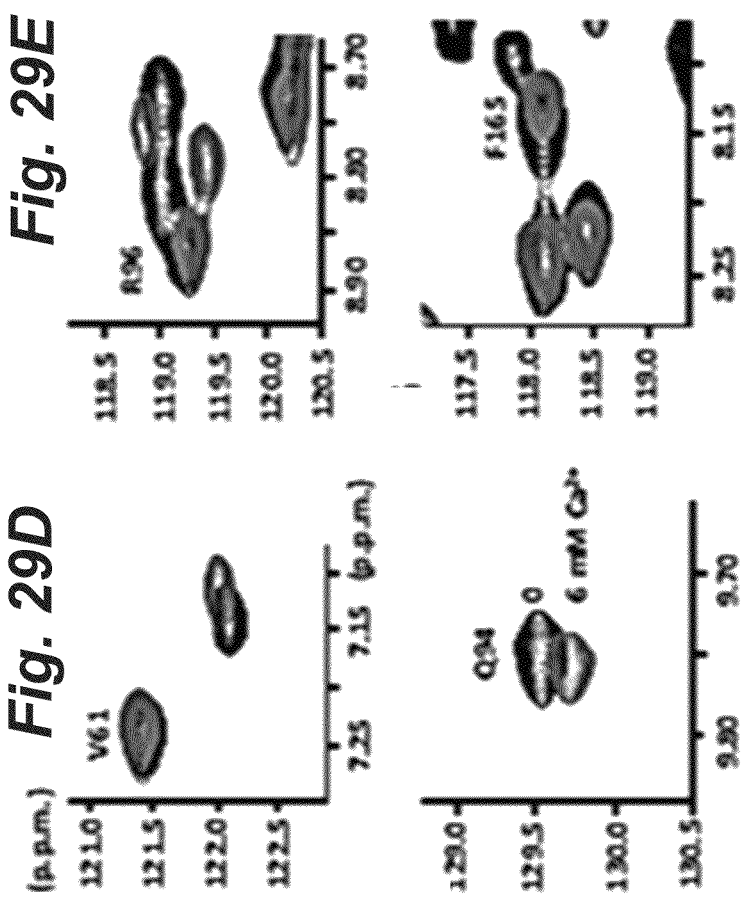

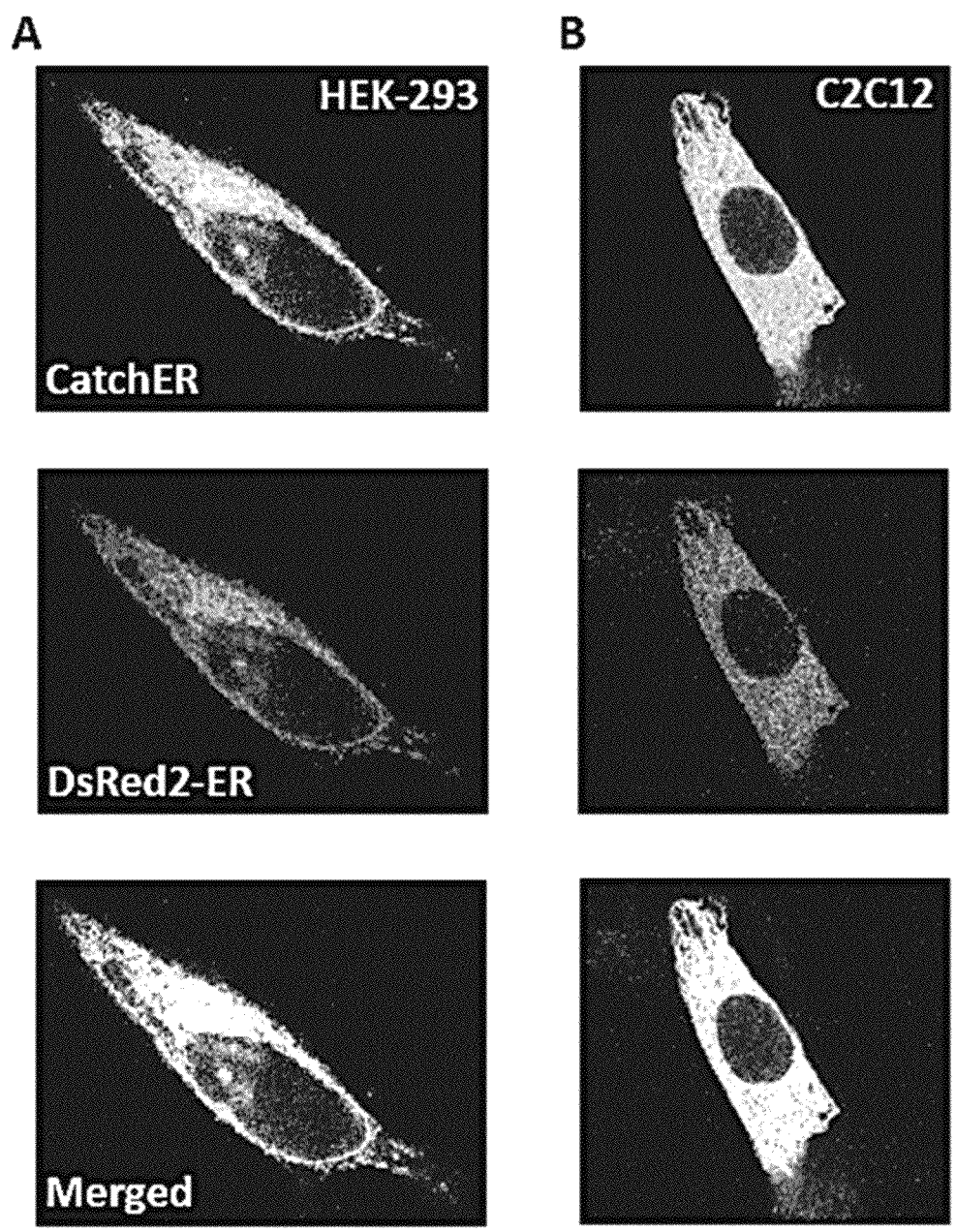
*Fig. 30A*  *Fig. 30B*

ANALYTE SENSORS, METHODS FOR PREPARING AND USING SUCH SENSORS, AND METHODS OF DETECTING ANALYTE ACTIVITY

CROSS-REFERENCE TO RELATED APPLICATIONS

This application is a continuation application of U.S. patent application Ser. No. 13/879,656, now issued as U.S. Pat. No.: 8,865,416 and entitled "ANALYTE SENSORS, METHODS FOR PREPARING AND USING SUCH SENSORS, AND METHODS OF DETECTING ANALYTE ACTIVITY", the entirety of which is hereby incorporated by reference, and which claims priority to PCT Application No. US2011/056952, filed Oct. 19, 2011 and entitled "ANALYTE SENSORS, METHODS FOR PREPARING AND USING SUCH SENSORS, AND METHODS OF DETECTING ANALYTE ACTIVITY", the entirety of which is hereby incorporated by reference, and which also claims priority to U.S. Provisional Patent Application Ser. No. 61/394,501, entitled "ANALYTE SENSORS, METHODS FOR PREPARING AND USING SUCH SENSORS, AND METHODS OF DETECTING ANALYTE ACTIVITY" filed on Oct. 19, 2010, the entirety of which is hereby incorporated by reference. This application also claims priority to U.S. Provisional Patent Application Ser. No. 61/526,420, entitled "ANALYTE SENSORS, METHODS FOR PREPARING AND USING SUCH SENSORS, AND METHODS OF DETECTING ANALYTE ACTIVITY" filed on Aug. 23, 2011, the entirety of which is hereby incorporated by reference.

FIELD OF THE DISCLOSURE

The present disclosure relates to fusion protein analyte sensors comprising an analyte binding region and a fluorescent polypeptide for the detection of metal ion analytes and to methods of their use in vivo and in vitro.

SEQUENCE LISTING

The present disclosure includes a sequence listing incorporated herein by reference in its entirety.

BACKGROUND $Ca^{2+}$ is the most ubiquitous signaling molecule in the human body, regulating numerous biological functions that include heart beat, muscle contraction, neural function, cell development, and proliferation, by fluxing between the subcellular compartments with different amplitudes and durations[1]. The membrane-based organelle endo/sarcoplasmic reticulum (ER/SR) lumen, which occupies less than 10% of cell volume, stores more than 90% of intracellular $Ca^{2+}$ and is pivotal in controlling $Ca^{2+}$ signaling. It can produce intrinsic $Ca^{2+}$ release and propagation of $Ca^{2+}$ oscillations[2-4]. $Ca^{2+}$-mobilization agonists such as ATP, ionomycin, histamine, and glutamine will activate $Ca^{2+}$ receptors and pumps, such as inositol 1,4,5-trisphosphate receptor ($IP_3R$), to release $Ca^{2+}$ from the ER into the cytosol[5-7], which results in a rapid decrease of ER $Ca^{2+}$ (from mM at the resting state to μM in excited state). The removal of these agonists will help $Ca^{2+}$ refill the ER through membrane channels such as sarco(endo) plasmic reticulum $Ca^{2+}$-ATPase (SERCA). The alternation of $Ca^{2+}$ concentration activates various intracellular $Ca^{2+}$ sensing (trigger) proteins, such as calmodulin (CaM), troponin C (TnC) and other ion channels, through conformational changes that occur upon binding to $Ca^{2+}$[8]. These activated $Ca^{2+}$-sensor receptors will further regulate numerous cellular processes and events. Recent studies indicate that $Ca^{2+}$ signaling is important for homeostatic handling of cardiovascular functions[9-11]. In cardiomyocytes, cardiac relaxation and contraction is regulated by the periodic change of intracellular $Ca^{2+}$ concentration and the proteins associated with the sarcoplasmic reticulum (SR), a homologue of ER[12, 13]. The cardiac ryanodine receptor (RyR2), inositol (1,4,5)-trisphosphate receptor ($IP_3R$) and the sarcoplasmic reticulum $Ca^{2+}$-ATPase 2a (SERCA2a) are three pivotal portals for the $Ca^{2+}$ mobilization during this agonist-induced process. Heart failure caused by dysfunction of these two proteins, associated with abnormal $Ca^{2+}$ handling, is becoming increasingly evident in data collected both from animals and humans[14-17]. A $Ca^{2+}$ indicator to monitor ER/SR $Ca^{2+}$ concentrations with fast release kinetics, and the capability to quantitatively detect $Ca^{2+}$ signaling in specific subcellular organelles will have a significant impact on the understanding of the molecular basis of $Ca^{2+}$ signaling and homeostasis in cardiac development and diseases.

The initial measure of ER $Ca^{2+}$ dynamics was achieved using the $Ca^{2+}$ dye Mag-fura-2 in plasma membrane-permeabilized live cells. In contrast to $Ca^{2+}$ dyes, fluorescent protein (FP)-based $Ca^{2+}$ indicators with genetically encoded chromophores can detect $Ca^{2+}$ signaling in subcellular organelles with high spatial and temporal resolution. They consist of a $Ca^{2+}$-modulated protein, either calmodulin or troponin C, coupled to a single fluorescent protein to generate sensors, such as GCaMP (11), or dual fluorescent proteins, such as Cameleon. Modifying Cameleon at its $Ca^{2+}$ binding loops or CaM's peptide-interaction surface generated several ER/SR sensors, which have been applied to excitable cells with some limitations. Directly monitoring fast ER/SR $Ca^{2+}$ dynamics in excitable cells is still new territory.

As a secondary messenger, calcium ions regulate many biological processes in various intracellular compartments through interactions with proteins. Calcium is involved in muscle contraction (including heartbeat), vision, and neuronal signaling. Calcium binding proteins exhibit different calcium binding affinities with $K_d$ ranging from 0.1 μM to mM, which are essential for their responses to various stimuli through the temporal and spatial changes of calcium and calcium homeostasis. For example, extracellular calcium-modulated proteins with multiple calcium binding sites, such as cadherins and calcium-sensing receptors, have dissociation constants in the submillimolar to millimolar range. Calsequestrin, a major calcium binding protein in the endoplasmic reticulum (ER), has a relatively weak calcium binding affinity that enables it to release or bind calcium in the ER calcium store.

The endoplasmic reticulum (ER) with a resting $Ca^{2+}$ concentration functions as the primary intracellular $Ca^{2+}$ store, which can produce both a synchronous $Ca^{2+}$ release and propagating $Ca^{2+}$ waves. $Ca^{2+}$-mobilizing agonists such as ATP, histamine, and glutamine, and second messengers, such as $IP_3$ and cADPR, generate an increase in the cytosolic $Ca^{2+}$ concentration ($[Ca^{2+}]_c$) with a defined spatio-temporal pattern. The release of $Ca^{2+}$ from the ER stores results in a rapid increase in $[Ca^{2+}]_c$ (from approximately $10^{-7}$ M at the resting state to approximately $10^{-6}$ M in the excited state) that activates a number of intracellular $Ca^{2+}$ sensing (trigger) proteins including calmodulin (CaM), troponin C (TnC), and other ion channels and enzymes (Protein Sci. 7: 270-282). While the prevalence of calcium throughout the biological system is well-known and extensive efforts have been made, understanding the calcium regulation of biological functions, stability, folding, and dynamic properties of proteins is limited largely due to the calcium-dependent conformational changes and cooperative calcium binding in natural proteins.

The study of the key determinants of calcium binding has been a continuing endeavor for decades. There are several factors, such as the type, charge, and arrangement of the calcium ligands that have been shown to be important in calcium binding. Calcium is mainly chelated by the oxygen atoms from the sidechains of Asp, Asn, and Glu, the main-chain carbonyl, and solvent water molecules in proteins; the pentagonal bipyramid geometry is the most popular binding geometry. Because of the electrostatic nature of calcium binding, charged Asp and Glu occur most often in calcium binding sites. The charge number in the coordination sphere also plays a role in calcium binding affinity. In addition, a more electronegative environment causes a stronger binding affinity for a given calcium site, and the electrostatic environment affects the cooperativity in multi-site systems. For these multi-site proteins, the apparent calcium affinity contains contributions from the metal-metal interactions and the cooperativity of the binding sites. However, quantitative estimation of the key factors for calcium binding is yet to be established. Therefore, the systematic study of the key determinants for calcium binding required a new strategy and model system.

Monitoring the effects of calcium on the abundant cellular processes has, thus far, been a difficult endeavor due to numerous factors, such as interference from endogenous proteins and perturbation of original calcium signal pathways. While commercially available dyes with binding affinities ranging from 60 nM to hundreds of micromolar can be loaded into mammalian cells through simple incubation, they cannot be targeted to specific cell compartments in a predictable amount, causing difficulty in accurately determining the dye concentration and monitoring calcium concentration. Many of these dyes were shown to have buffering effect in cells and do not provide the necessary sensitivity for thick tissues, intact organisms, or non-mammalian cells. Protein-based calcium sensors that can be directly expressed by the cells and reliably targeted to specific subcompartments have been used in a wide variety of cell types, including mammalian and bacteria. Aequorin was first applied to monitor calcium responses at different cellular environments. However, aequorin requires the constant addition of coelenterazine, which is consumed after each reaction.

FRET-based calcium sensors were then developed using two differently colored fluorescent proteins or their variants linked with a calmdoulin binding peptide and calmodulin (Cell Calcium 22: 209-216; Nature, 388: 882-887). To avoid using the essential trigger protein calmodulin, Troponin C (TnC) was used to sense calcium concentration change in the FRET pair of fluorescent proteins. To address the major concern regarding the competition of endogenous protein and the perturbation of the natural calcium signal systems using essential proteins such as calmodulin and troponin C and the potential perturbation of the natural calcium signal network, a modification of calmodulin binding sites and calmodulin to reduce the interaction was performed (Proc. Natl. Acad. Sci. U.S.A. 101: 17404-17409; Chem. Biol. 13: 521-530). Therefore, there remains a need to develop calcium sensors without using natural calcium binding proteins to monitor the spatial and temporal changes of calcium in the cell, especially at high concentration organelles such as the endoplasmic reticulum.

Endoplasmic reticulum/Sarcoplasmic reticulum calcium signaling are crucial for the research of muscle contraction, brain activity and all the other calcium mishandling related diseases. Different from bulk volume of cytosol in cells, ER/SR has well defined outline and only takes 3% of the total volume of the cell, which is challenged to be studies without highly specific-target calcium indicators. Unfortunately, there are only a few genetically encoded ER calcium sensor published, and all the Kds narrowed around tens of micromolar, while it is well known that free calcium concentration in SR of skeletal muscle cell is around 1 mM, with extra 20 mM calcium bound by calsequestrin. There is a strong need to design an SR calcium sensor with lower binding affinity which is appropriated to measure SR calcium in the muscle cells or tissues. Ideally, the calcium binding affinity should be around 1 mM or sub-millimolar range, similar to the overall calcium binding affinity of SR calcium buffer protein calsequestrin, which is based on the strategy that the cytosolic calcium indicators such as fura-2, camelone and GcamP2 and so on exhibit Kd around sub-micromolar, within the same magnitude of Kd of calmodulin.

The fluorescence change of calmodulin-based calcium sensors highly relies on the interaction between calcium bound form calmodulin and M13 peptide, which is a bulk complex with several different binding processes. The calcium binding affinities to C- and N-domain of calmodulin are in different magnitudes. Moreover, holo-form calmodulin and M13 peptide interact will add an additional Kd to the overall binding process, so the apparent Kd of the sensors does not directly come from the calcium binding, but in a mixture of two Kds with different magnitudes from calcium and calmodulin interaction and a sequential Kd from the calmodulin and M13 peptide interaction. The calmodulin based calcium indicator cannot quantitatively measure the calcium change, as the equation of D1ER binding process involving several constants such as Kd1, Kd2 and Hill coefficients which are difficult to be measured in situ. Furthermore, the kinetics of CaM and M13 peptide interaction could not be further accelerated due to complex delay.

SUMMARY

Embodiments of the present methodology provides designing $Ca^{2+}$ biosensor by creating a $Ca^{2+}$ binding site on GFP with site-direct mutagenesis, which not only overcomes the limitations of current $Ca^{2+}$ sensors, but also can be utilized in various other fluorescent proteins with different optical properties for the further application in tissue and animal imaging, to accurately measure the real-time $Ca^{2+}$ concentration in ER, which enhances our understanding of $Ca^{2+}$ signaling in ER, correlated to its biological function. Embodiments of the disclosure provides enhanced sensors with different signal peptides and multiple-magnitude binding affinities, which can help in detecting $Ca^{2+}$ signaling response to different agonists in various subcellular organelles of diverse cell types.

One aspect of the disclosure, therefore, encompasses embodiments of an engineered fluorescent host polypeptide having a metal ion binding site comprising a plurality of negatively charged residues, wherein the negatively charged residues comprise a plurality of carboxyl oxygens orientated in a pentagonal bipyrimdal geometry wherein said geometry provides a metallic ion binding site operatively interacting with a chromophore region of the engineered fluorescent host polypeptide such that binding of a metal ion analyte to the molecular recognition motif modulates the emission of a fluorescent signal emitted by the fluorescent host polypeptide, and optionally, the absorbance spectrum of the engineered fluorescent host polypeptide.

Another aspect of the disclosure encompasses embodiments of a composition comprising an embodiment of the analyte sensor, where the composition can be formulated for the detection of an analyte in a test sample.

Yet another aspect of the disclosure encompasses embodiments of a kit comprising an analyte sensor according to the disclosure and packaging, the packing comprising instructions for the use of the analyte sensor for the detection of an analyte by the analyte sensor.

Still another aspect of the disclosure encompasses embodiments of a method for detecting an analyte, comprising: (i) providing an analyte sensor according to the disclosure; (ii) providing a test sample suspected of comprising an analyte having affinity for the molecular recognition motif of the analyte sensor; (iii) detecting a first fluorescent signal emitted by the analyte sensor in the absence of a test sample suspected of comprising an analyte having affinity for the molecular recognition motif of the analyte sensor; (iv) contacting the analyte sensor with the test sample; (v) detecting a second fluorescent signal emitted by the analyte sensor in contact with the test sample; and (vi) comparing the first fluorescent signal and the second fluorescent signal, wherein a ratiometric change in the signal indicates an analyte in the test sample is interacting with the analyte sensor.

Another aspect of the disclosure encompasses embodiments of a recombinant nucleic acid encoding an analyte sensor according to the disclosure.

Another aspect of the disclosure encompasses embodiments of a method for characterizing the cellular activity of an analyte comprising: (i) providing a genetically modified cell comprising a recombinant nucleic acid expressing an analyte sensor according to claim 1; (ii) expressing the analyte sensor in the genetically modifying a cell measuring a signal produced from the analyte sensor; (iii) detecting a first fluorescent signal emitted by the analyte sensor; (iv) detecting a second fluorescent signal emitted by the analyte sensor after the induction of a physiological event in the cell; and (v) comparing the first fluorescent signal and the second fluorescent signal, wherein a ratiometric change in the signal indicates a change in the level of the analyte in the cell associated with the physiological in cell.

BRIEF DESCRIPTION OF THE FIGURES

Further aspects of the present disclosure will be more readily appreciated upon review of the detailed description of its various embodiments, described below, when taken in conjunction with the accompanying drawings.

FIG. 1A illustrates the domain structures of various GFP variants. CRsig: the calreticulin signal peptide MLLSVPLLLGLLGLAAAD (SEQ ID No.: 112); KDEL: ER retention signal; kz: Kozak consensus sequence for optimal translational initiation in mammalian cells. Constructs Ca-G1 and Ca-G2 contain the flanking sequences. Ca-G1', Ca-G2' and Ca-G3' do not contain flanking sequences.

FIG. 1B schematically illustrates the topology of Glu172-Asp173 (position 1), Gln157-Lys158 (position 2), and Asn144-Tyr145 (position 3) in EGFP.

FIG. 3A illustrates the visible absorption spectra for sensor Ca-G1-37 at 17 μM at various $Ca^{2+}$ concentrations. Arrows indicate the direction of signal change resulting from an increase in the $Ca^{2+}$ concentration.

FIG. 3B illustrates the $Ca^{2+}$ dependence of fluorescence emission spectra with excitation of $\lambda_{ex}$=398 nm at 1.7 μM at various $Ca^{2+}$ concentrations. Slit width of excitation and emission was 1 and 2 nm, respectively. Arrows indicate the direction of signal change resulting from an increase in the $Ca^{2+}$ concentration.

FIG. 3C illustrates the $Ca^{2+}$ dependence of fluorescence emission spectra with excitation of $\lambda_{ex}$=490 nm at 1.7 μM at various $Ca^{2+}$ concentrations. Slit width of excitation and emission was 1 and 2 nm, respectively. Arrows indicate the direction of signal change resulting from an increase in the $Ca^{2+}$ concentration.

FIG. 3D is a graph showing normalized $F_{(398nm)}/F_{(490nm)}$ ratio curve-fitting of $Ca^{2+}$ titration data.

FIG. 5A: Stopped-flow traces of fluorescence increase ($\lambda_{ex}$=398 nm) upon rapid mixing of Ca-G1 (final concentration of 20 μM) and $Ca^{2+}$ at concentrations indicated. FIG. 5B: Observed rates of fluorescence increases as a function of $Ca^{2+}$ concentration. FIG. 5C: Maximal changes in the amplitude of the fluorescence intensities observed in FIG. 5A as a function of $Ca^{2+}$ concentration. FIG. 5D: Stopped-flow trace of fluorescence decrease ($\lambda_{ex}$=398 nm) upon rapid mixing of 40 μM Ca-G1 preloaded with 0.8 mM $Ca^{2+}$. A 455 nm long pass filter was used to collect the emission with a main peak at 510 nm. Data were fit to Eq. 6 (FIGS. 5A and 5D), Eq. 8 (FIG. 5B) and Eq. 2 (FIG. 5C), respectively.

FIG. 6A: Localization of Ca-G1-ER; FIG. 6B: Localization of DsRed2-ER; FIG. 6C: overlay of Ca-G1-ER and DsRed2-ER in HeLa cells; FIG. 6D: Localization of Ca-G1-ER in BHK-21 cell. Confocal images of Ca-G1-ER and DsRed2-ER localization were with an argon laser 488 nm line for the green channel, and a He—Ne laser 543 nm line for the red channel. The scale bar indicates 10 μm.

FIG. 6E: Time course of $Ca^{2+}$ responses in response to different treatments. FIG. 6F: pseudo calibration of $Ca^{2+}$ concentrations in the ER. The time course expressed as the fluorescence emission ratio at 510 nm for excitation at 385 and 480 nm. The left-hand ordinate represents the 510 nm fluorescence emission ratio (excitation 385 and 480 nm) in both FIGS. 6E and 6F; right-hand ordinate represents the calibrated $Ca^{2+}$ concentration in the ER in FIG. 6F.

FIG. 12A is a graph illustrating EGFP-D2 series expression in HeLa cells at 30° C. and 37° C., respectively. Fluorescence intensity at 510 nm of different cell pellets was obtained for 2 days after transfection of the proteins. $\lambda_{ex}$=488 nm.

FIG. 12B is a graph illustrating EGFP-G1 series expression in HeLa cells at 30° C. and 37° C., respectively. Fluorescence intensity at 510 nm of different cell pellets was obtained for 2 days after transfection of the proteins. $\lambda_{ex}$=488 nm.

FIG. 19A illustrates titration of excess $Pb^{2+}$ with $Ca^{2+}$-loaded EGFP variant C2. Signal intensity decreases as Pb displaces Ca.

FIG. 19B illustrates the curve-fitting of C2-Pb complex to quantify Kd. The Kd for C2-$Pb^{2+}$ was 2 μM, and $Ca^{2+}$ was 440 μM.

FIGS. 20A-20L illustrate the structure and in vitro optical properties of $Ca^{2+}$ biosensor variants.

FIG. 20A schematically illustrates a truncated structure (left image) of the wild-type EGFP (1EMA) with the chromophore (CRO) shown as spheres. Residues 147, 202, 204, 223, and 225 sidechain protruding from the surface in close proximity to the chromophore were mutated to form the $Ca^{2+}$ binding ligands. Key residues H147, T203, and E222, involved in proton interaction with the chromophore are located near the designed $Ca^{2+}$ binding site.

FIG. 20B illustrates the spatial distribution of the five residues that are responsible for $Ca^{2+}$ chelation.

FIG. 20C illustrates the spatial organization of the five residues indicated in FIG. 20B and their relationship with the chromophore in the EGFP molecule, which shows nonacidic residues.

FIGS. 20D-20H, respectively illustrate constructs D8, D9, D10, CatchER, and D12 and show replacement at residues S147, S202, Q204, F223, and T225, respectively.

FIG. 20I illustrates the absorbance spectra of wild-type EGFP and the $Ca^{2+}$ sensors D8 to D12, with a normalized absorbance peak at 280 nm. The $Ca^{2+}$ sensors D8 to D12 exhibited a major absorbance peak at 398 nm and a lower peak at 490 nm.

FIG. 20J illustrates the absorbance intensity ratio at 395 nm and 488 nm for the $Ca^{2+}$ sensors D8 to D12 and wild-type EGFP. The ratio increased with the number of negatively charged residues introduced.

FIG. 20K illustrates the change in fluorescence intensity of EGFP variants in response to $Ca^{2+}$ recorded at 510 nm emission and 488/395 nm excitation with either 10 μM EGTA (black/grey bars) or 5 mM $Ca^{2+}$ (red/blue bars). EGFP emission maxima at 510 nm, excited at 488 nm, in the presence of 10 μM EGTA were normalized to 1.0.

FIG. 20L illustrates the correlation between the number of negatively charged residues and apparent $Ca^{2+}$ dissociation constants ($K_d$) for D9, D10, and CatchER, measured by fluorescence titration in the presence (square) and absence (circle) of 100 mM KCl.

FIG. 21A shows emission spectra in response to increased $Ca^{2+}$ concentrations.

FIG. 21B shows the CatchER apparent $K_d$ determined by fluorescence response in the presence or absence of 100 mM KCl, or by a main chain chemical shift change of residue Y143 in heteronuclear single quantum coherence (HSQC) spectra in the presence of 10 mM KCl (black). Titration results were fitted to a 1:1 binding mode.

FIG. 21C shows the fluorescence responses of various physiological molecules: 20 mM $Na^+$, 100 mM $K^+$, 2 μM $Cu^{2+}$, 2 μM $Zn^{2+}$, 1 mM $Mg^{2+}$, 0.2 mM ATP, 0.1 mM GTP, and 0.1 mM GDP in the presence of 1 mM $Ca^{2+}$. Values were normalized to 1 mM $Ca^{2+}$ in the absence of other metals. Emission maxima at 510 nm; excitation at 488 nm.

FIG. 21D shows the stopped-flow fluorescence using 10 μM CatchER at various $Ca^{2+}$ concentrations recorded at 395 nm excitation. CatchER's fluorescence response in 0 mM $Ca^{2+}$ was measured as the baseline.

FIG. 21E shows the stopped-flow traces showing decreased fluorescence upon rapid mixture of $Ca^{2+}$-loaded CatchER with 200 μM EGTA. Emission at 510 nm.

FIGS. 25A-25N illustrate the fluorescence and UV-absorbance changes of purified bacterially expressed EGFP-based sensors in response to $Ca^{2+}$ demonstrating adjustments of the sensor dynamic ranges.

FIG. 25A illustrates overlaid absorbance spectra from 220 nm to 600 nm of EGFP in the presence of 10 μM EGTA (solid line) or 5 mM $Ca^{2+}$ (dashed line).

FIGS. 25B-25F illustrate absorbance spectra from 220 nm to 600 nm of EGFP-based sensors D8, D9, D10, CatchER, and D12 in the presence of 10 μM EGTA (solid lines) or 5 mM $Ca^{2+}$ (dashed lines). The absorbance maxima at 488 nm increased and 395 nm decreased for D9, D10, and CatchER (C-E) in response to $Ca^{2+}$.

FIG. 25G illustrates overlaid fluorescence emission spectra from 500 nm to 600 nm of EGFP measured by a fluorometer in the presence of 10 μM EGTA (solid line) or 5 mM $Ca^{2+}$ (dashed line). The two overlaid emission spectra on the top were excited at 488 nm and the two or at 395 nm (bottom).

FIGS. 25H-25L illustrate the fluorescent emission spectra of the EGFP-based sensors D8, D9, D10, CatchER and D12, respectively.

FIG. 25N is a graph showing the comparison of the amplitudes of absorbance change at 488 nm (black bar) and 395 nm (gray bar) of EGFP and variants thereof in response to $Ca^{2+}$. The amplitude change is in the term of ($A_{Holo}/A_{Apo}-1$), and $A_{Holo}$ and $A_{Apo}$ represent the absorbance intensity in the presence of 5 mM $Ca^{2+}$ and 10 μM EGTA, respectively. The ratiometric absorbance change at 488 nm and 395 nm of D9, D10 and CatchER in response to $Ca^{2+}$ is presented in the positive and negative values of the bars, respectively. Absorbance at 280 nm of all the variants was normalized to 1.

FIG. 26A shows the fluorescence emission intensities at 510 nm were recorded in the presence of 10 μM EGTA (circle) or 4 mM $Ca^{2+}$ (square) with excitation at 488 nm at corresponding pH values. The apparent pKa was 7.59±0.03 (EGTA) and 6.91±0.03 ($Ca^{2+}$).

FIG. 26B shows the pH-dependence of the fluorescence emission intensities at 510 nm excited at 395 nm. The apparent pKa was 7.14±0.02 (EGTA) and 6.95±0.06 ($Ca^{2+}$).

FIG. 26C shows a Job's Plot of the relative amount of $Ca^{2+}$-bound CatchER as determined by fluorescence ($F_{488}$, $F_{395}$) and absorbance ($A_{488}$) as a function of the concentration of CatchER.

FIG. 26D shows the numerical results of the Job Plot of FIG. 26C.

FIG. 26E shows fluorescent spectra with the concentration of CatchER in μM 28.7, 23.3, 19.4, 15.1, and 11.6 (solid line) in response to [$Ca^{2+}$] (in μM)=11.3, 16.7, 20.6, 24.9, 28.4 (dashed line), excited at 488 nm.

FIG. 26F shows fluorescent spectra with the concentration of CatchER in μM 28.7, 23.3, 19.4, 15.1, and 11.6 (solid line) in response to [$Ca^{2+}$] (in μM)=11.3, 16.7, 20.6, 24.9, 28.4 (dashed line), excited at 395 nm.

FIG. 26G shows the corresponding absorbance change in the absence (solid line) or presence (dashed line) of $Ca^{2+}$.

FIG. 27A shows representative spectra of ICP-OES (Inductively Coupled Plasma Optical Emission Spectrometry) to determine the total $Ca^{2+}$ concentration (bound and unbound) outside a dialysis tube (buffer) and inside the dialysis tube with the samples of myoglobin, EGFP, CatchER and α-lactalbumin, respectively, with maximal intensity at 370.602 nm. Each spectrum is the average of three-time repeats with the error bars, and the amplitude of peak intensity of each sample represents the concentration of $Ca^{2+}$.

FIG. 27B shows the comparison of $Ca^{2+}$ concentration of each sample determined by ICP-OES. The peak intensities recorded at 396.847, 373.690, 219.779, 370.602, 317.933, 643.907 and 220.861 nm were converted to $Ca^{2+}$ concentration calibrated by the pre-determined $Ca^{2+}$ standard linear curve at each wavelength, respectively. The $Ca^{2+}$ concentration of the buffer outside the dialysis tube was 60.4±0.7 µM (unbound), and inside (both bound and unbound), containing myoglobin, EGFP, CatchER and α-lactalbumin was 61.5±1.2, 64.5±1.1, 74.6±1.5 and 79.1±1.7 µM (both bound and unbound), respectively.

FIGS. 28A-28C illustrate the monomerization of CatchER by measured rotational correlation time $\tau_C$ with high-field nuclear magnetic resonance spectroscopy.

FIG. 28A shows $\tau_C$ directly determined by the SCT-CCR experiment performed on an 800 MHz NMR spectrometer (gray square) or calculated using Eq. (16) and (17) with relaxation times $T_1$, $T_2$ determined on a 600 MHz NMR spectrometer (black circle). The secondary structures of corresponding residues are marked above.

FIG. 28B shows representative fitting of peaks integrations collected at 0, 30, 60, 100, 240, 480, 720, 1000, and 1500 ms $T_1$ delays.

FIG. 28C shows overlay of T1 delay spectra from selected region: 0 ms and 1500 ms.

FIGS. 29A-29H illustrate CatchER NMR assignment and $Ca^{2+}$ influence on residues interacting with the chromophore on the opposite side of the designed $Ca^{2+}$ binding site.

FIG. 29A shows selected CatchER 3D HNCA spectra from I14 to E17, with sequential and intraresidual Cα-Cα connections indicated by red lines.

FIG. 29B shows a CatchER 2D {$^1$H-$^{15}$N} HSQC spectrum.

FIG. 29C shows Cα chemical shifts. Most labeled residues exhibiting more than a 1.5 p.p.m. chemical shift difference were sequentially close to the chromophore or the designed $Ca^{2+}$ binding site. Nos. 1-5 represent E147, D202, E204, E223, and E225, respectively. All the data were recorded at 37° C. using an 800 MHz NMR spectrometer with a cryogenic probe and a 300 mM $^{13}$C-$^{15}$N double-labeled sample in 10 mM Tris, pH 7.4.

FIGS. 29D-29G show CatchER 2D {$^1$H-$^{15}$N} HSQC spectrum recorded at 0 mM $Ca^{2+}$ (black) and 6 mM $Ca^{2+}$ (red). A chemical shift change was observed for Q94 at 6 mM $Ca^{2+}$ but no change for R96, F165, or V61.

FIG. 29H shows sidechains of R96, Q94, F165, and V61 protruding toward the chromophore on the opposite side of the designed $Ca^{2+}$ binding site. Data were recorded at 37° C. using a 600 MHz NMR spectrometer with a 300 µM $^{15}$N labeled sample in 10 mM Tris and 10 mM KCl, pH 7.4.

FIGS. 30A-30B illustrate the localization of CatchER expressed in the ER of HEK-293 and C2C12 cells and SR of FDB fibers.

FIG. 30A shows colocalization of CatchER and DsRed2-ER in HEK-293 cells. CatchER and DsRed2-ER (were transiently co-transfected and expressed in two cell lines for confocal microscopy imaging. The overlay imaging shows the colocalization of CatchER corresponding to ER-tracker DsRed2-ER.

FIG. 30B shows co-localization of CatchER and DsRed2-ER in C2C12 cells. CatchER and DsRed2-ER (were transiently co-transfected and expressed in two cell lines for confocal microscopy imaging. The overlay imaging shows the co-localization of CatchER corresponding to ER-tracker DsRed2-ER.

FIG. 31A shows in situ determination of $K_d$ in ER of C2C12 myoblast cells. 1-5 correspond to 1, 3, 10, and 20 mM $Ca^{2+}$ and 3 mM EGTA, respectively.

FIG. 31B shows a $K_d$ determination in BHK cells. 1-7 represent 0.05, 0.1, 0.5, 1, 5, and 10 mM $Ca^{2+}$ and 200 µM EGTA. CatchER fluorescent signals of transfected permeabilized cells after equilibration with various extracellular $Ca^{2+}$ concentrations excited at 488 nm.

FIG. 31C shows a $K_d$ calculation with a 1:1 binding mode.

FIG. 31D shows a representative ER $Ca^{2+}$ signaling detected by CatchER in HeLa cells triggered by ATP.

FIG. 31E shows a representative ER $Ca^{2+}$ signaling detected by CatchER in HeLa cells triggered by histamine.

FIG. 31F shows a representative ER $Ca^{2+}$ signaling detected by CatchER in HeLa cells triggered by CPA.

FIG. 31G shows a representative ER $Ca^{2+}$ signaling detected by CatchER in HeLa cells triggered by ATP.

FIG. 31H reversible $Ca^{2+}$ release triggered by 50 µM histamine in HEK293 cells.

FIG. 31I shows quantification of irreversible ER $Ca^{2+}$ release in HEK293 cells induced by 2 µM thapsigargin in the presence of 1 mM extracellular $Ca^{2+}$. $F_{min}$ and $F_{max}$ were determined by adding 5 mM EGTA and 50 mM $Ca^{2+}$, respectively, to the intact cells in the presence of 5 µM ionomycin (n=6).

Figures 1A, 1B:
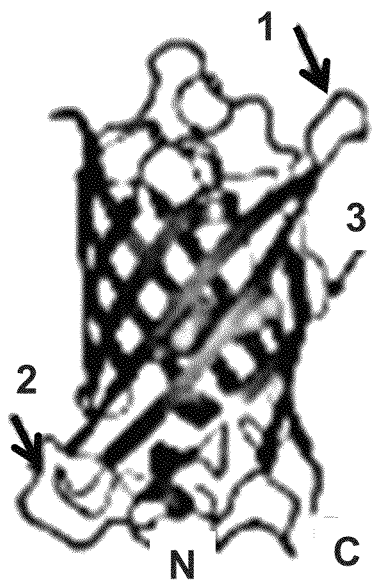
FIGS. 1A and 1B illustrate a model structure of EGFP-based $Ca^{2+}$ sensors based on 1ema.pdb. All $Ca^{2+}$ sensors were composed of a $Ca^{2+}$ binding motif integrated into an enhanced green fluorescent protein (EGFP).

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Definitions

In describing and claiming the disclosed subject matter, the following terminology will be used in accordance with the definitions set forth below.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001). As appropriate, procedures involving the use of commercially available kits and reagents are generally carried out in accordance with manufacturer defined protocols and/or parameters unless otherwise noted.

The term "polypeptide" as used herein refers to proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "variant" as used herein refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

The term "identity," as used herein refers to a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present invention.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially-available enzymes and other reagents. Proteins are purified by chromatography. (Robertson et al., (1991) J. Am. Chem. Soc. 113: 2722; Ellman et al., (1991) Methods Enzymol. 202: 301; Chung et al., Science (1993) 259: 806-809; and Chung et al., (1993) Proc. Natl. Acad. Sci. USA, 90: 10145-10149). In a second method, translation is carried out in *Xenopus* oocytes by microinjection of mutated mRNA and chemically aminoa-cylated suppressor tRNAs (Turcatti et al., (1996) J. Biol. Chem. 271: 19991-19998). Within a third method, *E. coli* cells are cultured in the absence of a natural amino acid that is to be replaced (e.g., phenylalanine) and in the presence of the desired non-naturally occurring amino acid(s) (e.g., 2-aza-phenylalanine, 3-azaphenylalanine, 4-azaphenylalanine, or 4-fluorophenylalanine). The non-naturally occurring amino acid is incorporated into the protein in place of its natural counterpart. (Koide et al., (1994) Biochem. 33: 7470-7476). Naturally occurring amino acid residues can be converted to non-naturally occurring species by in vitro chemical modifi-cation. Chemical modification can be combined with site-directed mutagenesis to further expand the range of substitu-tions (Wynn et al., (1993) Protein Sci. 2: 395-403).

The term "polynucleotide" as used herein refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs compris-ing unusual bases, such as inosine, or modified bases, such as tritylated bases, to name just two examples, are polynucle-otides as the term is used herein.

It will be appreciated that a great variety of modifications have been made to DNA and RNA that serve many useful purposes known to those of skill in the art. The term poly-nucleotide as it is employed herein embraces such chemi-cally, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either indi-vidually among the nucleotides in the reference sequence or in one or more contiguous groups within the reference sequence. The number of nucleotide alterations is determined by multiplying the total number of nucleotides in the refer-ence nucleotide by the numerical percent of the respective percent identity (divided by 100) and subtracting that product from said total number of nucleotides in the reference nucle-otide. Alterations of a polynucleotide sequence encoding the polypeptide may alter the polypeptide encoded by the poly-nucleotide following such alterations.

As used herein, DNA may obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

cDNA can be cloned from mRNA encoding the protein by, for example, the method described below:

First, the mRNA encoding the protein is prepared from the above-mentioned tissues or cells expressing and producing the protein. mRNA can be prepared by isolating total RNA by a known method such as guanidine-thiocyanate method (Chirgwin et al., Biochemistry, 18:5294, 1979), hot phenol method, or AGPC method, and subjecting it to affinity chro-matography using oligo-dT cellulose or poly-U Sepharose.

Then, with the mRNA obtained as a template, cDNA is synthesized, for example, by a well-known method using reverse transcriptase, such as the method of Okayama et al (Mol. Cell. Biol. 2:161 (1982); Mol. Cell. Biol. 3:280 (1983)) or the method of Hoffman et al. (Gene 25:263 (1983)), and converted into double-stranded cDNA. A cDNA library is prepared by transforming *E. coli* with plasmid vectors, phage vectors, or cosmid vectors having this cDNA or by transfect-ing *E. coli* after in vitro packaging.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by poly-merase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA mol-ecules, transfected cells, or cell clones, e.g., as these occur in a DNA library such as a cDNA or genomic DNA library.

The term "substantially pure" as used herein in reference to a given polypeptide means that the polypeptide is substan-tially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

The plasmid vectors used herein are not limited as long as they are replicated and maintained in hosts. Any phage vector that can be replicated in hosts can also be used. Examples of commonly used cloning vectors are pUC19, λgt10, λgt11, and so on. When the vector is applied to immunological screening as mentioned below, a vector having a promoter that can express a gene encoding the desired protein in a host is preferably used.

cDNA can be inserted into a plasmid by, for example, the method of Maniatis et al. (Molecular Cloning, A Laboratory Manual, second edition, Cold Spring Harbor Laboratory, p. 1.53, 1989). cDNA can be inserted into a phage vector by, for example, the method of Hyunh et al. (DNA cloning, a practical approach, 1, p. 49 (1985)). These methods can be simply performed by using a commercially available cloning kit (for example, a product from Takara Shuzo). The recombinant plasmid or phage vector thus obtained is introduced into an appropriate host cell such as a prokaryote (for example, *E. coli* strains HB101, DH5a, MC1061/P3, etc).

Examples of a method for introducing a plasmid into a host are, calcium chloride method, calcium chloride/rubidium chloride method, lipidsome method, and electroporation method, described in Molecular Cloning, A Laboratory Manual (second edition, Cold Spring Harbor Laboratory, p. 1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

The identification of cDNA encoding protein, its expression being augmented depending on the stimulation of cytokines like AID protein disclosed herein, can be carried out by for example suppression subtract hybridization (SSH) ((1996) Proc. Natl. Acad. Sci. USA. 93: 6025-6030; Anal. Biochem. (1996) 240: 90-97) taking advantage of suppressive PCR effect ((1995) Nucleic Acids Res. 23:1087-1088) using two cDNA libraries, namely, cDNA library constructed from mRNA derived from stimulated cells (tester cDNA library) and that constructed from mRNA derived from unstimulated cells (driver cDNA library).

Embodiments of the present disclosure relate to a recombinant vector comprising the DNA encoding the protein used herein. As a recombinant vector disclosed herein, any vector can be used as long as it is capable of retaining replication or self-multiplication in each host cell of prokaryotic and/or eukaryotic cells, including plasmid vectors and phage vectors. The recombinant vector can easily be prepared by ligating the DNA encoding protein with a vector for recombination available in the art (plasmid DNA and bacteriophage DNA) by the usual method.

Specific examples of the vectors for recombination used are *E. coli*-derived plasmids such as pBR322, pBR325, pUC12, pUC13, and pUC19, yeast-derived plasmids such as pSH19 and pSH15, and *Bacillus subtilis*-derived plasmids such as pUB110, pTP5, and pC194. Examples of phages are a bacteriophage such as lambda phage, and an animal or insect virus (pVL1393, Invitrogen) such as a retrovirus, vaccinia virus, and nuclear polyhedrosis virus.

An "expression vector" is useful for expressing the DNA encoding the protein used herein and for producing the protein. The expression vector is not limited as long as it expresses the gene encoding the protein in various prokaryotic and/or eukaryotic host cells and produces this protein. Examples thereof are pMAL C2, pEF-BOS ((1990) Nucleic Acids Res. 18:5322, and so on), pME18S pCDNA (Experimental Medicine: SUPPLEMENT, "Handbook of Genetic Engineering" (1992)), etc.

When bacteria, particularly *E. coli*, are used as host cells an expression vector generally comprises, at least, a promoter/operator region, an initiation codon, the DNA encoding the protein termination codon, terminator region, and replicon.

When yeast, animal cells, or insect cells are used as hosts, an expression vector is preferably comprised of, at least; a promoter, an initiation codon, the DNA encoding the protein and a termination codon. It may also comprise the DNA encoding a signal peptide, enhancer sequence, 5'- and 3'-untranslated region of the gene encoding the protein, splicing junctions, polyadenylation site, selectable marker region, and replicon. The expression vector may also contain, if required, a gene for gene amplification (marker) that is usually used. DNA plasmids can also be directly introduced to the mammalian cells of animals to express proteins.

A promoter/operator region to express the protein in bacteria comprises a promoter, an operator, and a Shine-Dalgarno (SD) sequence (for example, AAGG). For example, when the host is *Escherichia*, it preferably comprises Trp promoter, lac promoter, recA promoter, APL promoter, tac promoter, or the like. Examples of a promoter to express the protein in yeast are PH05 promoter, PGK promoter, GAP promoter, ADH promoter, and so on. When the host is *Bacillus*, examples thereof are SL01 promoter, SP02 promoter, penP promoter, and so on. When the host is a eukaryotic cell such as a mammalian cell, examples thereof are SV40-derived promoter, retrovirus promoter, heat shock promoter, and so on, and preferably SV-40 and retrovirus-derived one. As a matter of course, the promoter is not limited to the above examples. In addition, using an enhancer is effective for expression.

A preferable initiation codon is, for example, a methionine codon (ATG).

A commonly used termination codon (for example, TAG, TAA, TGA) is exemplified as a termination codon. Usually, used natural or synthetic terminators are used as a terminator region.

A "replicon" means a DNA capable of replicating the whole DNA sequence in host cells, and includes a natural plasmid, an artificially modified plasmid (DNA fragment prepared from a natural plasmid), a synthetic plasmid, and so on. Examples of preferable plasmids are pBR322 or its artificial derivatives (DNA fragment obtained by treating pBR322 or pRSET with appropriate restriction enzymes) for *E. coli*, yeast 2 µ plasmid or yeast chromosomal DNA for yeast, and pRSVneo ATCC 37198, pSV2dhfr ATCC 37145, pdBPV-MMTneo ATCC 37224, pSV2neo ATCC 37149, and such for mammalian cells.

An enhancer sequence, polyadenylation site, and splicing junction that are usually used in the art, such as those derived from SV40 can also be used.

A selectable marker usually employed can be used according to the usual method. Examples thereof are resistance genes for antibiotics, such as tetracycline, ampicillin, or kanamycin.

Examples of genes for gene amplification are dihydrofolate reductase (DHFR) gene, thymidine kinase gene, neomycin resistance gene, glutamate synthase gene, adenosine deaminase gene, ornithine decarboxylase gene, hygromycin-B-phosphotransferase gene, aspartate transcarbamylase gene, etc.

The expression vector used herein can be prepared by continuously and circularly linking at least the above-mentioned promoter, initiation codon, DNA encoding the protein, termination codon, and terminator region, to an appropriate replicon. If desired, appropriate DNA fragments (for example, linkers, restriction sites, and so on), can be used by the usual method such as digestion with a restriction enzyme or ligation using T4 DNA ligase.

Affinity tags such His-tag and GST can be added at the sequence end to facilitate protein purification and recognition by Western blot and pulldown assay. Examples of other tags such as HA and FLAG can also be added to allow further manipulation of the constructs.

As used herein, "transformants" can be prepared by introducing the expression vector mentioned above into host cells.

As used herein, "host" cells are not limited as long as they are compatible with an expression vector mentioned above and can be transformed. Examples thereof are various cells such as wild-type cells or artificially established recombinant cells usually used in technical field (for example, bacteria (*Escherichia* and *Bacillus*), yeast (*Saccharomyces, Pichia*, and such), animal cells, or insect cells).

*E. coli* or animal cells are preferably used. Specific examples are *E. coli* strains DH5 alpha, TB1, HB101, and the like, mouse-derived cells (COP, L, C127, Sp2/0, NS-1, NIH 3T3, and such), rat-derived cells (PC12, PC12h), hamster-derived cells (BHK, CHO, and such), monkey-derived cells (COS1, COS3, COS7, CV1, Velo, and such), and human-derived cells (Hela, diploid fibroblast-derived cells, myeloma cells, and HepG2, and such).

An expression vector can be introduced (transformed (transfected)) into host cells by known methods. Transformation can be performed, for example, according to the method of Cohen et al. ((1972) Proc. Natl. Acad. Sci. USA. 69: 2110), protoplast method ((1979) Mol. Gen. Genet. 168: 111), or competent method ((1971) J. Mol. Biol. 56: 209) when the hosts are bacteria (*E. coli, Bacillus subtilis*, and the like), the method of Hinnen et al. ((1978) Proc. Natl. Acad. Sci. USA. 75: 1927), or lithium method ((1983) J. Bacteriol. 153: 163) when the host is *Saccharomyces cerevisiae*, the method of Graham ((1973) Virology 52: 456) when the hosts are animal cells, and the method of Summers et al. ((1983) Mol. Cell. Biol. 3: 2156-2165) when the hosts are insect cells.

The protein disclosed herein, can be produced by cultivating transformants (in the following, this term includes transfectants) comprising an expression vector prepared as mentioned above in nutrient media.

The nutrient media preferably comprise a carbon source, an inorganic or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meat extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on).

Cultivation of cell lines is performed by a method known in the art. Cultivation conditions such as temperature, pH of the media, and cultivation time are selected appropriately so that the protein is produced in large quantities.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain or mRNA that make up an amino acid or termination signal.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins, or the nucleic acid may be incorporated into a vector.

"DNA regulatory sequences", as used herein, are transcriptional and translational control sequences, such as promoters, enhancers, polyadenylation signals, termination signals, and the like, that provide for and/or regulate expression of a coding sequence in a host cell.

A "promoter sequence" is a DNA regulatory region in an operon capable of binding RNA polymerase in a cell and initiating transcription of a downstream (3' direction) coding sequence. The promoter sequence is bound at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The terms "chimeric", "fusion" and "composite" are used to denote a protein, peptide domain or nucleotide sequence or molecule containing at least two component portions that are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences that encode them, are recombinant in the sense that they contain at least two constituent portions that are not otherwise found directly linked (covalently) together in nature.

The term "domain" in this context is not intended to be limited to a single discrete folding domain.

A "reporter polynucleotide" includes any gene that expresses a detectable gene product, which may be RNA or a reporter polypeptide. Reporter genes include coding sequences for which the transcriptional and/or translational products are readily detectable or selectable.

An "insertion" or "addition", as used herein, refers to a change in an amino acid or nucleotide sequence resulting in the addition or insertion of one or more amino acid or nucleotide residues, respectively, as compared to the corresponding naturally occurring molecule.

A "deletion" or "subtraction", as used herein, refers to a change in an amino acid or nucleotide sequence resulting in the deletion or subtraction of one or more amino acid or nucleotide residues, respectively, as compared to the corresponding naturally occurring molecule.

A "substitution", as used herein, refers to the replacement of one or more amino acids or nucleotides by different amino acids or nucleotides, respectively.

A "mutation" is an inheritable change in a DNA sequence relative to a reference "wild-type" DNA sequence. Mutations can occur as a result of a single base change, multiple base changes, or the addition or deletion of more than one nucleotide to a DNA sequence.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

A "gene mutation" refers to a mutation that occurs entirely within one gene, or its upstream regulatory sequences and can comprise either a point mutation or other disruption of normal chromosomal structure that occurs entirely within one gene.

A "wild-type" strain is capable of a full range of metabolic activities. For example, wild-type strains of *Salmonella* can synthesize all 20 amino acids from a single carbon source.

A "mutant" strain is not capable of all of the activities of the wild-type strain from which it is derived. For example, a mutant bacterial strain that is defective in its ability to synthesize the amino acid histidine (his strain) requires the presence of exogenous histidine in order to grow.

A "point mutation" is a change in one, or a small number of base pairs, in a DNA sequence. Point mutations may result from base pair substitutions or from small insertions or deletions.

A "transition" is a point mutation in which a purine is replaced with a purine or a pyrimidine is replaced with a pyrimidine.

A "transversion" is a point mutation in which a purine is replaced with a pyrimidine or a pyrimidine with a purine. Generally speaking, transitions are more common than transversions because the former are not detected by the proofreading enzymes.

Alternatively, point mutation can also cause a nonsense mutation resulting from the insertion of a stop codon (amber, ochre, opal). Base pair mutations that generate a translation stop codon causes premature termination of translation of the coded protein.

A "frameshift mutation" results from the insertion or deletion of one or more nucleotides within a gene. The "reading frame" of a gene refers to the order of the bases with respect to the starting point for translation of the mRNA. Deletion of a single base pair results in moving ahead one base in all of the codons, and is often referred to as a positive frameshift. Addition of one base pair (or loss of two base pairs) shifts the reading frame behind by one base, and is often referred to as a negative frameshift.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient corn plementarity to provide for the desired specificity. Stringent assay conditions are the summation or combination (totality) of both hybridization and wash conditions.

In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

By "administration" is meant introducing a sensor of the present disclosure into a subject. The preferred route of administration of the sensor is intravenous. However, any route of administration, such as oral, topical, subcutaneous, peritoneal, intraarterial, inhalation, vaginal, rectal, nasal, introduction into the cerebrospinal fluid, or instillation into body compartments can be used.

As used herein the term "isolated" is meant to describe a polynucleotide, a polypeptide, an antibody, or a host cell that is in an environment different from that in which the polynucleotide, the polypeptide, the antibody, or the host cell naturally occurs.

As used herein the phrase "beta-can structure of proteins" refers to a protein featured as a compact cylinder is formed with antiparallel beta strands.

"Fluorescent protein" refers to any protein capable of emitting light when excited with appropriate electromagnetic radiation. Fluorescent proteins include proteins having amino acid sequences that are either natural or engineered, such as the fluorescent proteins derived from *Aequorea*-related fluorescent proteins. A "fluorescent protein" as used herein is an *Aequorea victoria* green fluorescent protein (GFP), structural variants of GFP (i.e., circular permutants, monomeric versions), folding variants of GFP (i.e., more soluble versions, superfolder versions), spectral variants of GFP (i.e., YFP, CFP), and GFP-like fluorescent proteins (i.e., DsRed and mcherry). Fluorescent proteins can be from different resources. For class Hydrozoa, GFP can be from *Aequorea victoria, Mitrocoma* (synonym *Halistaura*), *Obelia, Phialidium* etc. For class Anthozoa, GFP can be from *Acanthopilum, Cavernularia, Renilla, Ptilosarcus* and *Pennatula, Stylatula*, etc. we also have GFP-like proteins from *Anemonia majna*, FP595 from *Anemonia sulcata*, FPs from *Zoanthus*, etc. The term "GFP-like fluorescent protein" is used to refer to members of the Anthozoa fluorescent proteins sharing the 11-beta strand "barrel" structure of GFP, as well as structural, folding and spectral variants thereof. The terms "GFP-like non-fluorescent protein" and "GFP-like chromophoric protein" (or, simply, "chromophoric protein" or "chromoprotein") are used to refer to the Anthozoa and Hydrozoa chromophoric proteins sharing the 11-beta strand "barrel" structure of GFP, as well as structural, folding and spectral variants thereof. GFP-like proteins all share common structural and functional characteristics, including without limitation, the capacity to form internal chromophores without requiring accessory co-factors, external enzymatic catalysis or substrates, other than molecular oxygen.

A variety of fluorescent proteins may be used in the present disclosure, including proteins that fluoresce due to intramolecular rearrangements or the addition of cofactors that promote fluorescence. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, and a blue fluorescent protein ("BFP") is a protein that emits blue light. GFPs have been isolated from the Pacific Northwest jellyfish *Aequorea victoria*; the sea pansy Renilla *reniformis*; and *Phialidium gregarium* (see Ward et al., (1982) Photochem. Photobiol. 35: 803-808 and Levine et al., (1982) Comp. Biochem. Physiol., 72B: 77-85). Red fluorescent protein mCherry with the excitation wavelength at 587 nm and emission maxima at 610 nm. (Shaner, N. C. et. al., (2004) Nat. Biotech.)

A variety of *Aequorea*-related GFPs having useful excitation and emission spectra have been engineered by modifying the amino acid sequence of a naturally occurring GFP from *Aequorea victoria*. See Prasher et. al., (1992) Gene 111: 229-233; Heim et al., (1994) Proc. Natl. Acad. Sci., USA 91: 12501-12504; U.S. Ser. No. 08/337,915, filed Nov. 10, 1994; International application PCT/US95/14692, filed Nov. 10, 1995; and U.S. Ser. No. 08/706,408, filed Aug. 30, 1996. The cDNA of GFP can be concatenated with those encoding many other proteins; the resulting fusions often are fluorescent and retain the biochemical features of the partner proteins. See, Cubitt et al., (1995) Trends Biochem. Sci. 20: 448-455. Mutagenesis studies have produced GFP mutants with shifted wavelengths of excitation or emission. See, Heim & Tsien (1996) Current Biol. 6: 178-182. Suitable pairs, for example a blue-shifted GFP mutant P4-3 (Y66H/Y145F) and an improved green mutant S65T can respectively serve as a donor and an acceptor for fluorescence resonance energy transfer (FRET). See, Tsien et al., (1993) Trends Cell Biol. 3: 242-245. A fluorescent protein is an *Aequorea*-related fluorescent protein if any contiguous sequence of 150 amino acids of the fluorescent protein has at least 85% sequence identity with an amino acid sequence, either contiguous or non-contiguous, from the wild type *Aequorea* green fluorescent protein. More preferably, a fluorescent protein is an *Aequorea*-related fluorescent protein if any contiguous sequence of 200 amino acids of the fluorescent protein has at least 95% sequence identity with an amino acid sequence, either contiguous or non-contiguous, from the wild type *Aequorea* green fluorescent protein. Similarly, the fluorescent protein can be related to *Renilla* or *Phialidium* wild-type fluorescent proteins using the same standards.

A variant of GFP with two mutations at F64L and S65 used in embodiments of the present disclosure includes enhanced green fluorescent protein (EGFP). Its chromophore has an excitation maximum at 488 nm and emission maxima at 510 nm. Its fluorescent signal is significantly greater than that of wildtype GFP without these two mutations.

Another variant of GFP is called Cycle 3 (See, Patterson et al., (1997) Biophys. J. 73: 2782-2790, which is included herein by reference). This GFP variant with mutations at F99S, M153T and V163A at w.t. GFP has improved folding and chromophore formation at 37° C. or above.

Other fluorescent proteins can be used in the fluorescent indicators, such as, for example, yellow fluorescent protein from *Vibrio fischeri* strain Y-1, Peridinin-chlorophyll a binding protein from the dinoflagellate *Symbiodinium* sp., phycobiliproteins from marine cyanobacteria such as *Synechococcus*, e.g., phycoerythrin and phycocyanin, or oat phytochromes from oat reconstructed with phycoerythrobilin. These fluorescent proteins have been described in Baldwin et al., (1990) Biochemistry 29: 5509-5515, Morris et al., (1994) Plant Mol. Biol., 24: 673-677, and Wilbanks et al., (1993) J. Biol. Chem. 268: 1226-1235, and Li et al., (1995) Biochemistry 34: 7923-7930.

The term "link" as used herein refers to a physical linkage as well as linkage that occurs by virtue of co-existence within a biological particle, e.g., phage, bacteria, yeast or other eukaryotic cell.

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods that are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

A variety of host-expression vector systems may be utilized to express the bioluminescent indicator coding sequence. These include, but are not limited to, microorganisms such as bacteria transformed with recombinant bacteriophage DNA, plasmid DNA or cosmid DNA expression vectors containing the calcium sensing system sequences; yeast transformed with recombinant yeast expression vectors vectors containing the calcium sensing system sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid vectors containing the calcium sensing system sequences; insect cell systems infected with recombinant virus expression vectors (e.g., baculovirus) vectors containing the calcium sensing system sequences; or animal cell systems infected with recombinant virus expression vectors (e.g., retroviruses, adenovirus, vaccinia virus vectors containing the calcium sensing system sequences, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (See, e.g., Bitter, et al., Methods in Enzymology 153:516-544, 1987). For example, when cloning in bacterial systems, inducible promoters such as pL of bacteriophage lamda, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted fluorescent indicator coding sequence.

In bacterial systems a number of expression vectors may be advantageously selected depending upon the use intended for calcium sensing system.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516-544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673-684, 1987; and The Molecular Biology of the Yeast *Saccharomyces*, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

An alternative expression system, which could be used to express mutation assay system, is an insect system. In one such system, *Autographa californica* nuclear polyhedrosis virus (AcNPV) is used as a vector to express foreign genes. The virus grows in *Spodoptera frugiperda* cells. The calcium sensing system sequences may be cloned into non-essential regions (for example, the polyhedrin gene) of the virus and placed under control of an AcNPV promoter (for example the polyhedrin promoter). Successful insertion of the calcium sensing system sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., J. Viol. 46:584, 1983; Smith, U.S. Pat. No. 4,215,051.

DNA sequences encoding the mutation assay system of the present disclosure can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications.

"Analytes" are atoms, molecules or ions that can bind to proteins or peptides. An analyte may bind reversibly or irreversibly and such a bond may be covalent or non-covalent. While $Ca^{2+}$, $Ln^{3+}$ and $Pb^{2+}$ are used in preferred embodiments of this disclosure as an exemplary analyte, it is understood that analytes suitable with this disclosure include, but are not limited to, metal ions including Group IIA metal ions, transition metal ions, and Lanthanide Series ions.

"Analytes" can also be $H^+$ or $OH^-$ that can bind to the proteins to change the optical properties of the sensors.

"Binding site" refers to any section of a peptide or protein involved in forming bonds with an analyte.

"Binding motif" is part of a binding site, often in a larger protein. The term binding site may be used interchangeably with the term binding motif and vice versa.

"Chemical reactions" can include the formation or dissociation of ionic, covalent, or noncovalent structures through known means. Chemical reactions can include changes in environmental conditions such as pH, ionic strength, and temperature.

"Conformation" is the three-dimensional arrangement of the primary, secondary, and tertiary structures of a molecule, and in some instances the quaternary structure of a molecule, including side groups in the molecule; a change in conformation occurs when the three-dimensional structure of a molecule changes. A conformational change may be a shift from an alpha-helix to a beta-sheet or a shift from a beta-sheet to an alpha-helix.

"Detectable changes" or "responsiveness" means any response of a protein to its microenvironment. Such detectable changes or responsiveness may be a small change or shift in the orientation of an amino acid or peptide fragment of the sensor polypeptide as well as, for example, a change in the primary, secondary, or tertiary structure of a polypeptide, and in some instances the quaternary structure of a polypeptide, including changes in protonation, electrical and chemical potential and or conformation.

A "measurable difference" in any fluorescent properties between the active and inactive states suffices for the utility of the fluorescent protein substrates of the disclosure in assays for activity. A measurable difference can be determined by measuring the amount of any quantitative fluorescent property, e.g., the fluorescence signal at a particular wavelength or the integral of fluorescence over the emission spectrum.

"Operatively inserted" or "linked" refers to a juxtaposition wherein the components so described are in a relationship permitting them to function in their intended manners. A control sequence operatively linked to a coding sequence is ligated such that expression of the coding sequence is achieved under conditions compatible with the control sequences.

"Responsive" is intended to encompass any response of a polypeptide or protein to an interaction with an analyte.

"Fluorescence lifetime: refers to the lifetime of the fluorophore signal, rather than its intensity. The fluorescence lifetime can be measured using fluorescence-lifetime imaging microscopy (FLIM), which is an imaging technique for producing an image based on the differences in the exponential decay rate of the fluorescence from a fluorescent sample. It can be used as an imaging technique in confocal microscopy, two-photon excitation microscopy, and multiphoton tomography. Measuring fluorescence lifetime has the advantage of minimizing the effect of photon scattering in thick layers of sample.

Description

Analyte sensors, methods for producing and using analyte sensors, methods of detecting and/or measuring analyte activity, detecting pH change, and/or, controlling the concentration of an analyte in a system, are disclosed. Embodiments of the analyte sensors according to the disclosure can provide an accurate and convenient method for characterizing analyte activity, detecting pH change, controlling the concentration of an analyte in a system, and the like, in both in vivo and in vitro environments, in particular in living cell imaging.

$Ca^{2+}$ regulates numerous biological processes through spatio-temporal changes in the cytosolic $Ca^{2+}$ concentration and subsequent interactions with $Ca^{2+}$ binding proteins. The endoplasmic reticulum (ER) serves as an intracellular $Ca^{2+}$ store and plays an essential role in cytosolic $Ca^{2+}$ homeostasis. There is a strong need to develop $Ca^{2+}$ sensors capable of real-time quantitative $Ca^{2+}$ measurements in specific subcellular environments without using natural $Ca^{2+}$ binding proteins such as calmodulin, which themselves participate as signaling molecules in cells. Strategies are disclosed for creating such sensors by integrating a $Ca^{2+}$-binding motif into chromophore sensitive locations in green fluorescence protein. The engineered $Ca^{2+}$ sensors exhibit large ratiometric fluorescence and absorbance changes upon $Ca^{2+}$ binding with affinities corresponding to the $Ca^{2+}$ concentrations found in the ER ($K_d$ values range from 0.4-2 mM). In addition to characterizing the optical and metal binding properties of the newly developed $Ca^{2+}$ sensors with various spectroscopic methods, the kinetic properties were also examined using stopped-flow spectrofluorimetry to ensure accurate monitoring of dynamic $Ca^{2+}$ changes. The developed $Ca^{2+}$ sensor was targeted to the ER of mammalian cell lines to monitor $Ca^{2+}$ changes occurring in this compartment in response to stimulation with agonists. It is contemplated that this class of $Ca^{2+}$ sensors can be modified further to measure $Ca^{2+}$ in other cellular compartments, providing tools to study the contribution of these compartments to cellular $Ca^{2+}$ signaling.

An EGFP-based $Ca^{2+}$ sensor was successfully created by grafting an EF-hand motif with a continuous $Ca^{2+}$ binding site into wild type EGFP as scaffold protein[35]. The generated $Ca^{2+}$ sensor (G1) exhibits a dual 510 nm fluorescence intensity ratiometric change accordingly when excited at 398 and 490 nm was monitored to decide the concentration of $Ca^{2+}$. Although the dynamic range is relative small (only 10-15% change) in mammalian cell imaging, this work strongly supports the hypothesis that GFP chromophore can be altered by introducing a $Ca^{2+}$ induced conformational change. The advantages of $Ca^{2+}$ sensors by site-directed mutagenesis are listed as follows: 1) Direct design of a $Ca^{2+}$ binding site on the surface of EGFP is supposed to create a bigger dynamic range of the signal change if its distance to chromophore is shorter than the grafting approach. This is because the shortest distance between the surface of GFP to the chromophore is only around 10 Å while $Ca^{2+}$ bound to the grafted EF-hand should crosstalk to the chromophore at more than 30 Å far away. This new strategy may have a more direct influence on the chromophore. 2) We chose EGFP (S65T mutant of wt.GFP) as the scaffold protein, as it is stable, non toxic, and exhibits robust optical fluorescence under physiological conditions [36]. The cycle 2 mutations (M153G, V163A)[37] were created in scaffold protein to improve the protein folding efficiency at high temperature, as poor folding will cause not only unqualify the cell imaging due to low fluorescent intensity, but also the dysfunction of the $Ca^{2+}$-binding site. The physiological temperature of mammalian cell is unfavorably high, due to the wtGFP encoded by Aequor Jellyfish inhabitance in the deep cold ocean. 3) Protein with different $Ca^{2+}$ binding affinities can be easily developed by alternating the electrostatic potential of the binding sites originated from the local negatively charged coordination ligands, according to the success of CD2-based $Ca^{2+}$ binding protein design[38]. 4) The designed GFP-based $Ca^{2+}$ sensor can specifically target various cellular organelles or tissues by fusing different signal peptides. 5) It can overcome the limitation of currently reported $Ca^{2+}$ sensors based on natural $Ca^{2+}$ binding proteins due to the perturbation of $Ca^{2+}$ signaling[39]. Furthermore, we propose to conduct nuclear magnetic resonance analysis to explore the mechanism of particular molecules influencing the chromophore environment and the chromophore conformational change. This will provide solid theoretical evidences for the development of GFP-based biosensors detecting diverse molecules.

Rationale of design $Ca^{2+}$ binding site on the surface of GFP by site-direct mutagenesis: FIG. 1 shows the designed $Ca^{2+}$ sensor in EGFP (7E15.EGFP) based on following considerations: First, this $Ca^{2+}$ binding site was designed to mimic that of 7E15 in CD2, formed by five negatively charged residues with their sidechain carboxyl oxygen orientated in a pentagonal by prymidal geometry to enabling similar $Ca^{2+}$ binding affinity. Second, tolerance of mutation for protein folding was considered to avoid the perturbation of fluorescence intensity. We chose this site according to the published paper, where three bulky aromatic residues were mutated to be positively charged ones around this area to prevent the formation of dimerization.[40] Third, fluorescence sensitivity spots were determined by the chromophore solvent accessibility in particular location, as fluorescence tends to be quenched by exposing the chromophore to solvent. Richmond has reported the $Cu^{2+}$ indicator with more than 40% fluorescent quench in response to 10-100 µM $Cu^{2+}$ by site-directed mutagenesis of residue 204 and 147[41], which demonstrated the high water accessibility around this area. We applied all five negatively charged residues around this area, in order to weaken the hydrogen bonds between antiparallel beta sheets by sidechain charge repulsion. Fourth, the geological distance between chromophore and calcium binding site are minimized for biggest interaction of $Ca^{2+}$ with chromophore. Several residues such as 222 and 203 involved in hydrogen network with chromophore were reported with shortest distance compacted in this region.

Embodiments of the analyte sensors according to the disclosure comprise a fluorescent host polypeptide and a molecular recognition motif that interacts with an analyte (e.g., calcium (or other metal as noted herein) or a flux of calcium in its microenvironment). Upon interaction of an analyte with the molecular recognition motif, the analyte sensor generates an optically-detectable signal (or the optically-detectable signal is altered or the lifetime of the signal is changed) which is produced during exposure to an analyte. The molecular recognition motif is integrated or operatively linked into (within the amino acid sequence) a fluorescent host polypeptide. The interaction of the analyte with the molecular recognition motif produces a detectable change in fluorescence properties (e.g., change of the intensity, or maxima wavelength or the imaging of the absorption, transmitted light, fluorescent excitation or emission change, light scattering, lifetime of the signal, and/or energy transfer of the chromophore and the protein) of the analyte sensor based on the quantity of the analyte.

Using relevant molecular recognition motifs, the analyte sensor can be used to investigate the mechanisms of diseases, track the process of diseases and diagnose some diseases related to analyte activity in vitro, in living cells and in vivo. In addition, a specific signal peptide can also be useful for investigating mechanisms such as their activation or inhibition of diseases related to calcium (or other metals as noted herein) activities in various cellular compartments in real time and in situ, which is useful in biotechnology, cell biology and medicinal chemistry, disease diagnosis and prognosis, calcium inhibitor screening and drug development.

Embodiments of the analyte sensors include an engineered fluorescent host polypeptide having a metal ion binding site comprising a plurality of negatively charged residues, wherein the negatively charged residues comprise a plurality of carboxyl oxygens orientated in a pentagonal bipyrimdal geometry wherein said geometry provides a metallic ion binding site operatively interacting with a chromophore region of the engineered fluorescent host polypeptide such that binding of a metal ion analyte to the molecular recognition motif modulates the emission of a fluorescent signal emitted by the fluorescent host polypeptide, and optionally, the absorbance spectrum of the engineered fluorescent host polypeptide.

Upon interaction of the analyte (e.g., calcium, lead, a lanthanide, and the like) with the analyte binding site, the analyte sensor produces an altered signal relative to the analyte sensor prior to interaction. In this regard, the relative three dimensional position of the chromophore within the fluorescent host polypeptide is altered upon interaction of the analyte with the analyte binding site, where such alteration generates the altered signal.

In other words, the analyte sensors have a folding arrangement in a three-dimensional space that produces a specific signal. The analyte sensor can undergo a local conformational change into another folding arrangement with an alteration of the chromophore microenvironment under the inducement of an analyte (e.g., calcium, lead, or a lanthanide) with the analyte binding site. The conformational change can be detected and measured and compared to the signal generated by the calcium sensor prior to interaction with the analyte.

The advantages of embodiments of the present disclosure can include one or more of the following: (i) embodiments of the present disclosure are capable of monitoring numerous cellular events in living cells or organisms via live cell imaging. Embodiments of the present disclosure can provide continuous and dynamic movies of the cellular event and their responses by the stimuli or drugs. Embodiments of the present disclosure largely overcome the limitations of currently commercial available small molecule dyes, peptide/mimics probes with one snap shot of the analyte action; (ii) embodiments of the present disclosure include single fluorescent proteins that are more easily and better translocated under cellular environment to probe analyte reaction in situ than FRET pairs that used two fluorescent proteins. With the addition of signal peptides, these analyte sensors can be specifically expressed/placed at the cellular environments such as ER, mitochondrial, Golgi or nuclei to monitor cellular event with spatial resolution in addition to temporal resolution. Currently available dye detection methods simply rely on passive diffusion of the probe through the membrane, and permits only short snapshots of calcium actions without the capability of detecting reactions at targeted cellular locations. These probes do not provide continuous dynamic imaging of calcium actions due to limited cellular lifetime and specificity; (iii) embodiments of the present disclosure do not use existing/natural calcium binding proteins to sense metal ions (e.g., calcium, lead, or a lanthanide), thus they have minimized perturbation of cellular network; (iv) embodiments of the present disclosure include single fluorescent protein units that overcome the limitations observed with FRET-based sensors that are prone to fluorescence photobleaching, poor orientation and translocation in the cellular compartments due to their large size; (v) the ratiometric signal change of embodiments of the present disclosure with absorption or excitations at 398 and 490 nm permits quantitative and accurate measurement of the calcium (or other metal as noted herein) action by normalizing the concentration change of the sensors and cellular and instrumental interference of the fluorescence signal; (vi) creating different sensors with different analyte affinities allows for monitoring of cellular response with high accuracy and sensitivity; (vii) the structural motifs used in embodiments of the present disclosure allow the maximal optical responses as well the optimal molecular recognition required for chemical reactions; and (viii) the developed analyte sensors can be expressed in bacterial, mammalian cells, and animals such as mice with good optical properties such as those described herein. The changes in the fluorescent and absorbance properties of the engineered polypeptides of the disclosure inducible by metal ion binding may also be used to detect the removal of the metal ion resulting in a reverse change.

Thus, the systems, sensors, and methods of the present disclosure can be used to detect, measure, quantitate, and image interactions between the analytes with the analyte binding site, in vitro and in vivo. In particular, embodiments of the present disclosure can be used to detect (and visualize) and/or quantitate calcium interactions or events in vitro as well as in cells, tissues, and in vivo. In addition, the systems, sensors, and methods of the present disclosure can be used to detect, measure, quantitate pH change with the analyte binding site, in vitro and in vivo. Furthermore, the systems, sensors, and methods of the present disclosure can be used to control the concentration of an analyte in a system.

The analyte sensors according to the disclosure can include an engineered fluorescent host polypeptide having a metal ion binding site comprising a plurality of negatively charged residues, wherein the negatively charged residues comprise a plurality of carboxyl oxygens orientated in a pentagonal bipyrimdal geometry wherein said geometry provides a metallic ion binding site operatively interacting with a chromophore region of the engineered fluorescent host polypeptide such that binding of a metal ion analyte to the molecular recognition motif modulates the emission of a fluorescent signal emitted by the fluorescent host polypeptide, and optionally, the absorbance spectrum of the engineered fluorescent host polypeptide. In an embodiment, the negatively charged residues are on the surface of three anti-parallel beta-sheets. In an embodiment, the negatively charged residues are spread on three strands of the protein with beta-can structure.

The native signal of the fluorescent protein is altered by the inclusion of the analyte binding site within the amino acid sequence of the fluorescent host polypeptide and the structural motif. In particular, embodiments of the present disclosure provide for insertion positions of the analyte binding site so that the analyte sensor produces emissions at two or more wavelengths. In this regard, the relative three dimensional position of the chromophore within the fluorescent host polypeptide is altered by the inclusion of the analyte binding site and the structural motif, where such alteration generates the altered signal.

Upon interaction of the analyte (e.g., calcium, lead, and/or lanthanide) with the analyte binding site, the analyte sensor produces an altered signal relative to the analyte sensor prior to interaction. In this regard, the relative three dimensional position of the chromophore within the fluorescent host polypeptide is altered upon interaction of the analyte with the analyte binding site, where such alteration generates the altered signal. The ratiometric change of the signal (chromophore signal) after the interaction allows an accurate measurement of the analyte activity (e.g., in vitro and in vivo with normalized sensor concentration). The inclusion of the structure motif allows optimal molecular recognition by incorporating essential structural and chemical properties required for a specific type of analyte. For example, inclusion of the structure motif allows for: solvent accessibility for the easy access of calcium, flexibility required for the recognition, a special geometric pocket for the interaction, a hydrophilic surface or charged environments to facilitate the binding process and a required environment for the fast kinetic rates such as good off rate required for real time measurements.

Design of calcium-binding GFP: The design of calcium binding proteins in green fluorescent protein was carried out using the established design program and the given parameters based on the pentagonal bipyramidal geometry (Biochemistry 44: 8267-8273; J. Am. Chem. Soc. 127: 2085-2093; J. Am. Chem. Soc. 125: 6165-6171). More than 3000 potential calcium binding sites were computationally constructed.

Several criteria were applied to rank and to choose sites: (i) any sites that contained mutations in the central helix (i.e. amino acids 56 to 71) were removed; (ii) sites that replaced buried hydrophobic residues with charged residues were removed to avoid folding disruptions; (iii) sites involving solvent-inaccessible residues, such as Phe8, were eliminated since solvent accessibility is observed for many calcium binding sites. The solvent accessibility was evaluated with the program GetArea; (iv) the mutations in the loop regions with higher flexibility were considered "safe" without disrupting the protein folding, while sites involving the mutations on the β-strands were considered more aggressive; (v) since fewer mutations are less likely to perturb the native protein conformation, predicted sites with more existing residues as ligands are preferred; (vi) the distance from the chromophore was also evaluated for the potential development of calcium sensors. The over packing of protein was examined, and the clash with close residues was avoided. In addition, the sites with three to four negatively charged ligand residues were preferred based on the statistical results for calcium binding proteins; and (vii) to have a potential calcium-induced fluorescence change, chromophore sensitive locations were analyzed based on the dynamic and conformational properties of the fluorescent proteins.

Figure 14:
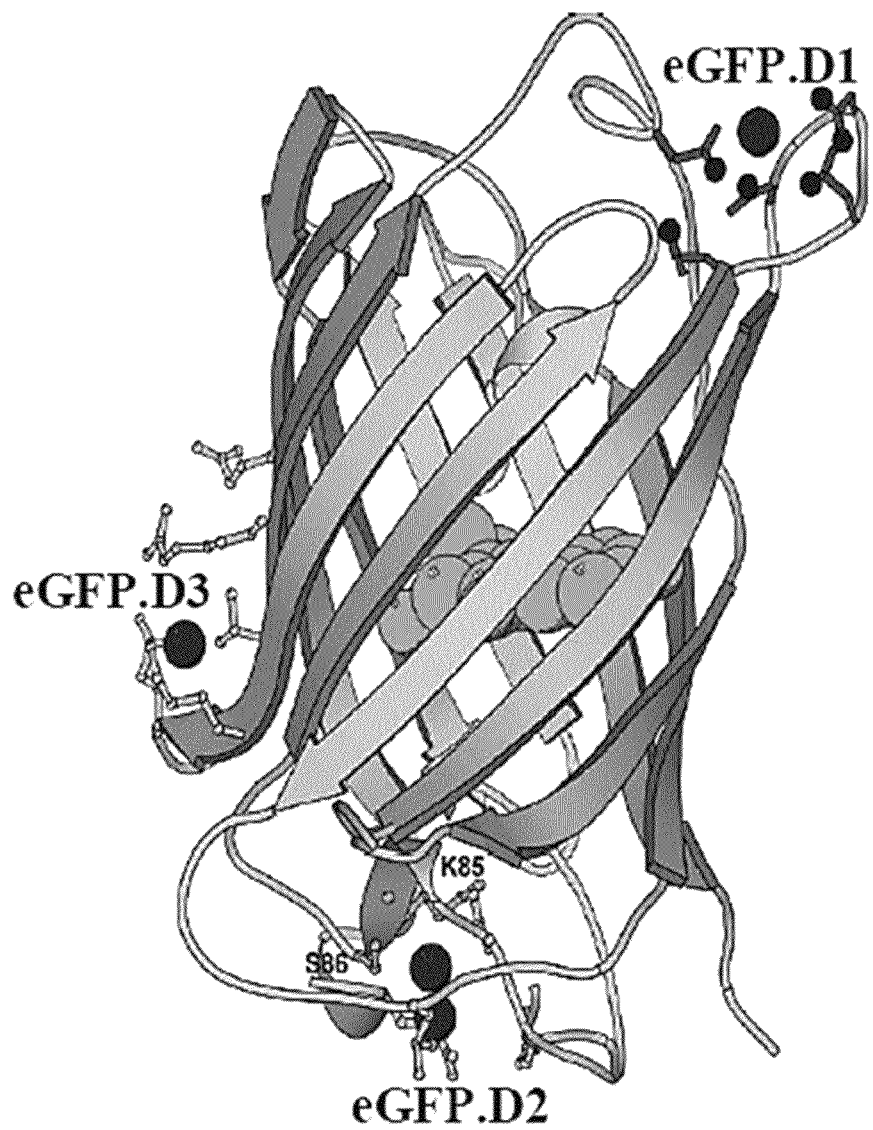
FIG. 14 schematically illustrates a calcium-binding protein based on GFP (pdb 1b9c). The binding geometry of GFP.D1 is shown in ball-and-stick. D2 is shown as a circle. The locations of GFP.D3 with the wild type residues are also indicted.

FIG. 14 shows five calcium binding sites (termed GFP.D1, GFP.D2, GFP.D2', GFP.D2", and GFP.D3) located in three different positions in GFP chosen based on the criteria (Table 1). GFP.D1 is located at the end of the barrel in the loop regions. It is expected to have less effect on the EGFP folding and structure due to the flexibility of the loop region. GFP.D2, GFP.D2', and GFP.D2" are located in the loop region on the opposite end of the barrel from GFP.D1. They contain four identical ligand residues and differ by one residue. GFP.D2 has ligands L194E, S86D, S2D, D82, and E5. L194 was mutated to be N in both GFP.D2' and GFP.D2". GFP.D2' contains K85D mutation whereas GFP.D2 and GFP.D2" contains S86D. This alters the sidechain packing and electrostatic interactions in the local environment due to the different size and charge natures of Lys, Glu, Asn, and Ser. GFP.D3 is located in the middle of the barrel, 14 Å to the chromophore. All ligand residues, including two natural ones and three mutations, are located on the β-strands.

Figure 15A:
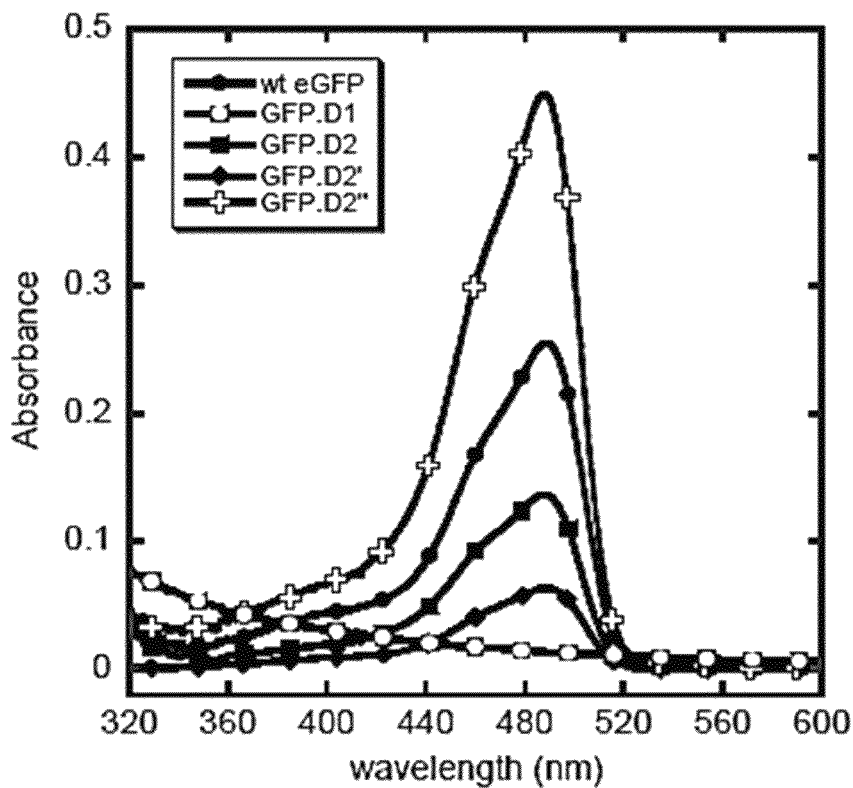
FIG. 15A is a graph illustrating the absorbance spectra of EGFP, GFP.D1, GFP.D2, GFP.D2' and GFP.D2" expressed in $E.\ coli$, indicate that the chromophore of GFP.D1 did not form.
Figure 15B:
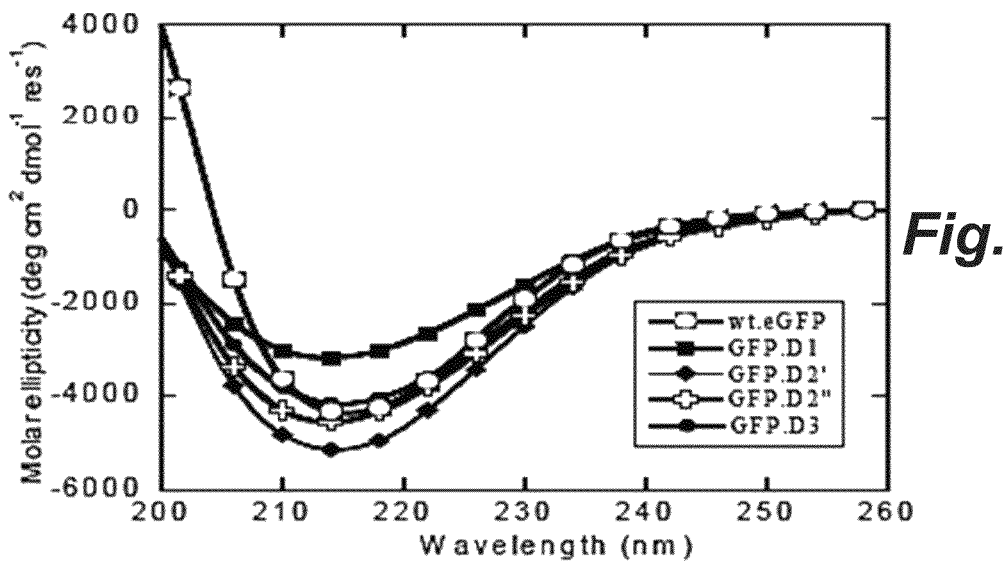
FIG. 15B illustrates the far UV CD spectra of EGFP, GFP.D1, GFP.D2, GFP.D2' and GFP.D2" indicating the formation of $\beta$-sheet secondary structures with a negative maximum at 216 nm.

Chromophore and conformational properties of designed proteins: Four calcium binding sites were engineered into EGFP, and they exhibit different optical properties. Among all of the bacterial-expressed proteins in E. coli, GFP.D2 is the only one that retains green fluorescence color. As shown in FIGS. 15A and 15B, the bacterial-expressed and purified GFP.D2 and its series and wildtype EGFP exhibit absorption maxima at 490 nm. The excitation at 490 nm results in an emission maximum at 510 nm. In contrast, the rest of the bacterial-expressed proteins GFP.D1 and GFP.D3 are colorless, indicating no chromophore formation in the bacterial-expression system. FIG. 15B shows that the far UV CD spectra of these designed proteins have a negative maximum at 216 nm similar to EGFP, indicating that a dominant β-sheet structure was not altered after introducing calcium binding ligand residues although the chromophore formation was perturbed.

Figure 16:
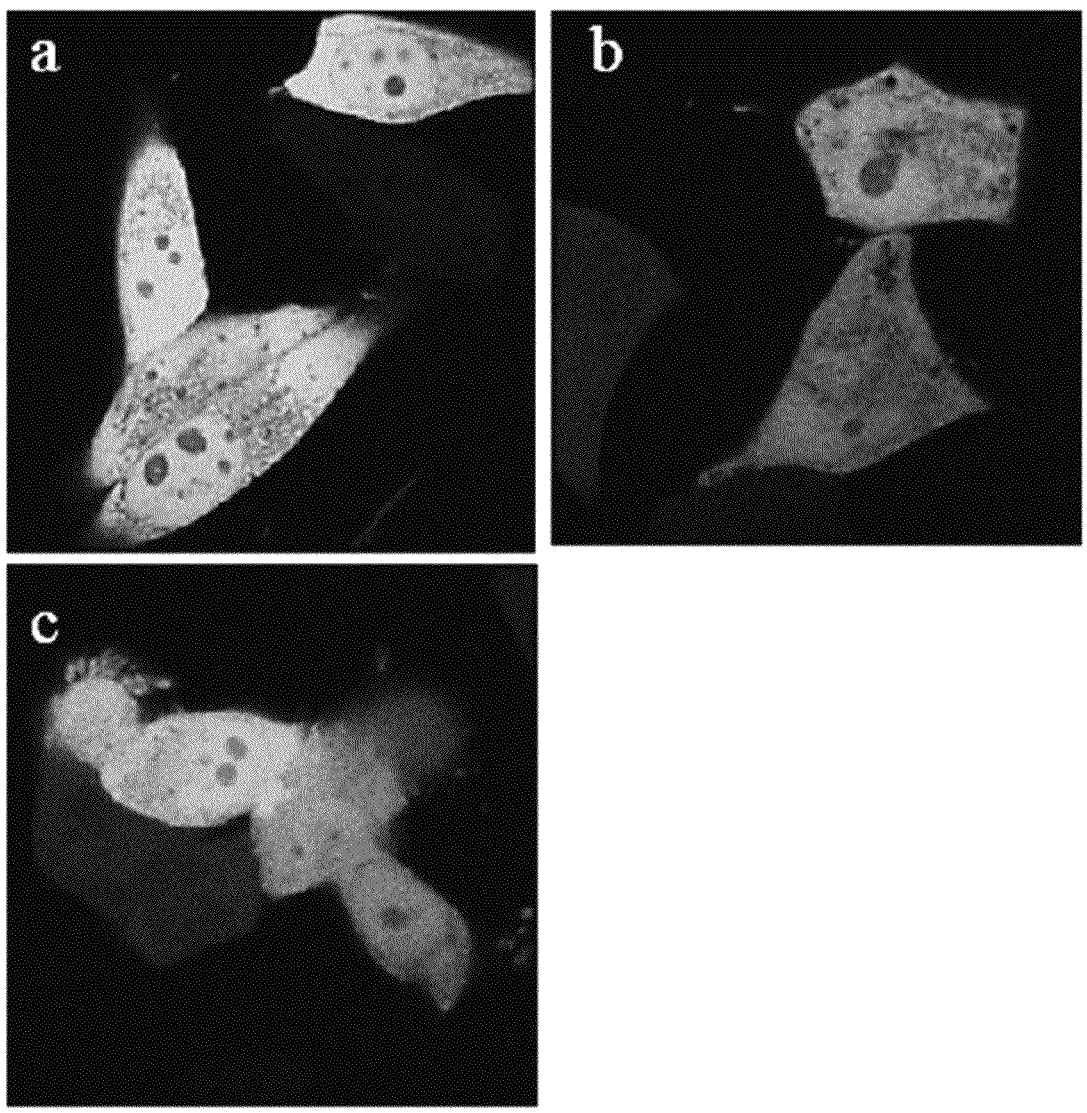
FIG. 16 is a series of digital images illustrating the inverted epifluorescence image of HeLa cells expressing: (a) wild-type EGFP; (b) GFP.D1; and (c) GFP.D2.

GFP is originally from jellyfish and it was reported that a eukaryotic expression system can facilitate chromophore formation since eukaryote cells contain machinery to aid in protein folding (J. Mol. Biol. 353: 397-409). FIG. 16 shows that both GFP.D1 and GFP.D2 exhibit fluorescence when expressed in Hela cell. In contrast, GFP.D3 remains colorless when expressed in the mammalian cells, similar to its expression in bacterial system. These results suggest that introducing several charged residues for calcium binding does not affect the folding and structure of the protein but does affect the synthesis and formation of the chromophore, which has less tolerance for environmental modifications.

Figure 17A:
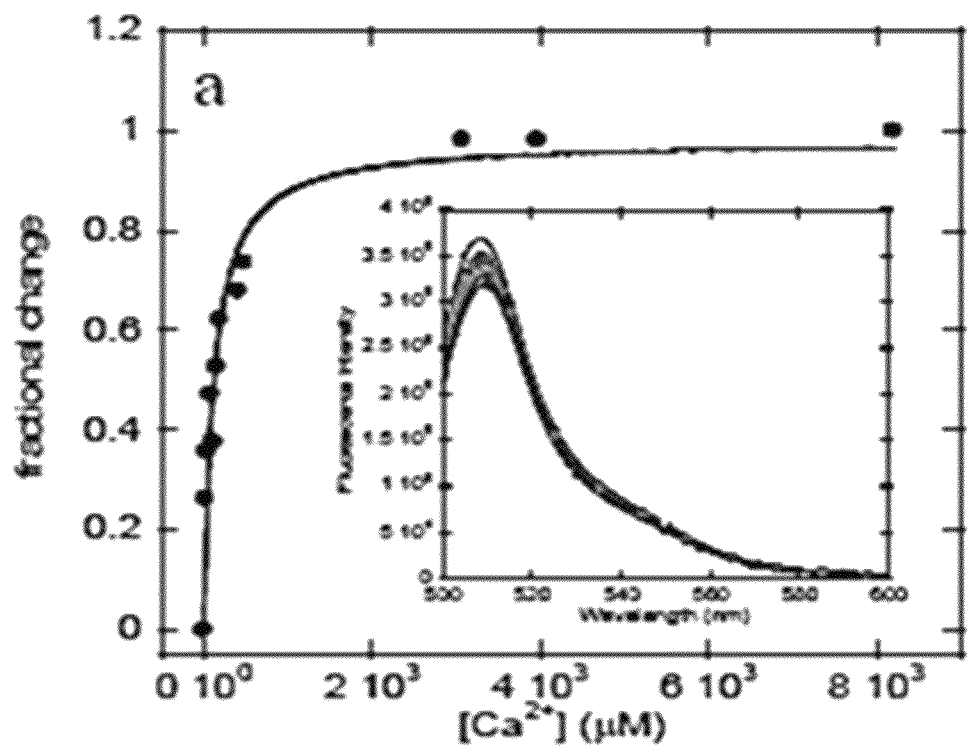
FIG. 17A illustrates the calcium-induced chromophore emission change for GFP.D2 expressed in $E.\ coli$ with excitation at 482 nm. The fit of the data using the 1:1 binding equation (Eq. 2.3) gives a $K_d$ of 107 μM.

Metal binding affinities and selectivity of designed GFP variants: Metal binding capabilities for calcium and its analog lanthanide ions of designed GFP variants were examined using four different methods using bacterial expressed and purified proteins. For GFP.D2 with a correct formed chromophore, metal binding affinity was directly determined by monitoring fluorescence signal change as a function of metal concentration. As shown in FIG. 17A, the addition of calcium from 0 to 10 mM results in a gradually decrease of fluorescent signal at 510 nm when excited at 398 nm. The fractional change at 510 nm can be well fitted with the equation forming 1:1 calcium: protein complex. The dissociate constants for calcium is 107±13. On the other hand, wildtype EGFP does not have any significantly fluorescence signal change upon addition of the metal ions.

Figure 17B:
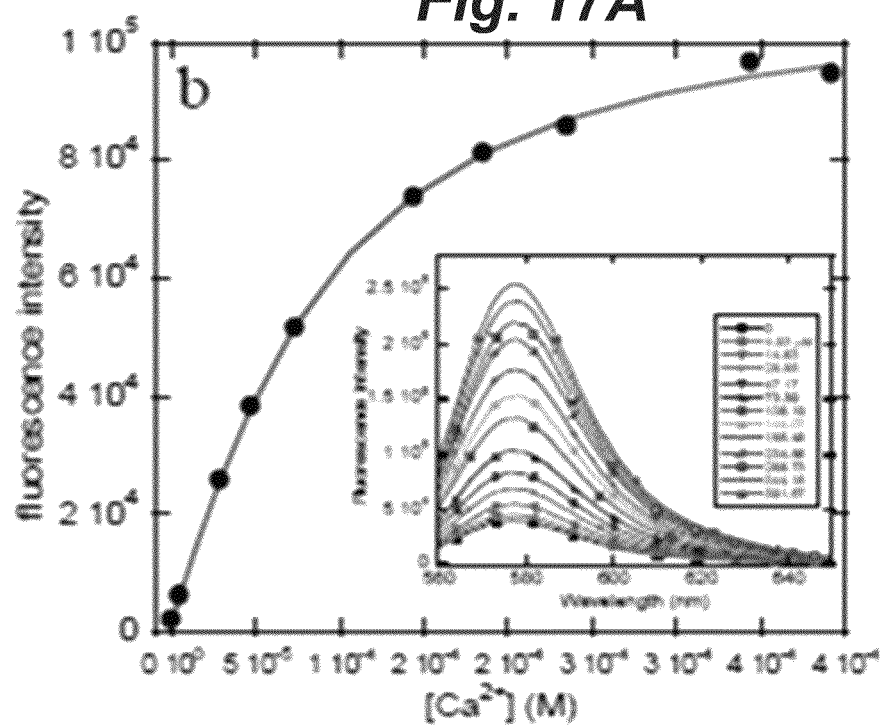
FIG. 17B illustrates the rhodamine-5N competition with GFP.D2 for calcium binding fluorescence emission with excitation at 552 nm. The inset shows the spectra of the Rhodamine-5N with the concentration change of $Ca^{2+}$.

Rhodamine-5N (Molecular Probes), a commercially available calcium binding dye to was used obtain calcium and lanthanide affinity by a dye competition assay. As shown in FIG. 17B, Rodmine-5N shows a large fluorescence signal increase when calcium is bound in GFP.D1. In the dye competition assay, the solutions with constant dye and protein concentration were titrated with calcium until saturation was observed (FIG. 17B insertion). The binding affinities for the designed proteins were obtained by globally fitting the spectra with the metal-and-two-ligand model. As shown in Table 1, the calcium binding affinities of GFP.D2 obtained by directly measurement of fluorescence signal change are in agreement with that obtained by dye the competition method.

teins GFP.D1, GFP.D2, GFP.D2' and GFP.D2" and GFP.D3. Their calcium-binding affinities are 60±5, 57±2, 96±7 and 38±5 μM, respectively.

Figure 17C:
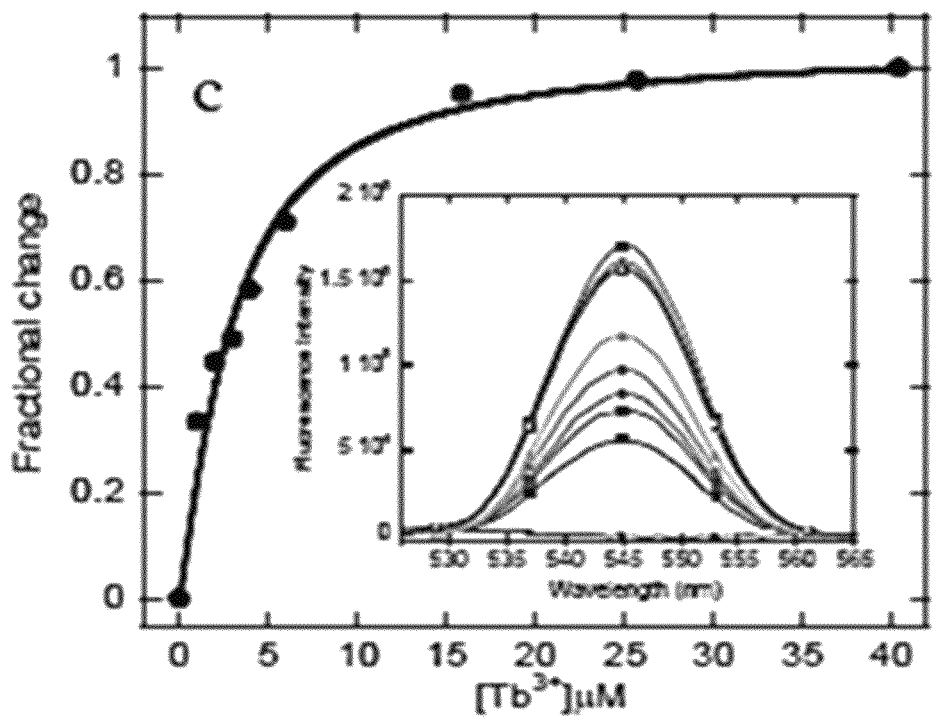
FIG. 17C illustrates the fluorescence change of 3 μM GFP.D1 in 20 mM PIPES, 10 mM KCl, 1 mM DTT, 1% glycerol, pH 6.8 at increasing terbium concentrations assuming a 1:1 binding. The inset shows the spectra peaks increase at 545 nm.

To further characterize the metal binding of the designed proteins, terbium sensitized fluorescence resonance energy transfer was used. Terbium, a calcium analog with similar ionic size and binding geometry, is intrinsically fluorescent at 545 nm and able to accept energy transferred from aromatic residues. EGFP contains 1 Trp and 10 Tyr, and the Trp is within 30 Å of GFP.D1 and GFP.D2 and 17 Å of GFP.D3 and GFP.D4 (Table 1). As shown in FIG. 17C, the addition of terbium into the protein results in a large increase in terbium-FRET signal at 545 nm with excitation at 280 nm. The enhancement as a function of terbium concentration with the assumption of a 1:1 metal:protein complex provided the binding affinities (Table 1). Of the three proteins tested at pH 7.4, GFP.D1 has the strongest terbium affinity (1.9±0.4 μM). GFP.D2 has a slightly weaker affinity of 4.9±0.2 μM while GFP.Ca2' exhibits a 15-foldweaker affinity of 32±13 μM. At pH 6.8, GFP.D2" exhibits a binding affinity for terbium of 2.9±0.3 μM. The addition of calcium and lanthanum into the terbium-protein complex significantly reduced the fluorescence enhancement of terbium due to competition.

Figure 17D:
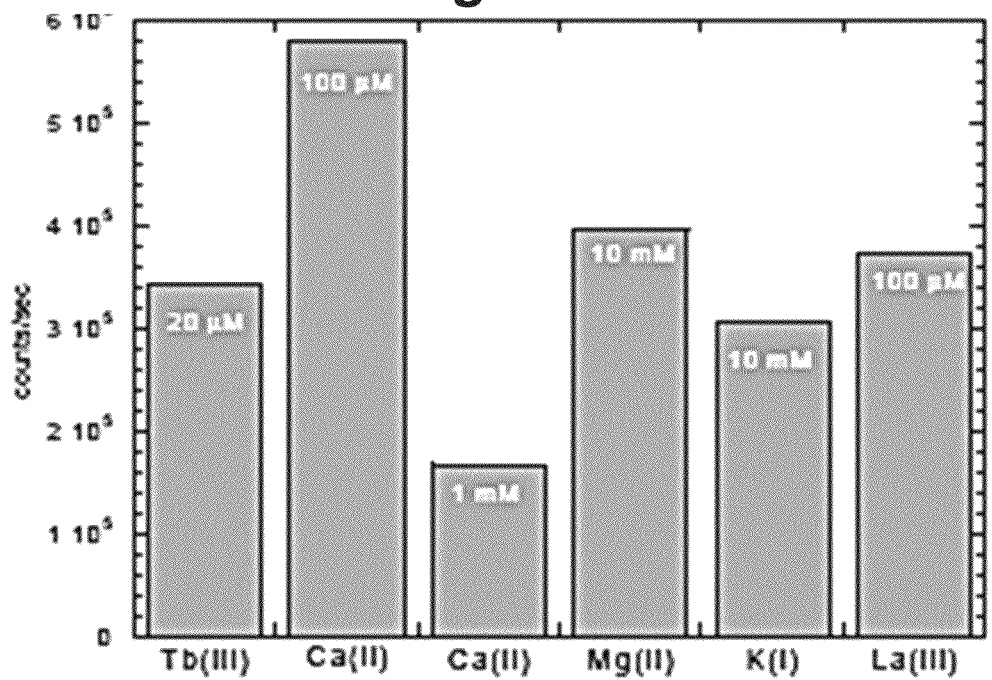
FIG. 17D illustrates the metal competition of GFP.D1.

As shown in FIG. 17D, addition of 1 mM calcium resulted in a large decrease in terbium fluorescence for GFP.D1, suggesting that calcium binds to the protein and competes for terbium binding. Addition of 100 μM lanthanum resulted in a fluorescence decrease to half, suggesting an estimated 5-fold lower metal binding affinity (about 10 μM). On the other hand, addition of higher concentrations of magnesium (10 mM) resulted in a relatively smaller decrease, indicating a relatively weaker binding affinity. Similarly, GFP.D2' exhibits a half maximal decrease in fluorescence with 1 mM calcium or 100 μM lanthanum, which is also more effective than magnesium. Taken together, calcium and lanthanides bind to the protein in the same pocket and have a greater than 20-fold selectivity over magnesium. The calcium binding sites of the present disclosure have calcium binding affinities with $K_d$ in the range of 38-96 μM. The metal selectivity is also sufficient for the proteins to bind calcium without interference from magnesium in the extracellular environment or in the ER where calcium concentration is much higher than in the cytosol.

TABLE 1

Design sites engineered into Green Fluorescent Protein.

| Design Site | Calcium-binding Ligands | Average distance to Chromophore (Å) | Charge of a.a. in binding site | Average distance binding site-Trp (A) | Tb (III) $K_d$ (μM) | Ca (II) $K_d$ (μM) |
|---|---|---|---|---|---|---|
| GFP.DI | Q177N, I171D, D173, S175O, N135 | 22 | −3 | 17 | 1.9 ± 0.4 | 60 ± 5 |
| GFP.D2 | E5, D82, S2D, S86D, L194E | 15 | −5 | 29 | N/A | 107 ± 13 |
| GFP.D2' | E5, D82, K79D, L194N, K85D | 15 | −4 | 29 | 32 ± 13 | 96 ± 7 |
| GFP.D2" | E5, O82, K79D, L194N, S86D | 15 | −4 | 30 | 2.9 ± 0.3 | 38 ± 5 |
| GFPD3 | E115, V120N, R122D, K113D | 14 | −4 | 15 | 4.9 ± 0.2 | 57 ± 2 |

For 120, 177, and 194 the terbium affinities were measured in a 20 mM PIPES, 10 mM KCl, 1 mM DTT, 1% glycerol, pH 6.8. For 194, the terbium affinity was measured in 10 mM Tris, 1 mM DTT, 1% glycerol, pH 7.4. The calcium affinities for all four sites were measured in 10 mM Tris, 1 mM DTT, 1% glycerol, pH 7.4.

Calcium binding dye competition was then used to obtain calcium binding affinities for these bacteria expressed pro- Embodiments of the present disclosure provide for analyte sensors including a molecular recognition motif that binds an analyte (e.g., calcium, lead, and/or lanthanide) and a fluorescent host polypeptide in which the molecular recognition motif is operatively linked to or integrated therein. Interaction of the analyte with the molecular recognition motif produces a detectable change. Table 2 lists some embodiments of the analyte sensors, the corresponding SEQ ID NO, and characteristics of the particular analyte sensor, while other analyte sensors are described in SEQ ID. Nos. 115-159. Although SEQ ID NOS. 1-99, and 104-105 and 115-159 includes specific order of amino acids, each of the groups (e.g., molecular recognition motif, fluorescent host polypeptide, and the like) could be positioned differently as long as the analyte sensor produces results consistent with the embodiments disclosed herein.

TABLE 2

| SEQ ID No. | Designator (Alternatives) | Amino acid positions of EGFP | Amino acid positions | Correspond to |
|---|---|---|---|---|
| 1 | EGFP-III-172 (Ca-G1') | 1-173, 186-256 | 174-185 | III. |
| 2 | EGFP-E-III-172 | 1-173, 197-262 | 174-196 | E-III. |
| 3 | EGFP-III-F-172 | 1-173, 194-259 | 174-193 | III-F. |
| 4 | EGFP-E-III-F-172 (Ca-G1, EGFP-G1) | 1-173, 205-270 | 174-204 | E-III-F |
| 5 | EGFP-E-III-F-172-ER (Ca-G1-ER) | 25-197, 229-294 | 198-228 | E-III-F |
| 6 | EGFP-E-III-F-172-mito | 36-213, 245-310 | 214-244 | E-III-F |
| 7 | EGFP-E-III-F-172-SKEAA | 1-173, 206-271 | 174-205 | E-III-F |
| 8 | EGFP-E-III-F-172-D/N | 1-173, 205-270 | 174-204 | E-III-F |
| 9 | EGFP-E-III-F-172-DD/NN | 1-173, 205-270 | 174-204 | E-III-F |
| 10 | EGFP-E-III-F-172-L194N | 1-173, 205-270 | 174-204 | E-III-F |
| 11 | EGFP-I-172 | 1-173, 186-251 | 174-185 | I |
| 12 | EGFP-α-Lac1-172 | 1-173, 206-271 | 174-205 | α-Lac1 |
| 13 | EGFP-α-Lac2-172 | 1-173, 206-271 | 174-205 | α-Lac2 |
| 14 | EGFP-α-Lac3-172 | 1-173, 206-271 | 174-205 | α-Lac3 |
| 15 | EGFP-α-Lac4-172 | 1-173, 206-271 | 174-205 | α-Lac4 |
| 16 | EGFP-III-172-C2 | 1-173, 186-256 | 174-185 | III |
| 17 | EGFP-E-III-172-C2 | 1-173, 197-262 | 174-196 | E-III |
| 18 | EGFP-III-F-172-C2 | 1-173, 194-259 | 174-193 | III-F |
| 19 | EGFP-E-III-F-172-C2 (Ca-G1-37, EGFP-G1-C2) | 1-173, 205-270 | 174-204 | E-III-F |
| 20 | EGFP-E-III-F-172-ER-C2 | 25-197, 229-294 | 198-228 | E-III-F |
| 21 | EGFP-E-III-F-172-mito-C2 | 36-213, 245-310 | 214-244 | E-III-F |
| 22 | EGFP-E-III-F-172-SKEAA-C2 | 1-173, 206-271 | 174-205 | E-III-F |
| 23 | EGFP-E-III-F-172-D/N-C2 | 1-173, 205-270 | 174-204 | E-III-F |
| 24 | EGFP-E-III-F-172-DD/NN-C2 | 1-173, 205-270 | 174-204 | E-III-F |
| 25 | EGFP-E-III-F-172-L194N-C2 | 1-173, 205-270 | 174-204 | E-III-F |
| 26 | EGFP-I-172-C2 | 1-173, 186-251 | 174-185 | I |
| 27 | EGFP-α-Lac1-172-C2 | 1-173, 206-271 | 174-205 | α-Lac1 |
| 28 | EGFP-α-Lac2-172-C2 | 1-173, 206-271 | 174-205 | α-Lac2 |
| 29 | EGFP-α-Lac3-172-C2 | 1-173, 206-271 | 174-205 | α-Lac3 |
| 30 | EGFP-α-Lac4-172-C2 | 1-173, 206-271 | 174-205 | α-Lac4 |
| 31 | EGFP-III-172-C3 | 1-173, 186-256 | 174-185 | III |
| 32 | EGFP-E-III-172-C3 | 1-173, 197-262 | 174-196 | E-III |
| 33 | EGFP-III-F-172-C3 | 1-173, 194-259 | 174-193 | III-F |
| 34 | EGFP-E-III-F-172-C3 (EGFP-G1-C3) | 1-173, 205-270 | 174-204 | E-III-F |
| 35 | EGFP-E-III-F-172-ER-C3 | 25-197, 229-294 | 198-228 | E-III-F |
| 36 | EGFP-E-III-F-172-mito-C3 | 36-213, 245-310 | 214-244 | E-III-F |
| 37 | EGFP-E-III-F-172-SKEAA-C3 | 1-173, 206-271 | 174-205 | E-III-F |
| 38 | EGFP-E-III-F-172-D/N-C3 | 1-173, 205-270 | 174-204 | E-III-F |
| 39 | EGFP-E-III-F-172-DD/NN-C3 | 1-173, 205-270 | 174-204 | E-III-F |
| 40 | EGFP-E-III-F-172-L194N-C3 | 1-173, 205-270 | 174-204 | E-III-F |
| 41 | EGFP-I-172-C3 | 1-173, 186-251 | 174-185 | I |
| 42 | EGFP-α-Lac1-172-C3 | 1-173, 206-271 | 174-205 | α-Lac1 |
| 43 | EGFP-α-Lac2-172-C3 | 1-173, 206-271 | 174-205 | α-Lac2 |
| 44 | EGFP-α-Lac3-172-C3 | 1-173, 206-271 | 174-205 | α-Lac3 |
| 45 | EGFP-α-Lac4-172-C3 | 1-173, 206-271 | 174-205 | α-Lac4 |
| 46 | EGFP-III-157 (Ca-G2') | 1-158, 171-251 | 159-170 | III |
| 47 | EGFP-E-III-F-157 (Ca-G2) | 1-158, 190-270 | 159-189 | E-III-F |
| 48 | EGFP-III-157-C2 | 1-158, 171-251 | 159-170 | III |
| 49 | EGFP-E-III-F-157-C2 | 1-158, 190-270 | 159-189 | E-III-F |
| 50 | EGFP-III-157-C3 | 1-158, 171-251 | 159-170 | III |
| 51 | EGFP-E-III-F-157-C3 | 1-158, 190-270 | 159-189 | E-III-F |
| 52 | EGFP-E-III-F-170 | 1-171, 203-270 | 172-202 | E-III-F |
| 53 | EGFP-E-I-F-170 | 1-171, 206-273 | 172-205 | E-I-F |
| 54 | EGFP-E-III-F-170-C2 | 1-171, 203-270 | 172-202 | E-III-F |
| 55 | EGFP-E-I-F-170-C2 | 1-171, 206-273 | 172-205 | E-I-F |
| 56 | EGFP-E-III-F-170-C3 | 1-171, 203-270 | 172-202 | E-III-F |
| 57 | EGFP-E-I-F-170-C3 | 1-171, 206-273 | 172-205 | E-I-F |
| 58 | EGFP-120 (GFP-D3) | 1-239 | 16, 114, 116, 121, 123 | $Ca^{2+}$ binding site |
| 59 | EGFP-120b | 1-239 | 16, 112, 116, 121, 123 | $Ca^{2+}$ binding site |
| 60 | EGFP-177 (GFP-D1) | 1-239 | 136, 172, 174, 176, 178 | $Ca^{2+}$ binding site |

TABLE 2-continued

| SEQ ID No. | Designator (Alternatives) | Amino acid positions of EGFP | Amino acid positions | Correspond to |
|---|---|---|---|---|
| 61 | EGFP-194a (GFP-D2') | 1-239 | 6, 80, 83, 86, 195 | $Ca^{2+}$ binding site |
| 62 | EGFP-194b (GFP-D2") | 1-239 | 6, 80, 83, 87, 195 | $Ca^{2+}$ binding site |
| 63 | EGFP-229 | 1-239 | 79, 82, 198, 200, 230 | $Ca^{2+}$ binding site |
| 64 | EGFP-site1 (GFP-D2) | 1-239 | 3, 6, 83, 87, 195 | $Ca^{2+}$ binding site |
| 65 | EGFP-site1-ER | 25-263 | 27, 30, 107, 111, 219 | $Ca^{2+}$ binding site |
| 66 | EGFP-site1-mito | 36-274 | 38, 41, 118, 122, 230 | $Ca^{2+}$ binding site |
| 67 | EGFP-site2 | 1-239 | 16, 18, 116, 121, 123 | $Ca^{2+}$ binding site |
| 68 | EGFP-site3 | 1-239 | 84, 153, 155, 162, 195 | $Ca^{2+}$ binding site |
| 69 | EGFP-site4 | 1-239 | 60, 101, 137, 142, 178 | $Ca^{2+}$ binding site |
| 70 | EGFP-site5 | 1-239 | 8, 13, 89, 115, 120 | $Ca^{2+}$ binding site |
| 71 | EGFP-site6 | 1-239 | 8, 13, 89, 115, 120 | $Ca^{2+}$ binding site |
| 72 | EGFP-120-C2 | 1-239 | 16, 114, 116, 121, 123 | $Ca^{2+}$ binding site |
| 73 | EGFP-120b-C2 | 1-239 | 16, 112, 116, 121, 123 | $Ca^{2+}$ binding site |
| 74 | EGFP-177-C2 | 1-239 | 136, 172, 174, 176, 178 | $Ca^{2+}$ binding site |
| 75 | EGFP-194a-C2 | 1-239 | 6, 80, 83, 86, 195 | $Ca^{2+}$ binding site |
| 76 | EGFP-194b-C2 | 1-239 | 6, 80, 83, 87, 195 | $Ca^{2+}$ binding site |
| 77 | EGFP-229-C2 | 1-239 | 79, 82, 198, 200, 230 | $Ca^{2+}$ binding site |
| 78 | EGFP-site1-C2 | 1-239 | 3, 6, 83, 87, 195 | $Ca^{2+}$ binding site |
| 79 | EGFP-site1-ER-C2 | 25-263 | 27, 30, 107, 111, 219 | $Ca^{2+}$ binding site |
| 80 | EGFP-site1-mito-C2 | 36-274 | 38, 41, 118, 122, 230 | $Ca^{2+}$ binding site |
| 81 | EGFP-site2-C2 | 1-239 | 16, 18, 116, 121, 123 | $Ca^{2+}$ binding site |
| 82 | EGFP-site3-C2 | 1-239 | 84, 153, 155, 162, 195 | $Ca^{2+}$ binding site |
| 83 | EGFP-site4-C2 | 1-239 | 60, 101, 137, 142, 178 | $Ca^{2+}$ binding site |
| 84 | EGFP-site5-C2 | 1-239 | 8, 13, 89, 115, 120 | $Ca^{2+}$ binding site |
| 85 | EGFP-site6-C2 | 1-239 | 8, 13, 89, 115, 120 | $Ca^{2+}$ binding site |
| 86 | EGFP-120-C3 | 1-239 | 16, 114, 116, 121, 123 | $Ca^{2+}$ binding site |
| 87 | EGFP-120b-C3 | 1-239 | 16, 112, 116, 121, 123 | $Ca^{2+}$ binding site |
| 88 | EGFP-177-C3 | 1-239 | 136, 172, 174, 176, 178 | $Ca^{2+}$ binding site |
| 89 | EGFP-194a-C3 | 1-239 | 6, 80, 83, 86, 195 | $Ca^{2+}$ binding site |
| 90 | EGFP-194b-C3 | 1-239 | 6, 80, 83, 87, 195 | $Ca^{2+}$ binding site |
| 91 | EGFP-229-C3 | 1-239 | 79, 82, 198, 200, 230 | $Ca^{2+}$ binding site |
| 92 | EGFP-site1-C3 | 1-239 | 3, 6, 83, 87, 195 | $Ca^{2+}$ binding site |
| 93 | EGFP-site1-ER-C3 | 25-263 | 27, 30, 107, 111, 219 | $Ca^{2+}$ binding site |
| 94 | EGFP-site1-mito-C3 | 36-274 | 38, 41, 118, 122, 230 | $Ca^{2+}$ binding site |
| 95 | EGFP-site2-C3 | 1-239 | 16, 18, 116, 121, 123 | $Ca^{2+}$ binding site |
| 96 | EGFP-site3-C3 | 1-239 | 84, 153, 155, 162, 195 | $Ca^{2+}$ binding site |
| 97 | EGFP-site4-C3 | 1-239 | 60, 101, 137, 142, 178 | $Ca^{2+}$ binding site |

TABLE 2-continued

| SEQ ID No. | Designator (Alternatives) | Amino acid positions of EGFP | Amino acid positions | Correspond to |
|---|---|---|---|---|
| 98 | EGFP-site5-C3 | 1-239 | 8, 13, 89, 115, 120 | $Ca^{2+}$ binding site |
| 99 | EGFP-site6-C3 | 1-239 | 8, 13, 89, 115, 120 | $Ca^{2+}$ binding site |

SEQ ID. No. 105 corresponds to the CaratER sensor. Residues for the ER targeting sequence from calreticulin signal peptide is attached to the N-terminal and the ER retention sequence is attached to the C-terminal. SEQ ID. No.: 105 includes mutations for the new binding site and the ER targeting and retention sequences at the N and C terminii, respectively. Additional sequences of the sensor are described in SEQ ID. No. 115 to 159.

The fluorescent host polypeptide can have the molecular recognition motif inserted or integrated into the fluorescent host polypeptide at one of a number of locations, where each different insertion point provides an analyte sensor with different characteristics. For example, when the fluorescent host polypeptide is an enhanced fluorescent protein (EGFP), the molecular recognition motif can be inserted into the positions 152, 172, or 170.

It should also be noted that the fluorescent host polypeptide can be modified to enhance the thermal stability and/or the fluorescent properties of the analyte sensor by including two or three mutations to the fluorescent host polypeptide. In particular, the EGFP can include two mutations (M153T, V163A) and/or three mutations (F99S, M153T, V163A), which increase thermal stability and or fluorescence properties, as described herein. These mutations are noted in SEQ ID Nos.: 16 to 45, SEQ ID Nos.: 48 to 51, SEQ ID Nos.: 54 to 57, and SEQ ID Nos.: 72 to 99, respectively. Additional details and the examples that describe specific embodiments of the present disclosure are provided below.

Based on the fluorescence properties of the analyte sensor, a DNA construct of the analyte sensor may be inserted into a recombinant vector or any suitable vectors that may conveniently be subjected to recombinant DNA procedures. The specific vector can depend on the type of host cells. For example, recombinant DNA plasmid vectors, which can exist as an extrachromosomal entity, may be a suitable vector. Alternatively, the vector may be one that, when introduced into a host cell, is integrated into the host cell genome and replicates together with the chromosome(s) into which it has been integrated. Once the analyte sensor has been constructed, vectors comprising the fluorescent nucleic acid molecules may be formulated into a variety of compositions, such as solutions (for example, buffer solutions) to be used in transfecting host cells.

A fluorescent host polypeptide or variant thereof can be linked to the molecule directly or indirectly, using any linkage that is stable under the conditions to which the protein-molecule complex is to be exposed. Thus, the fluorescent host polypeptide and molecule can be linked via a chemical reaction between reactive groups present on the protein and molecule, or the linkage can be mediated by a linker moiety, which contains reactive groups specific for the fluorescent host polypeptide and the molecule. It will be recognized that the appropriate conditions for linking the fluorescent host polypeptide variant and the molecule are selected depending, for example, on the chemical nature of the molecule and the type of linkage desired. Where the molecule of interest is a polypeptide, a convenient means for linking a fluorescent host polypeptide variant and the molecule is by expressing them as a fusion protein from a recombinant nucleic acid molecule, which includes a polynucleotide encoding, for example, a fluorescent host polypeptide operatively linked to a polynucleotide encoding the polypeptide molecule.

An embodiment of the analyte sensor may be produced as chimeric proteins by recombinant DNA technology. Recombinant production of proteins including fluorescent host polypeptides involves expressing nucleic acids having sequences that encode the proteins. Nucleic acids encoding fluorescent host polypeptides can be obtained by methods known in the art. For example, a nucleic acid encoding the protein can be isolated by a polymerase chain reaction of DNA from *A. victoria* using primers based on the DNA sequence of *A. victoria* GFP. Mutant versions of fluorescent host polypeptides can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

The molecular recognition motif can include the analyte binding site, one or more structural motif, and a targeting motif. The analyte binding site and the structural can include those described above. The targeting motif can target organelles and sub-organelles such as, but not limited to, ER, mitochondrion, Golgi, nucleus, channels, gap junctions, and extracellular spaces. The targeting motif includes, but is not limited to, signal peptides encoded in the proteins located in the target organelles. The targeting motif includes those listed in SEQ ID Nos.: 5-6, 20-21, 35-36, 65-66, 79-80, 93-94, where the specific amino acid sequences are noted above. As mentioned above, the motifs can be positioned differently than described herein as long as they have characteristics that are consistent with the embodiments disclosed. Additional details and the examples that describe specific embodiments of the present disclosure are provided below.

The present disclosure provides for analyte sensors that comprise a molecular recognition motif that binds a metal ion analyte (e.g., calcium, lead, and/or lanthanide) and a fluorescent host polypeptide in which the molecular recognition motif is operatively linked to or integrated therein. Interaction of the analyte with the molecular recognition motif produces a detectable change. The analyte sensor has a protein sequence that includes the molecular recognition motif and the fluorescent host polypeptide selected from: SEQ ID Nos.: 5, 6, 20, 21, 35, 36, 80, 81, 94, and 95.

An embodiment of the analyte sensor has at least one characteristic selected from the following: is stable at temperatures greater than about 30° C.; has enhanced fluorescent and optical properties (resulting, for example from mutations of the fluorescent protein (e.g., F99S, M153T and V163A)), and combinations thereof. In particular, embodiments of the analyte sensors (denoted as C2 or C3 variants) (SEQ ID NOS.: 16-45, 48-51, 54-57, and 72-99) are able to maintain fluorescence in both mammalian and bacterial cells. Each of the embodiments described herein are able to bind calcium and other metal ions (including but not limited to, $Pb^{2+}$, $Tb^{3+}$, $La^{3+}$, and $Gd^{3+}$).

An embodiment of the analyte sensor of the disclosure can be generated by first constructing a molecular recognition motif that includes the analyte binding site that is capable of responding to a metal ion analyte and then operatively inserting the molecular recognition motif into a fluorescent host polypeptide. Molecular recognition motifs typically have a primary structure, a secondary structure, and a tertiary structure in most cases and in some cases a quaternary structure, at least one of which can be tailored to the analyte sensor to achieve a desired level of analyte sensitivity. That is, each of the primary structure, the secondary structure, the tertiary structure, and if present, the quaternary structure can be tailored to the analyte sensor independently or in combination with one or more others of the structures to achieve a desired level of sensitivity for the sensor relative to the analyte. For example, the binding of the analyte to the molecular recognition motif preferably produces a change in a detectable signal (fluorescence, for example) and the manipulation of the molecular recognition motif manipulates the responsiveness of the sensor.

An embodiment of the analyte sensor also can allow the quantification of an analyte due to a molecular recognition motif able to produce a detectable change upon excitation, expressing the protein, providing excitement to the analyte sensor, and then quantifying the detectable change. Preferably, the protein can include a fluorescent host polypeptide, whose emission intensity is relative to the quantity of analyte in a microenvironment.

One method for creating a molecular recognition motif is through the use of an integrating method. The integration method focuses on engineering and constructing a molecular recognition motif by modifying the primary, secondary, tertiary, and/or quaternary structure of an identified binding site.

An illustrative method for constructing a molecular recognition motif using the integration method includes first identifying an analyte binding peptide that binds an analyte with specificity and then ascertaining at least a portion of a nucleic acid sequence encoding the analyte binding peptide. Once this is accomplished, the nucleic acid sequence encoding the analyte binding peptide is tailored into a molecular recognition motif that includes an analyte binding site. After the tailoring is completed, a fluorescent host polypeptide is selected and a relevant portion of the nucleic acid sequence of the fluorescent host polypeptide is identified, and the tailored nucleic acid sequence encoding the analyte binding peptide is operatively linked with the fluorescent host polypeptide nucleic acid sequence into a molecular recognition motif sequence. Finally, the molecular recognition motif sequence is expressed. In this method, the nucleic acid sequence encoding the analyte binding peptide is tailored so as to achieve the molecular recognition motif with a desired specificity for the analyte. Preferably, the nucleic acid sequence encoding the analyte binding peptide is tailored to have specificity for the analyte over other analytes. Resultant proteins encoded by the molecular recognition motif sequence are useful products of this disclosure.

The primary structure of an analyte binding site can be selectively modified by inserting at least one codon into the nucleic acid sequence encoding the analyte binding peptide. Similarly, codons for charged amino acids can be inserted into the nucleic acid sequence encoding the analyte binding peptide. The analyte binding site can also be modified by selectively manipulating and adding helices, loops, bridges or linkers, among other methods. Charged amino acids can be inserted into the amino acid sequence encoding the analyte binding peptide and or aromatic amino acids can be introduced into the amino acid sequence encoding the analyte binding peptide.

Another method for generating a desired molecular recognition motif is through the use of a computational approach in which a computational method for engineering and constructing a molecular recognition motif de novo is based on optimal binding characteristics of an analyte with other moieties. In one illustrative embodiment, using established criteria for evaluating $Ca^{2+}$ binding data, a $Ca^{2+}$ binding site of desired sensitivity may be constructed by molecular modeling. For example, such computation algorithms may be used to develop desired ion binding motifs based on parameters such as the metal's binding geometry, the folding of the host protein, the location of the charges on the fluorescent protein, the particular chromophores, and other criteria specific to the $Ca^{2+}$ binding data.

The computational approach can be used to construct a molecular recognition motif by accessing public and or private databases that include structural data on analyte binding sites, generating at least one preliminary analyte binding site from the structural data based on certain previously selected criteria, selecting one or more suitable analyte binding sites from the preliminary analyte binding sites, and constructing the analyte binding motif by tailoring the selected analyte binding site and operatively linking it with a host protein, keeping in mind that the molecular recognition motif preferably has a specificity for a selected analyte. The structural data typically can include amino acid sequences, secondary structures, nucleic acid sequences, geometric parameters, electrostatic properties, and coordination properties of the analyte binding sites, such as in protein and gene banks.

The computational approach can be performed on or by a system including at least one database that comprises the structural data on analyte binding sites, an algorithm for generating the preliminary analyte binding sites from portions of the structural data using selected criteria relevant to the molecular recognition motif and rating the preliminary analyte binding sites based on specificity for a selected analyte, and a computer for executing the algorithm so as to query the databases to generate the preliminary analyte binding sites. The algorithm generally is a relatively simple searching algorithm that will query the databases based on inputted criteria.

Once the molecular recognition motif has been tailored and operatively linked into the fluorescent host polypeptide, the analyte sensor may show responsiveness to analyte dependent fluorescence variations. The responsiveness of the analyte sensor is caused by the interaction of the fluorescent host polypeptide with the molecular recognition motif, which then may display fluorescence properties proportional to the analyte concentration or flux. In particular, the responsiveness is thought to be caused by changes in the orientation and protonation of the chromophore of the fluorescent protein. The interaction between the analyte and the fluorescent host polypeptide may result in a shift in the emission spectra, quantum yield, and/or extinction coefficient, which may be quantitatively analyzed in real-time to probe the microenvironment.

In use and application, an embodiment of the analyte sensor may be used to detect and quantify the analyte concentration and flux thereof in a sample as a non-ratiometric dye. More particularly, the analyte sensor is inserted into the sample, the sample then is excited by radiation, the fluorescence from the sample then is measured using an optical device, and the fluorescence or flux thereof then is analyzed to quantify or detect the analyte concentration in the sample. In order to analyze the sample, it may be necessary to generate a standard curve based on the fluorescence generated from known analyte concentrations. Specifically, the fluorescence signal of the analyte sensor is compared to the fluorescence of the standard curve so as to determine the concentration of analyte in the sample.

Fluorescent host polypeptides: The analyte sensors according to the disclosure may comprise a fluorescent host polypeptide or polypeptide (also referred to as "optically active fluorescent host polypeptide" or "optically active fluorescent protein"). The native signal of the fluorescent protein is altered by the inclusion of the analyte binding site within the amino acid sequence of the fluorescent host polypeptide. Embodiments of the present disclosure provide for specific insertion positions of the analyte binding site within the fluorescent host polypeptide so that the analyte sensor produces an emission that is altered upon interaction of the analyte with the analyte binding site. In this regard, the relative three dimensional position of the chromophore within the fluorescent host polypeptide is altered by the inclusion of the analyte binding site, where such alteration generates the altered signal. In an embodiment, the analyte sensors can emit at two or more distinguishable wavelengths.

Fluorescent host polypeptides suitable for use in the analyte sensors of the disclosure include, but are not limited to, Green Fluorescent Protein isolated from *Aequorea victoria* (GFP), as well as a number of GFP variants, such as enhanced fluorescent protein (EGFP). In particular, *Aequorea* green fluorescent protein (GFPs) and its enhanced fluorescent proteins have about 238 amino acid residues in a single polypeptide chain. The native molecule has been shown to regenerate its intrinsic fluorescence from the totally denatured state. GFPs display a strong visible absorbance and fluorescence that is thought to be generated by the autocyclization and oxidation of the chromophore having a tripeptide Ser-Tyr-Gly sequence at positions 65 to 67 of the 238 amino acid sequence. Mutations to GFPs have resulted in various shifts in absorbance and fluorescence. The usefulness of GFPs stems from fluorescence from GFP not requiring additional cofactors; the fluorophore is self-assembling via a cyclization reaction of the peptide backbone.

The chromophore of GFP is formed by the cyclization of the tripeptide Ser65-Tyr66-Gly67. This chromophore is located inside of the β-barrel that is composed of 11 antiparallel strands and a single central α-helix. There are short helices capping the ends of the β-barrel. The chromophore has extensive hydrogen bonding with the protein frame and can be affected by water molecules under the different folding states. The chromophore in a tightly constructed β-barrel that exhibits absorption peaks at 400 and 480 nm and an emission peak at 510 nm with a quantum yield of about 0.72 when excited at 470 nm. The chromophore in enhanced green fluorescent protein (EGFP), which is GFP with a mutation S65T, has an improved fluorescence intensity and thermo-sensitivity.

Two (M153T, V163A) or three additional mutations (F99S, M153T, V163A) were added to EGFP to increase the protein expression, stability, chromophore formation at 37° C., or above.

A linker comprising specific analyte binding sites can be grafted between the position 170, 172, and 157, as shown in SEQ ID Nos.: 1-58, as shown in Table 2, for example.

An embodiment of the analyte binding sites can be created by mutation in the fluorescent proteins to form a proper binding pocket without using amino acids from a contiguous stretch of the sequence. All of the sequences shown in SEQ ID Nos.: 59-99, as shown in Table 2, for example.

Analyte Binding Site: The analyte sensor according to the disclosure can have a molecular recognition motif that includes an analyte binding site. The native signal of the fluorescent protein can be altered by integration of the analyte binding site within the amino acid sequence of the fluorescent host polypeptide. The relative three dimensional position of the chromophore within the fluorescent host polypeptide may be altered by the inclusion of the analyte binding site, where such alteration generates the altered signal. This signal change in the sensors can results in a ratiometric change i.e. an increase, a decreases, or increases at one wavelength and an opposite change at another wavelength at both absorption and/or fluorescence excitations.

An embodiment of the analyte binding site functions by interacting with a metal ion analyte, such interaction causing the analyte sensor to produce an altered signal relative to the analyte sensor prior to interaction. The relative three-dimensional position of the chromophore within the fluorescent host polypeptide can be altered upon interaction of the analyte with the analyte binding site, where such alteration generates the altered signal.

The analyte binding site can include, but is not limited to, a binding site where the analyte binds to the analyte sensor. The binding site can be a location where the analyte binds to the analyte sensor. Usually specific types of amino acids in specific sequential or a particular spatial arrangement may be used for a specific type of analyte. Depending on the reaction and the nature of the binding and relative alteration of the chromophore, the binding of the analyte can cause an alteration in the analyte sensor signal. However, the cleavage reaction will cause large changes of the sensor signal. This can be due to the alteration of the local environment of the three dimensional position of the chromophore within the fluorescent host polypeptide which results in alteration of the signal. Such alteration can be due to the perturbation of the hydrogen network, the dynamic properties, the solvent accessibility or chemical properties such as hydrophobic and electrostatic interaction.

An embodiment of the site within the fluorescent host polypeptide for inserting the analyte binding site cleavage site preferably may be selected so that the location is accessible by a metal ion analyte. In addition, the location within the fluorescent host polypeptide can be selected so that the location does not substantially reduce the fluorescence from the fluorescent host polypeptide and so that the locations do not substantially denature or alter the protein folding of the fluorescent host polypeptide or chromophore. Furthermore, the site within the fluorescent host polypeptide for inserting the analyte binding site cleavage site can be selected based on one or more of the following criteria: maximization of solvent accessibility to allow efficient enzymatic action, maximization of fluorescent/optical signals once the analyte binding site is operatively incorporated into the fluorescent host polypeptide; minimization of the disruption to the chromophore environment after interaction of the analyte binding site with the analyte; minimizing the effects on the protein folding and packing of the fluorescent host polypeptide; and maximization of the ratiometric change of chromophore signal due to interaction of the analyte binding site with the analyte so to allow an accurate measurement of the analyte activity in vitro or in vivo. It should be noted that the analyte binding site can be include within or between motifs of the fluorescent host polypeptide, such as within or between a secondary structure motif, a tertiary structure motif, or a quaternary structure motif. In particular, the analyte binding site can be inserted in the loop of the β-barrel, and between loops.

Structure motifs: The inclusion of a structure motif in the molecular recognition motif allows optimal molecular recognition by incorporating essential structural and chemical properties required for a specific type of analyte. For example, good solvent accessibility for easier access by analytes, good flexibility required for recognition, a special geometric pocket for the interaction, a hydrophilic surface or charged environment to facilitate the binding process and a required environment for the fast kinetic rates such as good off rate required for real time measurements.

For example, but not intended to be limiting, for solvent accessibility and flexibility such as a helix-loop-helix or partial motif can be useful. These helix-loop-helix motifs can be from EF-hand motifs from calcium binding proteins such as calmodulin or trponic c, S100, or from nucleic binding motifs, and the like. Additionally, other structural motifs such as beta-loop-beta or beta-loop-helix, or coiled structures or domains and fragments that contain the cleavage sequence, and which are located at a sensitive location relative to the chromophore with the capability to alter the chromophore environment, can be used in embodiments of the present disclosure, as listed, for example in Table 2.

Targeting Motif: A target motif may have an affinity for a target such as a cell, a tissue, a small molecule, a protein, an organelle, a suborganelle, and the like related to a normal or pathological condition, biological or physiological event of the sample or host. The targeting motif can have an affinity for one or more targets. The targeting motif can be specific or non-specific.

The non-specific targeting moiety can be selected to do one or more of the following: enter a cell or a cell type, enter the vasculature, enter an extracellular space, enter an intracellular space, have an affinity for a cell surface, diffuse through a cell membrane, react with a non-specified moiety on the cell membrane, enter tumors due to leaky vasculature, and the like. The non-specific targeting moiety can include a chemical, biochemical, or biological entity that facilitates the uptake of the probe into a cell. The non-specific targeting moiety can include, but is not limited to, cell penetrating peptides, polyamino acid chains, small molecules, and peptide mimics.

The purified proteins of the disclosure can also be directly injected into the cells or cellular space to measure the analyte concentration. Sensor proteins selected from the SEQ ID Nos. 1-99, 104-105 and 115-159 can be also used to measure analyte changes in vitro such as in solution. The purified proteins can also function as a buffer or chelator to control the concentration of the analyte in vitro and in vivo.

Methods of Use: It is contemplated that the analyte sensors of the disclosure can be used in vivo and/or in vitro. The analyte sensors or systems of the disclosure can be introduced into a cell or host, the analyte sensors or systems can be expressed in the system, and/or the analyte sensors or systems can be included in a transgenic animal or plant. The analyte sensor can include a specific signal peptide for the delivery of the analyte sensor to different subcellular compartments such as cytosol, nucleus, mitochondrial matrix, endoplasmic reticulum, golgi and peroxisome, and the like.

Embodiments of the present disclosure provide for methods of detecting and measuring a metal ion analyte. The methods can include: introducing an analyte sensor into a system; allowing the analyte sensor to interact with the analyte of interest, which can interact with the analyte binding site of the analyte sensor; and detecting or measuring the fluorescent properties or changes derived from the fluorophore. As the change in fluorescent activity of the analyte sensor is a proxy for the activity of the analyte of interest, this method provides a means for studying and evaluating analyte activity.

Embodiments of the method of the disclosure can include: introducing a plasmid encoding the analyte sensor into a host cell by standard gene transfer methods; expressing the analyte sensor in the host cell; allowing the analyte sensor to interact with the analyte of interest, which can interact with the analyte binding site of the analyte sensor, and thereby detect or measure a fluorescent signal or changes. As the change in fluorescent activity of the analyte sensor is a proxy for the activity of the analyte of interest, this method provides a means for studying and evaluating analyte activity.

The methods can include: introducing an analyte sensor into a system; allowing the analyte sensor to interact with a metal ion analyte which can interact with the analyte binding site of the analyte sensor; and detecting or measuring the fluorescent properties or changes, which can be correlated to a pH change.

Embodiments of the present disclosure can further provide for methods of controlling the concentration of one or more metal ion analytes. In an embodiment, the methods can include: introducing an analyte sensor into a system; allowing the analyte sensor to interact with the analyte, which can interact with the analyte binding site of the analyte sensor. The bonding of the analyte with the analyte controls the amount of analyte in the cell or host.

Samples useful with this disclosure include biological samples, environmental samples, or any other samples for which it is desired to determine whether a particular molecule is present therein. The sample can be, but is not limited to, a living cell or a cell extract, which may be obtained from an animal or a plant. Alternatively, the cells can originate from or be derived from bacterial cells. Further, the cells may be obtained from a culture of such cells, for example, a cell line, or can be isolated from an organism. Where the method is performed using an intact living cell or a freshly isolated tissue or organ sample, the presence of a molecule of interest in living cells can be identified, thus providing a means to determine, for example, the intracellular compartmentalization of the molecule in real time.

Detecting with the analyte sensor: Methods for detecting with the analyte sensor or of a cell expressing containing an analyte sensor may include, but are not limited to, illuminating the analyte sensor or cell expressing the sensor with an illumination source such that the analyte sensor or cell expressing the analyte sensor emits a radiation. Such detection methods may use an illumination source such as an incandescent light source, a fluorescent light source, a halogen light source, sunlight, a laser light, and other equivalent sources. When illuminated by such an illumination source, the analyte sensor can emit fluorescent light that may be detected by unaided optical observation or by other qualitative or quantitative methods. Suitable methods for measuring fluorescence of samples are known and understood by those with ordinary skill in the art.

To overcome the limitation of slow kinetics (Zou et al., Brioche, 2007), an improvement of the off-rate constant $k_{off}$ to 256 s$^{-1}$ was obtained by redesigning the binding interface between calmodulin and its targeting peptide in GFP-based Ca$^{2+}$ sensors. Optimizing the protonation rate of the chromophore in GFP-based Ca$^{2+}$ sensors will provide a means to enhance further the accuracy with which Ca$^{2+}$ signals can be measured with high temporal resolution. Ca$^{2+}$-induced changes in CatchER's optical properties: The model structure of our designed $Ca^{2+}$ sensor, CatchER, was based on the scaffold protein EGFP. The binding site is adjacent to the chromophore (right on top of the Y66 phenolic oxygen) and next to H148, T203, and E222 (FIG. 20A); its fluorescence sensitivity may be due to hydrogen-bond interaction. The X-ray crystal structure shows mutated residue sidechains protruding from the protein surface, providing access to solvents. This putative $Ca^{2+}$ binding site is formed by residues 147, 202, 204, 223, and 225, which confer $Ca^{2+}$-preferred geometric properties (FIG. 20B). Five variants were created by introducing charged residues in these positions (FIGS. 20D-20H).

Figure 20I:
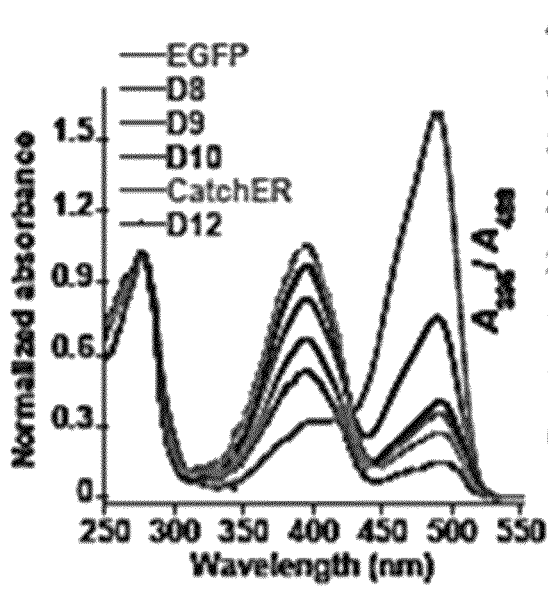
Figure 20J:
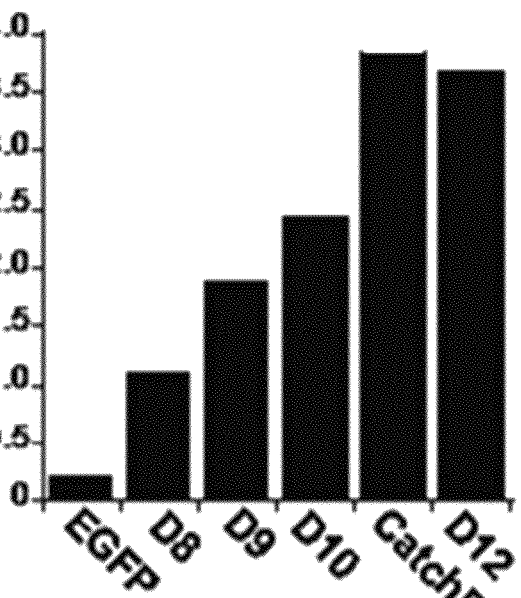
Figure 20K:
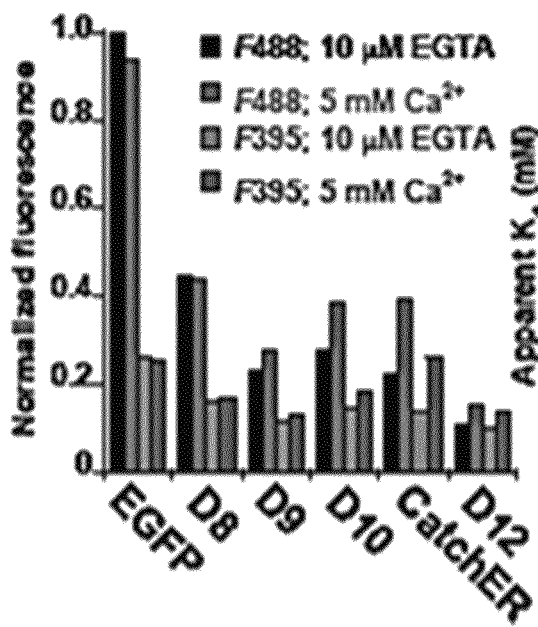

CatchER (D11) and its variants (D8-D10 and D12) were bacterially expressed and purified using established methods (Heim & Tsien (1996) Curr. Biol. 6: 178-182; Zou et al., (2007) Biochemistry 46: 12275-12288). Introducing acidic ligand residues added an absorption maximum at 398 nm at the expense of the 490 nm peak (FIG. 20I). This EGFP feature is associated with predominance of the anionic chromophore. The ratio of absorption maxima 395/488 increases from 0.2 for EGFP with no charged residue to 2.3 for D10 with four acidic residues (FIG. 20J). A fluorescence maximum of 510 nm excited at 488 nm parallels the absorbance maxima (FIGS. 25A-25L).

$Ca^{2+}$ binding to CatchER and its variants D9 and D10 increased absorbance at 490 nm and decreased it at 398 nm (FIG. 25C-25E, 25M), suggesting that $Ca^{2+}$ binding increases the anionic chromophore. In contrast, a 510 nm emission maximum increased when excited at both 395 and 488 nm (FIG. 25I-25K, 25M). Among all variants, CatchER had the largest fluorescence enhancement (about 80%) upon $Ca^{2+}$ binding (FIG. 25K and FIG. 25M) and attained approximately 50% of EGFP fluorescence intensity. D8's fluorescence response was negligible, possibly because it has few ligand residues and low $Ca^{2+}$ binding affinity.

Figure 26B:
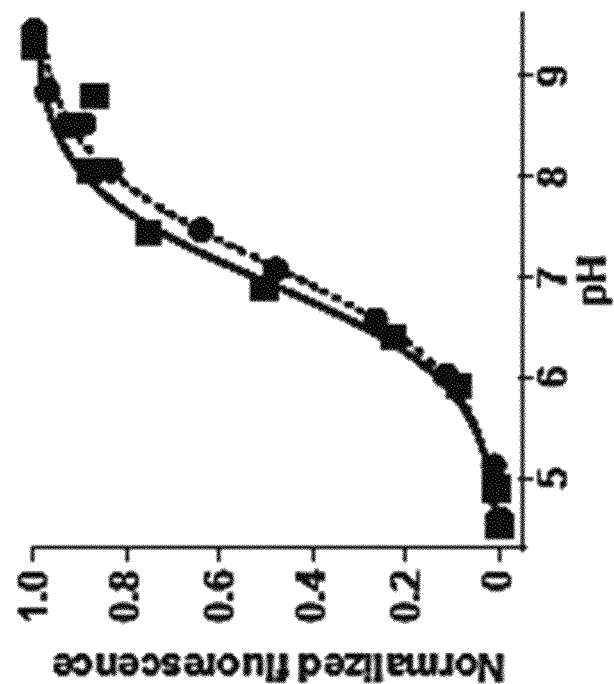
FIGS. 26A-26G illustrate the pH stability of CatchER before and after binding $Ca^{2+}$ as determined by measuring the apparent pKa values based on pH-dependence of the fluorescence intensity, and the stoichiometric interaction between CatchER and $Ca^{2+}$ is determined by Job's Plot.
Figure 26A:
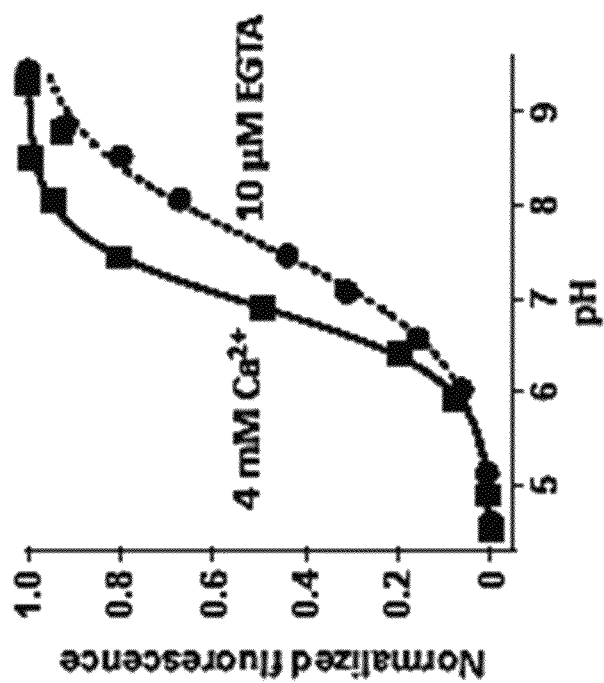

Metal binding assisted chromophore formation, as shown by a 0.7 unit decrease in CatchER's $pK_a$ in the presence of $Ca^{2+}$ (FIG. 26B) for a value of 6.9, which is closer to that for EGFP. $Ca^{2+}$ binding reverses changes in fluorescence properties associated with adding charged ligand residues presumably because it neutralizes the excess negative charge while enhancing fluorescence when excited at 488 and 395 nm. Taken together, these results suggest a unique mechanism for CatchER, involving a concomitant recovery of fluorescence and a switch in the chromophore's ionic form.

Figure 21A:
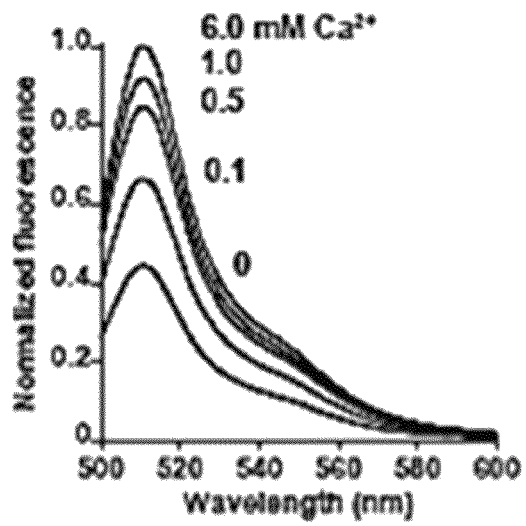
FIGS. 21A-21E illustrate the optical characterizations of CatchER in vitro.
Figure 21B:
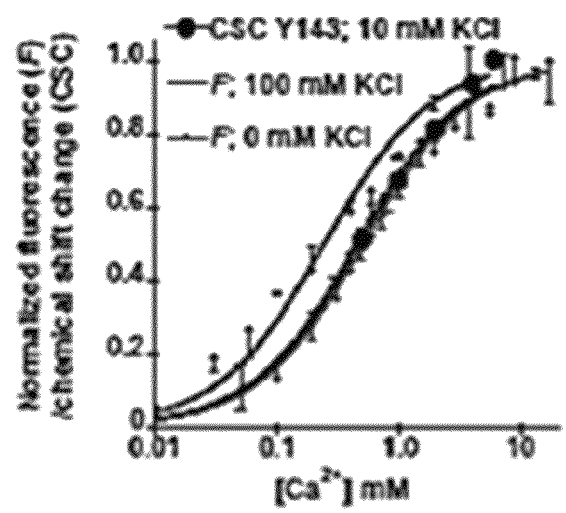
Figures 26C, 26D:
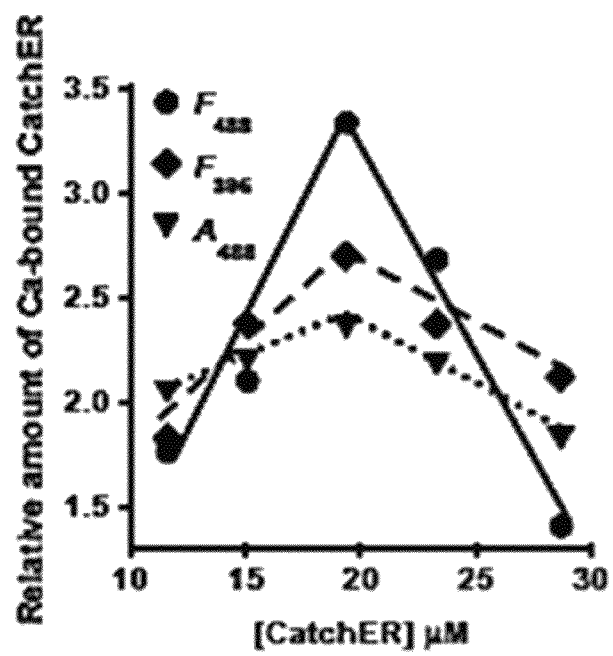
Figure 26G:
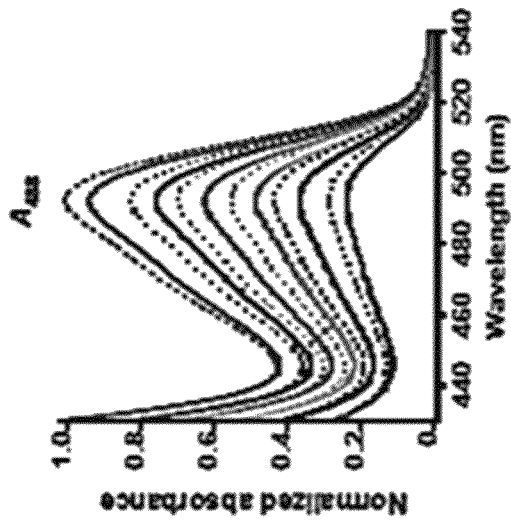
Figure 26F:
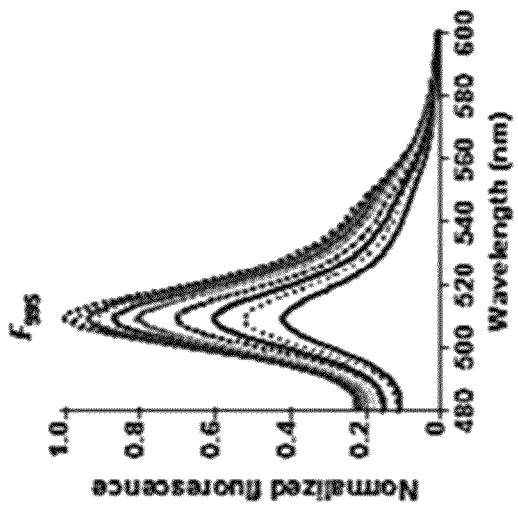
Figures 27A, 27B:
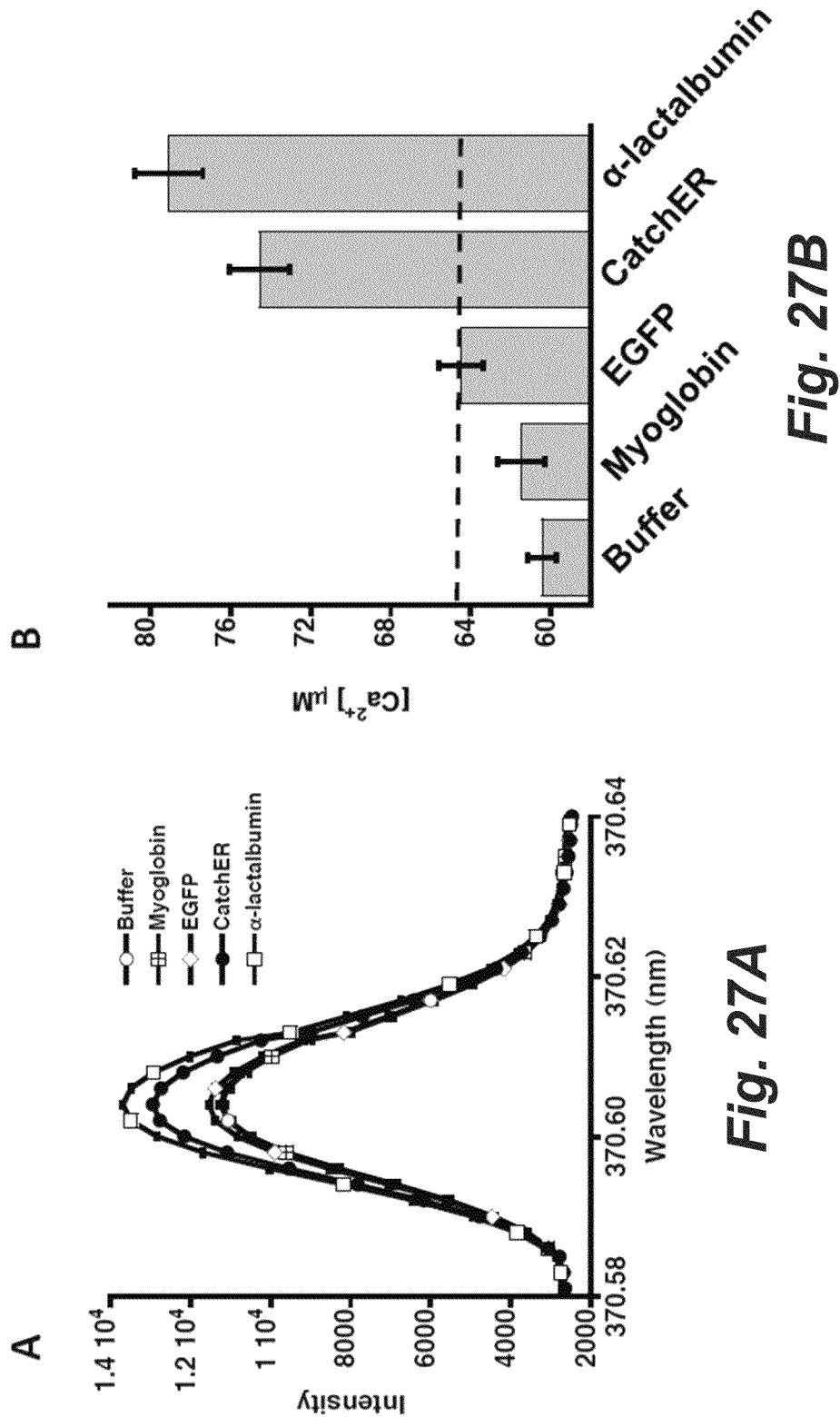
FIGS. 27A and 27B illustrate $Ca^{2+}$ binding by CatchER by equilibrium dialysis and an Inductively Coupled Plasma Optical Emission Spectrometer (ICP-OES).

Metal binding properties: Several lines of evidence support a simple CatchER-$Ca^{2+}$ stoichiometry reaction. The Job Plot suggests that $Ca^{2+}$ forms a 1:1 complex with CatchER (FIG. 26C), and the fluorescence change in response to $Ca^{2+}$ titration can be fitted to a 1:1 binding equation (FIG. 21B). The equilibrium dialysis experiments using myoglobin (noncalcium-binding protein), EGFP (noncalcium-binding protein), CatchER, and α-lactalbumin ($Ca^{2+}$-binding protein with $K_d=10^{-9}$ M) with $Ca^{2+}$ demonstrate that CatchER binds $Ca^{2+}$ with weak affinity (FIGS. 27A and 27B).

Figure 20L:
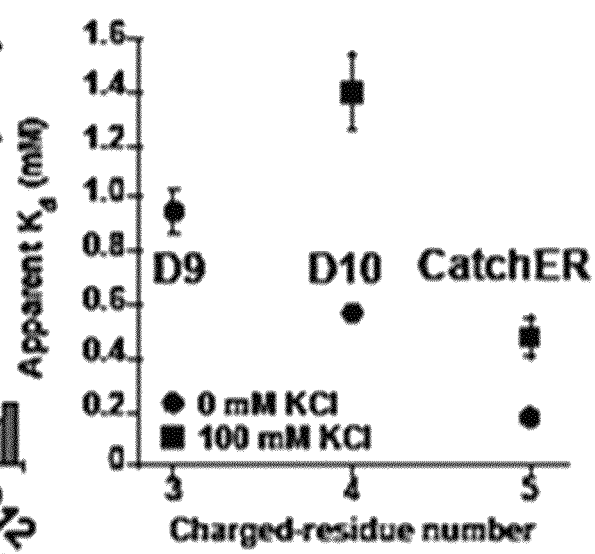
Figure 21C:
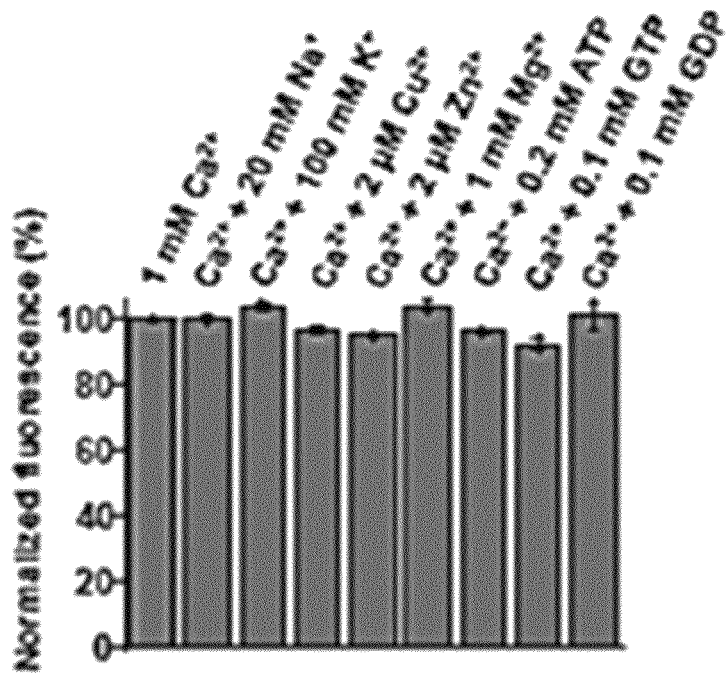
Figure 21D:
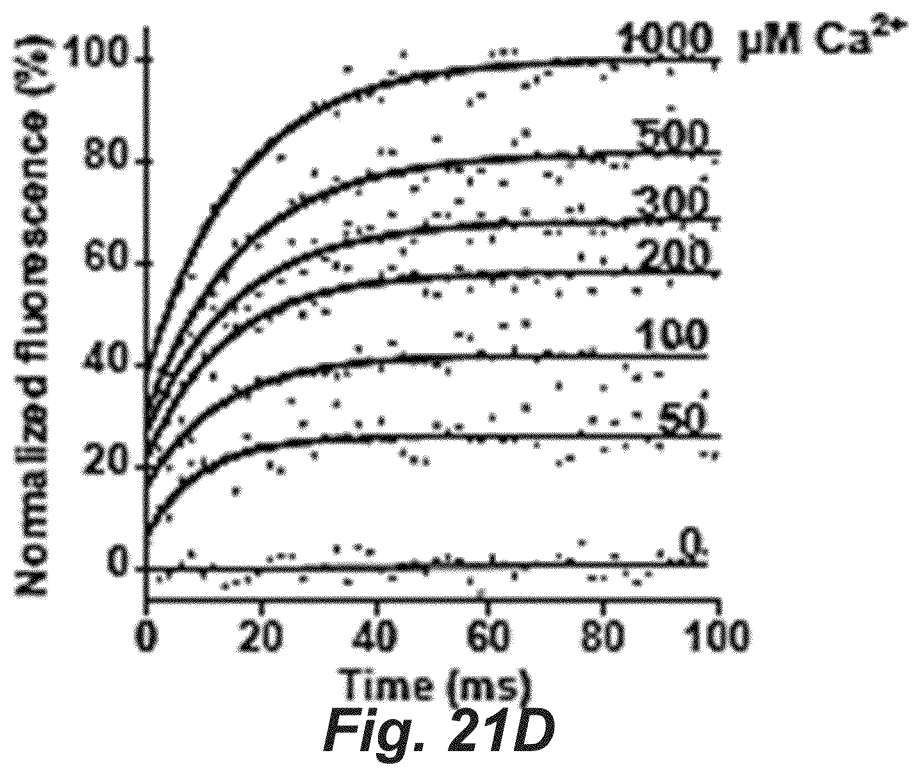
Figure 21E:
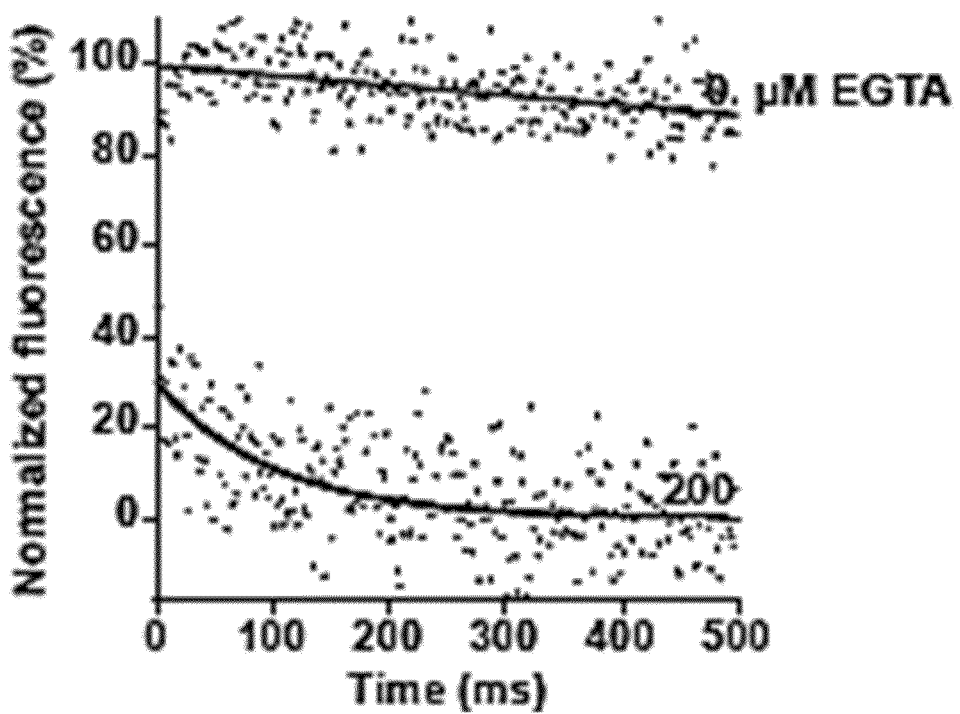
Figure 22A:
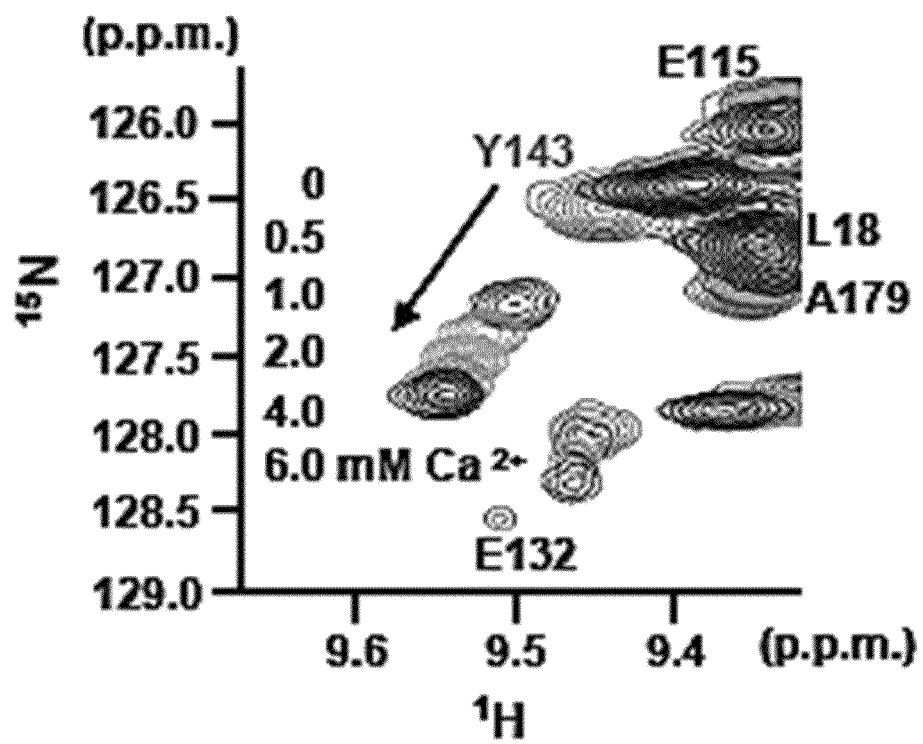
FIG. 22A shows a representative chemical shift of cross-peak Y143 at $[Ca^{2+}]$=0, 0.5, 1, 2, 4, and 6 mM, overlaid with 2D [$^1$H-$^{15}$N] HSQC spectra of 0.3 mM CatchER in response to $Ca^{2+}$.
Figure 22B:
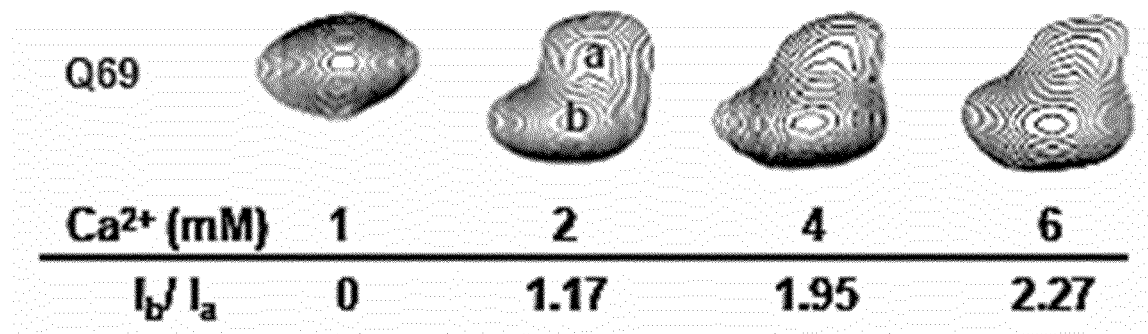
FIG. 22B shows a Q69 chemical shift perturbation induced by $Ca^{2+}$ titration. A minor peak was separated from the original single peak after adding 2 mM $Ca^{2+}$, and the ratio of integration of peak b to peak a increased from 0 to 2.27 as $Ca^{2+}$ concentration increased from 1 mM to 6 mM.
Figure 22C:
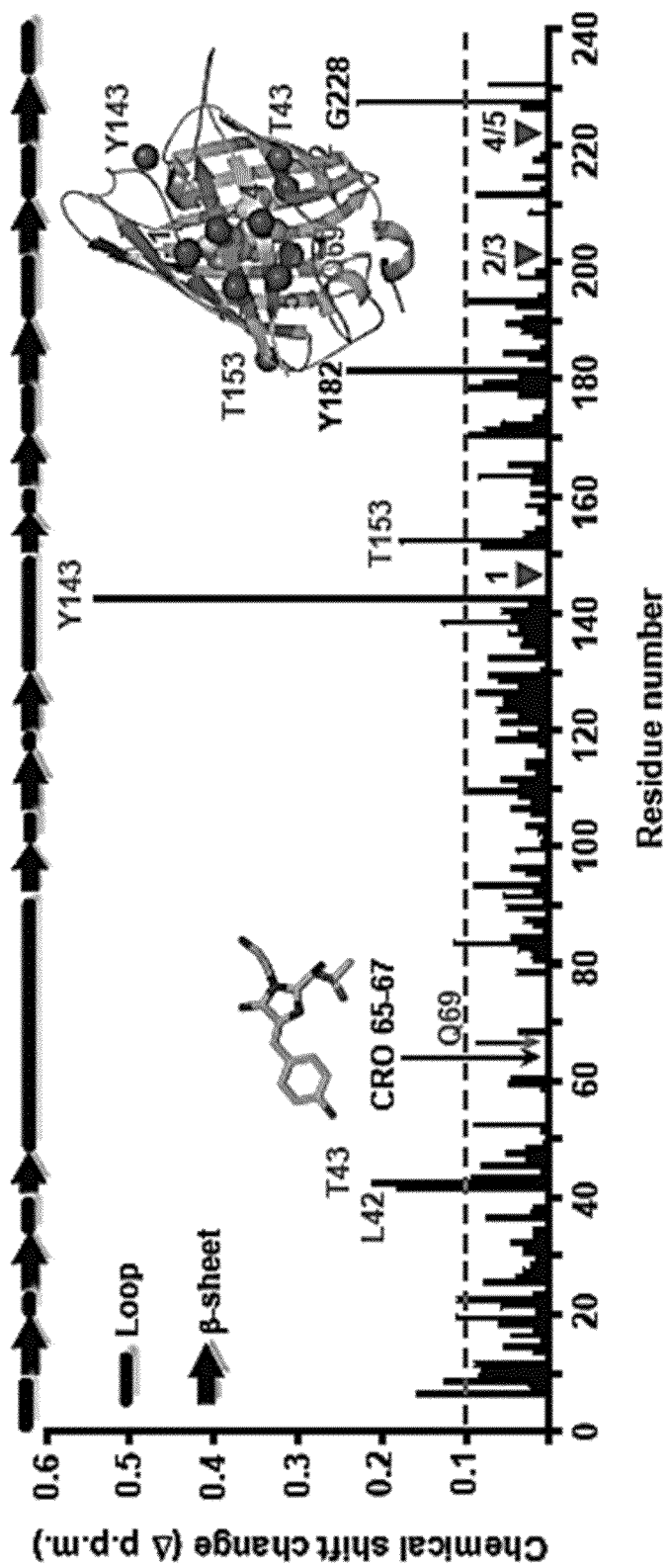
FIG. 22C shows combined chemical shift changes in combining a backbone amide proton and nitrogen between the $Ca^{2+}$-saturated and $Ca^{2+}$-free form. $Ca^{2+}$ influences the residues interacting with the chromophore or close to the designed $Ca^{2+}$ binding site. Y182, highly accessible to solvents, and G228 in the flexible C-terminal also exhibited more than a 0.2-ppm change in chemical shift. The secondary structure of CatchER, according to EGFP, was labeled on the top. All data were recorded at 37° C. using a 600 MHz NMR spectrometer with 300 μM $^{15}$N-labeled samples in 10 mM Tris, 10 mM KCl, pH 7.4.

$Ca^{2+}$-induced chemical shift changes of several residues close to the designed CatchER's $Ca^{2+}$ binding site (FIGS. 22A-22C) can also be fitted to a 1:1 binding process, with $K_d$ values consistent with those determined by fluorescence change. CatchER exhibits the strongest $Ca^{2+}$ binding affinity, with an apparent $K_d$ of 0.18±0.02 mM, while D9 has the weakest, with an apparent $K_d$ of 0.95±0.08 mM in 10 mM Tris pH 7.4 (FIG. 20L). CatchER's dissociation constant increases to 0.48±0.07 mM in the presence of 100 mM KCl, consistent with $Ca^{2+}$ electrostatic interaction. $Na^+$, $Cu^{2+}$, $Zn^{2+}$, $Mg^{2+}$, ATP, GTP, and GDP cannot compete with $Ca^{2+}$ for binding CatchER (FIG. 21C), which demonstrates its good selectivity. In vitro kinetic properties of CatchER: A stopped-flow spectrophotometer was used to record fluorescence changes upon mixing 10 μM CatchER with various $Ca^{2+}$ concentrations. Baseline corresponded to CatchER mixed with $Ca^{2+}$-free buffer. Between 40% and 60% of the initial fluorescence increase occurred within the lag-time of the stopped-flow spectrophotometer (i.e., 2.2 ms). A plot of ΔF as a function of $Ca^{2+}$ concentration yielded a hyperbolic pattern, where the $K_d$ value of 0.19±0.02 mM was in reasonable agreement with the $K_d$ of 0.18±0.02 mM determined by fluorescence equilibrium titration in the same condition (FIG. 20L). The observed rate constants were independent of the calcium concentration between 50 and 1000 μM, with an average value of 73±16 $s^{-1}$.

Figure 26E:
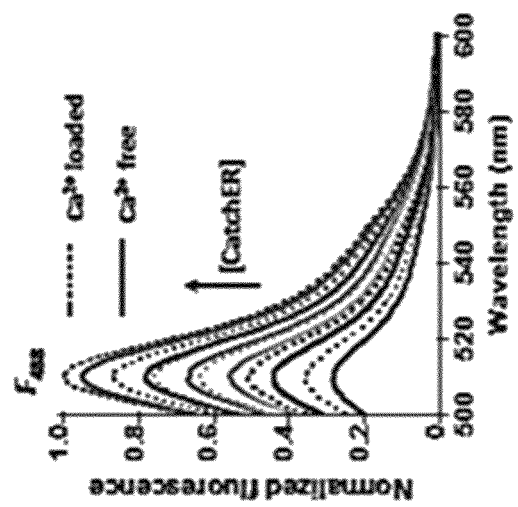

The CatchER:$Ca^{2+}$ off-rate was measured by directly monitoring changes in the fluorescence signal after equilibrating 10 μM CatchER with 10 μM $Ca^{2+}$ plus EGTA. About 70% of the fluorescence change was completed within the instrument lag-time (2.2 ms), consistent with very fast $Ca^{2+}$ release. If two half-lives would be required to complete 75% of a first-order process of the type required for $Ca^{2+}$ release from CatchER, a $k_{off}$ value of ~700 $s^{-1}$ can be estimated from the data in FIG. 26E). To our knowledge, CatchER exhibits the fastest off-rate of all reported $Ca^{2+}$ sensors.

Figure 29A:
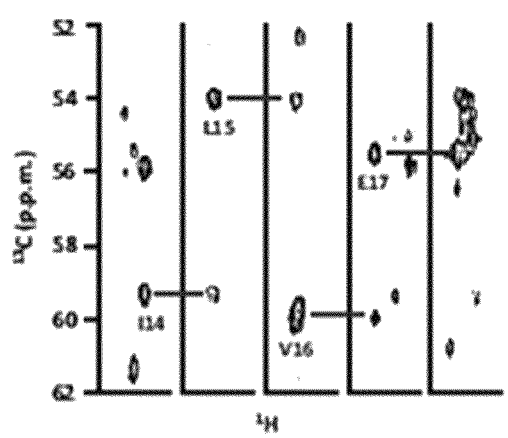
Figure 29B:
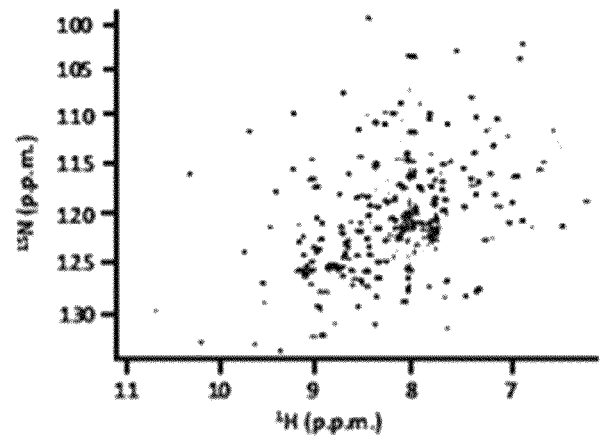
Figure 29C:
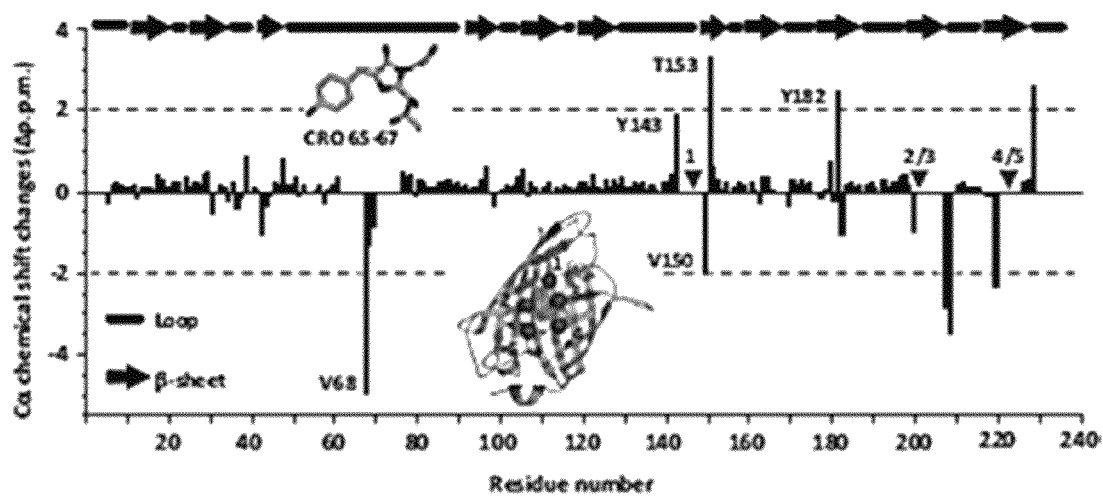
Figures 31A, 31B, 31C, 31D, 31E, 31F, 31G, 31H, 31I:
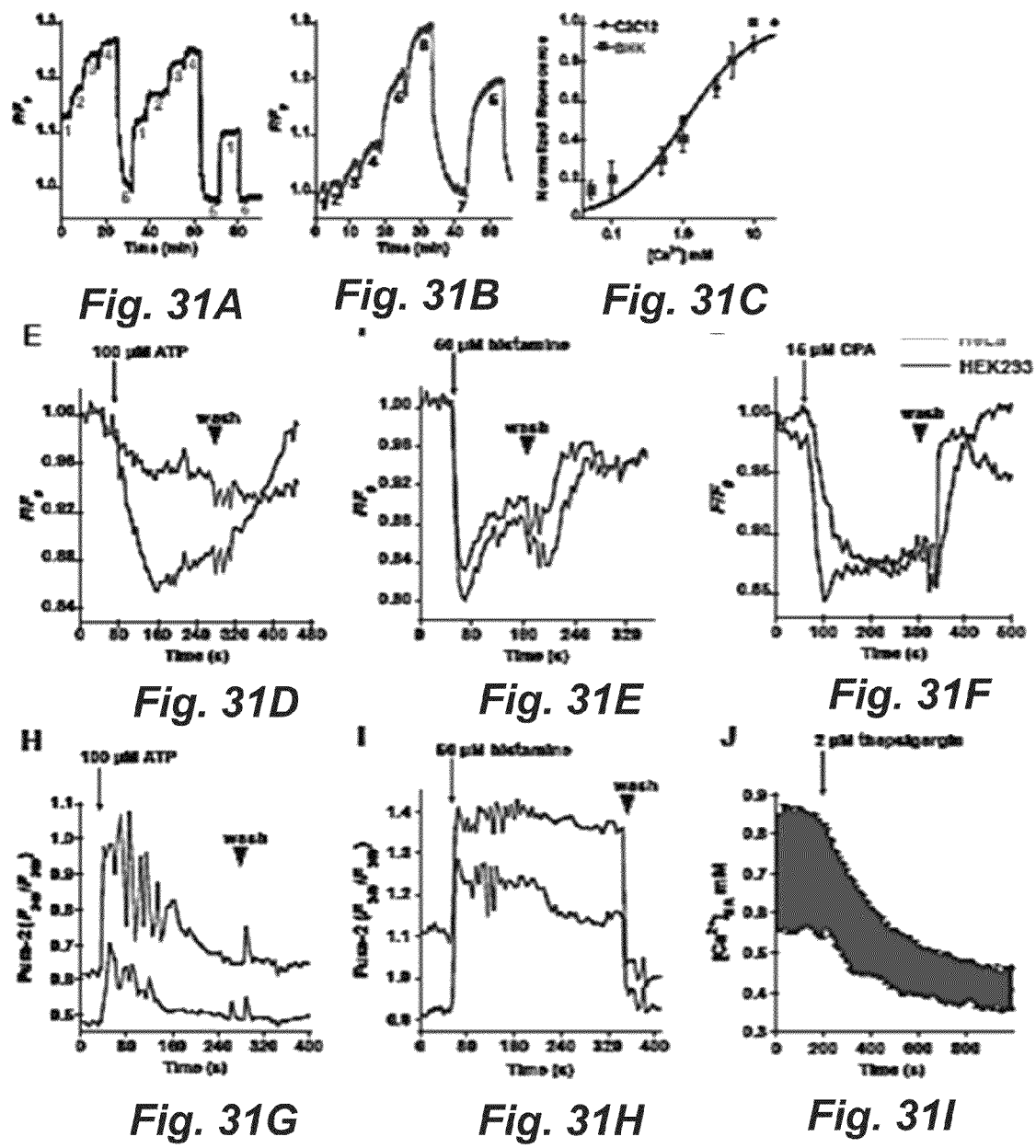
FIGS. 31A-31I illustrate the in situ determination of $K_d$ and endoplasmic reticulum $Ca^{2+}$ dynamics of HeLa and HEK293 cells.

Structural analysis of $Ca^{2+}$-CatchER interaction by high-resolution NMR: After introducing the designed $Ca^{2+}$ binding site, residues, such as Y143, T153, near binding sites or V68 around the chromophore exhibited more than a 1.5-ppm change, while most residues had less than a 0.4-ppm change in Ca chemical shift between CatchER and EGFP (FIG. 29C). This finding suggests that adding charged ligand residues changes local chromophore conformation, reduces fluorescence, and shifts the chromophore's ionic state toward its neutral state.

From dynamic NMR, the $Ca^{2+}$ sensor remains monomeric in solution. $Ca^{2+}$ binding leads to significant chemical shift changes in the HSQC spectra of the T153, Y143, L42, and T43 residues, located near the designed $Ca^{2+}$ binding site (FIG. 29C). Note that the main chain of Y143 close to the designed site showed the largest shift. These chemical shifts were fitted to a 1:1 binding equation with a $K_d$ value in agreement with that determined by fluorescence measurements (FIG. 21B), suggesting high correlation between these residues. On the other hand, residues R96, Q94, F165, and V61, which protrude toward the chromophore but away from the designed $Ca^{2+}$ binding site, showed no significant chemical shift changes, indicating that $Ca^{2+}$ binds specifically to the designed site.

NMR can further reveal $Ca^{2+}$-induced chromophore change, despite the lack of chromophore signal in the HSQC spectra. Q69 is buried inside the protein and forms hydrogen bonds with the chromophore. Its single resonance gradually becomes two with the addition of $Ca^{2+}$ (FIG. 22B), suggesting that $Ca^{2+}$ binding converts Q69 from a fast-exchange state to two different slow-exchange conformations. The hydrogen bond formed between E222 carboxyl group and the chromophore's phenolic oxygen is crucial to its fluorescence intensity; this residue forms a main chain hydrogen bond with L42 in the reported wild-type EGFP X-ray structure (pdb ID=1EMA). L42 also exhibits a significant $Ca^{2+}$-induced chemical shift change. From absorbance and fluorescence studies and high-resolution NMR, we can attribute the enhancement in $Ca^{2+}$-induced fluorescence with fast kinetics to a local conformational change close to the designed $Ca^{2+}$ binding site, which slows down the chemical exchange between two chromophore ionic states (kindle fluorescence by metal binding). Additionally, the fluorescence change via direct metal interaction is likely to be faster than indirect interactions via conformational changes. $Ca^{2+}$ binding-induced fluorescence changes also bypass the slow rate between ionic states, as we observed for G1, which distinguishes the sensor of the disclosure apart from GCaMP, although both exhibit a similar fluorescence enhancement at 488 nm in response to $Ca^{2+}$.

Figure 23A:
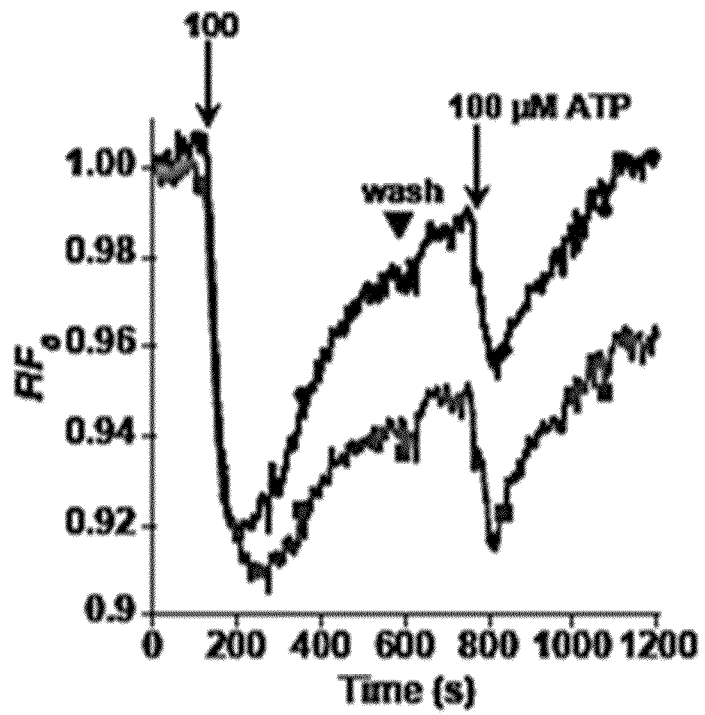
FIG. 23A illustrates C2C12 myoblast endoplasmic reticulum $Ca^{2+}$ dynamics monitored with CatchER. Two representative fluorescence responses to intact myoblasts without extracellular $Ca^{2+}$ or EGTA were evoked by 100 μM ATP (pH 7.0) twice separated by a Ringer buffer washout.
Figure 23B:
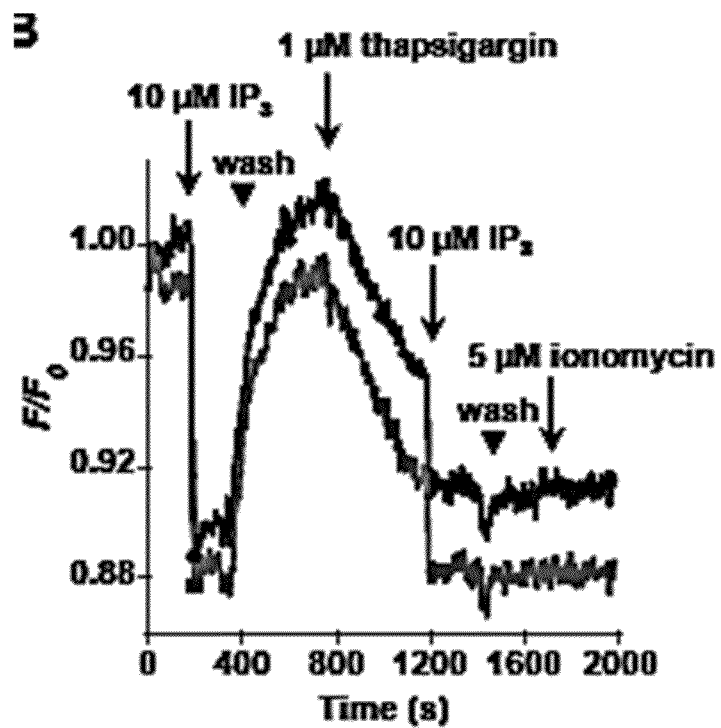
FIG. 23B illustrates the same batch of cells as in FIG. 23A when permeabilized with 25 μM digitonin in intracellular buffer for 3 mins and sequentially treated with $IP_3$, intracellular buffer washout, thapsigargin, $IP_3$ (arrow), washout (triangle), and ionomycin (arrow).

Endoplasmic Reticulum $Ca^{2+}$ concentration and release in various cell types: CatchER was fused with the calreticulin signal peptide and KDEL at the scaffold EGFP N- or C-terminus, respectively, to target it to the ER (FIG. 23B). Confocal microscopy of CatchER and the ER-tracker DsRed2-ER colocalized in HEK-293 and C2C12 cells further confirm CatchER's targeting specificity to the ER (FIGS. 30A and 30B).

To determine CatchER's $Ca^{2+}$ binding affinity, permeabilized C2C12 myoblasts were exposed to increasing $Ca^{2+}$ concentrations as described. CatchER's $K_d$ was 1.07±0.26 mM in BHK cells and 1.09±0.20 mM in C2C12 cells. The fluorescence intensity at the end of the experiment was fully recovered to the value prior to calibration, which demonstrates that CatchER was not washed out in permeabilized BHK and C2C12 cells, further supporting its targeting to, and retention in the ER. The resting ER $Ca^{2+}$ concentration in HeLa, HEK293, and C2C12 cells was: 396±13.2 (n=7), 742±134 (n=5), and 813±88.6 μM (n=11), respectively, in agreement with reported ER $Ca^{2+}$ concentrations of 100-900 μM using several Cameleon-based ER sensors.

ER $Ca^{2+}$ release evoked by ATP was measured in intact C2C12 myoblast cells (FIG. 23A), and the same batches of cell were permeabilized by digitonin to detect $IP_3$-induced $Ca^{2+}$ signaling (FIG. 23B). Fluorescence recovered when $IP_3$ was washed away, and adding thapsigargin slowed the decrease in ER $Ca^{2+}$ concentration. Again adding $IP_3$ caused fluorescence to decrease rapidly to the plateau as before, and no recovery was observed after washing, suggesting that thapsigargin completely inhibited the SERCA pumps.

Figure 23C:
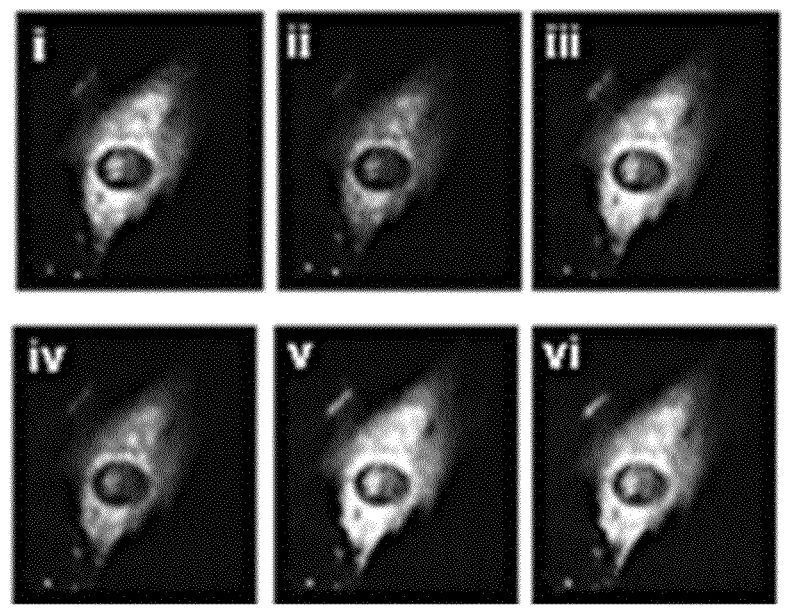
FIG. 23C illustrates representative fluorescent imaging of C2C12 co-expressing CatchER and mCherry-ER.
Figure 23D:
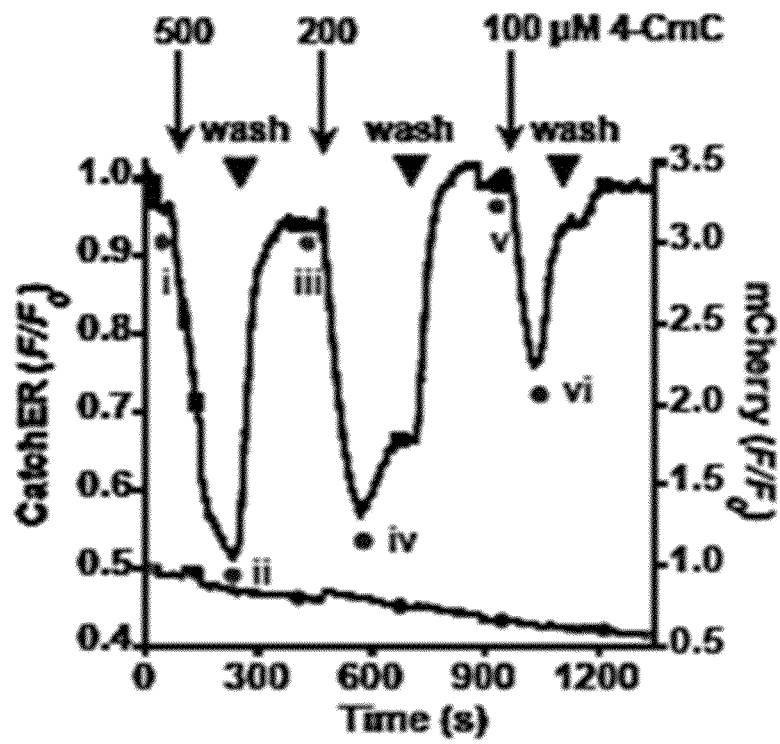
FIG. 23D illustrates CatchER (top) and mCherry-ER (bottom) fluorescence responses to 4-Chloro-m-Cresol (4-CmC) application. Time points of corresponding imaging in FIG. 23C are indicated.
Figure 23E:
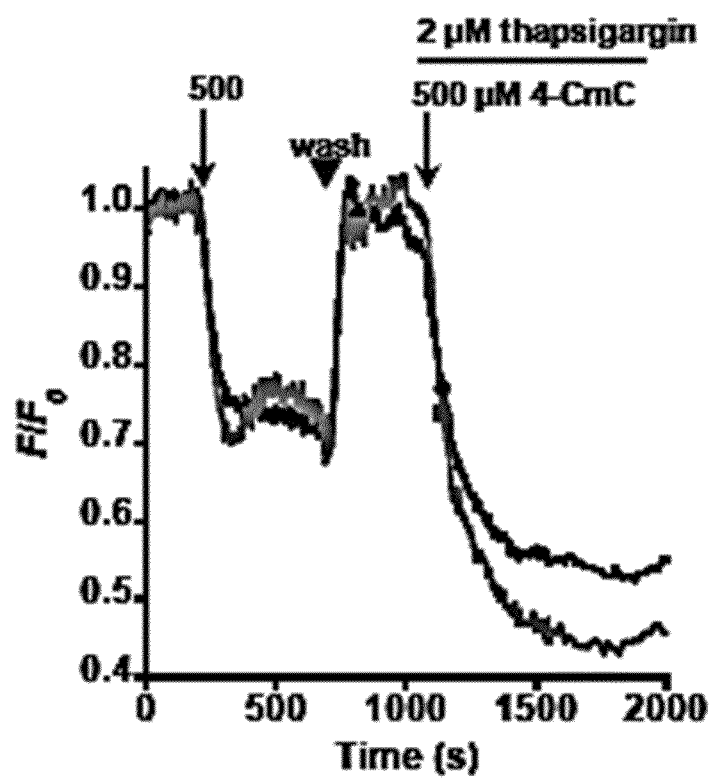
FIG. 23E illustrates 4-CmC evoked $Ca^{2+}$ release in the absence and presence of thapsigargin.
Figure 24:
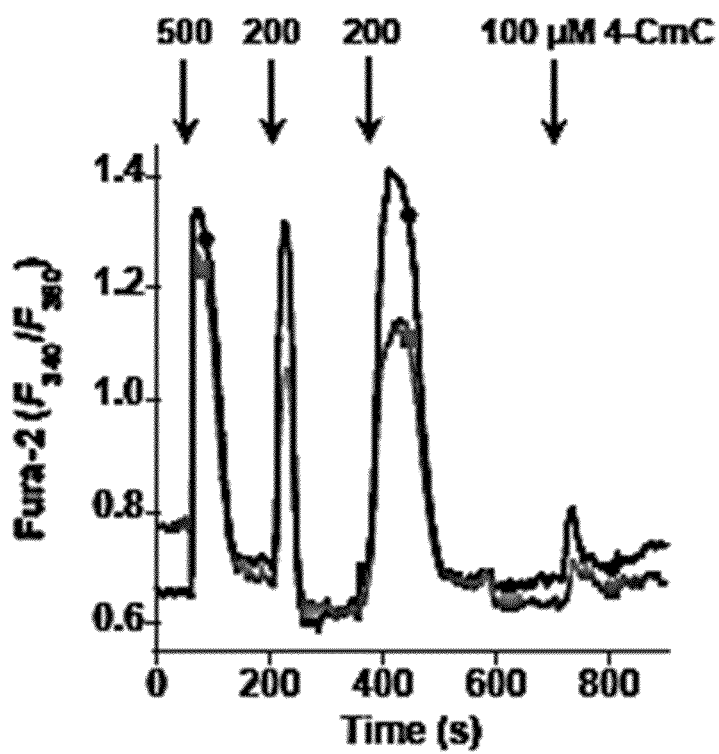
FIG. 24 illustrates 4-CmC evoked cytosolic $Ca^{2+}$ changes detected by Fura-2.
Figure 25M:
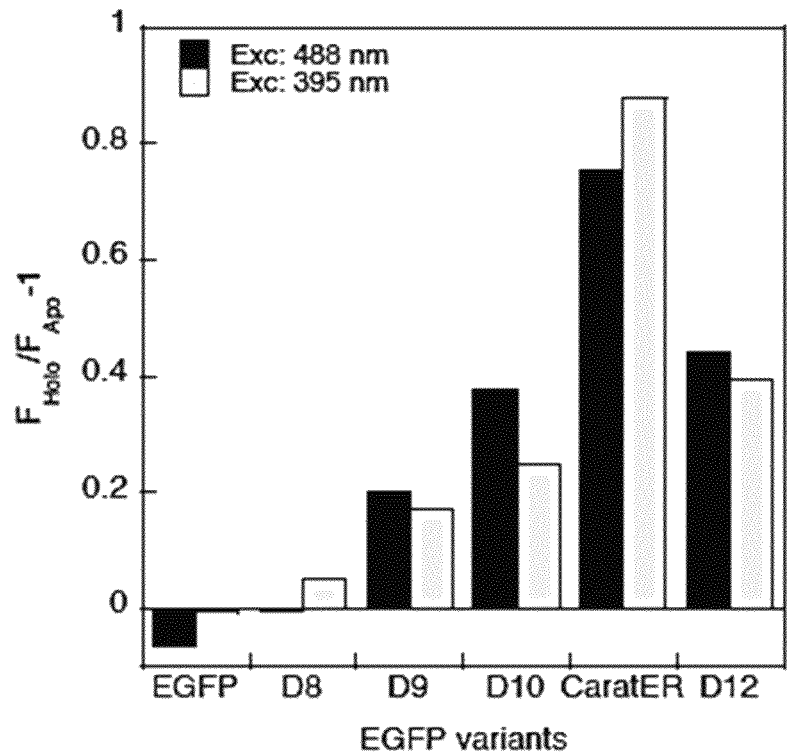
FIG. 25M is a graph showing the comparison of the amplitudes of fluorescence emission change at 510 nm excited at 488 nm (black bar) and 395 nm (gray bar) of EGFP and designed variants in response to $Ca^{2+}$. The amplitude change is in the term of ($F_{Holo}/F_{Apo}-1$), and $F_{Holo}$ and $F_{Apo}$ represent the absorbance intensity in the presence of 5 mM $Ca^{2+}$ and 10 μM EGTA, respectively. The non-ratiometric fluorescence change at 510 nm excited at either 488 nm and 395 nm of D9, D10, CatchER and D12 is presented in the positive values of the bars.
Figure 25N:
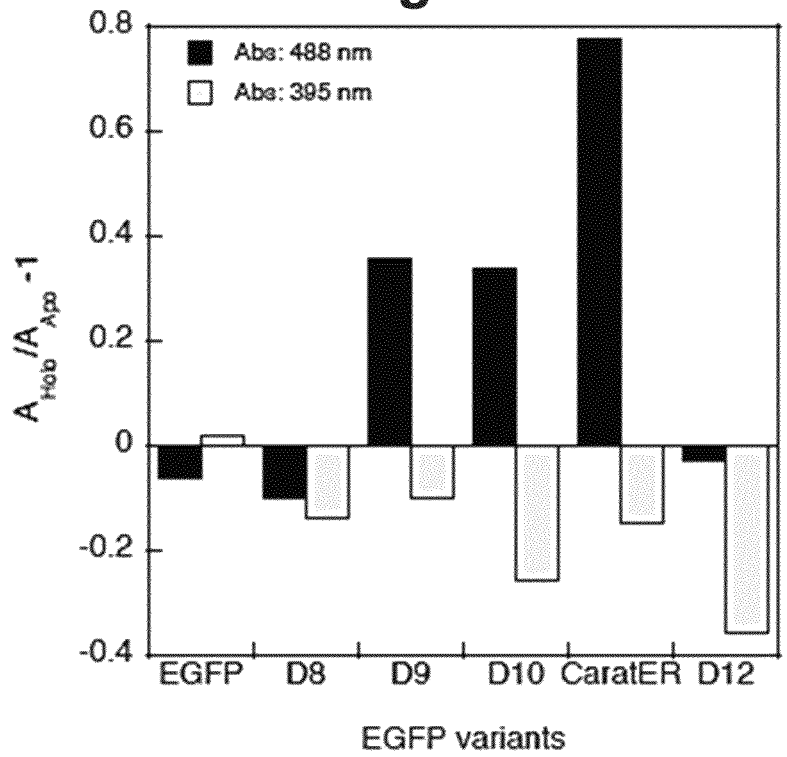

CatchER can detect $Ca^{2+}$ release through the ryanodine receptor elicited by 4-chloro-m-cresol (4-CmC) in intact cells. In contrast, no drug-related response was observed for mCherry co-expressed in the ER (FIGS. 23C and 23D). Cytosolic $Ca^{2+}$ was monitored in C2C12 myoblasts using Fura-2 (FIG. 24). 4-CmC elicited a concentration-dependent SR $Ca^{2+}$ depletion, while adding 500 μM 4-CmC and 2 μM thapsigargin together induced full SR $Ca^{2+}$ depletion (FIG. 23E). CatchER reports ER $Ca^{2+}$ release in excitable and non-excitable cells, such as HeLa and HEK 293, in response to ATP, histamine, thapsigargin, and cyclopiazonic acid (FIG. 31E-31G, 31J).

Kits: This disclosure further encompasses kits that can compromise, but are not limited to, an analyte sensor according to the disclosure, related agents that can facilitate the delivery of the protein to its desired destination and directions (written instructions for their use). The components listed above can be tailored to the particular biological event to be monitored as described herein. A kit for use in transfecting host cells may be assembled using the nucleic acid molecules encoding the analyte sensor, or for labeling target polypeptides with the analyte sensor. Host cell transfection kits may include at least one container containing one or more of the nucleic acid molecules encoding a analyte sensor (or a composition including one or more of the nucleic acid molecules or plasmids described above), which nucleic acid molecule preferably includes plasmid. The kit can further include appropriate buffers and reagents known in the art for administering various combinations of the components listed above to the host cell or host organism. The components of the present disclosure and carrier may be provided in solution or in lyophilized form. When the components of the kit are in lyophilized form, the kit may optionally contain a sterile and physiologically acceptable reconstitution medium such as water, saline, buffered saline, and the like.

One aspect of the disclosure, therefore, encompasses embodiments of an analyte sensor comprising an engineered fluorescent host polypeptide having a metal ion binding site comprising a plurality of negatively charged residues, wherein the negatively charged residues comprise a plurality of carboxyl oxygens orientated in a pentagonal bipyrimdal geometry wherein said geometry provides a metallic ion binding site operatively interacting with a chromophore region of the engineered fluorescent host polypeptide such that binding of a metal ion analyte to the molecular recognition motif modulates the emission of a fluorescent signal emitted by the fluorescent host polypeptide, and optionally, the absorbance spectrum of the engineered fluorescent host polypeptide.

In embodiments of this aspect of the disclosure, the negatively charged residues are on the surface of three anti-parallel beta-sheets.

In embodiments of this aspect of the disclosure, the negatively charged residues are spread on three strands of the protein with beta-can structure.

In embodiments of this aspect of the disclosure, the amino acid sequence of the analyte sensor can have at least 90% similarity to a sequence selected from the group consisting of SEQ ID Nos.: 104-105 and 113-159.

In embodiments of this aspect of the disclosure, the amino acid sequence of the analyte sensor can have at least 95% similarity to a sequence selected from the group consisting of SEQ ID Nos.: 105.

In embodiments of this aspect of the disclosure, the amino acid sequence of the analyte sensor is according to a sequence selected from the group consisting of SEQ ID Nos.: 104-105 and 113-159.

In embodiments of this aspect of the disclosure, the amino acid sequence of the analyte sensor can have at least 90% similarity to SEQ ID No.: 105.

In embodiments of this aspect of the disclosure, the amino acid sequence of the analyte sensor can have at least 95% similarity to a sequence selected from the group consisting of SEQ ID No.: 105.

In embodiments of this aspect of the disclosure, the amino acid sequence of the analyte sensor is according to SEQ ID No.: 105.

In embodiments of this aspect of the disclosure, the analyte sensor can bind to a metal ion selected from the group consisting of: calcium, lead, gadolinium, lanthanum, terbium, antimony, strontium, mercury, and cadmium.

In some embodiments of this aspect of the disclosure, the analyte sensor can binds to a metal ion selected from the group consisting of: calcium.

In embodiments of this aspect of the disclosure, the analyte sensor can further comprising a targeting motif for selectively targeting the endoplasmic reticulum or the sarcoplasmic reticulum of a cell.

In embodiments of this aspect of the disclosure, the analyte sensor in the presence of an analyte bound thereto can emit a fluorescent signal, the fluorescent signal indicating binding of the analyte to the analyte sensor.

In embodiments of this aspect of the disclosure, the analyte sensor in the absence of an analyte can emit a first fluorescent signal and in the presence of an analyte bound to the analyte sensor can emit a second fluorescent signal, wherein the first and the second fluorescent signals are distinguishably detectable.

In some embodiments of this aspect of the disclosure, the sensor is solubilized.

In some embodiments of this aspect of the disclosure, the sensor is attached to a solid surface.

Another aspect of the disclosure encompasses embodiments of a composition comprising an embodiment of the analyte sensor, where the composition can be formulated for the detection of an analyte in a test sample.

In some embodiments of this aspect of the disclosure, the composition can be formulated for detection of analyte in a tissue or a cell of an animal or human host.

In some embodiments of this aspect of the disclosure, the composition can be formulated for detection of analyte in an isolated cell or tissue, or in a cultured cell or tissue.

In embodiments of this aspect of the disclosure, the composition can be formulated for detection of analyte in a liquid.

In embodiments of this aspect of the disclosure, the composition can further comprise a pharmaceutically acceptable carrier.

Yet another aspect of the disclosure encompasses embodiments of a kit comprising an analyte sensor according to the disclosure and packaging, the packing comprising instructions for the use of the analyte sensor for the detection of an analyte by the analyte sensor.

Still another aspect of the disclosure encompasses embodiments of a method for detecting an analyte, comprising: (i) providing an analyte sensor according to the disclosure; (ii) providing a test sample suspected of comprising an analyte having affinity for the molecular recognition motif of the analyte sensor; (iii) detecting a first fluorescent signal emitted by the analyte sensor in the absence of a test sample suspected of comprising an analyte having affinity for the molecular recognition motif of the analyte sensor; (iv) contacting the analyte sensor with the test sample; (v) detecting a second fluorescent signal emitted by the analyte sensor in contact with the test sample; and (vi) comparing the first fluorescent signal and the second fluorescent signal, wherein a ratiometric change in the signal indicates an analyte in the test sample is interacting with the analyte sensor.

Still another aspect of the disclosure encompasses embodiments of a method for detecting an analyte, comprising: (i) providing an analyte sensor according to the disclosure; (ii) providing a test sample suspected of comprising an analyte having affinity for the molecular recognition motif of the analyte sensor; (iii) detecting a first absorption signal derived from the analyte sensor in the absence of a test sample suspected of comprising an analyte having affinity for the molecular recognition motif of the analyte sensor; (iv) contacting the analyte sensor with the test sample; (v) detecting a second absorption signal derived from the analyte sensor in contact with the test sample; and (vi) comparing the first absorption signal and the second absorption signal, wherein a ratiometric change in the absorption signal indicates an analyte in the test sample is interacting with the analyte sensor.

Still another aspect of the disclosure encompasses embodiments of a method for detecting an analyte, comprising: (i) providing an analyte sensor according to the present disclosure; (ii) providing a test sample suspected of comprising an analyte having affinity for the molecular recognition motif of the analyte sensor; (iii) detecting a first fluorescent signal emitted by the analyte sensor in the absence of a test sample suspected of comprising an analyte having affinity for the molecular recognition motif of the analyte sensor; (iv) contacting the analyte sensor with the test sample; (v) detecting a second fluorescent signal emitted by the analyte sensor in contact with the test sample; and (vi) comparing the first fluorescent signal and the second fluorescent signal, wherein a ratiometric change in the lifetime of the signal indicates an analyte in the test sample is interacting with the analyte sensor.

In some embodiments of this aspect of the disclosure, the first fluorescent signal in the absence of an analyte is a null emission.

In some embodiments of this aspect of the disclosure, the first fluorescent signal and the second fluorescent signal differ in wavelength, wherein the difference in the wavelengths, and optionally in the intensities thereof, indicates an analyte in the test sample is interacting with the analyte sensor.

In some embodiments of this aspect of the disclosure, the first fluorescent signal and the second fluorescent signal differ in intensity, wherein the difference in the intensities indicates an analyte in the test sample is interacting with the analyte sensor.

In embodiments of this aspect of the disclosure, the ratiometric change in the signal intensity provides a quantitative measurement of the analyte in the test sample.

In embodiments of this aspect of the disclosure, the ratiometric change in the signal intensity in the absorption provides a quantitative measurement of the analyte in the test sample.

In embodiments of this aspect of the disclosure, the changes in the life time signal provides a quantitative measurement of the analyte in the test sample.

In some embodiments of this aspect of the disclosure, the analyte is a metal ion selected from the group consisting of: calcium, lead, gadolinium, lanthanum, terbium, antimony, strontium, mercury, and cadmium.

In some embodiments of this aspect of the disclosure, the test sample is a cell or tissue of an animal or human subject, or a cell or tissue isolated from an animal or human subject.

In some embodiments of this aspect of the disclosure, the method is performed in vitro.

Another aspect of the disclosure encompasses embodiments of a recombinant nucleic acid encoding an analyte sensor according to the disclosure.

In embodiments of this aspect of the disclosure, the recombinant nucleic acid can further comprise a vector nucleic acid sequence.

Another aspect of the disclosure encompasses embodiments of a genetically modified cell comprising a recombinant nucleic acid according to the disclosure.

In embodiments of this aspect of the disclosure, the cell expresses the analyte sensor encoded by the recombinant nucleic acid.

In embodiments of this aspect of the disclosure, the analyte sensor expressed in the cell can provide a detectable fluorescent signal, absorbance signal, and/or life time change, said signal providing a qualitative or quantitative indicator of an analyte in the cell.

Another aspect of the disclosure encompasses embodiments of a method for characterizing the cellular activity of an analyte comprising: (i) providing a genetically modified cell comprising a recombinant nucleic acid expressing an analyte sensor according to claim 1; (ii) expressing the analyte sensor in the genetically modifying a cell measuring a signal produced from the analyte sensor; (iii) detecting a first fluorescent signal emitted by the analyte sensor; (iv) detecting a second fluorescent signal emitted by the analyte sensor after the induction of a physiological event in the cell; and (v) comparing the first fluorescent signal and the second fluorescent signal, wherein a ratiometric change in the signal indicates a change in the level of the analyte in the cell associated with the physiological in cell.

Another aspect of the disclosure encompasses embodiments of a method for characterizing the cellular activity of an analyte comprising: (i) providing a genetically modified cell comprising a recombinant nucleic acid expressing an analyte sensor according to the present disclosure; (ii) expressing the analyte sensor in the genetically modifying a cell measuring a signal produced from the analyte sensor; (iii) detecting a first absorption signal emitted by the analyte sensor; (iv) detecting a second absorption signal emitted by the analyte sensor after the induction of a physiological event in the cell; and (v) comparing the first absorption signal and the second absorption signal, wherein a ratiometric change in the absorption signal indicates a change in the level of the analyte in the cell associated with the physiological in cell.

Another aspect of the disclosure encompasses embodiments of a method for characterizing the cellular activity of an analyte comprising: (i) providing a genetically modified cell comprising a recombinant nucleic acid expressing an analyte sensor according to the present disclosure; (ii) expressing the analyte sensor in the genetically modifying a cell measuring a signal produced from the analyte sensor; (iii) detecting a first fluorescent signal emitted by the analyte sensor; (iv) detecting a second fluorescent signal emitted by the analyte sensor or absorbance signal after the induction of a physiological event in the cell; and (v) comparing the first fluorescent signal and the second fluorescent signal, wherein a ratiometric change in the lifetime of the signal indicates a change in the level of the analyte in the cell associated with the physiological in cell. In embodiments of this aspect of the disclosure, the genetically modified cell is an isolated genetically modified cell.

In embodiments of this aspect of the disclosure, the analyte is a metal ion selected from the group consisting of: calcium, lead, gadolinium, lanthanum, terbium, antimony, strontium, mercury, and cadmium.

In some embodiments of this aspect of the disclosure, the analyte is calcium.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Example 1

Construction of EGFP Based $Ca^{2+}$ Sensors: The $Ca^{2+}$ binding motifs of CaM, loop-III (DKDGNGYISAAE (SEQ ID NO.: 113) and the EF hand motif EEEIREAFRVFDKDGNGY-ISAAELRHVMTNL (SEQ ID NO.: 114)), were inserted into enhanced GFP (EGFP) as previously reported (J. Biotechnol. 119: 368-378, which is incorporated herein by reference) and the insertions were verified by automated DNA sequencing.

The cDNA encoding the EGFP variant grafted with a $Ca^{2+}$ binding motif was cloned into bacterial and mammalian expression vectors between BamH1 and EcoR1 restriction enzyme sites. For bacterial expression, the vector pET28(a) with a 6×His-tag was utilized. For mammalian expression, the protein-encoding DNA was subcloned into a pcDNA3.1+ vector. The ER retention sequence, KDEL, was attached to the C-terminus and the ER targeting sequence of calreticulin (CRsig), MLLSVPLLLGLLGLAAAD (SEQ ID NO.: 112), was attached to the N-terminus of the EGFP-based $Ca^{2+}$ sensors through PCR. The Kozak consensus sequence was placed at the N-terminus of the calreticulin sequence for the optimal initiation of protein expression in mammalian cells. DsRed2-ER (BD Biosciences Clontech), which contains CRsig and KDEL signal peptides at the N and C-terminals, respectively, was used as a marker for the ER in co-localization experiments. To improve the folding at 37° C., two additional mutations, M153T and V163A, were also added to the $Ca^{2+}$ sensors (Nature Biotechnol. 14: 315-319, Biochemistry 39: 12025-12032, each of which is incorporated herein by reference).

Example 2

Expression and Purification of EGFP and Its Variants: EGFP and its variants were expressed in *E. coli* BL21 (DE3). Cells were grown at 37° C. in LB medium containing 30 μg/ml kanamycin to an $O.D._{600}$ greater than 0.6 before protein induction with 0.2 mM isopropyl 13-D-thiogalactoside (IPTG). Since EGFP exhibits reduced fluorescence at 37° C. in vivo, high-level expression of the soluble mature form of EGFP was achieved by growing the cultures overnight in LB broth at 30° C. EGFP and its variants were purified by sonication of the cell pellet and centrifugation at 22,500×g for 20 min. The supernatant was injected into a fast performance liquid chromatography (FPLC) system, AKTAprime, connected to a Hitrap $Ni^{2+}$ chelating column (Amersham Biosciences). The protein was eluted from the column with a gradient of imidazole in 50 mM $NaH_2PO_4/Na_2HPO_4$ and 250 mM NaCl (pH 7.4) and identified by mass spectrometry. Imidazole was removed by dialysis against 10 mM Tris and 1 mM DTT (pH 7.4).

Ultra-violet and Visible Absorption Spectroscopy: Ultra-violet and visible absorption spectra of EGFP and its variants were determined with a Shimadzu UV-1601 Spectrophotometer. Protein concentration was determined by absorbance at 280 nm using the molar extinction coefficient of 21,890 $M^{-1}cm^{-1}$ for EGFP-wt calculated from the contribution from aromatic residues (1 Trp and 11 Tyr) (5500 and 1490 $M^{-1}cm^{-1}$ for Trp and Tyr, respectively). The extinction coefficients (at 398 nm or 490 nm) of the EGFP variants were obtained with the Eq. (1):

$$\varepsilon_P = \varepsilon_{P,280nm}\left(\frac{A_P}{A_{,280nm}}\right) \quad (1)$$

in which, the $\varepsilon_p$ is the extinction coefficient at 398 nm or 490 nm of EGFP variants, $\varepsilon_{p,280nm}$ is the extinction coefficient at 280 nm of EGFP variants, $A_p$ is the absorption of EGFP variants at 398 nm or 490 nm, and $A_{p,280nm}$ is the absorption of EGFP variants at 280 nm. EGFP was used as a reference in the measurement of the extinction coefficients of the EGFP variants.

Fluorescence Spectroscopy: The properties of EGFP and its variants were monitored using a Fluorescence Spectrophotometer (Photon Technology International, Inc.) with a 10 mm path length quartz cell at 20° C. Fluorescence spectra of the chromophore in proteins were measured in the emission region of 410 to 600 nm and 500 to 600 nm with 398 and 490 nm excitation wavelengths, respectively. The ratio of emission at 500 to 600 nm when excited at 398 and 490 nm as a function of $Ca^{2+}$ concentrations was utilized to calculate the apparent dissociation constant $K_d$ for $Ca^{2+}$ binding of various EGFP-based $Ca^{2+}$ sensors by fitting Eq 2 with a 1:1 metal binding equation:

$$f = \frac{([P]_r + [Ca]_r + K_d) - \sqrt{([P]_r + [Ca]_r + K_d)^2 - 4[P]_r[Ca]_r}}{2[P]_r} \quad (2)$$

in which f is the fraction of $Ca^{2+}$ bound protein, $[P]_T$ is the total protein concentration (mM), $[Ca]_T$ is the total $Ca^{2+}$ concentration (mM), and $K_d$ is the $Ca^{2+}$ dissociation constant of the protein. The fraction of the protein bound with $Ca^{2+}$ was calculated according to Eq. 3:

$$f = \frac{R - R_{min}}{R_{max} - R_{min}} \quad (3)$$

in which $R_{min}$, R, $R_{max}$ are the fluorescence emission ratios (excited at 398 and 490 nm) or the amplitudes measured with a stopped-flow spectrofluorimeter for $Ca^{2+}$-free, $Ca^{2+}$-bound, and $Ca^{2+}$-saturated protein, respectively. The fluorescence emission ratio (excited at 398 and 490 nm) was obtained by fitting the data to Eq. 4:

$$R = \frac{F_{(398nm)}}{F_{(490nm)}} \quad (4)$$

in which $F_{(398nm)}$ and $F_{(490nm)}$ are the integrated fluorescence intensities in the range of 500 to 600 nm excited at 398 and 490 nm, respectively. The dynamic range value of $Ca^{2+}$ sensors was calculated by dividing the fluorescence emission ratio excited at 398 and 490 nm of the $Ca^{2+}$ saturated state ($R_{max}$) with that of the $Ca^{2+}$-free state ($R_{min}$).

The apparent dissociation constant for $Ca^{2+}$ binding ($K_d$) of EGFP-based $Ca^{2+}$ sensors was also measured by competitive titration with Rhodamine-5N. Rhodamine-5N is a fluorescent dye (Molecular Probes) with a $K_d$ of 319±13 µM for $Ca^{2+}$ in 100 mM Tris, pH 7.4. The dye concentration was calculated using an extinction coefficient of 63,000 $M^{-1}cm^{-1}$ at 552 nm. Measurements with different $Ca^{2+}$ concentrations were performed by maintaining the concentration of dye (10 uM) and protein constant. The fluorescence emission signal from 560 to 650 nm was measured with a cell of 1 cm path length excited at 552 nm. The slit widths of excitation and emission were set at 2 and 4 nm, respectively. The apparent dissociation constants were obtained by globally fitting the spectra from 560 to 650 nm using Specfit/32 with the metal and two ligand model (Spectrum Software Associates).

The $Ca^{2+}$ selectivity of the EGFP-based $Ca^{2+}$ sensor was examined by monitoring the change of the fluorescence ratio $F_{(398nm)}/F_{(490nm)}$ with 1.0 mM $Ca^{2+}$ in the presence of metal ions including 0.1 µM $Cu^{2+}$, 0.1 mM $Zn^{2+}$, 10.0 mM $Mg^{2+}$, 5.0 µM $Tb^{3+}$, or 5.0 µM $La^{3+}$. The normalized change of the ratio (AR) was calculated using Eq. 5:

$$\Delta R = \frac{R_{metal} - R_0}{R_{Ca} - R_0} \times 100 \quad (5)$$

in which $R_0$ is ratio of the EGFP-based $Ca^{2+}$ sensor in the absence of $Ca^{2+}$ and metal ions, $R_{Ca}$ is the ratio of the EGFP-based $Ca^{2+}$ sensor with 1.0 mM $Ca^{2+}$ in the absence of metal ions, and $R_{metal}$ is the ratio of the EGFP-based $Ca^{2+}$ sensor with 1.0 mM $Ca^{2+}$ in the presence of the metal ions. Eq (5) was also used to examine the effect of small molecules including adenosine triphosphate (ATP), adenosine diphosphate (ADP), guanosine triphosphate (GTP), guanosine diphosphate (GDP), and Glutathione (GSH) on the $Ca^{2+}$ response of GFP-based $Ca^{2+}$ sensors. Data are expressed as a percentage.

Stopped-flow Spectrofluorometry: Stopped-flow kinetic measurements were performed on a Hi-Tech SF-61 stopped-flow spectrofluorometer (10 mm path length, dead time of <2 ms) with a 1:1 (v/v) ratio of the protein sensor and calcium at 20° C., as described previously (J. Am. Chem. Soc. 127: 2067-2074). Fluorescence emission changes associated with binding of $Ca^{2+}$ to Ca-G1 were determined by mixing $Ca^{2+}$ and Ca-G1 in 10 mM Tris and 1 mM DTT (pH 7.4) with excitation at 398 nm and a long-pass 455 nm filter. The concentrations of $Ca^{2+}$ ranged from 0 to 10 mM. Fluorescence emission changes associated with dissociation of $Ca^{2+}$ from Ca-G1 were measured upon mixing Ca-G1 preloaded with $Ca^{2+}$ in 10 mM Tris and 1 mM DTT (pH 7.4) with the same buffer. Generally, six duplicate measurements were carried out for each point and the last three were fitted to obtain the observed rate, $k_{obs}$. The $k_{obs}$ for each $Ca^{2+}$ concentration was obtained by fitting of the stopped-flow traces according to the single exponential function shown in Eq. 6:

$$F_t = F_0 + Amp[1 - \exp(-k_{obs}t)] \quad (6)$$

in which $F_t$ is the fluorescence intensity at any stopped-flow time, $F_0$ is the initial fluorescence intensity, Amp is the final value of the fluorescence signal at the end of the process at a given $Ca^{2+}$ concentration, $k_{obs}$ is the observed rate of fluorescence change ($s^{-1}$), and t is the reaction time (s). Measurements typically differed by less than 1% between duplicate experiments.

Example 3

Cell Culture and Transfection: Both BHK-21 and HeLa cells were grown on 100 mm culture dishes or glass coverslips (0.5-1.0×10$^6$ cells/dish) in 35 mm culture dishes in Dulbecco's Modified Eagles Medium (DMEM, Sigma Chemical Co., St. Louis, Mo.) with 44 mM $NaHCO_3$, pH 7.2 and supplemented with 10% (v/v) Fetal Bovine Serum (FBS), 100 U/ml penicillin and 0.1 mg/ml streptomycin (Pen/Strep) at 37° C. with 5% $CO_2$ in a humidified incubation chamber. The cells were seeded and grown overnight before transient transfection with $Ca^{2+}$ sensor plasmid constructs.

Plasmid DNA used for transfection was harvested from transformed E. coli (DH5□) using a QIAGEN Miniprep protocol (Qiagen). Each of the GFP variants was individually and transiently transfected into BHK-21 and HeLa cells with Lipofectamine-2000 (Invitrogen Life Technologies) and serum-free Opti-MEMI (Gibco Invitrogen Corporation) per the manufacturer's instructions. The plasmid DNA (2 μg) with a ratio of DNA to Lipofectamine between 1:1 and 1:3 (μg/μl) was generally used in a typical transfection. Following incubation at 37° C. for 4 hrs, the medium containing the DNA-Lipofectamine complex was removed and replaced with DMEM enriched with FBS and Pen/Strep. The cells were then grown for 1 to 3 days in a humidified chamber with 5% $CO_2$ at 30 or 37° C. before fluorescence or confocal microscope imaging.

Example 4

Confocal Microscope Imaging: BHK-21 and HeLa cells were transferred from DMEM to Hank's Balanced Salt Solution without divalent cations (HBSS(--), Sigma Chemical Co., St. Louis, Mo.) media with 10 mM HEPES, 5 mM $NaHCO_3$, 1 mM EGTA, and pH 7.2 for live imaging experiments on a LSM 510 laser confocal microscope (Carl Zeiss Inc., Thornwood, N.Y.) using a 100× oil-immersion objective (Zeiss, Fluar, 1.30 n.a.). Prior to imaging, cells and buffers were brought to ambient temperature and allowed to equilibrate to room air. The localization of EGFP-based $Ca^{2+}$ sensors was visualized by excitation of EGFP with the 488 nm line of an Argon laser and the narrowest bandpass filter (505-530 nm) was employed for emission. DsRed2-ER was excited with the 543 nm line of a He—Ne laser, and emission was detected through a long-pass filter (emission above 560 nm). Zeiss LSM 510 software (Carl Zeiss, Inc.) was used to control the image acquisition parameters. All images were acquired at high resolution (1024×1024).

Example 5

Fluorescence Microscope Imaging and Its Quantification: BHK-21 cells were imaged 1-3 days following transfection with GFP variants. A Nikon TE200 microscope running Metafluor software (Universal Imaging) with dual excitation capability was used for the cell imaging experiments. The ratio of fluorescence emission of EGFP-based $Ca^{2+}$ sensors (measured at 510 nm) in response to excitation wavelengths of 385 nm and 480 nm was measured to monitor changes in $[Ca^{2+}]_{ER}$ in time series experiments. The $[Ca^{2+}]_{ER}$ in BHK-21 cells was quantified according to Eq. 7:

$$[Ca^{2+}] = K_d \times \left(\frac{R - R_{min}}{R_{max} - R}\right)^{\frac{1}{n}} \quad (7)$$

in which R is the fluorescent emission ratio (measured at 510 nm) for 385 nm/480 nm excitation at the initial state, $R_{min}$ is the minimum of the emission ratio determined at the $Ca^{2+}$-free state, $R_{max}$ is the maximum of the emission ratio at the $Ca^{2+}$-saturated state, $K_d$ is the apparent dissociation constant (mM) and n is the Hill coefficient (n=1). $Ca^{2+}$-free and $Ca^{2+}$-saturated states were obtained on cells treated with 5 μM ionomycin and exposed to 1.0 mM EGTA and 1.0 mM $Ca^{2+}$, respectively.

Example 6

Design of EGFP-based $Ca^{2+}$ Sensors with a Single Inserted $Ca^{2+}$-binding Motif: FIG. 1 illustrates the design of $Ca^{2+}$ sensors made by integrating a $Ca^{2+}$-binding motif, a combination of CaM loop-III and its flanking helices, into EGFP based on the following criteria. First, $Ca^{2+}$-binding motifs such as loop-III or intact EF-hand motif III from CaM were used to create $Ca^{2+}$-binding sites in EGFP. $Ca^{2+}$ is chelated by 12-residues in the EF-hand motif. Thus, peptide fragments of an EF-motif of CaM interact with any CaM target enzymes, thereby producing a sensor that is unlikely to interfere with cellular signaling events. The $Ca^{2+}$-binding affinity of the grafted loop can be varied by modifying charged residues in the loop and flanking helices (J. Am. Chem. Soc. 127: 3743-3750; J. Inorg. Biochem. 99: 1376-1383, each of which are incorporated herein by reference), altering the $Ca^{2+}$ binding affinity of any designed sensor.

Three integration sites were selected: Glu172-Asp173 within Loop-9 of EGFP (position 1), Gln157-Lys158 within Loop-8 (position 2), and Asn144-Tyr145 within Loop-7 (position 3). Loop-III of CaM, with or without the flanking helices, was used as a $Ca^{2+}$ binding motif and grafted at these positions to construct EGFP-based $Ca^{2+}$ sensors (FIG. 1A). Next, mutations M153T and V163A were inserted into construct Ca-G1 to create a sensor with improved expression at 37° C. (Ca-G1-37) (Nature Biotechnol. 14: 315-319; Biochemistry 39: 12025-12032, each of which are incorporated herein by reference). Finally, a construct with both ER targeting sequence and retention sequence, which specifically targets Ca-G1 to the ER of mammalian cells, was designed and is referred to as Ca-G1-ER.

Example 7

Figure 2A:
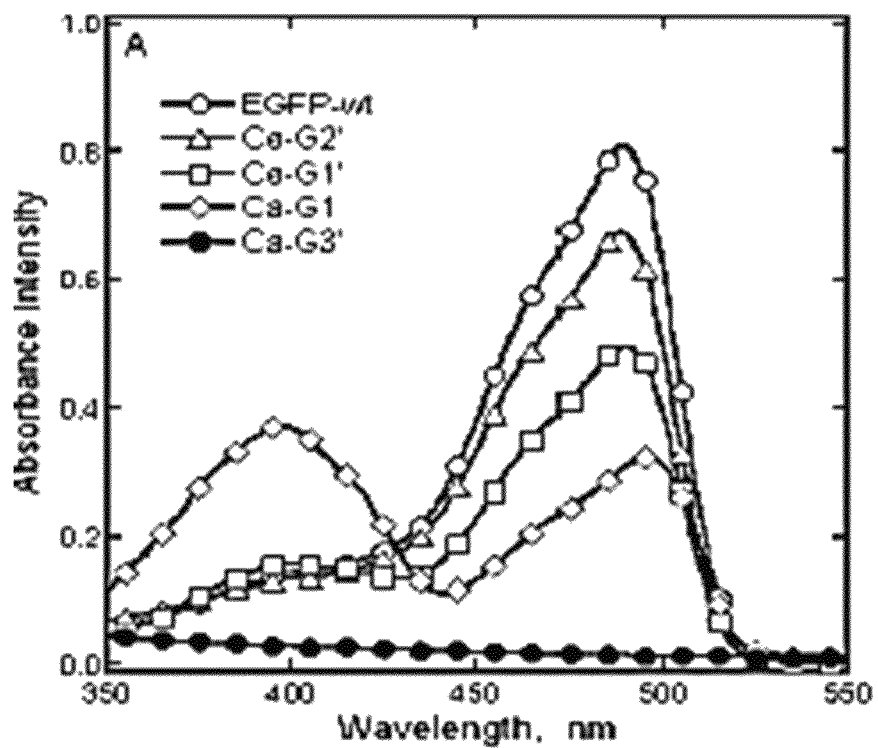
FIG. 2A illustrates the visible absorbances of EGFP-wt and variants thereof. Protein concentrations were 20 μM.
Figure 2B:
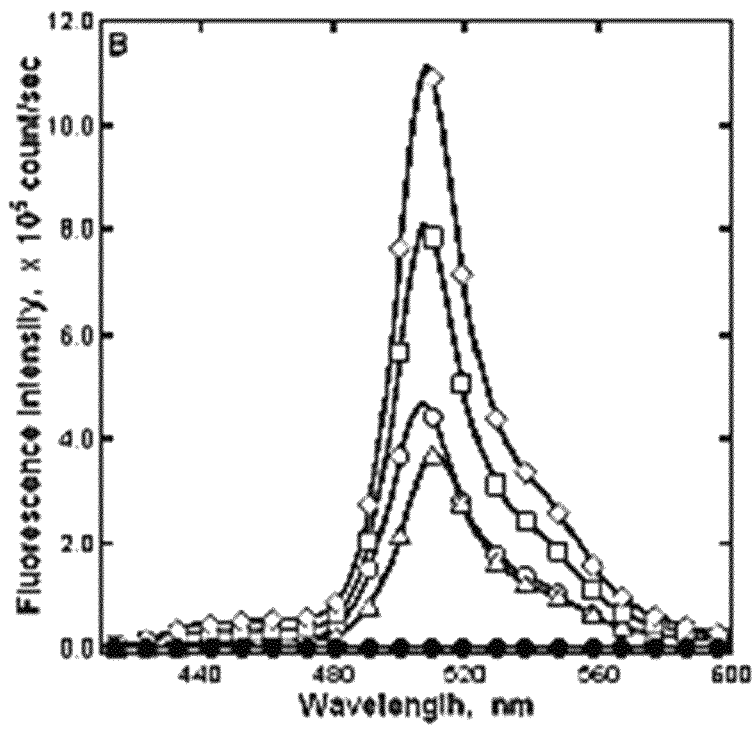
FIG. 2B illustrates the fluorescence spectra of EGFP-wt and variants thereof. Protein concentrations were 10 μM; slit width of 1 nm for both excitation and emission. $\lambda_{ex}$=398 nm.

Spectroscopic Properties of EGFP-based $Ca^{2+}$ Sensors and Sensitive Locations of EGFP: Spectroscopic properties of $Ca^{2+}$ sensors were first investigated using purified proteins (pH 7.4). FIGS. 2A and 2B show the visible absorbance and the fluorescence emission spectra of EGFP-wt and different $Ca^{2+}$ sensor constructs. The spectroscopic properties including extinction coefficients and quantum yields of $Ca^{2+}$ sensors are summarized in Table 3.

TABLE 3

Spectroscopic Properties of EGFP and $Ca^{2+}$ Sensor Constructs

| | Extinction coefficient | | | |
|---|---|---|---|---|
| | $\epsilon$ (398 nm)[a] | $\epsilon$ (490 nm) | $\epsilon$ (490 nm)/ $\epsilon$ (398 nm) | Quantum yield |
| EGFP[b] | 9.8 | 55.9 | 5.7 | 0.60 |
| Ca-G1' | 10.9 | 34.4 | 3.2 | 0.53 |
| Ca-G1 | 25.9 | 21.5 | 0.8 | 0.59 |
| Ca-G2' | 9.3 | 46.4 | 5.0 | 0.60 |
| Ca-G2 | 8.5 | 38.6 | 4.5 | 0.69 |
| Ca-G3'[c] | N/A[d] | N/A | N/A | N/A |

[a]□ is the extinction coefficient in units of $10^3$ $M^{-1}$ $cm^{-1}$. The wavelengths in absorption peaks are shown in the parentheses.
[b]EGFP-wt was used as a reference in the calculation of absorbance extinction coefficient ($\epsilon$) and fluorescent quantum yield of EGFP variants.
[c]The chromophore was not formed in Ca-G3'.
[d]N/A, not available.

The insertion of loop-III of CaM at Gln157-Lys158 of EGFP (Ca-G2' and Ca-G2 (only Ca-G2' is shown in FIGS. 2A and 2B), FIG. 1A) resulted in a protein with spectroscopic properties similar to EGFP-wt with a slight decrease in absorbance intensity. Note that the major absorbance peak at 490 nm and minor absorbance peak at 398 nm reflect the relative population of anionic and neutral states of the chromophore. FIG. 2B shows that excitation at 398 nm (the neutral state) contributed greatly to the emission peak at 510 nm.

As shown in Table 3, the constructs with a $Ca^{2+}$-binding motif grafted at Gln157-Lys158 (position 2) (Ca-G2' and Ca-G2) had spectroscopic properties (extinction coefficients and quantum yield constants at both 398 nm and 490 nm) similar to that of EGFP-wt. The integrating loop III of CaM at Glu172-Asp173 of EGFP (Ca-G1') resulted in the formation of a protein which showed a slight increase of absorbance at 398 nm and a decrease of absorbance at 490 nm compared to EGFP-wt. Moreover, the insertion of loop III containing the flanking EF-helices at the same location (Ca-G1) resulted in a protein which had a further increase in absorbance at 398 nm and a decrease at 490 nm. The extinction coefficients of Ca-G1 were increased 2.6-fold at 398 nm and decreased about 60% at 490 nm compared to EGFP-wt. Concurrently, a corresponding increase in fluorescence emission was observed for both Ca-G1' and Ca-G1 (FIG. 2B).

In contrast, the chromophore was not formed after insertion of loop III at Asn144-Tyr145 of EGFP (Ca-G3'), indicated by the lack of green fluorescence in the bacterial expression as well as in the purified protein. Thus, the integration of a $Ca^{2+}$ binding motif at Glu172-Asp173 in EGFP significantly shifts the population of the chromophore from the anionic state as indicated by the 490 nm peak to the neutral state as indicated by 398 nm peak. It is likely that Glu172-Asp173 of EGFP is a chromophore sensitive location.

Figure 7:
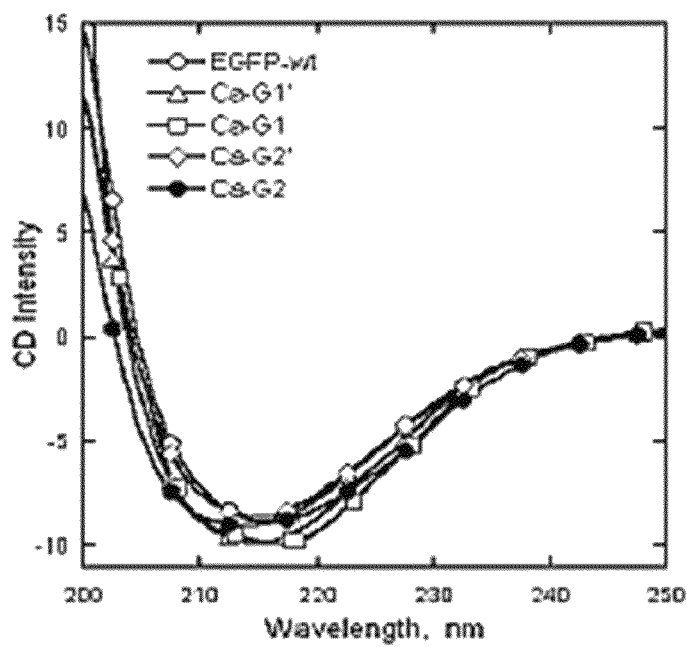
FIG. 7 illustrates CD spectra of EGFP-wt and variants thereof in 10 mM Tris and 1 mM DTT (pH 7.4). The protein concentrations were 10 μM for CD experiments.

CD analysis was performed to test whether the changes in the chromophore properties of the $Ca^{2+}$ sensor constructs were due to structural changes. All $Ca^{2+}$ sensor constructs exhibited CD spectra similar to that of EGFP-wt (FIG. 7), suggesting that the insertion of a $Ca^{2+}$ binding motif into EGFP did not significantly change the folding of the β-sheet structure of GFP.

Figure 8A:
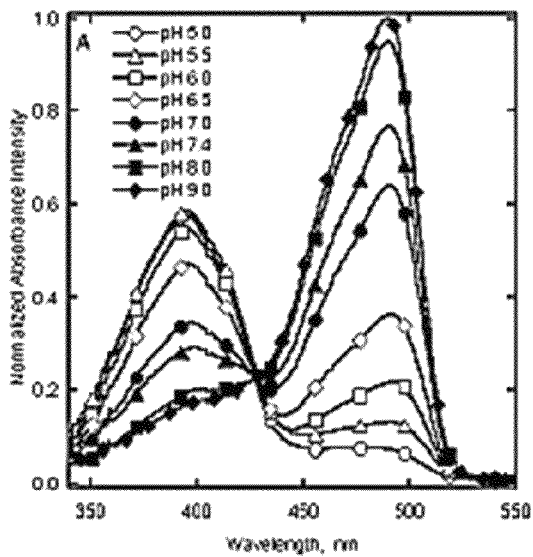
FIG. 8A illustrates visible absorbance spectra of Ca-G1' at various pHs. Measurements were performed in 1 mM DTT and 10 mM MES (pH 5.0, 5.5, 6.0), 10 mM PIPES (pH 6.5, 7.0), and 10 mM Tris (pH 7.4, 8.0, 9.0).
Figure 8B:
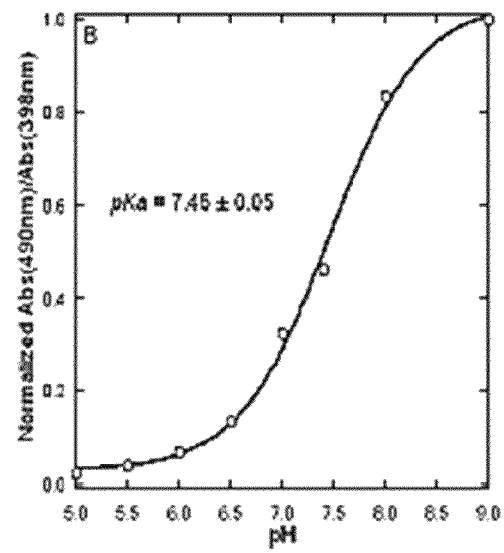
FIG. 8B illustrates the curve fitting of Ca-G1' at various pHs.

The pH sensitivity of the optical properties of Ca-G1', since a few GFP-based biosensors have been reported to be pH sensitive. FIGS. 8A and 8B shows the absorbance spectra of Ca-G1' as a function of pH. Changing pH from 9.0 to 5.0 resulted in an increase of the absorbance at 398 nm and a decrease of the absorbance at 488 nm. The $pK_a$ of Ca-G1' is 7.45±0.05 whereas the $pK_a$ of EGFP is 6.0. These data suggest that the optical properties of the designed $Ca^{2+}$ sensor are more sensitive to pH at physiological pH than those of EGFP-wt.

Example 8

Figure 3A:
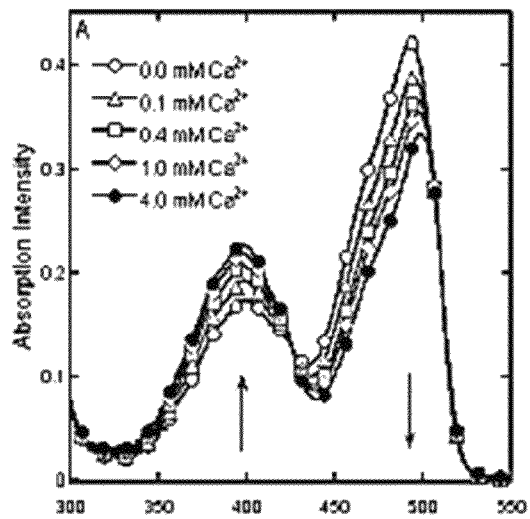
FIGS. 3A-3D illustrate the spectroscopic characterizations of the $Ca^{2+}$ sensor Ca-G1-37.
Figure 3B:
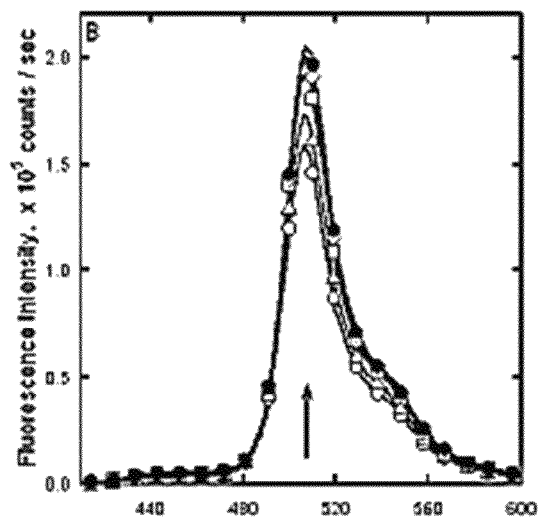
Figure 3C:
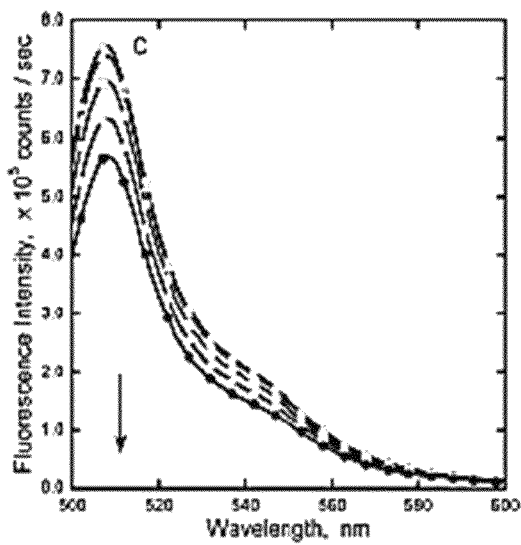

Effect of $Ca^{2+}$ Binding on Spectroscopic Properties of EGFP-based $Ca^{2+}$ Sensors: As shown in FIG. 3A, an increase in absorbance at 398 nm concomitant with a decrease at 490 nm was observed in response to the addition of $Ca^{2+}$ to Ca-G1-37. Similarly, $Ca^{2+}$ binding resulted in an increase in fluorescence with excitation at 398 nm (FIG. 3B) and a decrease with excitation at 490 nm (FIG. 3C).

Figure 3D:
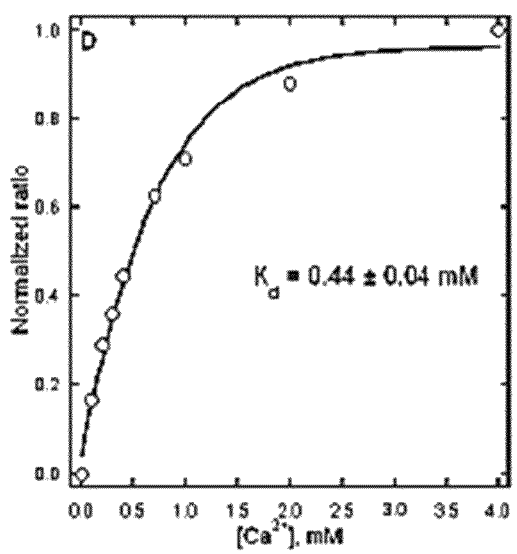

The dynamic range value was 1.8 and was calculated by dividing the fluorescence emission ratio excited at 398 and 490 nm of the $Ca^{2+}$ saturated state ($R_{max}$) by that of the $Ca^{2+}$-free state ($R_{min}$) (see Experimental procedures). FIG. 3D shows the fluorescence emission ratio, $F_{(398nm)}/F_{(490nm)}$, of Ca-G1-37 as a function of $Ca^{2+}$ concentration. The normalized fluorescence emission ratio change could be fitted as a 1:1 Ca-G1-37-$Ca^{2+}$ complex (Eq 2), yielding an apparent dissociation constant ($K_d$=0.44±0.04 mM) for its $Ca^{2+}$ binding affinity. The $Ca^{2+}$ binding affinity of EGFP-based $Ca^{2+}$ sensors was also determined using a Rhodamine-5N competition titration approach. The $Ca^{2+}$ binding affinities of these $Ca^{2+}$ sensors varied from 0.4 to 2 mM (Table 4), as determined by different techniques.

TABLE 4

Comparison of $Ca^{2+}$ Binding Affinities of Different EGFP-based $Ca^{2+}$ Sensors

| | $Ca^{2+}$ Binding Affinity, $K_d$ (mM) | |
|---|---|---|
| | $Ca^{2+}$ titration | Rhodamine-5N Competitive titration |
| Ca-G1' | 2.0 ± 0.4 | 0.9 ± 0.2 |
| Ca-G1 | 0.8 ± 0.1[a] | 0.4 ± 0.1 |
| | 0.8 ± 0.1[b] | |
| | 0.6 ± 0.1[c] | |
| Ca-G1-37 | 0.44 ± 0.04 | 0.2 ± 0.1 |
| Ca-G2' | N/A | 0.8 ± 0.2 |
| Ca-G2 | N/A | 0.2 ± 0.1 |
| Ca-G3' | N/A | 0.7 ± 0.2 |

[a]estimated with results of fluorescence spectrophotometer.
[b]estimated with fitting Scheme 1 using results from stopped-flow spectrofluorometer.
[c]estimated with fitting normalized changes (Amp) of stopped-flow spectrofluorimeter.

These values agreed with the approximate calcium concentration found in cellular compartments such as the ER, making these $Ca^{2+}$ sensors promising candidates for physiological experiments in living cells.

Example 9

$Ca^{2+}$ Selectivity of the EGFP-based $Ca^{2+}$ Sensor: The binding selectivity of the developed $Ca^{2+}$ sensors for $Ca^{2+}$ was examined by measuring the change of the ratio $F_{(398nm)}/F_{(490nm)}$ in the presence of 1.0 mM $Ca^{2+}$ before and following the addition of various metal ions. In cells, total metal concentrations for $Cu^{2+}$, $Zn^{2+}$, and $Mg^{2+}$ are estimated to be approximately 10 μM, approximately 0.1 mM, and greater than 10 mM, respectively. However, the free levels of these metal ions are significantly lower than the total concentrations, which protects the cell against potentially toxic reactions. For example, intracellular free copper is not detected and copper chaperone is used in vivo to allocate copper to its target proteins directly.

Figure 4B:
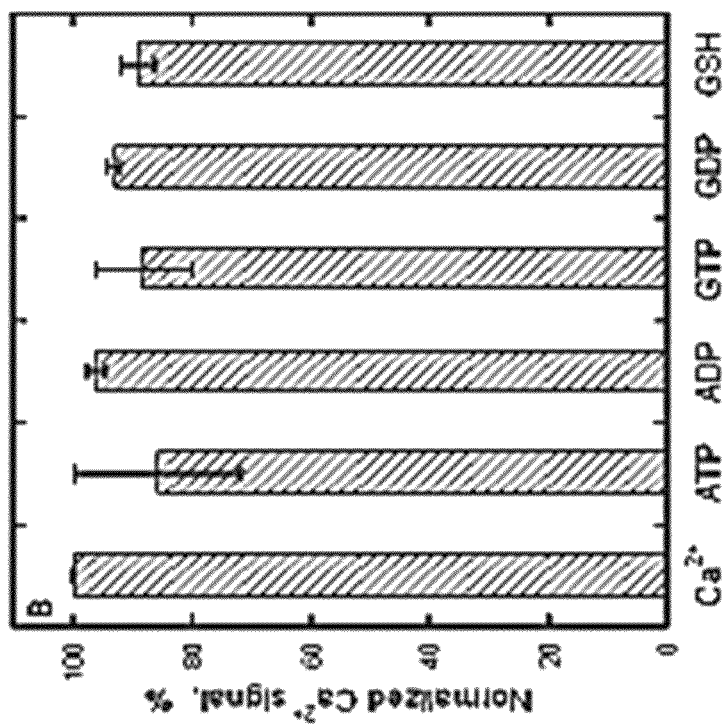
FIG. 4B illustrates $Ca^{2+}$ responses of Ca-G1-37 in the presence of: the intracellular molecules: ATP (0.2 mM), ADP (0.2 mM), GTP (0.1 mM), GDP (0.1 mM), and GSH (1.0 mM). The ratio of fluorescence emission of Ca-G1-37 with 398 nm and 490 nm excitation in the presence of 1.0 mM $Ca^{2+}$ was used to normalize the values using Eq. (5).
Figure 4A:
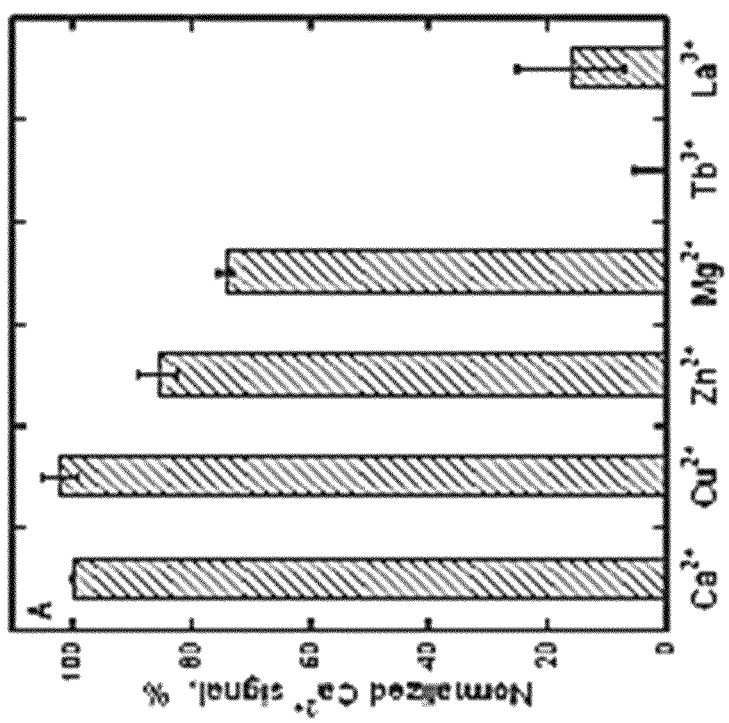
FIG. 4A illustrates $Ca^{2+}$ responses of Ca-G1-37 in the presence of: $Cu^{2+}$ (0.1 μM), $Zn^{2+}$ (0.1 mM), $Mg^{2+}$ (10.0 mM), $Tb^{3+}$ (5.0 μM) and $La^{3+}$ (5.0 μM). The ratio of fluorescence emission of Ca-G1-37 with 398 nm and 490 nm excitation in the presence of 1.0 mM $Ca^{2+}$ was used to normalize the values using Eq. (5).

FIG. 4A shows the $Ca^{2+}$ responses of sensor Ca-G1-37 in the presence of $Cu^{2+}$, $Zn^{2+}$, $Mg^{2+}$, $Tb^{3+}$, and $La^{3+}$. Note that no effect of $Cu^{2+}$ (0.1 μM) on the fluorescence response of the sensor for $Ca^{2+}$ was observed (101.95±3.02% compared to the reference value of 100% for 1.0 mM $Ca^{2+}$). $Zn^{2+}$ (0.1 mM) and $Mg^{2+}$ (10.0 mM) produced only a small change in the fluorescence response (reduction to 85.71±3.34% and 74.29±1.22%, respectively). Non-physiological metal ions, such as $Tb^{3+}$ (5.0 μM) and $La^{3+}$ (5.0 μM) have metal coordination properties similar to $Ca^{2+}$ and are able to compete more strongly with $Ca^{2+}$ responses of the sensor (0.15±5.4% and 16.0±9.0%, respectively). These results suggest that the developed $Ca^{2+}$ sensor, Ca-G1-37, has good metal selectivity for $Ca^{2+}$, $La^{3+}$ and $Tb^{3+}$ and only to a lesser degree with the other physiological metal ions.

The effects of small molecules including adenosine triphosphate (ATP), adenosine diphosphate (ADP), guanosine triphosphate (GTP), guanosine diphosphate (GDP), and Glutathione (GSH) on the $Ca^{2+}$ response of GFP-based $Ca^{2+}$ sensors were also analyzed by measuring the change of the ratio $F_{(398nm)}/F_{(490nm)}$ in the presence of 1.0 mM $Ca^{2+}$ before and following their addition.

FIG. 4B indicates that the addition of ATP (0.2 mM), ADP (0.2 mM), GTP (0.1 mM), GDP (0.1 mM), and GSH (1.0 mM) only resulted in a small decrease in the fluorescence response (reduction to 85.75±13.98%, 96.17±1.36%, 88.30±8.09%, 93.29±1.01%, and 89.18±2.90%, respectively). These results indicate that the developed $Ca^{2+}$ sensor, Ca-G1-37, has a high $Ca^{2+}$ binding affinity to compete with small molecules including ATP, ADP, GTP, GDP, and GSH in the intracellular environment.

Example 10

Figure 5A:
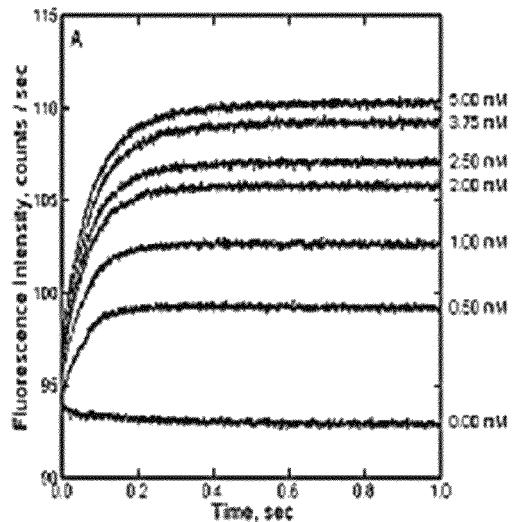
FIGS. 5A-5D illustrate a kinetic analysis of $Ca^{2+}$ association to Ca-G1.

Kinetics of $Ca^{2+}$ Binding to the EGFP-based $Ca^{2+}$ Sensor: As shown in FIG. 5A, mixing Ca-G1 with various concentrations of $Ca^{2+}$ resulted in a rapid increase in the fluorescence emission at 510 nm with excitation at 398 nm. The change in fluorescence signal is consistent with a single exponential function (Eq. 6) yielding observed rates for fluorescence emission change ($k_{obs}$) and amplitudes (Amp).

Figure 5B:
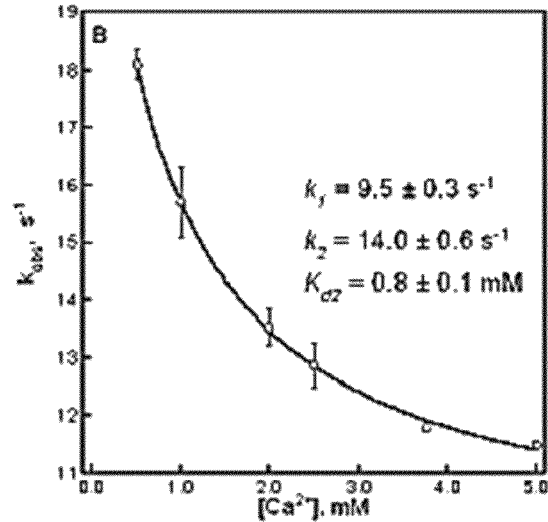

As shown in FIG. 5B, the $k_{obs}$ values of Ca-G1 decreased with increasing concentration of $Ca^{2+}$, consistent with the kinetic model of Scheme 1, in which $Ca^{2+}$ rapidly associates with one species of Ca-G1 that is in equilibrium with a second form of the biosensor. The increases in fluorescence emission excited at 398 nm of Ca-G1 observed upon $Ca^{2+}$ binding as shown in FIG. 5A further suggest that the neutral form of Ca-G1 is the species that binds $Ca^{2+}$ (E** in Scheme 1), whereas the anionic form of the biosensor (E*) does not bind $Ca^{2+}$.

According to this kinetic model, $k_1$ is the first order rate constant ($s^{-1}$) for the conversion of the anionic species to the neutral species of Ca-G1, $k_2$ is first order rate constant ($s^{-1}$) for the conversion of the neutral species to the anionic form of Ca-G1, and $K_{d2}$ represents the apparent dissociation constant for the binding of $Ca^{2+}$ to the neutral form of Ca-G1 (mM).

Scheme 1

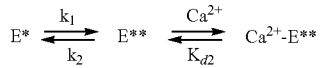

Figure 5C:
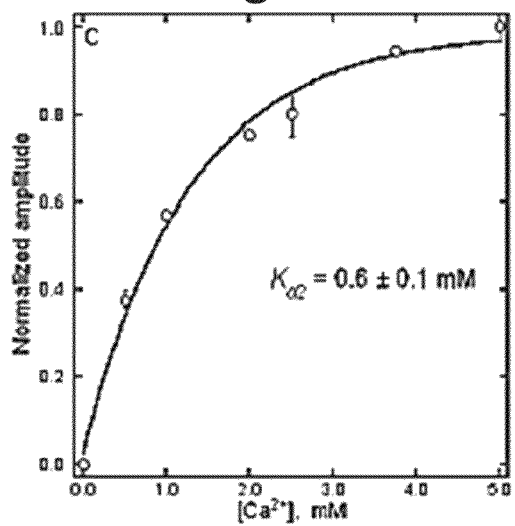

By fitting $k_{obs}$ values determined as a function of $Ca^{2+}$ concentration to Eq 8, the $k_1$ and $k_2$ values were estimated to be $9.5\pm0.3\ s^{-1}$ and $14.0\pm0.6\ s^{-1}$, respectively, and a $K_{d2}$ value of $0.8\pm0.1$ mM was determined. The $K_{d2}$ value was independently estimated to be $0.6\pm0.1$ mM by fitting the normalized amplitude in fluorescence emission as a function of the concentration of $Ca^{2+}$ by using Eq. 2 (FIG. 5C). Within errors associated with the measurements, the $K_d$ values determined using stopped-flow fluorescence spectroscopy are in agreement with the $K_d$ value independently determined in static titrations using a spectrofluorometer, which yielded a $K_d$ value of $0.8\pm0.1$ mM (Table 1). This, in turn, strongly supports the validity of the proposed minimal kinetic mechanism of Scheme 1 for $Ca^{2+}$ binding to Ca-G1, where rates of fluorescence changes associated with $Ca^{2+}$ binding to the neutral species of Ca-G1 reflect rates of interconversion of the neutral and anionic forms of Ca-G1, as compared to the rapid association and dissociation of $Ca^{2+}$ to and from the biosensor.

$$k_{obs} = k_1 + k_2\left(\frac{K_{d2}}{K_{d2} + [Ca^{2+}]}\right) \quad (8)$$

According to the minimal kinetic mechanism of Scheme 1 and the data shown in FIG. 5A, the release of $Ca^{2+}$ from preloaded Ca-G1 is expected to be associated with a decrease in fluorescence whose rate of fluorescence change represents the slow rate of conversion from the neutral to the anionic form of Ca-G1, i.e., $k_2$. Consequently, stopped-flow spectroscopy was utilized to independently determine $k_2$ by mixing equal volumes of $Ca^{2+}$-saturated sensor with 10 mM Tris and 1 mM DTT (pH 7.4). As expected, the fluorescence intensity at 510 nm decreased following $Ca^{2+}$ release and the time course of fluorescence change was consistent with a single exponential process (Eq. 6).

Figure 5D:
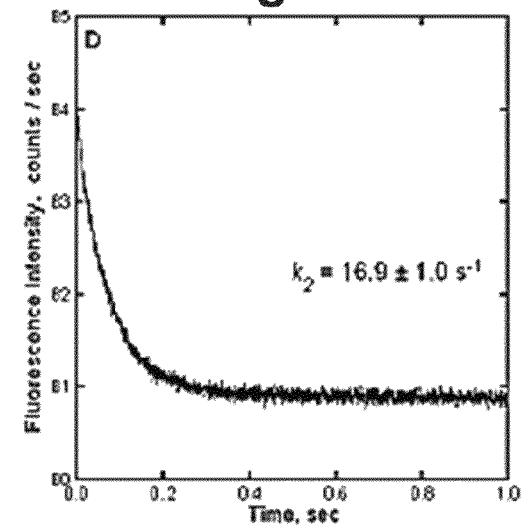

As shown in FIG. 5D, a $k_{obs}$ value of $16.9\pm1.0\ s^{-1}$ was estimated in this experiment by fitting the data to Eq. 6, in good agreement with the value of $14\ s^{-1}$ determined for $k_2$ from the data in FIG. 5B. Together, the kinetic data support the conclusion that $Ca^{2+}$ rapidly associates with and dissociates from the neutral form of Ca-G1, yielding a change in the relative amounts of neutral and anionic species that is associated with a change in the intensity of the fluorescence signal from Ca-G1.

$Ca^{2+}$ binding to Ca-G1 results in a rapid shift of the chemical equilibrium of the chromophore between its anionic and neutral states (Scheme 1). This conclusion is supported by visible absorption, fluorescence emission, and stopped-flow fluorescence data. Both kinetic and thermodynamic parameters, including the forward and reverse rate constants for the interconversion of the anionic and neutral states of the chromophore, as well as the apparent dissociation constant for binding of $Ca^{2+}$ to Ca-G1 were determined using stopped-flow fluorescence measurements. This approach established that the rates of $Ca^{2+}$ association and dissociation to and from the sensor must be significantly larger than both the forward and reverse first-order rate constants that define the chemical equilibrium of the chromophore ($k_1$ and $k_2$ in Scheme 1), which are between ~10 and ~20 $s^{-1}$. The rate of $Ca^{2+}$ association to proteins is generally a diffusion-limited process with an on-rate ($k_m$) equal or greater than $1\times10^6\ M^{-1}s^{-1}$. Since the apparent dissociation constant for the $Ca^{2+}$ binding process determined in this study for Ca-G1 is ~0.8 mM for Ca-G1, an off-rate ($k_{off}$) of ~800 $s^{-1}$ can be estimated from $k_{off}=k_{on}\times K_d$. Whereas the on-rate of GFP-based $Ca^{2+}$ sensors is generally not the limiting factor in $Ca^{2+}$ measurements, the slow off-rate exhibited by $Ca^{2+}$ sensors limits their usefulness in monitoring changes in $Ca^{2+}$ concentration in vivo, especially for fast $Ca^{2+}$ oscillations. To overcome this limitation, an improvement of the off-rate constant $k_{off}$ to 256 $s^{-1}$ was obtained by redesigning the binding interface between calmodulin and its targeting peptide in GFP-based $Ca^{2+}$ sensors. Optimizing the protonation rate of the chromophore in GFP-based $Ca^{2+}$ sensors will provide a means to enhance further the accuracy with which $Ca^{2+}$ signals can be measured with high temporal resolution.

Example 11

Figure 6A:
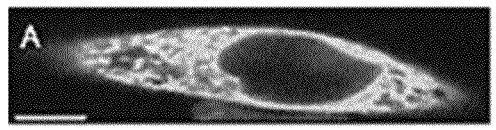
FIGS. 6A-6D is a series of digital images illustrating the localization of sensor Ca-G1-ER in HeLa and BHK-21 cells.
Figure 6B:
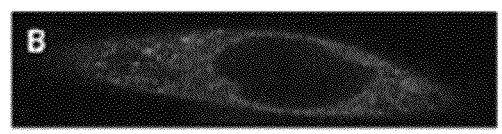
Figure 6C:
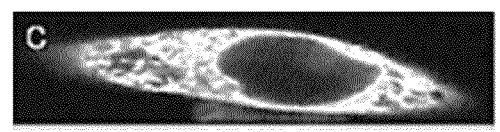
Figure 6D:
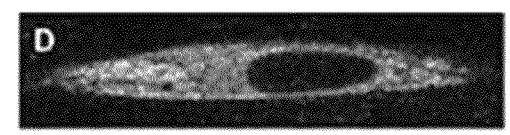

Monitoring ER $Ca^{2+}$ Responses in Cells: Localization of the $Ca^{2+}$ sensor, Ca-G1-ER, was confirmed in HeLa cells by co-transfecting the cells with the ER marker DsRed2-ER that has been shown to localize exclusively to this region in mammalian cells. FIG. 6 shows images taken through the green (A, Ca-G1-ER) and red (B, DsRed2-ER) channels which were excited at 488 and 543 nm, respectively. The merged image (FIG. 6C) indicates the complete co-localization of Ca-G1-ER with the ER marker DsRed2-ER in the ER of HeLa cells. FIG. 6D shows the ER distribution of Ca-G1-ER in a BHK-21 cell, a mammalian fibroblast cell line. Note the same granular distribution of Ca-G1-ER in FIGS. 6A and 6D, suggesting that the $Ca^{2+}$ sensor also specifically localizes to the ER of BHK cells. In contrast, Ca-G1, which lacked the ER signal peptides, was expressed diffusely throughout the cytoplasm of the cells, thereby serving as a negative control (data not shown).

Figure 6E:
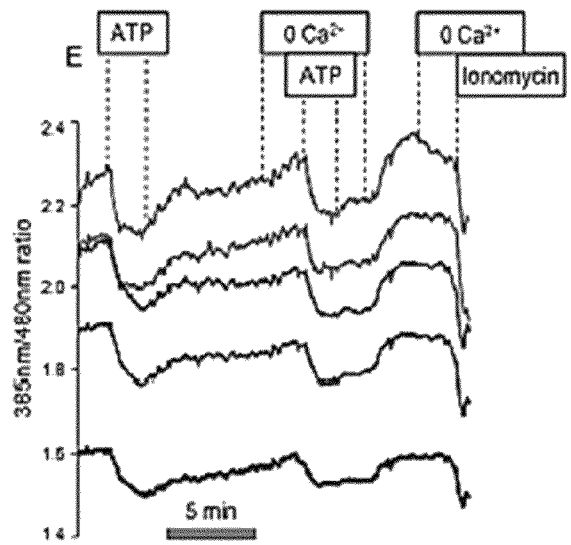
FIGS. 6E and 6F illustrate the calcium response of the sensor Ca-G1-ER in BHK-21 cells.
Figure 6F:
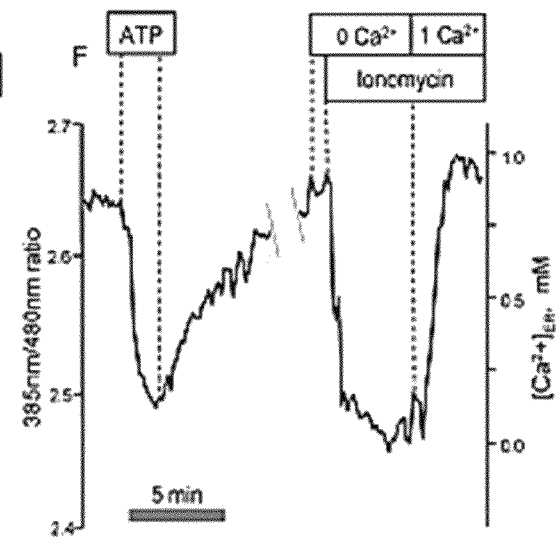

BHK-21 cells have been used previously to investigate the physiological roles of $[Ca^{2+}]_{ER}$ in intact cells by using small, low-affinity $Ca^{2+}$ indicators. ATP (100 µM) is a $Ca^{2+}$-mobilizing agonist of this cell type and elicits $Ca^{2+}$ release from the ER through Ins(1,4,5)P$_3$-mediated pathways. As shown in FIG. 6E, the addition of ATP (100 µM) resulted in a significant decrease (7.3±0.6% relative change) in the fluorescence ratio measured at 510 nm (excitation at 385 and 480 nm). The experiment shows five representative cells imaged in the same experiment and the results are typical of results obtained in 5 independent experiments. This decrease of $[Ca^{2+}]_{ER}$ was also observed following application of ATP in $Ca^{2+}$-free buffer, suggesting that ATP released $Ca^{2+}$ from the ER independent of extracellular $Ca^{2+}$. The refilling of the $Ca^{2+}$ store required several minutes in the presence of normal extracellular $Ca^{2+}$ in the medium. Similarly, the addition of the $Ca^{2+}$ ionophore, ionomycin, under $Ca^{2+}$ free conditions significantly emptied the ER store as indicated by the decreased 385 nm/480 nm fluorescence ratio. To obtain an estimate of $[Ca^{2+}]_{ER}$, a pseudo-calibration was performed in BHK-21 cells using Eq. 7 and a $K_d$ of 0.8 mM for Ca-G1 as shown in Table 1 (FIG. 6F). The 385 nm/480 nm fluorescence ratio decreased to a minimum value ($R_{min}$) following a wash with $Ca^{2+}$ free medium (EGTA) and the subsequent addition of ionomycin (approximately 5 µM) to the $Ca^{2+}$-free medium (estimated to contain less than 10 nM $Ca^{2+}$ using the freeware program 'Bound and Determined'). The addition of millimolar extracellular $Ca^{2+}$ (approximately 1 mM) resulted in a large increase in the $Ca^{2+}$ signal with a plateau that approached the saturation state with a maximum of 385 nm:480 nm fluorescence ratio ($R_{max}$) The initial $Ca^{2+}$ concentration in the ER of the BHK-21 cell was estimated to be less than 1 mM using Eq 7 and addition of ATP (100 µM) reduced $[Ca^{2+}]_{ER}$ to approximately 0.15 mM (FIG. 6F). As expected, no significant fluorescence signal change was observed in response to the above experimental protocol in cells transfected with the wild type control construct, EGFP-wt-ER (data not shown). These imaging experiments demonstrate the usefulness of this novel class of $Ca^{2+}$ sensors in living cells and it is anticipated that their future application will facilitate the investigation of the role of the ER in $Ca^{2+}$ signaling and $Ca^{2+}$ homeostasis.

Example 12

Variant Constructs: The GFP variant EGFP-D2 (SEQ ID No.: 64) with a discontinuous calcium binding site (S2D, S86D, L194E), cycle 3 (F99S, M153T, V163A) mutations was made through site-directed mutagenesis with PCR and turbo pfu (Strategene) following the manufacturer's suggestions with EGFP (S65T, F64L, V22L, M218I, H231L) as the initial template.

EGFP-G1 contains a continuous EF-hand $Ca^{2+}$ binding motif III that was inserted by several rounds of PCR utilizing turbo pfu. The linear DNA was ligated with T4 DNA ligase (Promega) following the manufacturer's instructions, and the circular DNA was transformed into E. coli DH5α competent cells for DNA amplification. The variant DNA was verified by automated sequencing. The cDNA encoding the EGFP variants with BamH I and EcoR I restriction enzyme sites between the N and C terminals were subcloned into mammalian expression vector pcDNA3.1+ that uses the CMV promoter.

Example 13

Bacterial Expression and Purification: The proteins were expressed from the vector pet28a (EMD Biosciences) with a 6×His-tag using E. coli BL21(DE3) in LB-kanamycin (30 µg/mL). Expression was induced at an O.D$_{600}$ of 0.6 with 0.2 mM IPTG and expression was allowed to continue for 21 hrs before the cells were harvested by centrifugation. For these studies, the temperature was controlled at both 30° C. and 37° C. after induction. The expression of EGFP and its variants was monitored with the fluorescence intensity at 510 nm with a Fluo-star instrument and an excitation wavelength of 488 nm.

Protein purification was with an Amersham-Pharmacia 5 mL HiTrap chelating HP column charged with nickel. The cell pellets were resuspended in 20 mM Tris, 10 mM NaCl, 0.1% Triton X-100, pH 8.8 and sonicated. The cellular debris was removed by centrifugation and the protein was loaded onto the prepared HiTrap column connected to an Amersham-Pharmacia AktaPrime FPLC. After washing to remove contaminant proteins, the protein of interest was eluted with an imidazole gradient. Contaminant imidazole was removed by dialysis, and the protein was further purified using a HiTrap Q ion-exchange column (Amersham) with a NaCl gradient at pH 8.0. Protein purity was verified by SDS-PAGE.

Example 14

Mammalian Cell Culture: HeLa cells were grown on 60 mm culture dishes in Dulbecco's Modified Eagles Medium (DMEM, Sigma Chemical Co., St. Louis, Mo.) with 44 mM NaHCO$_3$, pH 7.2, and supplemented with 10% (v/v) fetal bovine serum (FBS), 100 U/ml penicillin and 0.1 mg/ml streptomycin (Pen/Strep) at 37° C. with 5% CO$_2$ humidified incubation chamber. HeLa cells were grown to confluency before transient transfection.

Plasmid DNA used for transfection was harvested from transformed E. coli (DH5α) using QIAGEN's miniprep protocol (Qiagen). Each of the nine GFP variants were individually and transiently transfected into HeLa cells with Liptofectamine-2000 (Invitrogen Life Technologies) and serum-free Opti-MEMI (Gibco Invitrogen Corporation) as per the manufacturer's instructions. A typical transfection consisted of 1 or 2 µg plasmid DNA with a ratio of DNA to Liptofectamine between 1:1 and 1:3 (µg/µl) dependent upon the protein construct. Protein expression was allowed to proceed for 48 and 72 h before inverted epifluorescence imaging. Control transfections with EGFP were performed in the same conditions as each construct.

Example 15

Measurement of fluorescent intensity: Three 1 ml samples were collected at time points throughout the expression, and centrifuged at 14 K rpm for 3 min. The cell pellets were resuspended in 1 ml of Tris buffer at pH 7.4, and 200 µl was analyzed using a FLUOstar OPTIMA (BMG Labtech) plate reader with excitation filters of 390 and/or 460 nm and an emission filter at 510 nm.

Example 16

Fluorescence microscopy/imaging and its quantifications: An inverted epifluorescence microscope (Zeiss Axiovert 200) was utilized for fluorescence intensity screening in vivo. The microscope was equipped with a xenon arc Lamp, filters for Sapphire GFP with 398 nm excitation and 510 nm emission, with standard DAPI, FITC, and Texas Red filters, and transmitted light. An Axiocam 5 CCD camera was connected to the microscope at a right angle to the stage, and Zeiss Axiovision Rel 4.3 software was used for data collection and analysis.

For fluorescence intensity measurements a 40× dry objective was used with Sapphire GFP and FITC filters and exposure times from 50 to 2000 ms. The images with exposure allowing for fluorescence intensity within the dynamic range were utilized for data analysis. The fluorescence intensity measured in this time range was a linear function of the exposure time.

Both the area and mean fluorescence intensity of transfected cells (n>20 cells per image) were measured and the total mean fluorescence intensity of cells in each imaged field was obtained with the calculation of Eq. (9):

$$F = \frac{\sum_{i=1}^{n} S_i F_i}{\sum_{i=1}^{n} S_i} \quad (9)$$

in which, F is the total mean fluorescence intensity excited at 398 nm or 480 nm of cells in each image, and n is the number of fluorescent cells. $S_i$ is the area of $i^{th}$ fluorescent cell and $F_i$ is the mea fluorescent intensity excited at 398 nm or 480 nm of $i^{th}$ fluorescent cell.

The total mea fluorescent intensity excited at 398 nm or 480 nm of the HeLa cells three days after transfection with EGFP-G1-C3 was used as a reference, and the fluorescence intensity excited at different wavelengths of the HeLa cells grown for different times with other GFP variants was expressed as a percentage of EGFP-G1-C3 fluorescence according to Eq. (10):

$$F' = \frac{F}{F_0} \times 100 \quad (10)$$

in which, the F' is the relative fluorescent intensity excited at 398 nm or 480 nm of the HeLa cells, F is the total mean fluorescence intensity excited at 398 nm or 480 nm of the HeLa cells, and $F_0$ is the total mea fluorescent intensity excited at 398 nm or 480 nm of the HeLa cells incubated for three days after transfection with EGFP-G1-C3.

Example 17

Measurement of ultra-violet (UV) and visible absorption spectrum: Spectroscopic properties of EGFP and its variants were measured by UV and visible absorption spectra with a Shimadzu UV and Visible Light Spectrophotometer from 600 to 220 nm. The concentrations of the proteins were determined by UV-vis absorbance at 280 nm using the molar extinction coefficient of 21,890 $M^{-1}cm^{-1}$ calculated from the contribution from aromatic residues (1 Trp and 11 Tyr) (5500 and 1490 $M^{-1}cm^{-1}$ for Trp and Tyr, respectively). The extinction coefficient at 398 nm or 490 nm of the EGFP variants were obtained with the Eq. (11):

$$\varepsilon_P = \varepsilon_{P,280nm} \left( \frac{A_P}{A_{P,280nm}} \right) \quad (11)$$

in which, $\varepsilon_p$ is the extinction coefficient at 398 nm or 490 nm of EGFP variants, $\varepsilon_{p,280nm}$ is the extinction coefficient at 280 nm of EGFP variants, $A_p$ is the absorption of EGFP variants at 398 nm or 490 nm, and $A_{p,280nm}$ is the absorption of EGFP variants at 280 nm. EGFP was used as a reference in the measurement of the extinction coefficients of the variants.

Example 18

Fluorescence excitation and emission spectra: Spectroscopic properties of EGFP and its variants were also monitored with their fluorescence spectra, measured in a Fluorescence Spectrophotometer (Hitachi Co. Ltd.) with a 1 cm path length quartz cell at room temperature and at 1 µM concentration in 10 mM Tris and 1 mM DTT (pH 7.4). Slit widths of 3 nm and 5 nm were used for excitation and emission, respectively. The quantum yield of EGFP variants with different excitation wavelengths was obtained with a calculation of equation Eq. (12):

$$\varphi_p = \varphi_r \left( \frac{A_r}{A_p} \right) \left( \frac{F_p}{F_r} \right) \left( \frac{n_p^2}{n_r^2} \right) \quad (12)$$

in which, $\phi_p$ is the relative quantum yield excited at 398 nm or 490 nm of EGFP variants; $\phi_r$ is the relative quantum yield excited at 398 nm or 490 nm of the reference sample; $A_p$ is the absorption of EGFP variants at 398 nm or 490 nm; $A_r$ is the absorption of the reference sample at 398 nm or 490 nm; $F_p$ is the integrated fluorescence intensity in the range of 500 nm to 600 nm excited at 398 nm or 490 nm of EGFP variants; $F_r$ is the integrated fluorescence intensity in the range of 500 nm to 600 nm excited at 398 nm or 490 nm of the reference sample; $n_p$ is the refractive index of EGFP variants; and $n_r$ is the refractive index of the reference sample.

EGFP was used as the reference sample in the measurement of quantum yield of EGFP variants.

Example 19

Statistical analysis: Statistical analysis was performed with the software package SuperANOVA (Abacus Concepts, Berkeley, Calif.). Values were expressed as mean±SEM. Control and treatment groups were compared by performing an analysis of variance (ANOVA). Fisher's Protected Least Significance Difference Test (Fisher's PLSD) was employed for post-hoc tests of statistical significance. Significance levels compared to day 1 are indicated as follows: *$p \leq 0.05$; $p \leq 0.01$; *$p \leq 0.001$.

Example 20

Figure 9A:
FIG. 9A illustrates a model structure of calcium binding fluorescent protein with the addition of the EGFP.D2 (site 1) by computational design or EGFP-G1 (172EF) by inserting the EF-hand motif III from calmodulin into position 172-173. Residues involved in the formation of the chromophore are highlighted. The structure of EGFP around the chromophore based on 1EMA.pdb.

Design of EGFP-based calcium binding proteins: Two different types of calcium binding sites were created in enhanced green fluorescent protein (EGFP). FIG. 9A shows the design of EGFP-D2 (SEQ ID No.: 64) containing a discontinuous calcium binding site based on common pentagonal bipyramidal geometry and chemical properties (J. Am. Chem. Soc. 127: 2085-2093; J. Am. Chem. Soc. 125: 6165-6171). It was formed by oxygen from five negatively charged ligand residues from sidechain carboxyl groups by the mutated amino acid positions, S2D L194E, S86D, and the natural ligands of D82 and E5. FIG. 9A also shows the engineering of a continuous calcium binding site EGFP-G1 (SEQ ID No.: 4) by integrating the EF hand calcium binding motif III of calmodulin inserted on loop 9 between residues E172 and D173 of EGFP. In addition to fulfilling the required criteria for calcium binding to have proper local calcium binding geometric properties and charge arrangement, these calcium binding sites were also selected based on criteria to assist chromophore formation: (i) site location and residue mutations should not abolish the chromophore synthesis or folding of the protein. Any residues that are conserved in fluorescent proteins and essential for protein structure and folding are not mutated; (ii) the location should be in a solvent-exposed region to have a good accessibility to enable calcium binding; (iii) to avoid drastic alterations of protein folding and chromophore formation by the introduced charged calcium ligand residues, a calcium binding pocket with few mutations necessary is preferred.

Additional mutants were also created to test the effect of folding mutations on the fluorescence at both temperatures. The cycle 3 mutations were applied in sets of two or three of each calcium binding site to examine the differences in fluorescence in accordance with the applied mutations. Two mutations, M153T and V163A, were applied to EGFP-D2 and EGFP-G1 to create EGFP-D2-C2 and EGFP-G1-C2 (SEQ ID No.: 19) constructs, respectively. The last mutation F99S was further incorporated to create the C3 constructs, EGFP-D2-C3 and EGFP-G1-C3 (SEQ ID No.: 34). The same mutations (C2 and C3) were also applied to EGFP-wt.

Figure 9B:
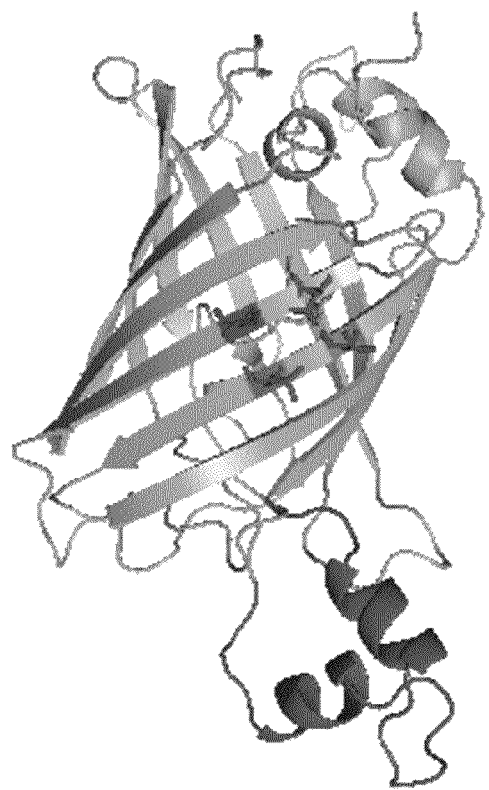
FIG. 9B illustrates a model structure of modified grafting EGFP sensor. One EF-hand was inserted in the fluorescent sensitive location of EGFP, generating EGFP-G1. A site-directed mutagenesis on the beta-sheet surface introducing a negatively charged residue to form a $Ca^{2+}$ binding site with three existed negatively charged resiudes.

FIG. 9B illustrates a model structure of modified grafting EGFP sensor. One EF-hand was inserted in the fluorescent sensitive location of EGFP, generating EGFP-G1. A site-directed mutagenesis on the beta-sheet surface introducing a negatively charged residue to form a $Ca^{2+}$ binding site with three existed negatively charged residues.

Bacteria expression of the EGFP calcium binding proteins: The nine proteins, EGFP, EGFP-C2, EGFP-C3, EGFP-D2 (SEQ ID No 64), EGFP-D2-C2, EGFP-D2-C3, EGFP-G1 (SEQ ID No.: 4), EGFP-G1-C2 (SEQ ID No.: 19), and EGFP-G1-C3 (SEQ ID No.: 34) were first expressed in bacteria at 30° C. and 37° C. to examine the differences in the chromophore maturation by monitoring the fluorescence intensity at 510 nm (excited at 490 nm). Average intensities of the nine proteins were taken at five time points throughout the expression.

Figure 10:
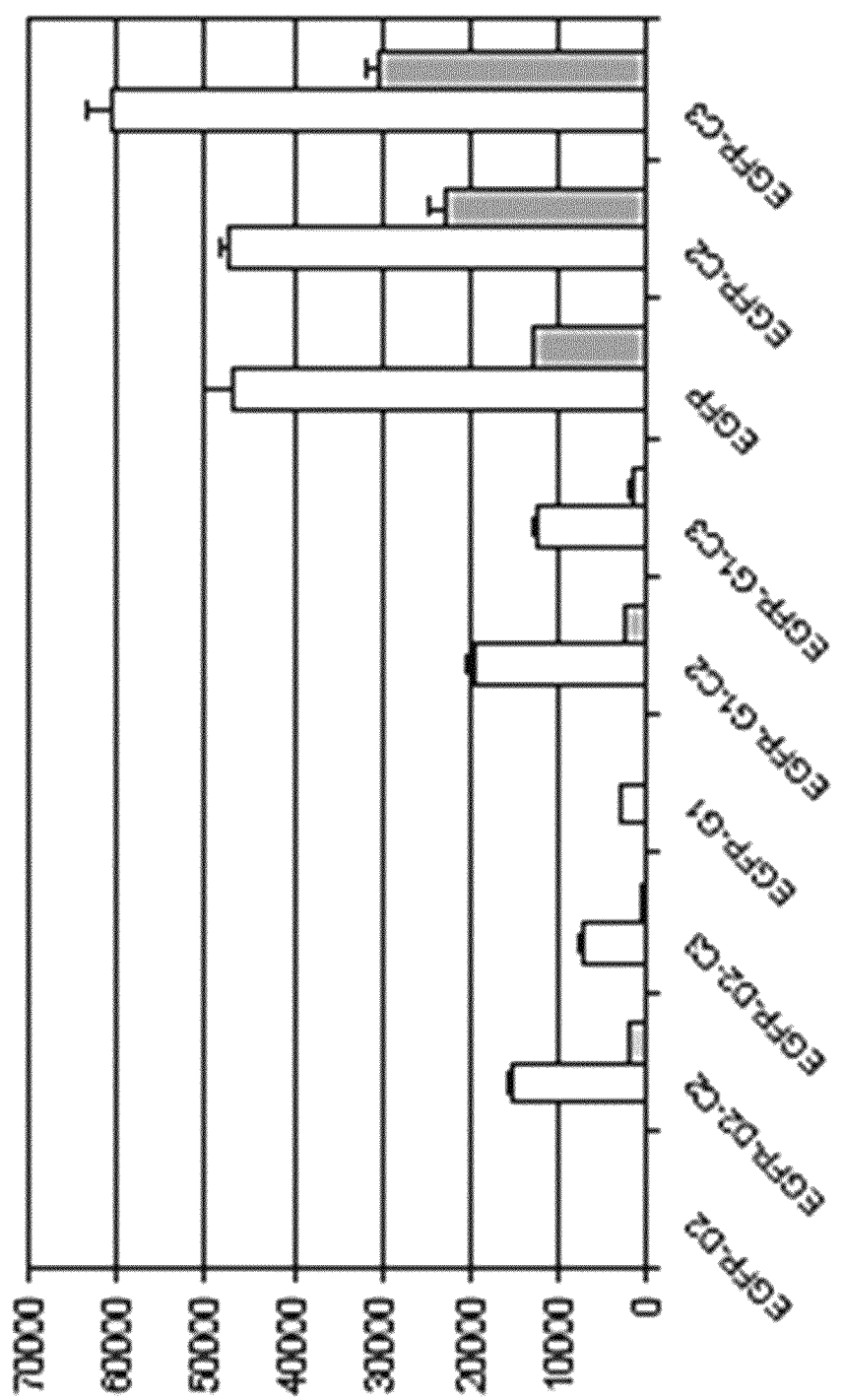
FIG. 10 is a graph illustrating expression of EGFP and variants thereof in $E.\ coli$ BL21-DE3 22 hrs after 200 mM IPTG induction and at 30° C. (open bars) and 37° C. (closed bars), respectively. $\lambda$ex=488 nm.

FIG. 10 lists the average fluorescence intensities for 22 hrs after IPTG induction. The differences between the 30° C. and 37° C. expression fluorescence intensities were also calculated. As shown in FIG. 10, at 30° C. the addition of both types of calcium binding sites into EGFP does not alter the chromophore formation. However, the fluorescent intensities of expressed properties in bacteria were significantly decreased.

The fluorescent intensities of both EGFP-D2 (SEQ ID No.: 64) and EGFP-G1 (SEQ ID No.: 4) is significantly lower than in EGFP at both 30° C. and 37° C. The C2 and C3 mutations in EGFP-D2 (SEQ ID No.: 64) resulted in 37- and 18-fold increases of its fluorescence intensity at 30° C., respectively. The fluorescence intensity increase (6- and 4-fold) was also observed with C2 and C3 mutations in EGFP-G1 (SEQ ID No.: 4) at 30° C. However, the similar fluorescence intensity increase was not observed with C2 and C3 mutations in EGFP at 30° C. The fluorescent intensities at 510 nm of the proteins with the addition of calcium binding sites D2 and G1 at 30° C. were greater than that at 37° C., respectively. While EGFP does not have any significantly difference in fluorescent intensity for both C2 and C3 variants, the C2 constructs for D2 and G1 surprisingly exhibited an increased fluorescence over the C3 variants. Though it is not as low in fluorescence as the protein variants with none of the cycle 3 mutations added, this indicates that F99S actually interferes with the folding of the protein variant when applied to the M153T/V163A construct.

Example 21

Figure 11:
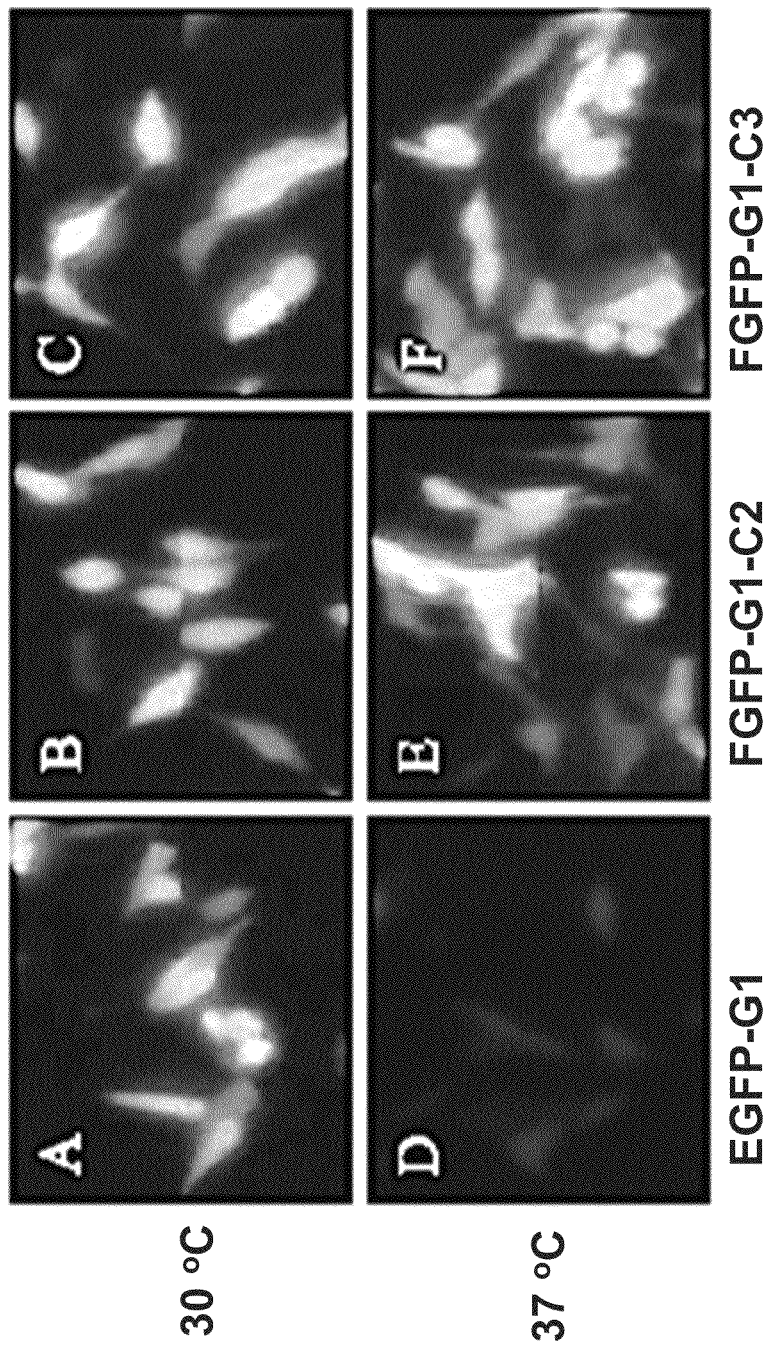
FIG. 11 is a series of digital images illustrating fluorescence microscope imaging of HeLa cells. The imaging was performed two days (48 hrs) after HeLa cells were transfected with EGFP-G1, EGFP-G1-C2, and EGFP-G1-C3. The exposure time was 200 ms.

Mammalian cell expression of EGFP-based calcium binding proteins: The effect of the C2 and C3 mutations on the expression of EGFP calcium proteins in mammalian cells was also monitored using fluorescence microscopy. FIG. 11 shows the fluorescence microscope imaging of the HeLa cells at two day expression at 30° C. and 37° C. after transfection of EGFP-G1, EGFP-G1-C2, and EGFP-G1-C3. As shown in FIGS. 11A-11C, after two days transfection and expression at 30° C., EGFP-G1 (SEQ ID No.: 4) variant and its C2 and C3 mutations were expressed and folded in the majority of the HeLa cells as indicated by their strong fluorescence signals. However, as shown in FIG. 11D, EGFP-G1 (SEQ ID No.: 4) lost its fluorescence signal at 37° C. indicating that this temperature was not suitable to the maturation of EGFP-G1 (SEQ ID No.: 4) in HeLa cells. In contrast, the addition of C2 and C3 mutations in EGFP-G1 (SEQ ID No.: 4) resulted in a maturation of the proteins at 37° C. in HeLa cells, as shown in FIGS. 11E and 11F.

FIGS. 12A and 12B show the quantitative analysis of fluorescence intensity of HeLa cells (more than 20 cells per image) transfected with both EGFP-D2 and EGFP-G1 series at both 30° C. and 37° C. A low fluorescence intensity of HeLa cells transfected with EGFP-D2 (SEQ ID No.: 64) was observed at both 30° C. and 37° C. (FIG. 12A) compared with that of EGFP-G1 (SEQ ID No.: 4). The C2 mutation in EGFP-D2 resulted in the increase of fluorescence intensity, but further increase was not observed in the C3 mutation. This result with mammalian cells corresponded with that observed in *E coli*. A similar result was also indicated with a C2 mutation in EGFP-G1 at 37° C. although the effect of C2 and C3 mutations of EGFP-G1 was not observed at 30° C., shown in FIG. 12B.

Example 22

Spectroscopic properties of the calcium binding GFPs: To further explore this phenomenon, the proteins were purified. EGFP-D2-C2 and EGFP-G1-C2 (SEQ ID No.: 19) were much harder to purify than the parent proteins at the increased concentrations of the protein, indicating that the protein folds more efficiently and there were more soluble fractions that could easily be released during sonication. This was expected as EGFP-D2-C2 and EGFP-G1-C2 (SEQ ID No.: 19) had 37- and 19-fold higher fluorescence than their counterparts with no "folding mutations".

Figure 13A:
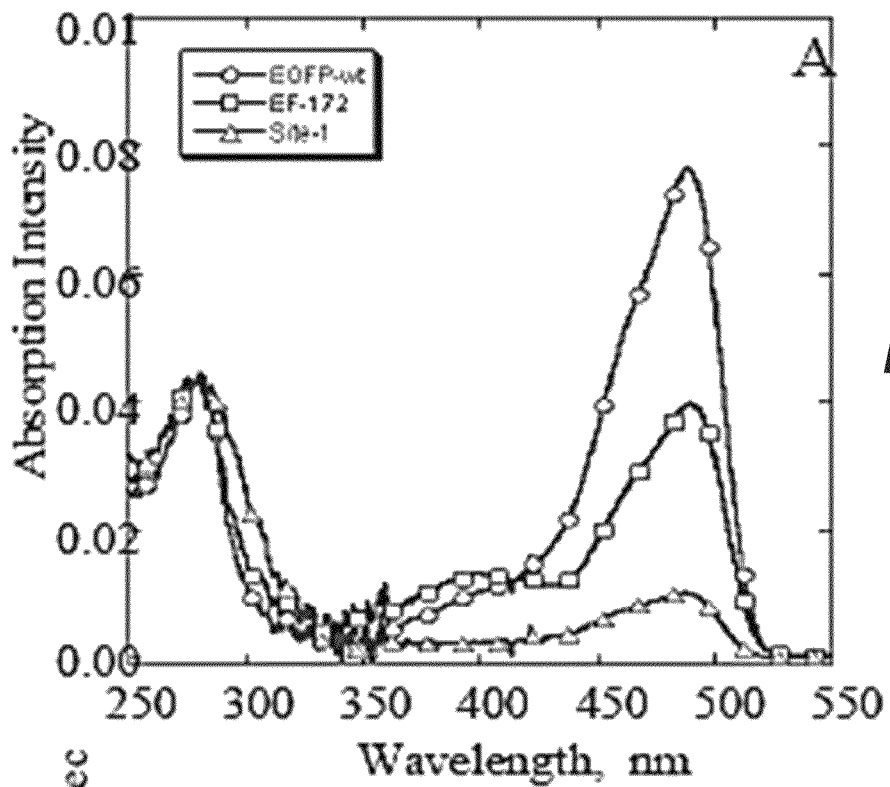
FIG. 13A illustrates the visible absorbance spectra of EGFP, EF-172, and Site 1. The protein concentrations were 2 mM.
Figure 13B:
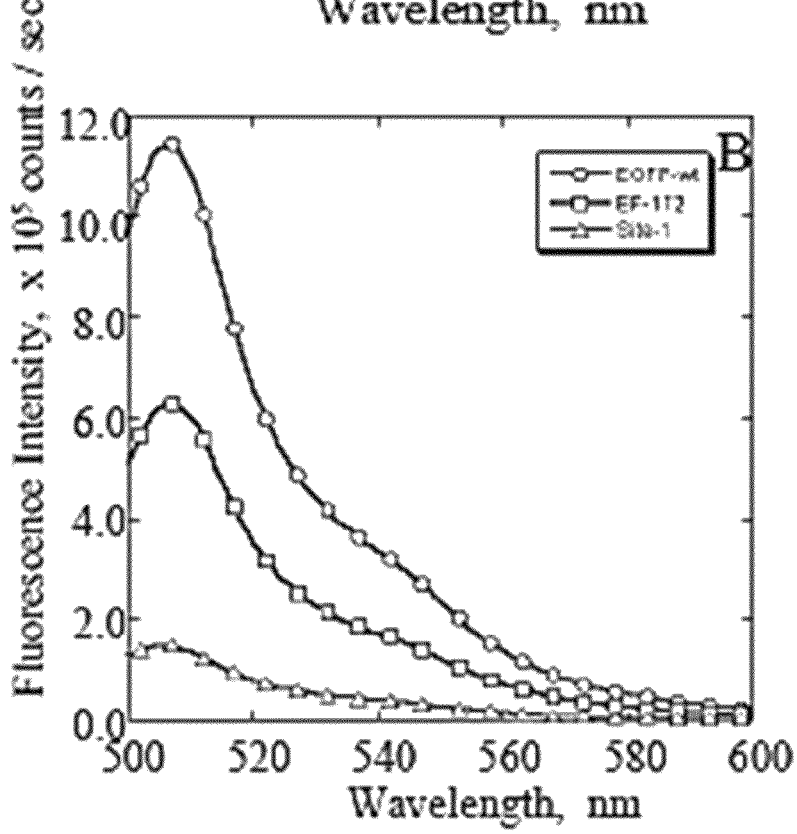
FIG. 13B illustrates the fluorescence spectra of EGFP, EF-172, and Site 1. The protein concentrations were 2 mM. Slit width of 1 nm for both excitation and emission; $\lambda_{ex}$=488 nm.

Spectroscopic properties of EGFP-based $Ca^{2+}$ binding proteins were investigated using purified proteins. FIGS. 13A and 13B show the visible absorbance and fluorescence emission spectra of EGFP, EGFP-D2 (SEQ ID No.: 64), and EGFP-G1 (SEQ ID No.: 4) at pH 7.4.

TABLE 5

Spectroscopic property of EGFP, EGFP-D2, and EGFP-G1 and their C2 and C3 mutations

|  | Extinction Coefficient ($\epsilon$), M−1cm−1 | | Quantum Yield |
|---|---|---|---|
|  | 398 nm | 488 nm | 488 nm |
| EGFP | 5126.6 | 55900 | 0 |
| EGFP-C2 | 7184.3 | 55506 | 0 |
| EGFP-C3 | 6672.1 | 55840 | 0 |
| EGFP-G1 | 9228.1 | 28463 | 0 |
| EGFP-G1-C2 | 14063 | 26999 | 0 |
| EGFP-G1-C3 | 9906.1 | 28401 | 0 |
| EGFP-D2 | 1291.5 | 9323.8 | 0 |
| EGFP-D2-C2 | 5490.0 | 52989 | 0 |
| EGFP-D2-C3 | 5404.6 | 56416 | 0 |

Table 5 summarizes the spectroscopic properties of EGFP, EGFP-D2, and EGFP-G1 and their C2 and C3 mutations. As shown in FIG. 13A, a major absorbance peak at 488 nm and a minor absorbance peak at 398 nm appeared in the visible spectra of EGFP, indicating that the anionic state of chromophore was the main form in EGFP. A fluorescence emission peak at 510 nm was observed in EGFP fluorescence spectrum (FIG. 13B). The similar spectroscopic properties including both extinction coefficients and quantum yield constant at 398 nm and 488 nm (Table 1) indicate that there is no effect of C2 and C3 mutations on the visible absorption spectra in EGFP-C2 and EGFP-C3. The formation of a $Ca^{2+}$-binding site by using three mutated ligands S2D, L194E and S86D and two natural ligands D82 and E5 of EGFP (EGFP-D2 (SEQ ID No.: 64)) resulted in a decrease of visible absorption at both 398 nm and 488 nm as observed in FIG. 13A. Comparing to EGFP, for example, the extinction coefficient at 488 nm of EGFP-D2 (SEQ ID No.: 64) was decreased from 55900 $M^{-1}cm^{-1}$ to 9324 $M^{-1}cm^{-1}$. Concurrently, the fluorescence emission peak at 510 nm was decreased in its fluorescence spectrum (FIG. 13B) although the quantum yield of EGFP-D2 (SEQ ID No.: 64) was almost same with that of EGFP. Strikingly, both C2 and C3 mutations in EGFP-D2 (SEQ ID No.: 64) reproduced the major absorbance peak at 488 nm and minor absorbance peak at 398 nm similar to that of EGFP (Table 5). Taken together, while the quantum yield is significantly increased for EGFP variants with both types of calcium binding sites, the relative distribution of ionic-neutral states of the chromophore was not altered by the addition of folding mutations.

Example 23

Computational Design: The design of calcium-binding sites used the GFPc3 structure, 1b9c, due to its 30,000-fold greater fluorescence than wild type GFP with expression at 37° C. The potential calcium binding sites were computationally constructed with the desired oxygen-calcium-oxygen angle, oxygen-calcium distance, ligand type, and number of ligands. One anchor Asp and four additional potential ligands from Asp, Asn, Glu, or the backbone were utilized. The calcium-oxygen length was in the range of 2.0 to 3.0 Å. The oxygen-calcium-oxygen angles ranged ±45° from the theoretical angles of the ideal pentagonal bipyramid geometry (Biochemistry 44: 8267-73; J. Am. Chem. Soc. 127: 2085-2093; J. Am. Chem. Soc. 125: 6165-6171).

Example 24

Cloning and purification of GFP variants: Site-directed mutagenesis was carried out by the classical polymerase chain reaction with pfu or turbo pfu (Invitrogen) and with EGFP DNA as the initial template and the forward primer sequence 5'-ACGGCGACGCGAACCTCGCCGACC-3' (SEQ ID No.: 106) and the reverse sequence is 5'-CCTCGTCGTTGTGGCGGATCTTG-3' (SEQ ID No.: 107). The linear DNA was ligated with T4 DNA ligase (Promega), and the circular DNA was amplified in E. coli (either DH5α or Top10) competent cells. The mutations to engineer 177c3 included the above mutations, with the addition of F99S, M153T, and V163A, known as cycle 3 (C3). The F99S forward and reverse primers 5'-CGCACCATCTCCTT-CAAGGACG-3' (SEQ ID No.: 108) and 5'-CTCCTGGACG-TAGCCTTCCC-3' (SEQ ID No.: 109), respectively. M153T and V163A were made, together with the forward primer 5'-GAACGGCATCAAGGCGAACTTCAA-3' (SEQ ID No.: 110) and the reverse primer 5'-TTCTGCTTGTCGGCCGT-GATATAGA-3' (SEQ ID No.: 111). The mutations were carried out utilizing turbo pfu (Stratagene), following the manufacturer's protocol with annealing temperatures of 61° C. for F99S and 63° C. for 153/163. The DNA was purified with a Qiagen Miniprep kit, and the circular variant DNA was verified by automated sequencing at the GSU core facility.

The vector pcDNA3.1+ (Invitrogen) was utilized during the mutagenesis and for the expression of the protein in mammalian cells in the cytosol. For expression of the protein in the ER, the pcDNA3.1+ vector was modified through PCR to contain the calreticulin signal peptide at the N-terminus of the protein and the KDEL retention sequence at the C-terminus. The N-terminal tag from calreticulin, MLLSVPLLLGLLG-LAAAD (SEQ ID No.: 112) directs the expression of the gene to commence in the ER. The C-terminal tag, KDEL, is a retention sequence that retains the expressed protein in the ER and does not allow it to be shuffled to the Golgi. The N-terminus tag was inserted in two rounds of PCR with four primers due to its length. The proteins were expressed fused to a 6× histidine tag with a pet28a vector (EMD Biosciences) in LB medium containing 30 μg/mL kanamycin. Protein expression was induced at an $OD_{600}$ of 0.6 with 0.2 mM IPTG, and growth was continued for 3-4 hr before harvesting by centrifugation at 9500 g for 20 min. After breaking the cells with sonication, the proteins were dissolved with 8 M urea. The denatured protein was refolded by 10× dilution into the buffer (10 mM Tris, 1 mM DTT, 1% glycerol, pH 7.4) and was centrifuged to remove cellular debris. The refolded protein was purified using Sephadex G-75 size exclusion FPLC (10 mM Tris, pH 7.3) to greater than 95% purity. The expression and purity of the protein were analyzed by SDS-PAGE. The protein concentration was estimated using a calculated extinction coefficient of 21,890 $M^{-1}cm^{-1}$ at 280 nm. The histidine tag used for purification did not have any effect on calcium and terbium binding.

Example 25

Terbium fluorescence: All buffers for the metal binding and conformational analysis studies in this work were pretreated with Chelex-100 Resin (Bio-Rad). The terbium binding of the proteins was measured with a PTI fluorimeter following the emission at 545 nm with an excitation at 280 nm. For terbium titration, the initial protein concentration was 3 μM in 20 mM PIPES, 10 mM KCl, 1 mM DTT, 1% glycerol, pH 6.8, for proteins GFP.Ca1-3 and 10 mM Tris, 1 mM DTT, 1% glycerol, pH 7.4 for GFP.Ca2". A 1.0 or 5.0 mM stock terbium containing the same concentration of protein was added directly into the protein samples. Blank samples consisted of the buffer with increasing terbium without protein. The data were baseline corrected, and the integrated area of the peak at 545 nm was fitted by assuming a 1:1 terbium:protein binding (J. Am. Chem. Soc. 125: 6165-6171). The data were also analyzed using Specfit/32 (Talanta, 33, 943). Each binding affinity is an average of 4 to 6 titrations. To investigate the metal selectivity, GFP.Ca1 and GFP.Ca2' (3 μM) with 20 μM terbium were incubated with 0.1 and 1 mM calcium, 10 mM magnesium, or 100 μM lanthanum in 10 mM Tris, 1 mM DTT, 1% glycerol, pH 7.4; and the terbium fluorescence of each sample was measured.

Example 26

Calcium binding dye competition: The protein (30 or 40 μM) and Rhodamine-5N (approximately 20 μM, Molecular Probes) (J. Biol. Chem. 264: 19449-19457) were incubated in 10 mM Tris, 1 mM DTT, 1% glycerol, pH 7.4. A 100 mM CaCl$_2$ stock containing the same concentrations of dye. Protein was gradually added into the mixture, and the fluorescence was measured with a 1 cm path length cell and an excitation of 552 nm. After the titration, the dye concentration was verified by absorbance at 552 nm with an extinction coefficient of 63,000 M$^{-1}$cm$^{-1}$. The data were analyzed by globally fitting the spectra from 560 to 650 nm using Specfit/32 with the metal-ligand-ligand model (Talanta, 33, 943).

Example 27

Mammalian cell transfection: Untransfected HeLa cells were maintained on 100 mm tissue culture dishes in filter-sterilized Dubelcco's Modified Eagle's Medium (DMEM, Sigma Chemical Co.) with 44 mM NaHCO$_3$, pH 7.2, and were supplemented with 10% v/v Fetal Calf Serum (FCS, Hyclone), 100 U/ml penicillin and 0.1 mg/ml streptomycin (Pen/Strep, Sigma) at 37° C. with 5% CO$_2$ in a humidified incubation chamber. The designed protein DNA was subcloned into pcDNA3.1+ vector (Invitrogen) for expression in mammalian cells through EcoRI and BamHI digestion, followed by ligation with T4 DNA Ligase. The DNA, confirmed by automated sequencing, was transfected into previously prepared 90% confluent HeLa (HEK293, Vero, or CHO) cells using Lipofectamine 2000 (Invitrogen) on 60 mm cell-culture-treated dishes. The DNA (3 µg) was mixed with Lipofectamine 2000 in a 1:3 ratio in Opti-MEMI serum-free medium (Invitrogen) and was allowed to equilibrate at room temperature for 20 min in the dark before being added to the cells in Opti-MEMI medium. The transfection was allowed to proceed for 4 hrs at 37° C. and 5% CO$_2$. The transfection medium was removed and was replaced with DMEM, 10% FCS, 1% Penicillin-Streptomycin Solution; and the cells were grown at 30° C. at 5% CO$_2$ for 72 hrs. Mock-transfected HeLa cells were treated in the same way without DNA addition for a background control.

Example 28

Microscopy Imaging: HeLa cells transfected with GFP.Ca1 were imaged 72 hrs following transfection. Coverslips with cells were transferred to a micro-incubation chamber (model MSC-TD, Harvard Apparatus, Holliston, Mass.). Briefly, imaging of GFP.Ca1 fluorescence was performed on a Nikon TE300 (Nikon Inc., Melville, N.Y.) inverted microscope equipped with a Nikon filter block optimized for GFP optics ($\lambda_{ex480}$, $\lambda_{em\ 510}$; Chroma Technology Corp, Rockingham, Vt.), a Metaltek filter wheel (Metaltek Instruments, Raleigh, N.C.) to regulate excitation light exposure times, a 75 watt xenon short arc lamp, a Hamamatsu CCD digital camera (Hamamatsu Corporation, Bridgewater, N.J.), and supported on a vibration isolation table. MetaFluor software (Universal Imaging Corp., v 3.5, Downington, Pa.) was utilized for image acquisition. Acquisition time was 50 ms with a gain of 1-3, depending upon the transfection efficiency.

The fluorescence intensity of the transiently transfected GFP.Ca1 or GFP.Ca1c3 was monitored for several minutes to obtain a baseline value before the addition of ionomycin to the bath buffer to a final concentration of 2 µM. The designed protein's fluorescence was imaged until the fluorescence intensity was stable (typically 2 min), and the intracellular calcium concentration was then manipulated by the subsequent addition of concentrated CaCl$_2$ to obtain the targeted extracellular calcium concentration. Multiple additions of CaCl$_2$ were typically spaced 1 min apart. Extracellular calcium concentrations were returned to basal levels by bath perfusion of HBSS$^{++}$ buffer. EGFP without a calcium binding site was utilized as a control.

To test the calcium response of the sensor expressed in the ER, 50-100 µM ATP and 100 µM histamine were added to the bathing medium to induce calcium release from the ER. Higher concentrations of ionomycin (2.5-5 µM) were utilized to permeabilize the ER membrane and to allow for calcium uptake with addition of calcium to the bathing medium (10-100 mM). Thapsigargin (1 µM) and calmidozolium (2 µM) were added to the bathing medium to empty slowly the ER of calcium.

Example 29

Application of engineered variants of EGFP as analyte sensors with high affinity and selectivity for Pb$^{2+}$ and Gd$^{3+}$ ions: Toxic metals (e.g. Gd$^{3+}$, La$^{3+}$, Tb$^{3+}$, Pb$^{2+}$, Sm$^{3+}$, Sr$^{2+}$, Hg$^{2+}$ and Cd$^{2+}$) can interact adversely with biological systems. While the toxicological effects of metals have been extensively studied, the mechanisms of toxicity relative to interaction with proteins are not fully-understood. Lead (Pb$^{2+}$) is a persistent, anthropogenic toxic metal responsible for a variety of health problems related to neurological disorders, anemia, kidney damage, hypertension and male fertility decrease (Reprod. Toxicol. (2005). 20: 221-228; (2000) Am. J. Ind. Med. 38: 310-315; (2005) Neurotoxicol. Teratol. 27: 245-257; (1997) Annu. Rev. Nutr. 17: 37-50; (2001) Int. J. Toxicol. 20: 113-120; (2000) Int. J. Dev. Neurosci. 18: 791-795; (1987) Ann. N.Y. Acad. Sci. 514: 191-203). Lanthanides are known to block calcium channels in human and animal cells, and Pb$^{2+}$, Cd$^{2+}$, and Hg$^{2+}$ will specifically target voltage-gated calcium channels ((2003) J. Bioenerg. Biomembr. 2003. 35: 507-532). There is, therefore, a strong need to develop inexpensive, benign materials for the detection and neutralization of toxic metals in natural systems, and for biological remediation. The present disclosure, therefore, encompasses the application of the engineered variants of EGFP of the disclosure as analyte sensors with high affinity and selectivity for such as Pb$^{2+}$ and Gd$^{3+}$ ions. The autofluorescence of GFP and its variants make it a versatile tag for metal-binding studies where the close proximity of a metal cation to a chromophore in the protein results in a detectable quenching of the fluorescent peaks ((2000) Biochem. Biophys. Res. Commun. 268: 462-465.)

Example 30

Development of EGFP-Based Pb$^{2+}$ and Ln$^{3+}$ Sensors: EGFP protein variants designed for metal-binding and protease studies were developed via sub-cloning using PCR. Proteins were prepared for purification on a Ni$^{2+}$-chelating sepharose column by the addition of a 6xHis-tag. These variants provide the scaffold for mutagenesis studies to provide protein variants with high metal selectivity, and for use as a protease sensor. EMD Omnipur tris(hydroxymethyl)aminoethane (EMD Chemicals, Inc., Gibbstown, N.J.), or TRIS, was the buffering agent for the expressed proteins.

Transformation: Recombinant pET28a vector comprising regions encoding EGFP variants were transformed into *E. coli* cell strain DE3 by heat shock for 90 s at 42° C. The sample was placed on ice for 2 minutes. LB Medium (50 µL) was added and the sample incubated for 30 mins at 37° C. before plating on selective media.

Expression: Kanamycin was used at 0.03 mg/mL. 1.0 L LB media cultures were incubated to an A$_{600}$ of 0.6±0.1 isopropyl-beta-D-thiogalactopyranoside (IPTG) was added to a concentration of 0.2 mM, and the temperature reduced to 20-25° C. 1.0 mL samples were removed every hour for three hrs, followed by a final sample on the following day, to evaluate protein expression using SDS-PAGE gels. Cells were harvested and stored at 4° C.

Purification: A cell pellet was suspended in about 20 mL of extraction buffer (20 mM TRIS, 100 mM NaCl, 0.1% Triton x-100) and placed on ice. The sample was sonicated 6×30 s periods, with about 5 min intervals between sonications and centrifuged for 20 min at about $5 \times 10^4$ g. The supernatant was filtered with 0.45 μm pore size filter (Whatman, Florham Park, N.J.) and diluted with the appropriate binding buffer prior to injection into an FPLC system.

Purification of EGFP variants was completed using an Aktaprime FPLC (Amersham Biosciences, Piscataway, N.J.) equipped with a UV detector and a 280 nm optical filter. For most purifications, a Hitrap 5 mL HP Chelating sepharose column was used. The binding Buffer A was 1 M $K_2HPO_4$, 1 M $KH_2PO_4$, 250 mM NaCl, pH 7.4 and elution Buffer B was of Buffer A and 0.5 M imidazole.

The column was first rinsed with 100 mM EDTA, 1 M NaCl, pH 8.0 to remove metals, and rinsed with distilled water. The column was then washed with 0.1 M $NiSO_4$ to bind $Ni^{2+}$ onto the column, which was rinsed again with distilled water to remove unbound $NiSO_4$.

For additional protein purification, a Hitrap Q Ion Exchange column (GE Healthcare, Piscataway, N.J.) was used. The binding Buffer A was 20 mM TRIS, pH 8.0 and the elution Buffer B was of 20 mM TRIS, 1 M NaCl, and pH 8.0.

Protein injections onto the column were limited to 5-8 mL and eluted bound protein was collected in 8 mL fractions that were then further purified by dialysis in 2.0 L of 10 mM TRIS, 1 mM Dithiothreitol, pH 7.4. Protein fractions were dialysed in dialysis bags with a molecular weigh cutoff value of 3,500 Da for 72 hrs to remove imidazole and other impurities. Purity was evaluated using SDS-PAGE gels.

Example 31

Spectroscopic Analysis: Fluorometric spectral analyses of EGFP variants were conducted with excitation slit widths set at 1 nm, to reduce photobleaching of the proteins, and the emission slit widths were set at 2 nm. Excitation wavelengths of 398 nm and 490 nm were used. Data from the fluorometers were collected at 1 nm intervals.

The selectivity of the EGFP-based sensors for $Pb^{2+}$ and $Gd^{3+}$ was examined by monitoring the change of the fluorescence ratio $F_{(398nm)}/F_{(490nm)}$ obtained with 1.0 mM $Ca^{2+}$ in the presence of the test metal ions.

The ratiometric change from the metal-free protein to the metal-protein complex was calculated by integrating the peak areas for each of the emissions scans (398 nm and 488 nm) from 500-600 nm as a sum of the intensities recorded at each 1 nm interval, and then evaluating the ratio of (F398/F488), as seen in Eq. 13.

$$\text{Ratiometric change} = (F398/F488) \quad \text{(Eq. 13)}$$

$$= \left( \frac{\sum_{500}^{600} \text{Counts398}}{\sum_{500}^{600} \text{Counts488}} \right)$$

The ratio eliminates possible errors associated of absolute intensity values due to instrumental variations.

The fluorescent ratiometric change (F398/F490) was evaluated for 1.0 μM of the EGFP variants to evaluate selectivity between $Ca^{2+}$ and either $Pb^{2+}$ or $Gd^{3+}$ in 10 mM TRIS-Cl, pH 7.4. First, 1 mM $Ca^{2+}$ was added to the protein, followed by aliquots of the competing metal.

The affinity of a competing ion was assumed to be directly proportional to the change in the ratio (F398/F490), as calculated using Equation 11. To calculate the $K_{eq}$ for the competitive titration, the value for the fraction of the competing ion (F) was normalized across the range of concentrations evaluated. This F Normalized value ($F_{Norm}$) was calculated with Eq. 14.

$$F_{Norm} = (F_{Ca\ initial} - F_{M+})/(F_{Ca\ initial} - F_{M+final}) \quad \text{(Eq. 14)}$$

In Equation 3, $F_{Ca\ initial}$ is the initial ratio (F398/F490) following addition of $Ca^{2+}$, $F_{M+}$ is the ratio at each point of addition of a competing metal ion, and $F_{M+final}$ is the ratio at the final concentration of metal. K for the competitive titration was the calculated in using the curve-fitting equation:

$$F_{Norm} = ((([P]_t + [M]_t + K) - ((([P]_t + [M]_t + K)^2 - 4[P]_t[M]_t)^{1/2})/2[P]_t) + (C^*[M]_t) \quad \text{(Eq. 15)}$$

where the final term, $(C^*[M]_t)$, accounts for non-specific binding. The $K_d$ for $Pb^{2+}$ or $Gd^{3+}$ was calculated using Eq. 4, with K calculated from Eq. 15, and the $K_d$ for $Ca^{2+}$ which was previously determined for the EGFP-C2 variant to be 440 μM.

$$K_{dM+} = K/(1 + ([Ca^{2+}]/K_{dCa})) \quad \text{(Eq. 16)}$$

The absorbance scan encompassed the range of 600-220 nm.

Example 32

Figure 18:
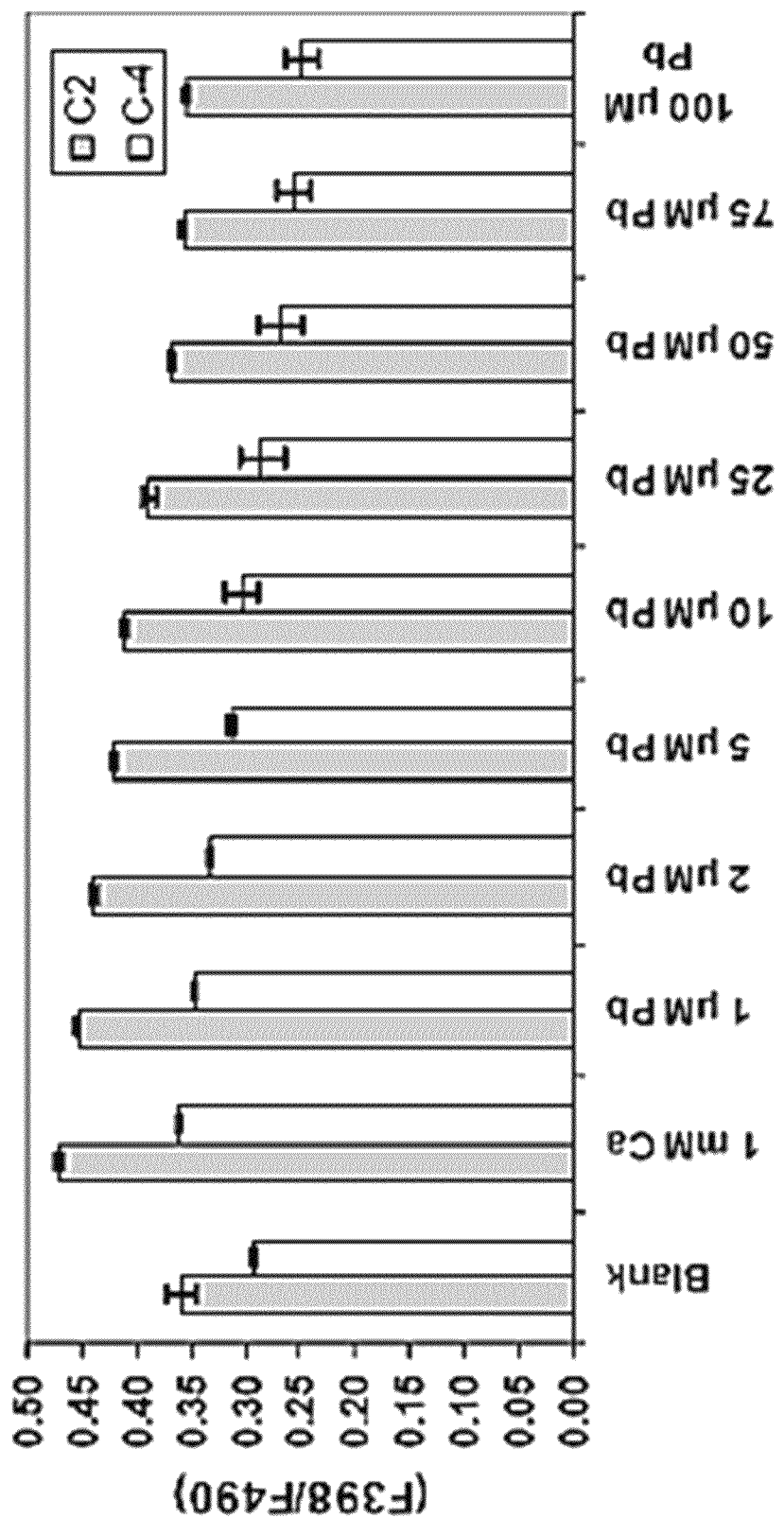
FIG. 18 illustrates competitive titration of $Pb^{2+}$ and $Ca^{2+}$-loaded EGFP variants C2 and C4.

It was determined from competitive titrations that $Gd^{3+}$ and $Pb^{2+}$ displace $Ca^{2+}$ in the binding sites of the engineered EGFP variants of the disclosure. FIG. 18 shows the normalized ratiometric changes associated with displacement of $Ca^{2+}$ by $Pb^{2+}$. FIGS. 19A to D show changes in fluorescence intensity resulting from displacement of $Ca^{2+}$ by $Pb^{2+}$, and a 2-3 nm red shift in the spectra near 10 μM $Pb^{2+}$. This red shift is believed to be the result of conformational changes relative to the chromophore, unrelated to displacement of $Ca^{2+}$ which had already occurred. These data were then used to calculate binding affinities for both $Gd^{3+}$ and $Pb^{2+}$.

Figure 19D:
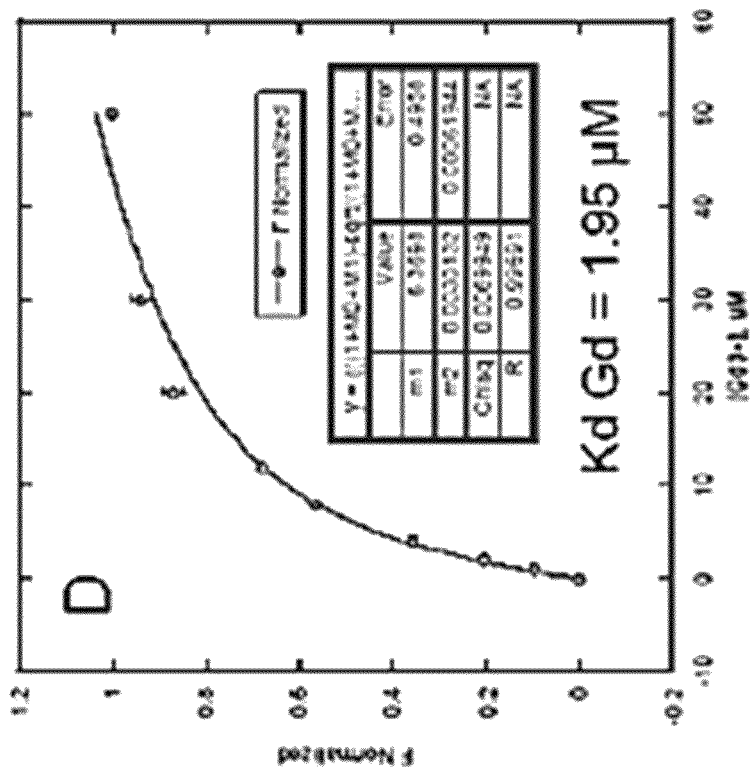
FIG. 19D illustrates curve-fitting of C2-Gd complex to quantify Kd. The Kd for $Gd^{3+}$ was 2.0 μM.
Figure 19C:
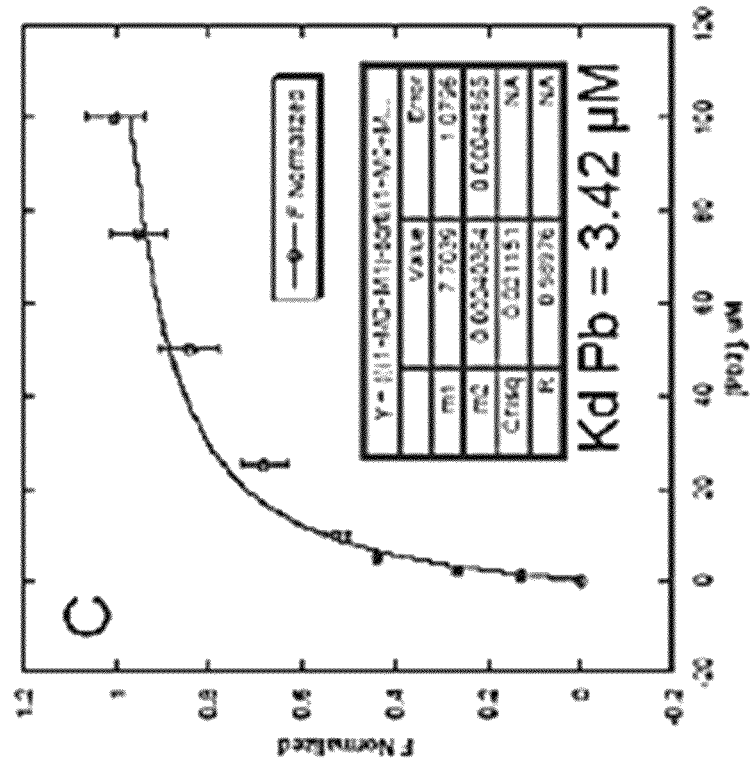
FIG. 19C illustrates curve fitting of EGFP/$Pb^{2+}$ complex to quantify Kd. The Kd was 3.5 μM.

For the EGFP-C2 variant analyzed in this work, the binding affinities for $Pb^{2+}$ and $Gd^{3+}$ were both found to be approximately 200 times higher than for $Ca^{2+}$ (FIGS. 19B and 19D). For the other EGFP variant (SEQ ID Nos.: 18 and 19), the binding affinity for $Pb^{2+}$ was found to be over 100 times higher than $Ca^{2+}$. (FIG. 19C). These higher affinities, coupled with the conformational changes associated with the binding of these metals, suggests an important relationship to toxicity. It also provides for a sensor capable of high-affinity binding for $Pb^{2+}$ and $Gd^{3+}$.

Example 33

CatchER biosensor family design strategy: Based on key determinants for fine-tuning $Ca^{2+}$ binding affinity and $Ca^{2+}$-induced conformational changes and the established chromophore properties of fluorescent proteins, $Ca^{2+}$ sensors with fast fluorescence response were designed by coupling $Ca^{2+}$ binding sites directly to the chromophore rather than relying on stretched protein-protein interaction to modulate chromophore conformation.

The computationally-assisted design was based on the following criteria and considerations: (i) it requires four or five oxygen ligand atoms from protein residues (typically, carboxyl groups of D, E, N, Q) situated in the spherical geometry characteristic of natural $Ca^{2+}$ binding proteins; (ii) appropriate choice of residue charge and type can be chosen to fine-tune $Ca^{2+}$ binding affinity and metal selectivity; (iii) diffusion-limited access of $Ca^{2+}$ to the site requires good solvent accessibility; (iv) propagating $Ca^{2+}$-induced, local conformational and electrostatic changes to the chromophore can be achieved by properly locating of the charged ligand residues with respect to it; (v) these changes must occur rapidly than the rate of conversion from a neutral to anionic state ascribed to these chromophores; and (v), the created binding site must not interfere with the chromophore's synthesis and formation. The EGFP variant with the M153T/V163A mutation (EGFP Cycle 2) was chosen as the scaffold protein because of its high fluorescence intensity, folding efficiency, and thermostability.

Example 34

Plasmid construction, protein expression, and purification: Bacterial expression plasmids for EGFP variants D8 to D12 were constructed by site-directed mutagenesis on cycle 2 EGFP (F64L/S65T/M153T/T163A) inserted in the pET28a vector (EMD Biosciences, San Diego, Calif.) vector between the BamHI and EcoRI restriction enzyme cleavage sites. The DNA sequence of the designed EGFP variants between these two restriction sites were cleaved and inserted into pcDNA3.1+ vector (Invitrogen, Carlsbad, Calif.). Calreticulin ER targeting sequence (CRsig) MLLSVPLLLGLLG-LAAAD (SEQ ID No.: 112) and ER retention sequence KDEL were added to the N- and C-termini, respectively, to construct the mammalian cell expression plasmids. CatchER (D11) and its variants (D8-D10 and D12) were bacterially expressed in *Escherichia coli* BL21(DE3) and purified using established methods (Heim & Tsien (1996) Curr. Biol. 6:178-182; Zou et al., (2007) Biochemistry 46: 12275-12288).

Example 35

In situ measurement of CatchER's $Ca^{2+}$ dissociation constant: CatchER's $Ca^{2+}$ dissociation constant ($K_d$) was measured in BHK and C2C12 cells. ER $Ca^{2+}$ in BHK cells was depleted by applying 100 μM histamine and 5 μM thapsigargin in Ringer 0 $Ca^{2+}$ buffer. Cells were permeabilized in 100 μM digitonin in intracellular-like solution containing 140 mM KCl, 10 mM NaCl, 1 mM $MgCl_2$, 20 mM Hepes, pH 7.25. Calibration buffers were prepared by adding $Ca^{2+}$ to the intracellular-like solution, reaching final concentrations of 0.05, 0.1, 0.5, 1, 5, and 10 mM, and 200 μM EGTA buffer. $F_{min}$ and $F_{max}$ were determined in 200 μM EGTA and 10 mM $Ca^{2+}$ with no $Ca^{2+}$ ionophore, respectively.

Similar in situ $K_d$ calibration was conducted in C2C12 myoblasts. ER $Ca^{2+}$ of permeabilized cells was depleted in intracellular buffer containing 10 μM IP3 and 2 μM thapsigargin. For calibration, 1, 3, 10, and 20 mM $Ca^{2+}$ buffers were applied in the presence of 5 μM ionomycin. $F_{min}$ and $F_{max}$ were determined in 3 mM EGTA and 20 mM $Ca^{2+}$, respectively.

The fluorescence was normalized according to the equation:

$$f = \frac{F - F_{min}}{F_{max} - F_{min}}$$

and $K_d$ determined by the Hill-equation:

$$f = \frac{[Ca^{2+}]^n}{K_d + [Ca^{2+}]^n}$$

The Kd was 1.07±0.26 mM (0.90±0.19 Hill coefficient) in BHK cells and 1.09±0.20 mM (0.94±0.17 Hill coefficient) in C2C12 cells.

Example 36

Kinetic analysis of $Ca^{2+}$ binding to CatchER by stopped-flow: The fluorescence kinetics of bacterially expressed CatchER was investigated using an SF-61 stopped-flow spectrofluorometer (Hi-Tech Scientific, Salisbury, UK; 10-mm path length, 2.2-ms deadtime at room temperature) at 22° C. Fluorescence intensity changes were recorded with a 455 nm long-pass filter with excitation at 395 nm. Equal volumes of $Ca^{2+}$-free protein in 10 mM Tris-Cl at pH 7.4 and $Ca^{2+}$ in the same buffer were mixed in the stopped-flow spectrofluorometer, yielding final concentrations of 10 μM CatchER and 50, 100, 200, 300, 500, and 1000 μM $Ca^{2+}$. The stopped-flow traces were fit to Eq. (1), which describes F, the fluorescence intensity at any given time; $F_\infty$, the fluorescence at infinite time; and ΔF, the amplitude of the fluorescence change.

$$F = F_\infty - \Delta F \exp(-k_{obs} \cdot t) \quad 17)$$

$$F = F_\infty + \Delta F \exp(-k_{obs} \cdot t) \quad 18)$$

$$k_{obs} \cdot \tau = \ln 2 \quad 19)$$

Example 37 sApparent $pK_a$ determination by pH profile: The apparent $pK_a$ of $Ca^{2+}$-free or $Ca^{2+}$-loaded CatchER was determined with bacterially expressed protein by fitting the fluorescence intensity change at 510 nm (λex=488/395 nm). 5 μM protein was dissolved in different buffers with pH ranging from 4.5 to 9.5 in the presence of either 10 μM EGTA (apo) or 4 mM $Ca^{2+}$ (holo), and the actual pH was determined after measuring fluorescence. The proposed interaction scheme is

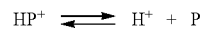

$$pH = pKa + \log \frac{[P]}{[HP^+]} \quad 20)$$

$$f = \frac{F - F_{min}}{F_{max} - F_{min}} \quad 21)$$

$$F_{min} = [P]_T c_1 \quad 22)$$

$$F_{max} = [P]_T c_2 \quad 23)$$

$$F = ([P]_T - [P])c_1 + [P]c_2 \quad 24)$$

$$f = \frac{[P]_T c_1 - [P]c_1 + [P]c_2 - [P]_T c_1}{[P]_T c_2 - [P]_T c_1} = \frac{[P]}{[P]_T} \quad 25)$$

$$\frac{[P]}{[HP^+]} = \frac{1}{1/f - 1} \quad 26)$$

-continued $$f = \frac{1}{1 + \exp\left(\frac{pKa - pH}{c}\right)} \quad 27)$$

H+ is the proton; P is the CatchER protein; f, the normalized ΔF change; [P]$_T$, the total protein concentration; $c_1$ or $c_2$ is the extinction coefficient of HP+ or P fluorescence, respectively; F is the real-time fluorescence; F$_{min}$, the fluorescence at the lowest pH; F$_{max}$, the fluorescence at the highest pH; c is a constant for adjustment. The value theoretically equals Ige. The apparent pK$_a$, fitted by a single exponential (Eq. 11), were 7.59±0.03 and 6.91±0.03 for apo and holo forms excited at 488 nm and 7.14±0.02 and 6.95±0.06 at 395 nm, respectively.

Example 38

CatchER:Ca$^{2+}$ stoichiometry studied by the Job Plot: The stoichiometry of the CatchER and Ca$^{2+}$ interaction was determined at the maximal relative amount of Ca$^{2+}$-bound CatchER in the Job Plot (15). Ca$^{2+}$-free and bound [CatchER] were converted to fluorescence intensity following the equation: F=S$_f$·C$_f$+S$_b$·C$_b$, where F is the apparent fluorescence intensity; S$_f$ and S$_b$ are the coefficients of Ca$^{2+}$ free and bound CatchER, respectively; and C$_f$ and C$_b$ are the concentration of Ca$^{2+}$ free and bound CatchER, respectively. The relative amount of Ca$^{2+}$ bound CatchER (C$_b$·V, V=1) was calculated using the Eq. (12). Fluorescence emission ($\lambda_{ex}$=488/395 nm) and absorbance spectra were recorded with [CatchER]: 28.7, 23.3, 19.4, 15.1, 11.6 μM in response to [Ca$^{2+}$]: 11.3, 16.7, 20.6, 24.9, 28.4 μM, respectively.

$$\frac{F_{Ca^{2+}-bound}}{F_{Ca^{2+}-free}} = \frac{S_f \cdot C_f + S_b \cdot C_b}{S_f \cdot C_T} \quad 28)$$

$$= \frac{S_f(C_T - C_b) + S_b \cdot C_b}{S_f \cdot C_T}$$

$$= 1 + \frac{C_b \cdot (S_b - S_f)}{S_f \cdot C_T}$$

$$a = \frac{S_b - S_f}{S_f} \quad 29)$$

$$\frac{C_b}{C_T} \cdot a = \frac{F_{Ca^{2+}-bound}}{F_{Ca^{2+}-free}} - 1 \quad 30)$$

$$C_b \cdot V = \left(\frac{F_{Ca^{2+}-bound}}{F_{Ca^{2+}-free}} - 1\right) \cdot \frac{C_T}{a} \quad 31)$$

Example 39

NMR Spectroscopy: All NMR experiments were performed at 37° C. using a Varian 800 or 600 MHz spectrometer. Typically, NMR samples contained 0.3 mM $^{15}$N- or $^{13}$C, $^{15}$N-labeled protein in 10 mM Tris, 10 mM KCl, 10% D$_2$O, pH 7.4. For backbone assignment of $^1$H, $^{13}$C, and $^{15}$N resonances, a HNCA was collected on a Varian (nova 800 MHz spectrometer, and a CBCA(CO)NH was collected on a Varian (nova 600 MHz spectrometer, both equipped with a cryogenic probe. For Ca$^{2+}$ titration, {$^1$H, $^{15}$N} HSQC spectra were collected, and chemical shift perturbations calculated using the equation $\Delta\delta_{av} = \{0.5[\Delta\delta(^1H^N)^2 + (0.2\Delta\delta(^{15}N))^2]\}^{1/2}$, where Δδ is the change in chemical shift between the apo and Ca$^{2+}$-loaded form. Rotational correlation time ($\tau_c$) was measured using a shared, constant-time, cross-correlated relaxation (SCT-CCR) pulse sequence. In this measurement, a series of highly sensitive HSQC spectra were collected at relaxational acquisition times from 0 to about 100 ms. Residue-specific $\tau_c$ values were then extracted from the exponential decay rates. T1 and T2 were collected on a Varian (nova 600 MHz spectrometer. Integrations of peak collected at 0, 30, 60, 100, 240, 480, 720, 1000, and 1500 ms (T1) and 10, 30, 50, 70, 90, 110, 130, and 150 ms (T2) were fitted with I=I$_0$exp(-t/T$_{1/2}$), where I$_0$ is the intensity at zero decay, and t, the relaxation decay. $\tau_c$ values were calculated following the equation below:

$$\tau_c = (2\omega_N)^{-1} \cdot \sqrt{(6T_1/T_2 - 7)} \quad 32)$$

$$\omega_N = 2\pi \cdot f_N \quad 33)$$

Example 40

Structure Analysis of Catcher and its Variants by NMR and Verified by X-Ray

Figure 32:
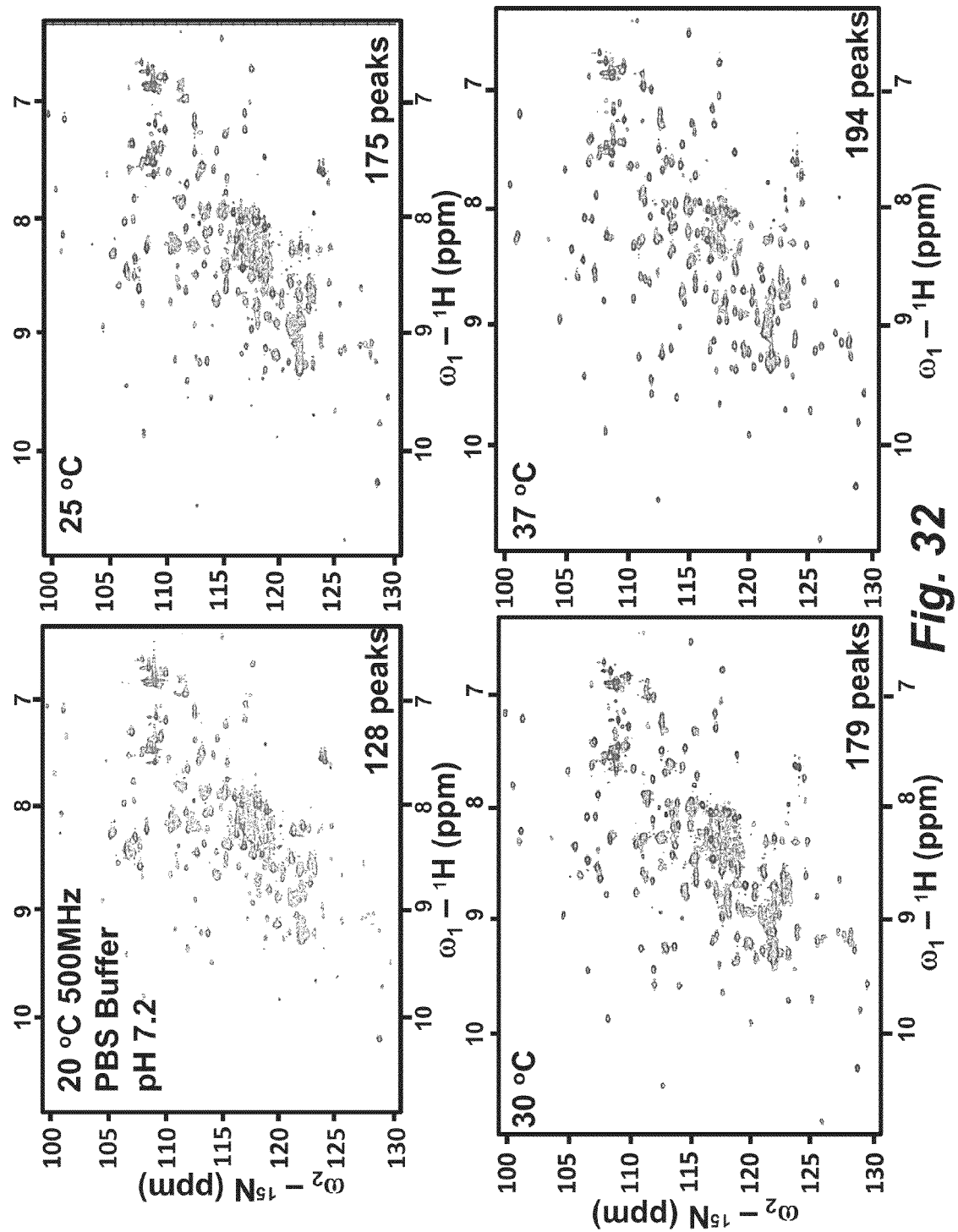
FIG. 32 shows the temperature dependent NMR HSQC spectra changes of CatchER.

The reality of calcium binding to the sensor can be further proved by calcium titration by NMR after the construction of the relationship between fluorescence intensity and calcium concentration. The condition of sample preparation is very important to affect the quality of the NMR spectra as the protein is the beta-sheet protein which has the tendency to be aggregation. One of the factors is the temperature that will influence the desperation of the peaks, so we test the D11 spectra quality in different temperatures in 500 MHz NMR. FIG. 32 shows the temperature dependent NMR HSQC spectra changes of CatchER.

The peak number increases from 128 to 194 along with the temperature raise from 20° C. to 37° C. As the total amino acid number of EGFP is 238, the optimal temperature for the experiment operation is above 37° C.

Figure 33:
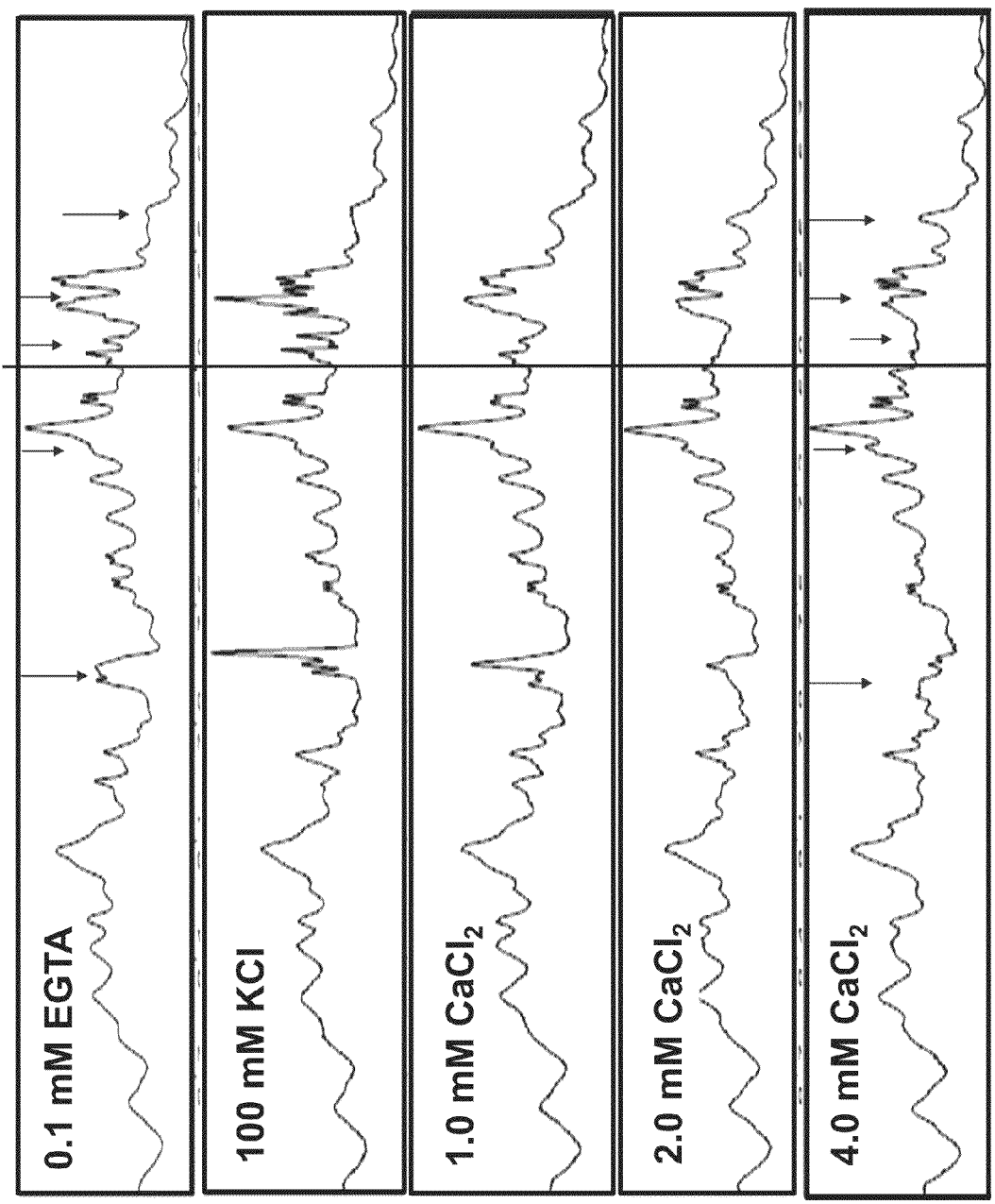
FIG. 33 shows a 1D NMR spectra of chemical shift changes of CatchER triggered by $Ca^{2+}$.

Prior to the gNhsqc calcium titration, 1D NMR calcium titration was operated to roughly detect chemical shifts and besides the sidechains dispersed around 0 to 6 ppm, the major chemical shifts of the NH group were approximate 6.6 to 7.8 ppm which was later proved to be from sidechain NH. The region of 8 to 11 ppm did not exhibit obvious shift due to the huge number of peaks overlap together what was insensitive to be distinguished.

gNhsqc is conducted to verify the chemical shift of each residues as 1D experiment is not effective enough to explore such a huge protein. The protein with the concentration of 0.3 mM is dissolved in 10 mM pH 7.4 Tris buffer and 10% of D$_2$O for the final concentration. The operation temperature is 40° C. for 600 MHz NMR. FIG. 33 shows a 1D NMR spectra of chemical shift changes of CatchER triggered by Ca$^{2+}$.

Salt effect should firstly be examined to verify whether D11 can nonspecifically bind to monovalent cations. 0.1 mM EGTA was added into the sample as the starting points and then titrated with 10 mM KCl to monitor the chemical shifts. After these two spectra overlapped, they perfectly matched. It hinted that high concentration salt could not cause conformation change of the protein so that there is no nonspecific binding.

Figure 34:
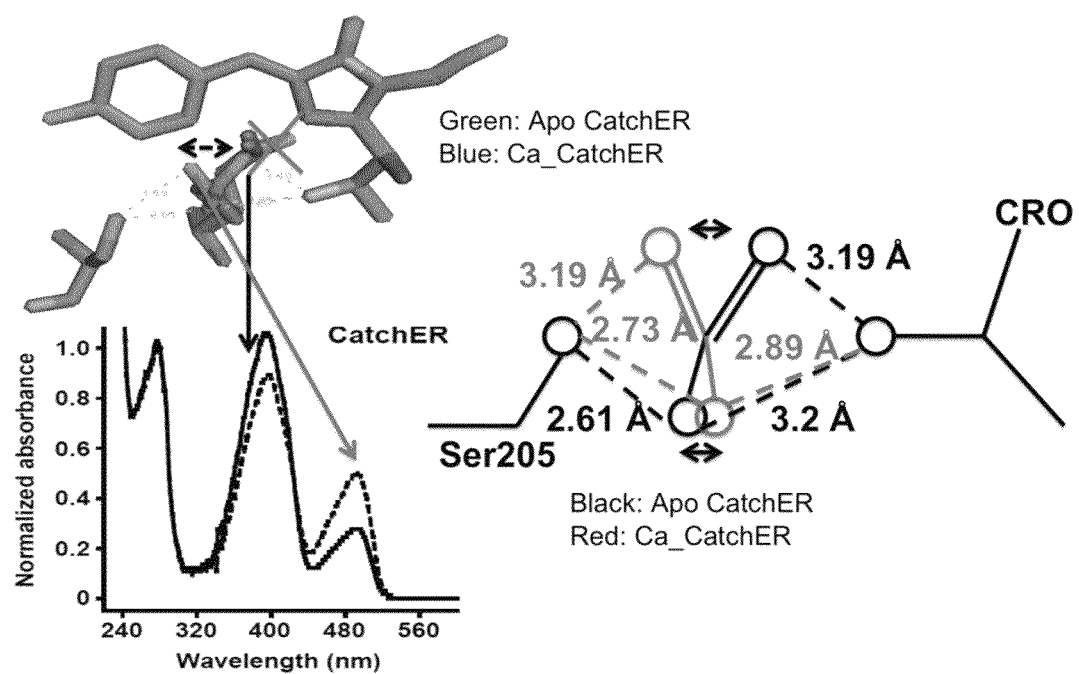
FIG. 34 illustrates X-ray crystal structures of chromophore conformation change of Apo_CatchER and $Ca^{2+}$_loaded CatchER, and correlated absorption spectra. (red is light grey, blue is dark grey, green is medium grey, cyan is light grey)
Figure 35:
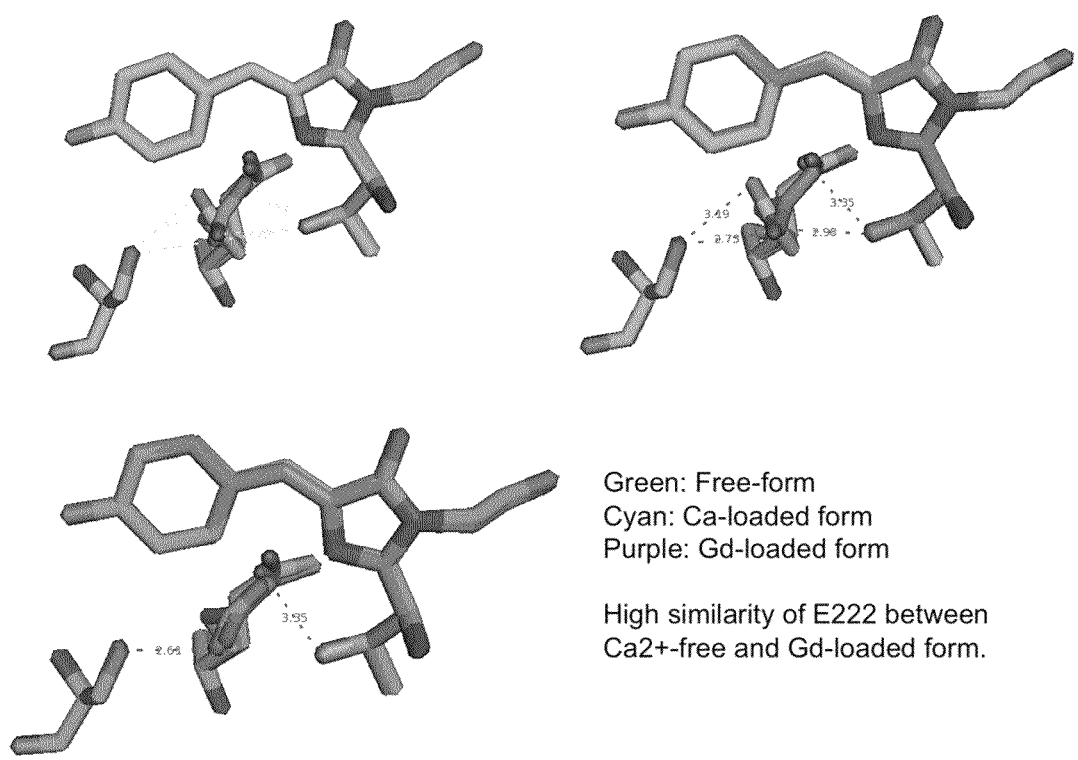
FIG. 35 illustrates X-ray crystal structures of chromophore conformation change of Apo_CatchER, $Ca^{2+}$_loaded CatchER, and $Gd^{3+}$_loaded CatchER. (cyan is light grey, purple is dark grey, green is medium grey)

X-ray crystal structure of Ca2+_free_CatchER, Ca2+_loaded CatchER Ca2+-free CatchER exhibited a major absorption peak at 395 nm and a minor peak at 490 nm, which is similar to the wtGFP, with a ratio of 395 nm to 490 nm 3.0 measured in vitro (Tang, et. al.). From the crystal structures of Ca2+ free and loaded form CatchER (FIG. 34), the sidechain of 222 rotated to change the distance of hydrogen bonds between carboxyl group of sidechain Glu222 and Ser205 and hydroxyl group of chromophore. The proposed hydrogen networks surrounding the chromophore are based on the previous reported crystal structure of wtGFP (pdb code: 1EMB) and EGFP (pdb code: 1EMA). The previous reported wtGFP from A jellyfish has two absorption peaks at 390 nm (major) and 490 nm (minor), suggesting a mixture of two forms of chromophore co-existed in one fluorescent protein (Heim, 1996). Though from the DNA sequence alignment, the site directed mutagenesis S65T is the cause of the major difference, however, the chromophore of wtGFP and EGFP can be overlapped well from the crystal structure, but the sidechain surrounding the chromophore exhibited different conformation, especially for Thr203 and Glu222 (Baird, 1997). In wtGFP, the mainchain of Thr203 distantly interacts with the chromophore through a water molecule (Remington, 1996 and Tsien, 1998), while for EGFP, the polar sidechain hydroxyl oxygen interact oxygen atom of chromophore directly, forming a short hydrogen bond 2.5 A, and stabilize the chromophore at anionic form, causing a major absorption peak at 490 nm. This stabilization is further enhanced by the special orientation of sidechain carboxyl group of E222, the only negative charged residue protrude toward the chromophore, forming a restricted hydrogen network among E222, V61 and T65 conjugated within the chromophore. However, the oxygen of Tyr66 of wtGFP only directly interacts with H2O without forming hydrogen bonds with polar residues, maintained neutral form, contributing to the major absorption peak at 395 nm. The two oxygen atoms of the carboxyl group of E222 are equally partially charged forming hydrogen bonds with Ser205 and chromophore. A hydrogen bridge between the hydroxyl group of T65 and Y66 is formed via E222, S205 and a water molecule, ensuring an efficient electron transfer between polar residues within the chromophore. An interesting observation of carboxyl group of E222 rotating between Ca2+ free and loaded form CatchER from the crystal structure, altering the distance of the hydrogen bonds between the carboxyl group of E222 to S205 and chromophore. Up to now, the rotation of Glu222 triggered by analyte binding has not been reported, especially correlated with the optical properties change. It is possible that the E222 sidechain rotation in response to Ca2+ may contribute to the fast kinetics of CatchER as a single residue rotation is faster than long-range protein-protein interaction in FRET pair based sensor. However, this sidechain rotation of Glu222 was not observed in comparison of Gd3+_free and Gd3+_soaking CatchER structure (FIG. 35, it is plausible that the residues buried inside the beta-barrel structure of GFP did not exhibit further conformational change after crystallization, even during the metal soaking, though fluorescent intensity of CatchER was dramatically enhanced after adding Gd3+ during in vitro titration. The other key residue Thr203 of CatchER maintained one hydrogen bond between the main chain oxygen and water close to chromophore in all of metal-free, Ca2+_loaded and Gd3+_loaded form CatchER, similar to the wtGFP, suggesting that the fluorescent intensity of Ca2+_loaded CatchER only recover 50% of EGFP is possibly due to the fixe hydrogen bond network close to the phenol group of Tyr66 of chromophore maintained similar to wtGFP.
Sequence Listings:

```
<SEQ ID No.: 1; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsnGlyIleLys
ValAsnPheLysIleArgHisAsnIleGluAspLysAspGlyAsnGlyTyrIleSerAlaAlaGluAlaGlySerValGlnLeu
AlaAspHisTyrGlnGlnAsnThrProIleGlyAspGlyProValLeuLeuProAspAsnHisTyrLeuSerThrGlnSer
AlaLeuSerLysAspProAsnGluLysArgAspHisIleValLeuLeuGluPheValThrAlaAlaGlyIleThrLeuGly
MetAspGluLeuTyrLys <SEQ ID No.: 2; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsnGlyIleLys
ValAsnPheLysIleArgHisAsnIleGluGluGluIleArgGluAlaPheArgValPheAspLysAspGlyAsnGly
TyrIleSerAlaAlaGluAlaGlyAspGlySerValGlnLeuAlaAspHisTyrGlnGlnAsnThrProIleGlyAspGlyProValLeu
LeuProAspAsnHisTyrLeuSerThrGlnSerAlaLeuSerLysAspProAsnGluLysArgAspHisIleValLeuLeu
GluPheValThrAlaAlaGlyIleThrLeuGlyMetAspGluLeuTyrLys <SEQ ID No.: 3; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsnGlyIleLys
ValAsnPheLysIleArgHisAsnIleGluAspLysAspGlyAsnGlyTyrIleSerAlaAlaGluLeuArgHisValMetThr
AsnLeuAspGlySerValGlnLeuAlaAspHisTyrGlnGlnAsnThrProIleGlyAspGlyProValLeuLeuProAsp
AsnHisTyrLeuSerThrGlnSerAlaLeuSerLysAspProAsnGluLysArgAspHisIleValLeuLeuGluPheVal
ThrAlaAlaGlyIleThrLeuGlyMetAspGluLeuTyrLys <SEQ ID No.: 4; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsnGlyIleLys
```

-continued

ValAsnPheLysIleArgHisAsnIleGluGluGluIleArgGluAlaPheArgValPheAspLysAspGlyAsnGly
TyrIleSerAlaAlaGluLeuArgHisValMetThrAsnLeuAspGlySerValGlnLeuAlaAspHisTyrGlnGlnAsnThr
ProIleGlyAspGlyProValLeuLeuProAspAsnHisTyrLeuSerThrGlnSerAlaLeuSerLysAspProAsnGlu
LysArgAspHisIleValLeuLeuGluPheValThrAlaAlaGlyIleThrLeuGlyMetAspGluLeuTyrLys

<SEQ ID No.: 5; PRT3; Artificial sequence>
MetLeuLeuSerValProLeuLeuLeuGlyLeuLeuGlyLeuAlaAlaAlaAspGlySerGlyProSerArgMetValSer
LysGlyGluGluLeuPheThrGlyValValProIleLeuValGluLeuAspGlyAspLeuAsnGlyHisLysPheSerVal
SerGlyGluGlyGluGlyAspAlaThrTyrGlyLysLeuThrLeuLysPheIleCysThrThrGlyLysLeuProValProTrp
ProThrLeuValThrThrLeuThrTyrGlyValGlnCysPheSerArgTyrProAspHisMetLysGlnHisAspPhePhe
LysSerAlaMetProGluGlyTyrValGlnGluArgThrIlePhePheLysAspAspGlyAsnTyrLysThrArgAlaGlu
ValLysPheGluGlyAspThrLeuValAsnArgIleGluLeuLysGlyIleAspPheLysGluAspGlyAsnIleLeuGly
HisLysLeuGluTyrAsnTyrAsnSerHisAsnValTyrIleMetAlaAspLysGlnLysAsnGlyIleLysValAsnPheLys
IleArgHisAsnIleGluGluGluIleArgGluAlaPheArgValPheAspLysAspGlyAsnGlyTyrIleSerAlaAla
GluLeuArgHisValMetThrAsnLeuAspGlySerValGlnLeuAlaAspHisTyrGlnGlnAsnThrProIleGlyAsp
GlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLysLysAspGluLeu <SEQ ID No.: 6; PRT3; Artificial sequence>
MetSerValLeuThrProLeuLeuLeuArgGlyLeuThrGlySerAlaArgArgLeuProValProArgAlaLysIleHisSer
LeuGlySerGlyProSerArgMetValSerLysGlyMetValSerLysGlyGluGluLeuPheThrGlyValValProIle
LeuValGluLeuAspGlyAspLeuAsnGlyHisLysPheSerValSerGlyGluGlyGluGlyAspAlaThrTyr8GlyLys
LeuThrLeuLysPheIleCysThrThrGlyLysLeuProValProTrpProThrLeuValThrThrLeuThrTyrGlyVal
GlnCysPheSerArgTyrProAspHisMetLysGlnHisAspPhePheLysSerAlaMetProGluGlyTyrValGlnGlu
ArgThrIlePhePheLysAspAspGlyAsnTyrLysThrArgAlaGluValLysPheGluGlyAspThrLeu160ValAsn
ArgIleGluLeuLysGlyIleAspPheLysGluAspGlyAsn1IleLeuGlyHisLysLeuGluTyrAsnTyrAsnSerHis
AsnValTyrIleMetAlaAspLysGlnLysAsnGlyIleLysValAsnPheLysIleArgHisAsnIleGluGluGluIle
ArgGluAlaPheArgValPheAspLysAspGlyAsnGlyTyrIleSerAlaAlaGluLeuArgHisVal240MetThrAsn
LeuAspGlySerValGlnLeuAlaAspHisTyrGlnGln2AsnThrProIleGlyAspGlyProValLeuLeuProAspAsn
HisTyrLeuSerThrGlnSerAlaLeuSerLysAspProAsnGluLysArgAspHisIleValLeuLeuGluPheValThr
AlaAlaGlyIleThrLeuGlyMetAspGluLeuTyrLys310

<SEQ ID No.: 7; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluSerGluGluLeuArgGluAlaGluArgValPheAspLysAspGlyAsn
GlyTyrIleSerAlaAlaGluLeuArgHisAlaAlaThrAsnLeuAspGlySerValGlnLeuAlaAspHisTyrGlnGln
AsnThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 8; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluGluGluGluIleArgGluAlaPheArgValPheAsnLysAspGlyAsnGly
TyrIleSerAlaAlaGluLeuArgHisValMetThrAsnLeuAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 9; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluGluGluIleArgGluAlaPheArgValPheAsnLysAspGlyAsnGly
TyrIleSerAlaAlaGluLeuArgHisValMetThrAsnLeuAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 10; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluGluGluIleArgGluAlaPheArgValPheAspLysAspGlyAsnGly
TyrIleSerAlaAlaGluLeuArgHisValMetThrAsnLeuAspGlySerValGlnLeuAlaAspHisTyrGlnGlnAsn
ThrProIleGlyAspGlyProValAsnLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

-continued

<SEQ ID No.: 11; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluAspLysAspGlyAspGlyThrIleThrThrLysGluAspGlySerValGln
LeuAlaAspHisTyrGlnGlnAsnThrProIleGlyAspGlyProValLeuLeuProAspAsnHisTyrLeuSerThrGln
SerAlaLeuSerLysAspProAsnGluLysArgAspHisIleValLeuLeuGluPheValThrAlaAla24GlyIleThrLeu
GlyMetAspGluLeuTyrLys <SEQ ID No.: 12; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluSerArgAsnIleCysAspIleSerCysAspLysPheLeuAspAspAspIle
ThrAspAspIleMetCysAlaLysLysIleLeuAspIleLysGlyAspGlySerValGlnLeuAlaAspHisTyrGlnGln
AsnThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 13; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluSerArgAsnIleCysAspIleSerAlaAspLysPheLeuAspAspAspIle
ThrAspAspIleMetCysAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 14; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluSerArgAsnIleCysAspIleSerCysAspLysPheLeuAspAspAspIle
ThrAspAspIleMetAlaAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 15; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluSerArgAsnIleCysAspIleSerAlaAspLysPheLeuAspAspAspIle
ThrAspAspIleMetAlaAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 16; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspLysAspGlyAsnGlyTyrIleSerAlaAlaGluAspGlySerValGln
LeuAlaAspHisTyrGlnGlnAsnThrProIleGlyAspGlyProValLeuLeuProAspAsnHisTyrLeuSerThrGln
SerAlaLeuSerLysAspProAsnGluLysArgAspHisIleValLeuLeuGluPheValThrAlaAla24GlyIleThrLeu
GlyMetAspGluLeuTyrLys <SEQ ID No.: 17; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle LysAlaAsnPheLysIleArgHisAsnIleGluGluGluIleArgGluAlaPheArgValPheAspLysAspGlyAsnGly
TyrIleSerAlaAlaGluAspGlySerValGlnLeuAlaAspHisTyrGlnGlnAsnThrProIleGlyAspGlyProValLeu
LeuProAspAsnHisTyrLeuSerThrGlnSerAlaLeuSerLysAspProAsnGluLysArgAsp24HisIleValLeu
LeuGluPheValThrAlaAlaGlyIleThrLeuGlyMetAspGluLeuTyrLys <SEQ ID No.: 18; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspLysAspGlyAsnGlyTyrIleSerAlaAlaGluLeuArgHisValMet
ThrAsnLeuAspGlySerValGlnLeuAlaAspHisTyrGlnGlnAsnThrProIleGlyAspGlyProValLeuLeuPro
AspAsnHisTyrLeuSerThrGlnSerAlaLeuSerLysAspProAsnGluLysArgAspHisIleVal24LeuLeuGluPhe
ValThrAlaAlaGlyIleThrLeuGlyMetAspGluLeuTyrLys <SEQ ID No.: 19; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluGluGluIleArgGluAlaPheArgValPheAspLysAspGlyAsnGly
TyrIleSerAlaAlaGluHisValMetThrAsnLeuAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 20; PRT3; Artificial sequence>
MetLeuLeuSerValProLeuLeuLeuGlyLeuLeuGlyLeuAlaAlaAlaAspGlySerGlyProSerArgMetValSer
LysGlyGluGluLeuPheThrGlyValValProIleLeuValGluLeuAspGlyAspLeuAsnGlyHisLysPheSerVal
SerGlyGluGlyGluGlyAspAlaThrTyrGlyLysLeuThrLeuLysPheIleCysThrThrGlyLysLeuProValProTrp
ProThrLeuValThrThrLeuThrTyrGlyValGlnCysPheSerArgTyrProAspHisMetLysGlnHisAspPhePhe
LysSerAlaMetProGluGlyTyrValGlnGluArgThrIlePhePheLysAspAspGlyAsnTyrLysThrArgAlaGlu
ValLysPheGluGlyAspThrLeuValAsnArgIleGluLeuLysGlyIleAspPheLysGluAspGlyAsn16IleLeu
GlyHisLysLeuGluTyrAsnTyrAsnSerHisAsnValTyrIleThrAlaAspLysGlnLysAsnGlyIleLysAlaAsnPhe
LysIleArgHisAsnIleGluGluGluIleArgGluAlaPheArgValPheAspLysAspGlyAsnGlyTyrIleSerAla
AlaGluLeuArgHisValMetThrAsnLeuAspGlySerValGlnLeuAlaAspHisTyrGlnGln24AsnThrProIle
GlyAspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLysLysAspGluLeu <SEQ ID No.: 21; PRT3; Artificial sequence>
MetSerValLeuThrProLeuLeuLeuArgGlyLeuThrGlySerAlaArgArgLeuProValProArgAlaLysIleHisSer
LeuGlySerGlyProSerArgMetValSerLysGlyMetValSerLysGlyGluGluLeuPheThrGlyValValProIle
LeuValGluLeuAspGlyAspLeuAsnGlyHisLysPheSerValSerGlyGluGlyGluGlyAspAlaThrTyrGlyLys
LeuThrLeuLysPheIleCysThrThrGlyLysLeuProValProTrpProThrLeuValThrThrLeuThrTyrGlyValGln
CysPheSerArgTyrProAspHisMetLysGlnHisAspPhePheLysSerAlaMetProGluGlyTyrValGlnGlu
ArgThrIlePhePheLysAspAspGlyAsnTyrLysThrArgAlaGluValLysPheGluGlyAspThrLeu16ValAsn
ArgIleGluLeuLysGlyIleAspPheLysGluAspGlyAsnIleLeuGlyHisLysLeuGluTyrAsnTyrAsnSerHisAsn
ValTyrIleThrAlaAspLysGlnLysAsnGlyIleLysAlaAsnPheLysIleArgHisAsnIleGluGluGluIleArg
GluAlaPheArgValPheAspLysAspGlyAsnGlyTyrIleSerAlaAlaGluLeuArgHisVal24MetThrAsnLeuAsp
GlySerValGlnLeuAlaAspHisTyrGlnGlnAsnThrProIleGlyAspGlyProValLeuLeuProAspAsnHisTyr
LeuSerThrGlnSerAlaLeuSerLysAspProAsnGluLysArgAspHisIleValLeuLeuGluPheValThrAlaAla
GlyIleThrLeuGlyMetAspGluLeuTyrLys31

<SEQ ID No.: 22; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluSerGluGluGluIleArgGluAlaPheArgValPheAspLysAspGlyAsn
GlyTyrIleSerAlaAlaGluLeuArgHisAlaAlaThrAsnLeuAspGlySerValGlnLeuAlaAspHisTyrGlnGln
AsnThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 23; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluGluGluIleArgGluAlaPheValPheAsnLysAspGlyAsnGly
TyrIleSerAlaAlaGluLeuArgHisValMetThrAsnLeuAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

-continued

<SEQ ID No.: 24; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluGluGluGluIleArgGluAlaPheArgValPheAsnLysAsnGlyAsnGly
TyrIleSerAlaAlaGluLeuArgHisValMetThrAsnLeuAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 25; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluGluGluGluIleArgGluAlaPheArgValPheAspLysAspGlyAsnGly
TyrIleSerAlaAlaGluLeuArgHisValMetThrAsnLeuAspGlySerValGlnLeuAlaAspHisTyrGlnGlnAsn
ThrProIleGlyAspGlyProValAsnLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 26; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspLysAspGlyAspGlyThrIleThrThrLysGluAspGlySerValGln
LeuAlaAspHisTyrGlnGlnAsnThrProIleGlyAspGlyProValLeuLeuProAspAsnHisTyrLeuSerThrGln
SerAlaLeuSerLysAspProAsnGluLysArgAspHisIleValLeuLeuGluPheValThrAlaAla24GlyIleThrLeu
GlyMetAspGluLeuTyrLys <SEQ ID No.: 27; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluSerArgAsnIleCysAspIleSerCysAspLysPheLeuAspAspAspIle
ThrAspAspIleMetCysAlaLysLysIleLeuAspIleLysGlyAspGlySerValGlnLeuAlaAspHisTyrGlnGln
AsnThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 28; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluSerArgAsnIleCysAspIleSerAlaAspLysPheLeuAspAspAspIle
ThrAspAspIleMetCysAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 29; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluSerArgAsnIleCysAspIleSerCysAspLysPheLeuAspAspAspIle
ThrAspAspIleMetAlaAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 30; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluSerArgAsnIleCysAspIleSerAlaAspLysPheLeuAspAspAspIle
ThrAspAspIleMetAlaAlaLysLysIleLeuAspIleLysGlyAspGlySerValGlnLeuAlaAspHisTyrGlnGlnAsn ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 31; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspLysAspGlyAsnGlyTyrIleSerAlaAlaGluAspGlySerValGlnLeu
AlaAspHisTyrGlnGlnAsnThrProIleGlyAspGlyProValLeuLeuProAspAsnHisTyrLeuSerThrGlnSer
AlaLeuSerLysAspProAsnGluLysArgAspHisIleValLeuLeuGluPheValThrAlaAla24GlyIleThrLeu
GlyMetAspGluLeuTyrLys <SEQ ID No.: 32; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluGluGluGluIleArgGluAlaPheArgValPheAspLysAspGlyAsnGly
TyrIleSerAlaAlaGluAspGlySerValGlnLeuAlaAspHisTyrGlnGlnAsnThrProIleGlyAspGlyProValLeu
LeuProAspAsnHisTyrLeuSerThrGlnSerAlaLeuSerLysAspProAsnGluLysArgAsp24HisIleValLeuLeu
GluPheValThrAlaAlaGlyIleThrLeuGlyMetAspGluLeuTyrLys <SEQ ID No.: 33; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspLysAspGlyAsnGlyTyrIleSerAlaAlaGluAspGlyAsnGlyTyrIleSerAlaAlaGluLeuArgHisValMetThr
AsnLeuAspGlySerValGlnLeuAlaAspHisTyrGlnGlnAsnThrProIleGlyAspGlyProValLeuLeuProAsp
AsnHisTyrLeuSerThrGlnSerAlaLeuSerLysAspProAsnGluLysArgAspHisIleVal24LeuLeuGluPhe
ValThrAlaAlaGlyIleThrLeuGlyMetAspGluLeuTyrLys <SEQ ID No.: 34; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluGluGluGluIleArgGluAlaPheArgValPheAspLysAspGlyAsnGly
TyrIleSerAlaAlaGluLeuArgHisValMetThrAsnLeuAspGlySerValGlnLeuAlaAspHisTyrGlnGlnAsnThr
ProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 35; PRT3; Artificial sequence>
MetLeuLeuSerValProLeuLeuLeuGlyLeuLeuGlyLeuAlaAlaAlaAspGlySerGlyProSerArgMetValSer
LysGlyGluGluLeuPheThrGlyValValProIleLeuValGluLeuAspGlyAspLeuAsnGlyHisLysPheSerVal
SerGlyGluGlyGluGlyAspAlaThrTyrGlyLysLeuThrLeuLysPheIleCysThrThrGlyLysLeuProValProTrp
ProThrLeuValThrThrLeuThrTyrGlyValGlnCysPheSerArgTyrProAspHisMetLysGlnHisAspPhePhe
LysSerAlaMetProGluGlyTyrValGlnGluArgThrIleSerPheLysAspAspGlyAsnTyrLysThrArgAlaGlu
ValLysPheGluGlyAspThrLeuValAsnArgIleGluLeuLysGlyIleAspPheLysGluAspGlyAsn16IleLeu
GlyHisLysLeuGluTyrAsnTyrAsnSerHisAsnValTyrIleThrAlaAspLysGlnLysAsnGlyIleLysAlaAsnPhe
LysIleArgHisAsnIleGluAspLysGluGluGluIleArgGluAlaPheArgValPheAspLysAspGlyAsnGlyTyrIleSerAla
AlaGluLeuArgHisValMetThrAsnLeuAspGlySerValGlnLeuAlaAspHisTyrGlnGln24AsnThrProIle
GlyAspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLysLysAspGluLeu <SEQ ID No.: 36; PRT3; Artificial sequence>
MetSerValLeuThrProLeuLeuLeuArgGlyLeuThrGlySerAlaArgArgLeuProValProArgAlaLysIleHisSer
LeuGlySerGlyProSerArgMetValSerLysGlyMetValSerLysGlyGluGluLeuPheThrGlyValValProIle
LeuValGluLeuAspGlyAspLeuAsnGlyHisLysPheSerValSerGlyGluGlyGluGlyAspAlaThrTyrGlyLys
LeuThrLeuLysPheIleCysThrThrGlyLysLeuProValProTrpProThrLeuValThrThrLeuThrTyrGlyValGln
CysPheSerArgTyrProAspHisMetLysGlnHisAspPhePheLysSerAlaMetProGluGlyTyrValGlnGlu
ArgThrIleSerPheLysAspAspGlyAsnTyrLysThrArgAlaGluValLysPheGluGlyAspThrLeu16ValAsnArg
IleGluLeuLysGlyIleAspPheLysGluAspGlyAsnIleLeuGlyHisLysLeuGluTyrAsnTyrAsnSerHisAsn
ValTyrIleThrAlaAspLysGlnLysAsnGlyIleLysAlaAsnPheLysIleArgHisAsnIleGluGluGluGluIleArgGlu
AlaPheArgValPheAspLysAspGlyAsnGlyTyrIleSerAlaAlaGluLeuArgHisVal24MetThrAsnLeuAsp
GlySerValGlnLeuAlaAspHisTyrGlnGlnAsnThrProIleGlyAspGlyProValLeuLeuProAspAsnHisTyrLeu
SerThrGlnSerAlaLeuSerLysAspProAsnGluLysArgAspHisIleValLeuLeuGluPheValThrAlaAlaGly
IleThrLeuGlyMetAspGluLeuTyrLys31

<SEQ ID No.: 37; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu -continued ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluSerGluGluGluIleArgGluAlaPheAspLysAspGlyAsn
GlyTyrIleSerAlaAlaGluLeuArgHisAlaAlaThrAsnLeuAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 38; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluGluGluIleArgGluAlaPheArgValPheAsnLysAspGlyAsnGly
TyrIleSerAlaAlaGluLeuArgHisValMetThrAsnLeuAspGlySerValGlnLeuAlaAspHisTyrGlnGlnAsnThr
ProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 39; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluGluGluIleArgGluAlaPheArgValPheAsnLysAsnGlyAsnGly
TyrIleSerAlaAlaGluLeuArgHisValMetThrAsnLeuAspGlySerValGlnLeuAlaAspHisTyrGlnGlnAsnThr
ProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 40; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluGluGluIleArgGluAlaPheArgValPheAspLysAspGlyAsnGly
TyrIleSerAlaAlaGluLeuArgHisValMetThrAsnLeuAspGlySerValGlnLeuAlaAspHisTyrGlnGlnAsnThr
ProIleGlyAspGlyProValAsnLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 41; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspLysAspGlyAspGlyThrIleThrThrLysGluAspGlySerValGlnLeu
AlaAspHisTyrGlnGlnAsnThrProIleGlyAspGlyProValLeuLeuProAspAsnHisTyrLeuSerThrGlnSer
AlaLeuSerLysAspProAsnGluLysArgAspHisIleValLeuLeuGluPheValThrAlaAla24GlyIleThrLeu
GlyMetAspGluLeuTyrLys <SEQ ID No.: 42; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAsppheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluSerArgAsnIleCysAspIleSerCysAspLysPheLeuAspAspAspIle
ThrAspAspIleMetCysAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 43; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluSerArgAsnIleCysAspIleSerAlaLysPheLeuAspAspAspIleThr
AspAspIleMetCysAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspProAsn
GluLysArgAspHisIleValLeuLeuGluPheValThrAlaAlaGlyIleThrLeuGlyMetAspGluLeuTyrLys -continued <SEQ ID No.: 44; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluSerArgAsnIleCysAspIleSerCysAspLysPheLeuAspAspAspIle
ThrAspAspIleMetAlaAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspPro
AsnGluLysArgAspHisIleValLeuLeuGluPheValThrAlaAlaGlyIleThrLeuGlyMetAspGluLeuTyrLys <SEQ ID No.: 45; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluSerArgAsnIleCysAspIleSerAlaAspLysPheLeuAspAspAspIleThr
AspAspIleMetAlaAlaLysLysIleLeuAspIleLysGlyAspGlySerValGlnLeuAlaAspHisTyrGlnGlnAsn
ThrProIleGlyAspGlyProValLeuLeuProAspAsnHisTyrLeuSerThrGlnSerAlaLeu24SerLysAspProAsn
GluLysArgAspHisIleValLeuLeuGluPheValThrAlaAlaGlyIleThrLeuGlyMetAspGluLeuTyrLys <SEQ ID No.: 46; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnAspLys16AspGly
AsnGlyTyrIleSerAlaAlaGluLysAsnGlyIleLysValAsnPheLysIleArgHisAsnIleGluAspGlySerValGln
LeuAlaAspHisTyrGlnGlnAsnThrProIleGlyAspGlyProValLeuLeuProAspAsnHisTyrLeuSerThrGln
SerAlaLeuSerLysAspProAsnGluLysArgAspHisIleValLeuLeuGluPheValThrAlaAla24GlyIleThrLeu
GlyMetAspGluLeuTyrLys <SEQ ID No.: 47; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysGlu16GluIle
ArgGluAlaPheArgValPheAspLysAspGlyAsnGlyTyrIleSerAlaAlaGluLeuArgHisValMetThrAsnLeu
LysAsnGlyIleLysValAsnPheLysIleArgHisAsnIleGluAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspPro
AsnGluLysArgAspHisIleValLeuLeuGluPheValThrAlaAlaGlyIleThrLeuGlyMetAspGluLeuTyrLys27

<SEQ ID No.: 48; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnAspLys16AspGly
AsnGlyTyrIleSerAlaAlaGluLysAsnGlyIleLysAlaAsnPheLysIleArgHisAsnIleGluAspGlySerValGln
LeuAlaAspHisTyrGlnGlnAsnThrProIleGlyAspGlyProValLeuLeuProAspAsnHisTyrLeuSerThrGln
SerAlaLeuSerLysAspProAsnGluLysArgAspHisIleValLeuLeuGluPheValThrAlaAla24GlyIleThrLeu
GlyMetAspGluLeuTyrLys <SEQ ID No.: 49; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnGluGlu16GluIle
ArgGluAlaPheArgValPheAspLysAspGlyAsnGlyTyrIleSerAlaAlaGluLeuArgHisValMetThrAsnLeu
LysAsnGlyIleLysAlaAsnPheLysIleArgHisAsnIleGluAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspPro
AsnGluLysArgAspHisIleValLeuLeuGluPheValThrAlaAlaGlyIleThrLeuGlyMetAspGluLeuTyrLys27

<SEQ ID No.: 50; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnAspLys16AspGly AsnGlyTyrIleSerAlaAlaGluLysAsnGlyIleLysAlaAsnPheLysIleArgHisAsnIleGluAspGlySerValGlnLeu
AlaAspHisTyrGlnGlnAsnThrProIleGlyAspGlyProValLeuLeuProAspAsnHisTyrLeuSerThrGlnSer
AlaLeuSerLysAspProAsnGluLysArgAspHisIleValLeuLeuGluPheValThrAlaAla24GlyIleThrLeu
GlyMetAspGluLeuTyrLys <SEQ ID No.: 51; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleGluPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnGluGlu16GluIleArg
GluAlaPheArgValPheAspLysAspGlyAsnGlyTyrIleSerAlaAlaGluLeuArgHisValMetThrAsnLeuLys
AsnGlyIleLysAlaAsnPheLysIleArgHisAsnIleGluAspGlySerValGlnLeuAlaAspHisTyrGlnGlnAsnThr
ProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 52; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnGluGluGluIleArgGluAlaPheArgValPheAspLysAspGlyAsnGlyTyrIle
SerAlaAlaGluLeuArgHisValMetThrAsnLeuIleGluAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 53; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnThrGluGluGlnIleAlaGluPheLysGluAlaPheSerLeuPheAspLysAsp
GlyAspGlyThrIleThrThrLysGluLeuGlyThrValMetArgSerIleGluAspGlySerValGlnLeuAlaAspHisTyr
GlnGlnAsnThrProIleGlyAspGlyProValLeuLeuProAspAsnHisTyrLeuSerThrGlnSer24AlaLeuSerLys
AspProAsnGluLysArgAspHisIleValLeuLeuGluPheValThrAlaAlaGlyIleThrLeuGlyMetAspGluLeu
TyrLys <SEQ ID No.: 54; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnGluGluGluIleArgGluAlaPheArgValPheAspLysAspGlyAsnGlyTyrIle
SerAlaAlaGluLeuArgHisValMetThrAsnLeuIleGluAspGlySerValGlnLeuAlaAspHisTyrGlnGlnAsn
ThrProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

<SEQ ID No.: 55; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnThrGluGluGlnIleAlaGluPheLysGluAlaPheSerLeuPheAspLysAsp
GlyAspGlyThrIleThrThrLysGluLeuGlyThrValMetArgSerIleGluAspGlySerValGlnLeuAlaAspHisTyr
GlnGlnAsnThrProIleGlyAspGlyProValLeuLeuProAspAsnHisTyrLeuSerThrGlnSer24AlaLeuSerLys
AspProAsnGluLysArgAspHisIleValLeuLeuGluPheValThrAlaAlaGlyIleThrLeuGlyMetAspGluLeu
TyrLys <SEQ ID No.: 56; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnGluGluGluIleArgGluAlaPheArgValPheAspLysAspGlyAsnGlyTyrIle
SerAlaAlaGluLeuArgHisValMetThrAsnLeuIleGluAspGlySerValGlnLeuAlaAspHisTyrGlnGlnAsnThr
ProIleGlyAspGlyProValLeuLeuProAspAsnHisTyrLeuSerThrGlnSerAlaLeuSer24LysAspProAsn
GluLysArgAspHisIleValLeuLeuGluPheValThrAlaAlaGlyIleThrLeuGlyMetAspGluLeuTyrLys27

-continued

<SEQ ID No.: 57; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnThrGluGluGlnIleAlaGluPheLysGluAlaPheSerLeuPheAspLysAspGly
AspGlyThrIleThrThrLysGluLeuGlyThrValMetArgSerIleGluAspGlySerValGlnLeuAlaAspHisTyrGln
GlnAsnThrProIleGlyAspGlyProValLeuLeuProAspAsnHisTyrLeuSerThrGlnSer24AlaLeuSerLys
AspProAsnGluLysArgAspHisIleValLeuLeuGluPheValThrAlaAlaGlyIleThrLeuGlyMetAspGluLeuTyr
Lys <SEQ ID No.: 58; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValAspPheGluGlyAspThrLeuAsnAsnAspIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys <SEQ ID No.: 59; PRT3; Artificial sequence>
MetValSerLysGlyGluGluLeuPheThrGlyValValProIleAsnValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuAsnAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys <SEQ ID No.: 60; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnAspGluAspGlyAspGlySerValGlnLeuAlaAspHisTyrGlnGlnAsnThrProIle
GlyAspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys <SEQ ID No.: 61; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetAspGln
HisAspPhePheAspSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluAspGlySerValGlnLeuAlaAspHisTyrGlnGlnAsnThrProIleGly
AspGlyProValAsnLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 62; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetAspGln
HisAspPhePheLysAspAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluAspGlySerValGlnLeuAlaAspHisTyrGlnGlnAsnThrProIleGly
AspGlyProValAsnLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 63; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisAsnLysGln
AspAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluAspGlySerValGlnLeuAlaAspHisTyrGlnGlnAsnThrProIleGly
AspGlyProValLeuLeuProAspAsnAspTyrLeuSerThrGlnSerAlaLeuSerLysAspProAsnGluLysArgAsp
HisIleValLeuLeuGluPheValThrAlaAlaGlyAspThrLeuGlyMetAspGluLeuTyrLys

```
<SEQ ID No.: 64; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysAspAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluAspGlySerValGlnLeuAlaAspHisTyrGlnGlnAsnThrProIleGly
AspGlyProValGluLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 65; PRT3; Artificial sequence>
MetLeuLeuSerValProLeuLeuLeuLeuGlyLeuLeuLeuGlyLeuAlaAlaAlaAspGlySerGlyProSerArgMetValSer
LysGlyGluGluLeuPheThrGlyValValProIleLeuValGluLeuAspGlyAspLeuAsnGlyHisLysPheSerVal
SerGlyGluGlyGluGlyAspAlaThrTyrGlyLysLeuThrLeuLysPheIleCysThrThrGlyLysLeuProValProTrp
ProThrLeuValThrThrLeuThrTyrGlyValGlnCysPheSerArgTyrProAspHisMetLysGlnHisAspPhePhe
LysAspAlaMetProGluGlyTyrValGlnGluArgThrIlePhePheLysAspAspGlyAsnTyrLysThrArgAlaGlu
ValLysPheGluGlyAspThrLeuValAsnArgIleGluLeuLysGlyIleAspPheLysGluAspGlyAsn16IleLeu
GlyHisLysLeuGluTyrAsnTyrAsnSerHisAsnValTyrIleMetAlaAspLysGlnLysAsnGlyIleLysValAsnPhe
LysIleArgHisAsnIleGluAspGlySerValGlnLeuAlaAspHisTyrGlnGlnAsnThrProIleGlyAspGlyPro
ValGluLeuProAspAsnHisTyrLeuSerThrGlnSerAlaLeuSerLysAspProAsnGluLysArg24AspHisIleVal
LeuLeuGluPheValThrAlaAlaGlyIleThrLeuGlyMetAspGluLeuTyrLysLysAspGluLeu <SEQ ID No.: 66; PRT3; Artificial sequence>
MetSerValLeuThrProLeuLeuLeuArgGlyLeuThrGlySerAlaArgArgLeuProValProArgAlaLysIleHisSer
LeuGlySerGlyProSerArgMetValSerLysGlyGluGlyLeuPheThrGlyValValProIleLeuValGluLeuAsp
GlyAspLeuAsnGlyHisLysPheSerValSerGlyGluGlyGluGlyAspAlaThrTyrGlyLysLeuThrLeuLysPhe
IleCysThrThrGlyLysLeuProValProTrpProThrLeuValThrThrLeuThrTyrGlyValGlnCysPheSerArg
TyrProAspHisMetLysGlnHisAspPhePheLysAspAlaMetProGluGlyTyrValGlnGluArgThrIlePhePhe
LysAspAspGlyAsnTyrLysThrArgAlaGluValLysPheGluGlyAspThrLeuValAsnArgIleGluLeu16LeuLys
GlyIleAspPheLysGluAspGlyAsnIleLeuGlyHisLysLeuGluTyrAsnTyrAsnSerHisAsnValTyrIleMetAla
AspLysGlnLysAsnGlyIleLysValAsnPheLysIleArgHisAsnIleGluAspGlySerValGlnLeuAlaAspHisTyr
GlnGlnAsnThrProIleGlyAspGlyProValGluLeuProAspAsnHisTyrLeuSerThrGln24SerAlaLeuSer
LysAspProAsnGluLysArgAspHisIleValLeuLeuGluPheValThrAlaAlaGlyIleThrLeuGlyMetAspGluLeu
TyrLys <SEQ ID No.: 67; PRT3; Artificial sequence>
MetValSerLysGlyGluGluLeuPheThrGlyValValProIleAspValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuSerAsnGluIleGluLeuLysGlyIleAspPheLysGluAspGly
AsnIleLeuGlyHisLysLeuGluTyrAsnTyrAsnSerHisAsnValTyrIleMetAlaAspLysGlnLysAsn16GlyIle
LysValAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 68; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspAspPheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrGluMetAspAspLysGlnLysAsn16GlyAsp
LysValAsnPheLysIleArgHisAsnIleGluAspGlySerValGlnLeuAlaAspHisTyrGlnGlnAsnThrProIleGly
AspGlyProValGluLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys <SEQ ID No.: 69; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProAspLeuValThrThrLeuThrTyrGlyValGlnCysPheSerArgTyrProAspHisMetLysGln
HisAspPhePheLysSerAlaMetProGluGlyTyrValGlnGluArgThrIlePheGluLysAspAspGlyAsnTyrLys
ThrArgAlaGluValLysPheGluGlyAspThrLeuValValLysGlyIleAspPheLysGluAspGlyAsn
SerLeuGlyHisLysAsnGluTyrAsnTyrAsnSerHisAsnValTyrIleMetAlaAspLysGlnLysAsn16GlyIle
LysValAsnPheLysIleArgHisAsnIleGluAspGlySerValGluLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 70; PRT3; Artificial sequence>
MetValSerLysGlyGluGluAspPheThrGlyValAsnProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaSerProGluGlyTyrValGlnGluArgThrIlePhePheLysAspAspGlyAsnTyrLys
ThrArgAlaGluValLysAspGluGlyAspThrAspValAsnArgIleGluLeuLysGlyIleAspPheLysGluAspGlyAsn
IleLeuGlyHisLysLeuGluTyrAsnTyrAsnSerHisAsnValTyrIleMetAlaAspLysGlnLysAsn16GlyIleLys
ValAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys
```

-continued

<SEQ ID No.: 71; PRT3; Artificial sequence>
MetValSerLysGlyGluGluAspPheThrGlyValAsnProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaThrProGluGlyTyrValGlnGluArgThrIlePhePheLysAspAspGlyAsnTyrLys
ThrArgAlaGluValLysAspGluGlyAspThrGluValAsnArgIleGluLeuLysGlyIleAspPheLysGluAspGlyAsn
IleLeuGlyHisLysLeuGluTyrAsnTyrAsnSerHisAsnValTyrIleMetAlaAspLysGlnLysAsn16GlyIleLys
ValAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 72; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValAspPheGluGlyAspThrLeuAsnAsnAspIleGluLeuLysGlyIleAspPheLysGluAspGly
AsnIleLeuGlyHisLysLeuGluTyrAsnTyrAsnSerHisAsnValTyrIleThrAlaAlaLysGlnLysAsn16GlyIle
LysAlaAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 73; PRT3; Artificial sequence>
MetValSerLysGlyGluGluLeuPheThrGlyValValProIleAsnValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuAsnAsnAspIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 74; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnAspGluAspGlyAspValAsnLeuAlaAspHisTyrGlnGlnAsnThrProIle
GlyAspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys <SEQ ID No.: 75; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetAspGln
HisAspPhePheAspSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValAsnLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 76; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetAspGln
HisAspPhePheLysAspAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValAsnLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 77; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisAsnLysGln
AspAspPhePheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValLeuLeuProAspAsnAspTyrLeuSerThrGlnSerAlaLeuSerLysAspProAsnGluLysArgAsp
HisIleValLeuLeuGluPheValThrAlaAlaGlyAspThrLeuGlyMetAspGluLeuTyrLys <SEQ ID No.: 78; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln -continued HisAspPhePheLysAspAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValGluLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 79; PRT3; Artificial sequence>
MetLeuLeuSerValProLeuLeuLeuGlyLeuLeuGlyLeuAlaAlaAlaAspGlySerGlyProSerArgMetValSer
LysGlyGluGluLeuPheThrGlyValValProIleLeuValGluLeuAspGlyAspLeuAsnGlyHisLysPheSerVal
SerGlyGluGlyGluGlyAspAlaThrTyrGlyLysLeuThrLeuLysPheIleCysThrThrGlyLysLeuProValProTrp
ProThrLeuValThrThrLeuThrTyrGlyValGlnCysPheSerArgTyrProAspHisMetLysGlnHisAspPhePhe
LysAspAlaMetProGluGlyTyrValGlnGluArgThrIlePhePheLysAspAspGlyAsnTyrLysThrArgAlaGlu
ValLysPheGluGlyAspThrLeuValAsnArgIleGluLeuLysGlyIleAspPheLysGluAspGlyAsn16IleLeu
GlyHisLysLeuGluTyrAsnTyrAsnSerHisAsnValTyrIleThrAlaAspLysGlnLysAsnGlyIleLysAlaAsnPhe
LysIleArgHisAsnIleGluAspGlySerValGlnLeuAlaAspHisTyrGlnGlnAsnThrProIleGlyAspGlyProVal
GluLeuProAspAsnHisTyrLeuSerThrGlnSerAlaLeuSerLysAspProAsnGluLysArg24AspHisIleVal
LeuLeuGluPheValThrAlaAlaGlyIleThrLeuGlyMetAspGluLeuTyrLysLysAspGluLeu <SEQ ID No.: 80; PRT3; Artificial sequence>
MetSerValLeuThrProLeuLeuLeuArgGlyLeuThrGlySerAlaArgArgLeuProValProArgAlaLysIleHisSer
LeuGlySerGlyProSerArgMetValSerLysGlyGluGluLeuPheThrGlyValValProIleLeuValGluLeuAsp
GlyAspLeuAsnGlyHisLysPheSerValSerGlyGluGlyGluGlyAspAlaThrTyrGlyLysLeuThrLeuLysPhe
IleCysThrThrGlyLysLeuProValProTrpProThrLeuValThrThrLeuThrTyrGlyValGlnCysPheSerArg
TyrProAspHisMetLysGlnHisAspPhePheLysAspAlaMetProGluGlyTyrValGlnGluArgThrIlePhePhe
LysAspAspGlyAsnTyrLysThrArgAlaGluValLysPheGluGlyAspThrLeuValAsnArgIleGlu16LeuLys
GlyIleAspPheLysGluAspGlyAsnIleLeuGlyHisLysLeuGluTyrAsnTyrAsnSerHisAsnValTyrIleThrAla
AspLysGlnLysAsnGlyIleLysAlaAsnPheLysIleArgHisAsnIleGluAspGlySerValGlnLeuAlaAspHisTyr
GlnGlnAsnThrProIleGlyAspGlyProValGluLeuProAspAsnHisTyrLeuSerThrGln24SerAlaLeuSer
LysAspProAsnGluLysArgAspHisIleValLeuLeuGluPheValThrAlaAlaGlyIleThrLeuGlyMetAspGluLeu
TyrLys <SEQ ID No.: 81; PRT3; Artificial sequence>
MetValSerLysGlyGluGluLeuPheThrGlyValValProIleAspValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIlePhePheLysAspAspGlyAsnTyrLys
ThrArgAlaGluValLysPheGluGlyAspThrLeuSerAsnGluIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 82; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspAspPheLysSerAlaMetProGluGlyTyrValGlnGluArgThrIlePhePheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrGluThrAspAspLysGlnLysAsn16GlyAsp
LysAlaAsnPheLysIleArgHisAsnIleGluAspGlySerValLeuAlaAspHisTyrGlnGlnAsnThrProIleGly
AspGlyProValGluLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys <SEQ ID No.: 83; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProAspLeuValThrThrLeuThrTyrGlyValGlnCysPheSerArgTyrProAspHisMetLysGln
HisAspPhePheLysSerAlaMetProGluGlyTyrValGlnGluArgThrIlePheGluLeuLysAspAspGlyAsnTyrLys
ThrArgAlaGluValLysPheGluGlyAspThrLeuValAsnArgIleGluLeuLysGlyIleAspPheLysGluAspGlyAsn
SerLeuGlyHisLysAsnGluTyrAsnTyrAsnSerHisAsnValTyrIleThrAlaAspLysGlnLysAsn16GlyIleLys
AlaAsnPheLysIleArgHisAsnIleGluAspGlySerValGluLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 84; PRT3; Artificial sequence>
MetValSerLysGlyGluGluAspPheThrGlyValAsnProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaSerProGluGlyTyrValGlnGluArgThrIlePhePheLysAspAspGlyAsnTyrLys
ThrArgAlaGluValLysAspGluGlyAspThrAspValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspGlySerValGlnLeuAlaAspHisTyrGlnGlnAsnThrProIleGlyAsp
GlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 85; PRT3; Artificial sequence>
MetValSerLysGlyGluGluAspPheThrGlyValAsnProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaThrProGluGlyTyrValGlnGluArgThrIlePhePheLysAspAspGlyAsnTyrLys <SEQ ID No.: 86; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValAspPheGluGlyAspThrLeuAsnAsnAspIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 87; PRT3; Artificial sequence>
MetValSerLysGlyGluGluLeuPheThrGlyValValProIleAsnValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuAsnAsnAspIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 88; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnGluAspGlyAspValAsnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 89; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetAspGln
HisAspPhePheAspSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspGlySerValGlnLeuAlaAspHisTyrGlnGlnAsnThrProIleGlyAsp
GlyProValAsnLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 90; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetAspGln
HisAspPhePheLysAspAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspGlySerValGlnLeuAlaAspHisTyrGlnGlnAsnThrProIleGlyAsp
GlyProValAsnLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 91; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisAsnLysGln
AspAspPhePheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGly
AsnIleLeuGlyHisLysLeuGluTyrAsnTyrAsnSerHisAsnValTyrIleThrAlaAspLysGlnLysAsn16GlyIle
LysAlaAsnPheLysIleArgHisAsnIleGluAspGlySerValGlnLeuAlaAspHisTyrGlnGlnAsnThrProIleGly
AspGlyProValLeuLeuProAspAsnAspTyrLeuSerThrGlnSerAlaLeuSerLysAspProAsnGluLysArgAsp
HisIleValLeuLeuGluPheValThrAlaAlaGlyAspThrLeuGlyMetAspGluLeuTyrLys <SEQ ID No.: 92; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysAspAlaMetProGluGlyTyrValGlnGluArgThrIleSerPheLysAspAspGlyAsnTyrLys -continued ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspGlySerValGlnLeuAlaAspHisTyrGlnGlnAsnThrProIleGlyAsp
GlyProValGluLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 93; PRT3; Artificial sequence>
MetLeuLeuSerValProLeuLeuLeuGlyLeuLeuGlyLeuAlaAlaAlaAspGlySerGlyProSerArgMetValSer
LysGlyGluGluLeuPheThrGlyValValProIleLeuValGluLeuAspGlyAspLeuAsnGlyHisLysPheSerVal
SerGlyGluGlyGluGlyAspAlaThrTyrGlyLysLeuThrLeuLysPheIleCysThrThrGlyLysLeuProValProTrp
ProThrLeuValThrThrLeuThrTyrGlyValGlnCysPheSerArgTyrProAspHisMetLysGlnHisAspPhePhe
LysAspAlaMetProGluGlyTyrValGlnGluArgThrIleSerPheLysAspAspGlyAsnTyrLysThrArgAlaGlu
ValLysPheGluGlyAspThrLeuValAsnArgIleGluLeuLysGlyIleAspPheLysGluAspGlyAsn16IleLeu
GlyHisLysLeuGluTyrAsnTyrAsnSerHisAsnValTyrIleThrAlaAspLysGlnLysAsnGlyIleLysAlaAsnPhe
LysIleArgHisAsnIleGluAspGlySerValGlnLeuAlaAspHisTyrGlnGlnAsnThrProIleGlyAspGlyProVal
GluLeuProAspAsnHisTyrLeuSerThrGlnSerAlaLeuSerLysAspProAsnGluLysArg24AspHisIleVal
LeuLeuGluPheValThrAlaAlaGlyIleThrLeuGlyMetAspGluLeuTyrLysLysAspGluLeu <SEQ ID No.: 94; PRT3; Artificial sequence>
MetSerValLeuThrProLeuLeuLeuArgGlyLeuThrGlySerAlaArgArgLeuProValProArgAlaLysIleHisSer
LeuGlySerGlyProSerArgMetValSerLysGlyGluGluLeuPheThrGlyValValProIleLeuValGluLeuAsp
GlyAspLeuAsnGlyHisLysPheSerValSerGlyGluGlyGluGlyAspAlaThrTyrGlyLysLeuThrLeuLysPhe
IleCysThrThrGlyLysLeuProValProTrpProThrLeuValThrThrLeuThrTyrGlyValGlnCysPheSerArg
TyrProAspHisMetLysGlnHisAspPhePheLysAspAlaMetProGluGlyTyrValGlnGluArgThrIleSerPhe
LysAspAspGlyAsnTyrLysThrArgAlaGluValLysPheGluGlyAspThrLeuValAsnArgIleGlu16LeuLys
GlyIleAspPheLysGluAspGlyAsnIleLeuGlyHisLysLeuGluTyrAsnTyrAsnSerHisAsnValTyrIleThrAla
AspLysGlnLysAsnGlyIleLysAlaAsnPheLysIleArgHisAsnIleGluAspGlySerValGlnLeuAlaAspHisTyr
GlnGlnAsnThrProIleGlyAspGlyProValGluLeuProAspAsnHisTyrLeuSerThrGln24SerAlaLeuSer
LysAspProAsnGluLysArgAspHisIleValLeuLeuGluPheValThrAlaAlaGlyIleThrLeuGlyMetAspGluLeu
TyrLys <SEQ ID No.: 95; PRT3; Artificial sequence>
MetValSerLysGlyGluGluLeuPheThrGlyValValProIleAspValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaMetProGluGlyTyrValGlnGluArgThrIleSerPheLysAspAspGlyAsnTyrLys
ThrArgAlaGluValLysPheGluGlyAspThrLeuSerAsnGluIleGluLeuLysGlyIleAspPheLysGluAspGly
AsnIleLeuGlyHisLysLeuGluTyrAsnTyrAsnSerHisAsnValTyrIleThrAlaAspLysGlnLysAsn11GlyIle
LysAlaAsnPheLysIleArgHisAsnIleGluAspGlySerValGlnLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 96; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspAspPheLysSerAlaMetProGluGlyTyrValGlnGluArgThrIleSerPheLysAspAspGlyAsnTyrLys
ThrArgAlaGluValLysPheGluGlyAspThrLeuValAsnArgIleGluLeuLysGlyIleAspPheLysGluAspGlyAsn
IleLeuGlyHisLysLeuGluTyrAsnTyrAsnSerHisAsnValTyrGluThrAspAspLysGlnLysAsn16GlyAsp
LysAlaAsnPheLysIleArgHisAsnIleGluAspGlySerValGlnLeuAlaAspHisTyrGlnGlnAsnThrProIleGly
AspGlyProValGluLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys <SEQ ID No.: 97; PRT3; Artificial sequence>
MetValSerLysGlyGluGluLeuPheThrGlyValValProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProAspLeuValThrThrLeuThrTyrGlyValGlnCysPheSerArgTyrProAspHisMetLysGln
HisAspPhePheLysSerAlaMetProGluGlyTyrValGlnGluArgThrIleSerGluLysAspAspGlyAsnTyrLys
ThrArgAlaGluValLysPheGluGlyAspThrLeuValValAsnArgIleGluLeuLysGlyIleAspPheLysGluAspGlyAsn
SerLeuGlyHisLysAsnGluTyrAsnTyrAsnSerHisAsnValTyrIleThrAlaAspLysGlnLysAsn16GlyIleLys
AlaAsnPheLysIleArgHisAsnIleGluAspGlySerValGluLeuAlaAspHisTyrGlnGlnAsnThrProIleGly
AspGlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 98; PRT3; Artificial sequence>
MetValSerLysGlyGluGluAspPheThrGlyValAsnProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaSerProGluGlyTyrValGlnGluArgThrIleSerPheLysAspAspGlyAsnTyrLys
ThrArgAlaGluValLysAspGluGlyAspThrAspValAsnArgIleGluLeuLysGlyIleAspPheLysGluAspGlyAsn
IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspGlySerValGlnLeuAlaAspHisTyrGlnGlnAsnThrProIleGlyAsp
GlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 99; PRT3; Artificial sequence>
MetValSerLysGlyGluGluAspPheThrGlyValAsnProIleLeuValGluLeuAspGlyAspLeuAsnGlyHisLys
PheSerValSerGlyGluGlyGluGlyAspAlaThrTyrGlyLysLeuThrLeuLysPheIleCysThrThrGlyLysLeu
ProValProTrpProThrLeuValThrThrLeuThrTyrGlyValGlnCysPheSerArgTyrProAspHisMetLysGln
HisAspPhePheLysSerAlaThrProGluGlyTyrValGlnGluArgThrIleSerPheLysAspAspGlyAsnTyrLys
ThrArgAlaGluValLysAspGluGlyAspThrGluValAsnArgIleGluLeuLysGlyIleAspPheLysGluAspGlyAsn -continued IleLeuGlyHisLysLeuGluTyrAsnTyrAsnSerHisAsnValTyrIleThrAlaAspLysGlnLysAsn16GlyIleLys
AlaAsnPheLysIleArgHisAsnIleGluAspGlySerValGlnLeuAlaAspHisTyrGlnGlnAsnThrProIleGlyAsp
GlyProValLeuLeuProAspAsnHisTyrLeuSerThrGlnSerAlaLeuSerLysAspProAsnGluLysArgAsp
HisIleValLeuLeuGluPheValThrAlaAlaGlyIleThrLeuGlyMetAspGluLeuTyrLys <SEQ ID No.: 100; PRT3; Artificial sequence>
MetLeuLeuSerValProLeuLeuLeuGlyLeuLeuGlyLeuAlaAlaAlaAspGlySerGlyProSerArg <SEQ ID No.: 101; PRT3; Artificial sequence>
LysAspGluLeu <SEQ ID No.: 102; PRT3; Artificial sequence>
MetSerValLeuThrProLeuLeuLeuArgGlyLeuThrGlySerAlaArgArgLeuProValProArgAlaLysIleHisSer
LeuGlySerGlyProSerArg <SEQ ID No.: 103; PRT3; Artificial sequence>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnSerHisAsnValTyrIleThrAlaAspLysGlnLysAsnGlyIleLysAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuSerThrGlnSerAlaLeuSerLysAspProAsnGluLysArgAspHisIleVal
LeuLeuGluPheValThrAlaAlaGlyIleThrLeuGlyMetAspGluLeuTyrLys <SEQ ID No.: 104; PRT3; Artificial sequence>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluValAlaAlaGlyIleThrLeuGlyMetAspGluLeuTyrLys <SEQ ID No.: 105; PRT3; Artificial sequence>
MetLeuLeuSerValProLeuLeuLeuGlyLeuLeuGlyLeuAlaAlaAlaAspValSerLysGlyGluGluLeuPheThr
GlyValValProIleLeuValGluLeuAspGlyAspLeuAsnGlyHisLysPheSerValSerGlyGluGlyGluGlyAsp
AlaThrTyrGlyLysLeuThrLeuLysPheIleCysThrThrGlyLysLeuProValProTrpProThrLeuValThrThr
LeuThrTyrGlyValGlnCysPheSerArgTyrProAspHisMetLysGlnHisAspPhePheLysSerAlaMetProGlu
GlyTyrValGlnGluArgThrIlePhePheLysAspAspGlyAsnTyrLysThrArgAlaGluValLysPheGluGlyAsp
ThrLeuValAsnArgIleGluLeuLysGlyIleAspPheLysGluAspGlyAsnIleLeuGlyHisLysLeuGluTyrAsn
TyrAsnGluHisAsnValTyrIleThrAlaAspLysGlnLysAsnGlyIleLysAlaAsnPheLysIleArgHisAsnIleGlu
AspGlySerValGlnLeuAlaAspHisTyrGlnGlnAsnThrProIleGlyAspGlyProValLeuLeuProAspAsnHis
TyrLeuAspThrGluSerAlaLeuSerLysAspProAsnGluLysArgAspHisIleValLeuLeuGluGluValGluAla
AlaGlyIleThrLeuGlyMetAspGluLeuTyrLysLysAspGluLeu <SEQ ID No.: 106; DNA; Artificial sequence>
ACGGCGACGCGAACCTCGCCGACC <SEQ ID No.: 107; DNA; Artificial sequence>
CCTCGTCGTTGTGGCGGATCTTG <SEQ ID No.: 108; DNA; Artificial sequence>
CGCACCATCTCCTTCAAGGACG <SEQ ID No.: 109; DNA; Artificial sequence>
CTCCTGGACGTAGCCTTCCC <SEQ ID No.: 110; DNA; Artificial sequence>
GAACGGCATCAAGGCGAACTTCAA <SEQ ID No.: 111; DNA; Artificial sequence>
TTCTGCTTGTCGGCCGTGATATAGA <SEQ ID No.: 112; PRT; Artificial sequence>
MLLSVPLLLGLLGLAAAD <SEQ ID No.: 113; PRT; Artificial sequence>
DKDGNGYISAAE <SEQ ID No.: 114; PRT; Artificial sequence>
EEEIREAFRVFDKDGNGYISAAELRHVMTNL <SEQ ID No.: 115; DNA; Artificial sequence>
TATTACGTGTTCGCTGGCTaGCGTTTaACTTaAGCTTATGGGGGCCAGAGCAGTGTCCGAG
CTGCGGCTGGCACTGCTGTTTGTACTGGTGCTAGGGACGCCCAGGTTAGGGGTCCAGGG
GGAAGATGGGTTGGACTTCCCTGAGTACGACGGTGTGGACCGTGTGATCAATGTGAATGC
CAAGAACTACAAGAACGTGTTTAAGAAGTATGAGGTGCTGGCCCTCCTCTACCATGAGCCC

```
CCTGAGGACGACAAGGCCTCGCAGAGACAATTTGAGATGGAGGAGCTAATCCTGGAGTTA
GCAGCCCAAGTCTTAGAAGACAAGGGTGTTGGCTTTGGCCTGGTGGACTCAGAGAAGGAT
GCAGCTGTGGCCAAGAAACTAGGACTAACTGAAGAAGACAGCGTTTATGTGTTCAAAGGA
GATGAAGTCATTGAATATGACGGCGAGTTTTCTGCAGACACTCTGGTGGAGTTTCTGCTTG
ATGTCCTAGAAGACCCTGTAGAGTTGATTGAAGGTGAACGAGAGCTGCAGGCATTTGAGA
ATATTGAAGATGAAATCAAACTCATTGGCTACTTCAAGAGCAAAGACTCAGAGCATTACAAA
GCCTACGAGGACGCAGCTGAAGAGTTCCATCCCTACATCCCTTTCTTCGCTACCTTCGACA
GCAAGGTGGCAAAGAAGCTGACTCTGAAGTTAATGAGATTGATTTCTACGAGGCCTTCAT
GGAAGAGCCTATGACCATCCCAGACAAGCCCAACAGTGAAGAGGAGATTGTGAGCTTCGT
GGAGGAGCACAGGAGATCAACCCTGAGGAAACTGAAGCCTGAGAGTATGTACGAGACTTG
GGAGGATGACCTGGATGGAATCCACACTGTCGCCTTTGCAGAGGAAGCAGATCCTGATGG
CTATGAGTTCTTAGAGACTCTCAAGGCTGTGGCCCAAGACAACACTGAGAACCCCGACCT
CAGTATCATCTGGATTGATCCTGATGACTTCCCGCTGCTGGTCCCGTACTGGGAGAAGAC
CTTTGACATTGACCTGTCAGCTCCACAAATAGGAGTTGTCAATGTTACAGACGCGGACAGC
ATATGGATGGAGATGGATAACGAGGAGGACCTGCCTTCTGCTGATGAGCTGGAGGACTGG
CTGGAGGACGTGCTGGAGGGCGAGATCAACACAGAGGATGACGACGACGATGACGACGA
TGACGATGATGACGATGATGACGACGACGGATCCGGGCCCTCTAGAATGGTGAGCAAGG
GCGAGGAGCTGTTCACCGGGGTTGGTGCCCATCCTGGTCGAGCTGGACGGCGACGTAAAC
GGCCACAAGTTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCCTCGTGACCAC
CCTGACCTACGGCGTGCAGTGCTTCAGCCGCTACCCCGACCACATGAAGCAGCACGACTT
CTTCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTGGAG
TACAACTACAACGAGCACAACGTCTATATCACGGCCGACAAGCAGAAGAACGGCATCAAG
GCGAACTTCAAGATCCGCCACAACATCGAGGACGGCAGCGTGCAGCTCGCCGACCACTA
CCAGCAGAACACCCCCATCGGCGACGGCCCCGTGCTGCTGCCCGACAACCACTACCTGG
ACACCGAATCCGCCCTGAGCAAAGACCCCAACGAGAAGCGCGATCACATGGTCCTGCTG
GAGGAGGTGGAGGCCGCCGGGATCACTCTCGGCATGGACGAGCTGTACAAGTAAGAATT
CTGCAGATATCCAGCACAGTGGCGGCCGCTCGAGTCTAGAGGGCCCGTTTAAACCCGCT
GATCAGCCTCGACTGTGCCTTCTAGTTGCCAGCCATCTGTTGT

<SEQ ID No.: 116; PRT; Artificial sequence>
ITCSLASVLKLMGARAVSELRLALLFVLVLGTPRLGVQGEDGLDFPEYDGVDRVINVNAKNYKN
VFKKYEVLALLYHEPPEDDKASQRQFEMEELILELAAQVLEDKGVGFGLVDSEKDAAVAKKLGL
TEEDSVYVFKGDEVIEYDGEFSADTLVEFLLDVLEDPVELIEGERELQAFENIEDEIKLIGYFKSK
DSEHYKAYEDAAEEFHPYIPFFATFDSKVAKKLTLKLNEIDFYEAFMEEPMTIPDKPNSEEEIVSF
VEEEHRRSTLRKLKPESMYETVVEDDLDGIHTVAFAEEEADPDGYEFLETLKAVAQDNTENPDLSII
WIDPDDFPLLVPYWEKTFDIDLSAPQIGVVNVTDADSIWMEMDNEEDLPSADELEDWLEDVLE
GEINTEDDDDDDDDDDDDDDDGSGPSRMVSKGEELFTGWPILVELDGDVNGHKFSVSGE
GEGDATYGKLTLKFICTTGKLPVPWPTLVTTLTYGVQCFSRYPDHMKQHDFFKSAMPEGYVQ
ERTIFFKDDGNYKTRAEVKFEGDTLVNRIELKGIDFKEDGNILGHKLEYNYNEHNVYITADKQKN
GIKANFKIRHNIEDGSVQLADHYQQNTPIGDGPVLLPDNHYLDTESALSKDPNEKRDHMVLLEE
VEAAGITLGMDELYK-EFXXQISSTVAAARV-RARLNPLISLDCAF-LPAICC <SEQ ID No.: 117; DNA; Artificial sequence>
TATTACGTGTTCGCTGGCTaGCGTTTaACTTaAGCTTATGGGGGCCAGAGCAGTGTCCGAG
CTGCGGCTGGCACTGCTGTTTGTACTGGTGCTAGGGACGCCCAGGTTAGGGGTCCAGGG
GGAAGATGGGTTGGACTTCCCTGAGTACGACGGTGTGGACCGTGTGATCAATGTGAATGC
CAAGAACTACAAGAACGTGTTTAAGAAGTATGAGGTGCTGGCCCTCCTCTACCATGAGCCC
CCTGAGGACGACAAGGCCTCGCAGAGACAATTTGAGATGGAGGAGCTAATCCTGGAGTTA
GCAGCCCAAGTCTTAGAAGACAAGGGTGTTGGCTTTGGCCTGGTGGACTCAGAGAAGGAT
GCAGCTGTGGCCAAGAAACTAGGACTAACTGAAGAAGACAGCGTTTATGTGTTCAAAGGA
GATGAAGTCATTGAATATGACGGCGAGTTTTCTGCAGACACTCTGGTGGAGTTTCTGCTTG
ATGTCCTAGAAGACCCTGTAGAGTTGATTGAAGGTGAACGAGAGCTGCAGGCATTTGAGA
ATATTGAAGATGAAATCAAACTCATTGGCTACTTCAAGAGCAAAGACTCAGAGCATTACAAA
GCCTACGAGGACGCAGCTGAAGAGTTCCATCCCTACATCCCTTTCTTCGCTACCTTCGACA
GCAAGGTGGCAAAGAAGCTGACTCTGAAGTTAATGAGATTGATTTCTACGAGGCCTTCAT
GGAAGAGCCTATGACCATCCCAGACAAGCCCAACAGTGAAGAGGAGATTGTGAGCTTCGT
GGAGGAGCACAGGAGATCAACCCTGAGGAAACTGAAGCCTGAGAGTATGTACGAGACTTG
GGAGGATGACCTGGATGGAATCCACACTGTCGCCTTTGCAGAGGAAGCAGATCCTGATGG
CTATGAGTICTTAGAGACTCTCAAGGCTGTGGCCCAAGACAACACTGAGAACCCCGACCT
CAGTATCATCTGGATTGATCCTGATGACTTCCCGCTGCTGGTCCCGTACTGGGAGAAGAC
CTTTGACATTGACCTGTCAGCTCCACAAATAGGAGTTGTCAATGTTACAGACGCGGACAGC
ATATGGATGGAGATGGATAACGAGGAGGACCTGCCTTCTGCTGATGAGCTGGAGGACTGG
CTGGAGGACGTGCTGGAGGGCGAGATCAACACAGAGTGATGACGATGATGACGACGACG
GATCCGGGCCCTCTAGAATGGTGAGCAAGGGCGAGGAGCTGTTCACCGGGGTGGTGCCC
ATCCTGGTCGAGCTGGACGGCGACGTAAACGGCCACAAGTTCAGCGTGTCCGGCGAGGG
CGAGGGCGATGCCACCTACGGCAAGCTGACCCTGAAGTTCATCTGCACCACCGGCAAGC
TGCCCGTGCCCTGGCCCACCCTCGTGACCACCCTGACCTACGGCGTGCAGTGCTTCAGC
CGCTACCCCGACCACATGAAGCAGCACGACTTCTTCAAGTCCGCCATGCCCGAAGGCTAC
GTCCAGGAGCGCACCATCTTCTTCAAGGACGACGGCAACTACAAGACCCGCGCCGAGGT
GAAGTTCGAGGGCGACACCCTGGTGAACCGCATCGAGCTGAAGGGCATCGACTTCAAGG
AGGACGGCAACATCCTGGGGCACAAGCTGGAGTACAACTACAACGAGCACAACGTCTATA
TCACGGCCGACAAGCAGAAGAACGGCATCAAGGCGAACTTCAAGATCCGCCACAACATCG
AGGACGGCAGCGTGCAGCTCGCCGACCACTACCAGCAGAACACCCCCATCGGCGACGGC
CCCGTGCTGCTGCCCGACAACCACTACCTGGACACCGAATCCGCCCTGAGCAAAGACCC
CAACGAGAAGCGCGATCACATGGTCCTGCTGGAGGAGGTGGAGGCCGCCGGGATCACTC
TCGGCATGGACGAGCTGTACAAGTAAGAATTCTGCAGATATCCAGCACAGTGGCGGCCGC
TCGAGTCTAGAGGGCCCGTTTAAACCCGCTGATCAGCCTCGACTGTGCCTTCTAGTTGCC
AGCCATCTGTTGT
```

-continued

<SEQ ID No.: 118; PRT; Artificial sequence>
ITCSLASVLKLMGARAVSELRLALLFVLVLGTPRLGVQGEDGLDFPEYDGVDRVINVNAKNYKN
VFKKYEVLALLYHEPPEDDKASQRQFEMEELILELAAQVLEDKGVGFGLVDSEKDAAVAKKLGL
TEEDSVYVFKGDEVIEYDGEFSADTLVEFLLDVLEDPVELIEGERELQAFENIEDEIKLIGYFKSK
DSEHYKAYEDAAEEFHPYIPFFATFDSKVAKKLTLKLNEIDFYEAFMEEPMTIPDKPNSEEEIVSF
VEEHRRSTLRKLKPESMYETWEDDLDGIHTVAFAEEADPDGYEFLETLKAVAQDNTENPDLSII
WIDPDDFPLLVPYWEKTFDIDLSAPQIGVVNVTDADSIWMEMDNEEDLPSADELEDWLEDVLE
GEINTEGSGPSRMVSKGEELFTGVVPILVELDGDVNGHKFSVSGEGEGDATYGKLTLKFICTTG
KLPVPWPTLVTTLTYGVQCFSRYPDHMKQHDFFKSAMPEGYVQERTIFFKDDGNYKTRAEVK
FEGDTLVNRIELKGIDFKEDGNILGHKLEYNYNEHNVYITADKQKNGIKANFKIRHNIEDGSVQLA
DHYQQNTPIGDGPVLLPDNHYLDTESALSKDPNEKRDHMVLLEEVEAAGITLGMDELYKEFXX
QISSTVAAARVRARLNPLISLDCAFLPAICC <SEQ ID No.: 119; PRT; Artificial sequence>
FCLTLRRRYTMGSSHHHHHHSSGLVPRGSHMASMTGGQQMGRGSGPSRMVSKGEELFTGV
VPILVELDGDVNGHKFSVSGEGEGDATYGKLTLKFICTTGKLPVPWPTLVTTLTYGVQCFSRYP
DHMKQHDFFKSAMPEGYVQERTIFFKDDGNYKTRAEVKFEGDTLVNRIELKGIDFKEDGNILGH
KLEYNYNEHNVYITADKQKNGIKANFKIRHNIEDGSVQLADHYQQNTPIGDGPVLLPDNHYLDIE
SALSKDPNEKRDHMVLLEEVEAAGITLGMDELYKEFELRRQACGRTRVPPPPPLRSGCQSPK
GSXGCCPTPLPXXRIRPXQRPXXSAXXXXCX <SEQ ID No.: 120; PRT; Artificial sequence>
XITCSLASVLKLGTELGSGPSRMVSKGEELFTGVVPILVELDGDVNGHKFSVSGEGEGDATYG
KLTLKFICTTGKLPVPWPTLVTTLTYGVQCFSRYPDHMKQHDFFKSAMPEGYVQERTIFFKDD
GNYKTRAEVKFEGDTLVNRIELKGIDFKEDGNILGHKLEYNYNEHNVYITADKQKNGIKANFKIR
HNIEDGSVQLADHYQQNTPIGDGPVLLPDNHYLDTESALSKDPNEKRDHMVLLEEVEAAGITLG
MDELYKFYTLRFLALFLAFAINFILLFYKVSEFCRYPAQWRPLESRGPVTRSASTVPSSCQPSV <SEQ ID No.: 121; PRT3; > (D8-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnSerHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGlnSerAlaLeuSerLysAspProAsnGluLysArgAspHisIleVal
LeuLeuGluGluValThrAlaAlaGlyIleThrLeuGlyMetAspGluLeuTyrLys <SEQ ID No.: 122; PRT3; > (D9-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGlnSerAlaLeuSerLysAspProAsnGluLysArgAspHisIleVal
LeuLeuGluGluValThrAlaAlaGlyIleThrLeuGlyMetAspGluLeuTyrLys <SEQ ID No.: 123; PRT3; > (D10-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGlnSerAlaLeuSerLysAspProAsnGluLysArgAspHisIleVal
LeuLeuGluGluValGluAlaAlaGlyIleThrLeuGlyMetAspGluLeuTyrLys <SEQ ID No.: 124; PRT3; > (D11-EGFP, CatchER without ER tag)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluGluValGluAlaAlaGlyIleThrLeuGlyMetAspGluLeuTyrLys <SEQ ID No.: 125; PRT3; > (D11-EGFP, CatchER with ER tag)
MetLeuLeuSerValProLeuLeuLeuGlyLeuLeuGlyLeuAlaAlaAlaAspValSerLysGlyGluGluLeuPheThr
GlyValValProIleLeuValGluLeuAspGlyAspLeuAsnGlyHisLysPheSerValSerGlyGluGlyGluGlyAsp
AlaThrTyrGlyLysLeuThrLeuLysPheIleCysThrThrGlyLysLeuProValProTrpProThrLeuValThrThr
LeuThrTyrGlyValGlnCysPheSerArgTyrProAspHisMetLysGlnHisAspPhePheLysSerAlaMetProGlu
GlyTyrValGlnGluArgThrIlePhePheLysAspAspGlyAsnTyrLysThrArgAlaGluValLysPheGluGlyAsp
ThrLeuValAsnArgIleGluLeuLysGlyIleAspPheLysGluAspGlyAsnIleLeuGlyHisLysLeuGluTyrAsn
TyrAsnGluHisAsnValTyrIleThrAlaAspLysGlnLysAsnGlyIleLysAlaAsnPheLysIleArgHisAsnIleGlu -continued AspGlySerValGlnLeuAlaAspHisTyrGlnGlnAsnThrProIleGlyAspGlyProValLeuLeuProAspAsnHis
TyrLeuAspThrGluSerAlaLeuSerLysAspProAsnGluLysArgAspHisIleValLeuLeuGluGluValGluAla
AlaGlyIleThrLeuGlyMetAspGluLeuTyrLysLysAspGluLeu <SEQ ID No.: 126; PRT3; > (D12-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluAspValGluAlaAlaGlyIleThrLeuGlyMetAspGluLeuTyrLys <SEQ ID No.: 127; PRT3; > (D13-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrAsnSerAlaLeuSerLysAspProAsnGluLysArgAspHisIle
ValLeuLeuGluAspValGluAlaAlaGlyIleThrLeuGlyMetAspGluLeuTyrLys <SEQ ID No.: 128; PRT3; > (D14-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisGluValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGlnSerAlaLeuSerLysAspProAsnGluLysArgAspHisIleVal
LeuLeuGluValThrAlaAlaGlyIleThrLeuGlyMetAspGluLeuTyrLys <SEQ ID No.: 129; PRT3; > (D15-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluGluValThrAlaAlaGlyIleThrLeuGlyMetAspGluLeuTyrLys <SEQ ID No.: 130; PRT3; > (D16-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisGluValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluGluValGluAlaAlaGlyIleThrLeuGlyMetAspGluLeuTyrLys <SEQ ID No.: 131; PRT3; > (D11-EGFP-203I, CatchER-203I)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspIleGluSerAlaLeuSerLysAspProAsnGluLysArgAspHisIleVal
LeuLeuGluGluValGluAlaAlaGlyIleThrLeuGlyMetAspGluLeuTyrLys <SEQ ID No.: 132; PRT3; > (D11-EGFP-203V, CatchER-203V)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspValGluSerAlaLeuSerLysAspProAsnGluLysArgAspHisIleVal
LeuLeuGluGluValGluAlaAlaGlyIleThrLeuGlyMetAspGluLeuTyrLys -continued

```
<SEQ ID No.: 133; PRT3; > (D11-EGFP-203D, CatchER-203D)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspAspGluSerAlaLeuSerLysAspProAsnGluLysArgAspHisIle
ValLeuLeuGluGluValGluAlaAlaGlyIleThrLeuGlyMetAspGluLeuTyrLys <SEQ ID No.: 134; PRT3; > (D11-EGFP-203F, CatchER-203F)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspPheGluSerAlaLeuSerLysAspProAsnGluLysArgAspHisIle
ValLeuLeuGluGluValGluAlaAlaGlyIleThrLeuGlyMetAspGluLeuTyrLys <SEQ ID No.: 135; PRT3; > (D11-EGFP-203E, CatchER-203E)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspGluGluSerAlaLeuSerLysAspProAsnGluLysArgAspHisIleVal
LeuLeuGluGluValGluAlaAlaGlyIleThrLeuGlyMetAspGluLeuTyrLys <SEQ ID No.: 136; PRT3; > (D11-EGFP-175G, CatchER-175G)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlyGlyValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluGluValGluAlaAlaGlyIleThrLeuGlyMetAspGluLeuTyrLys <SEQ ID No.: 137; PRT3; > (D11-EGFP-148D, CatchER-148D)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluAspAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGly
ProValLeuLeuProAspAsnHisTyrLeuAspThrGluSerAlaLeuSerLysAspProAsnGluLysArgAspHisIle
ValLeuLeuGluGluValGluAlaAlaGlyIleThrLeuGlyMetAspGluLeuTyrLys <SEQ ID No.: 138; PRT3; > (G1M1-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnAspIleGluLeuLysGlyIleAspPheLysGluAspGlyAsnIle
LeuGlyHisLysLeuGluTyrAsnTyrAsnSerHisAsnValTyrIleThrAlaAspLysGlnLysAsnGlyIleLysAlaAsn
PheLysIleArgHisAsnIleGluGluGluIleArgGluAlaPheArgValPheAspLysAspGlyAsnGlyTyrIleSer
AlaAlaGluLeuArgHisValMetThrAsnLeuAspGlySerValGlnLeuAlaAspHisTyrGlnGlnAsnThrProIle
GlyAspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys <SEQ ID No.: 139; PRT3; > (G1M2-EGFP)
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnSerHisAsnValTyrIleThrAlaAspLysGlnLysAsnGlyIleLysAlaAsn
PheLysIleArgHisAsnIleGluGluGluGluIleArgGluAlaPheArgValPheAspLysAspGlyAsnGlyTyrIleSer
AlaAlaGluLeuArgHisValMetThrAsnLeuAspGlySerValGlnLeuAlaAspHisTyrGlnGlnAsnThrProIle
GlyAspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys
```

```
<SEQ ID No.: 140; PRT; > (calsequestrin tethered CatchER)
ITCSLASVLKLMGARAVSELRLALLFVLVLGTPRLGVQGEDGLDFPEYDGVDRVINVNAKNYKN
VPKKYEVLALLYHEPPEDDKASQRQFEMEELILELAAQVLEDKGVGFGLVDSEKDAAVAKKLGL
TEEDSVYVFKGDEVIEYDGEFSADTLVEFLLDVLEDPVELIEGERELQAFENIEDEIKLIGYFKSK
DSEHYKAYEDAAEEFHPYIPFFATFDSKVAKKLTLKLNEIDFYEAFMEEPMTIPDKPNSEEEIVSF
VEEHRRSTLRKLKPESMYETVVEDDLDGIHTVAFAEEEADPDGYEFLETLKAVAQDNTENPDLSII
WIDPDDFPLLVPYWEKTFDIDLSAPQIGVVNVTDADSIWMEMDNEEDLPSADELEDWLEDVLE
GEINTEDDDDDDDDDDDDDDDDGSGPSRMVSKGEELFTGVVPILVELDGDVNGHKFSVSGE
GEGDATYGKLTLKFICTTGKLPVPWPTLVTTLTYGVQCFSRYPDHMKQHDFFKSAMPEGYVQ
ERTIFFKDDGNYKTRAEVKFEGDTLVNRIELKGIDFKEDGNILGHKLEYNYNEHNVYITADKQKN
GIKANFKIRHNIEDGSVQLADHYQQNTPIGDGPVLLPDNHYLDTESALSKDPNEKRDHMVLLEE
VEAAGITLGMDELYK-EFXXQISSTVAAARV-RARLNPLISLDCAF-LPAICC <SEQ ID No.: 141; PRT; > (calsequestrin 17 Asp deleted tethered CatchER)
ITCSLASVLKLMGARAVSELRLALLFVLVLGTPRLGVQGEDGLDFPEYDGVDRVINVNAKNYKN
VPKKYEVLALLYHEPPEDDKASQRQFEMEELILELAAQVLEDKGVGFGLVDSEKDAAVAKKLGL
TEEDSVYVFKGDEVIEYDGEFSADTLVEFLLDVLEDPVELIEGERELQAFENIEDEIKLIGYFKSK
DSEHYKAYEDAAEEFHPYIPFFATFDSKVAKKLTLKLNEIDFYEAFMEEPMTIPDKPNSEEEIVSF
VEEHRRSTLRKLKPESMYETVVEDDLDGIHTVAFAEEEADPDGYEFLETLKAVAQDNTENPDLSII
WIDPDDFPLLVPYWEKTFDIDLSAPQIGVVNVTDADSIWMEMDNEEDLPSADELEDWLEDVLE
GEINTEGSGPSRMVSKGEELFTGVVPILVELDGDVNGHKFSVSGEGEGDATYGKLTLKFICTTG
KLPVPWPTLVTTLTYGVQCFSRYPDHMKQHDFFKSAMPEGYVQERTIFFKDDGNYKTRAEVK
FEGDTLVNRIELKGIDFKEDGNILGHKLEYNYNEHNVYITADKQKNGIKANFKIRHNIEDGSVQLA
DHYQQNTPIGDGPVLLPDNHYLDTESALSKDPNEKRDHMVLLEEVEAAGITLGMDELYKEFXX
QISSTVAAARVRARLNPLISLDCAFLPAICC <SEQ ID No. 142: D8-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnSerHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGlnSerAlaLeuSerLysAspProAsnGluLysArgAspHisIleVal
LeuLeuGluGluValThrAlaAlaGlyIleThrLeuGlyMetAspGluLeuTyrLys <SEQ ID No. 143: D9-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGlnSerAlaLeuSerLysAspProAsnGluLysArgAspHisIleVal
LeuLeuGluGluValThrAlaAlaGlyIleThrLeuGlyMetAspGluLeuTyrLys <SEQ ID No. 144: D10-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGlnSerAlaLeuSerLysAspProAsnGluLysArgAspHisIleVal
LeuLeuGluGluValGluAlaAlaGlyIleThrLeuGlyMetAspGluLeuTyrLys <SEQ ID No. 145: D11-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluGluValGluAlaAlaGlyIleThrLeuGlyMetAspGluLeuTyrLys <SEQ ID No. 146: D12-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrAra
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluAspValGluAlaAlaGlyIleThrLeuGlyMetAspGluLeuTyrLys
```

<SEQ ID No. 147: D13-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsn
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrAsnSerAlaLeuSerLysAspProAsnGluLysArgAspHisIle
ValLeuLeuGluAspValGluAlaAlaGlyIleThrLeuGlyMetAspGluLeuTyrLys

<SEQ ID No. 148: D14-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisGluValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGlnSerAlaLeuSerLysAspProAsnGluLysArgAspHisIleVal
LeuLeuGluGluValThrAlaAlaGlyIleThrLeuGlyMetAspGluLeuTyrLys

<SEQ ID No. 149: D15-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisGluValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluGluValThrAlaAlaGlyIleThrLeuGlyMetAspGluLeuTyrLys

<SEQ ID No. 150: D16-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisGluValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspThrGluSerAlaLeuSerLysAspProAsnGluLysArgAspHisIleVal
LeuLeuGluGluValGluAlaAlaGlyIleThrLeuGlyMetAspGluLeuTyrLys

<SEQ ID No. 151: D11-EGFP-203I>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspIleGluSerAlaLeuSerLysAspProAsnGluLysArgAspHisIleVal
LeuLeuGluGluValGluAlaAlaGlyIleThrLeuGlyMetAspGluLeuTyrLys

<SEQ ID No. 152: D11-EGFP-203V>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspValGluSerAlaLeuSerLysAspProAsnGluLysArgAspHisIleVal
LeuLeuGluGluValGluAlaAlaGlyIleThrLeuGlyMetAspGluLeuTyrLys

<SEQ ID No. 153: D11-EGFP-203D>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspAspGluSerAlaLeuSerLysAspProAsnGluLysArgAspHisIle
ValLeuLeuGluGluValGluAlaAlaGlyIleThrLeuGlyMetAspGluLeuTyrLys

<SEQ ID No. 154: D11-EGFP-203F>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp

-continued

PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspPheGluSerAlaLeuSerLysAspProAsnGluLysArgAspHisIle
ValLeuLeuGluGluValGluAlaAlaGlyIleThrLeuGlyMetAspGluLeuTyrLys

<SEQ ID No. 155: D11-EGFP-203E>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlySerValGlnLeuAlaAspHisTyrGlnGlnAsnThrProIleGlyAspGlyPro
ValLeuLeuProAspAsnHisTyrLeuAspGluGluSerAlaLeuSerLysAspProAsnGluLysArgAspHisIleVal
LeuLeuGluGluValGluAlaAlaGlyIleThrLeuGlyMetAspGluLeuTyrLys

<SEQ ID No. 156: D11-EGFP-175G>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluHisAsnValTyrIleThrAlaAspLysGlnLysAsnGlyIleLysAlaAsn
PheLysIleArgHisAsnIleGluAspGlyValGlnLeuAlaAspHisTyrGlnGlnAsnThrProIleGlyAspGlyPro
ValLeuLeuProAspAsnHisTyrLeuProThrGluSerAlaLeuSerLysAspProAsnGluLysArgAspHisIleVal
LeuLeuGluGluValGluAlaAlaGlyIleThrLeuGlyMetAspGluLeuTyrLys

<SEQ ID No. 157: D11-EGFP-148D>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuLysGlyIleAspPheLysGluAspGlyAsnIle
LeuGlyHisLysLeuGluTyrAsnTyrAsnGluAspAsnValTyrIleThrAlaAspLysGlnLysAsnGlyIleLysAlaAsn
snPheLysIleArgHisAsnIleGluAspGlySerValGlnLeuAlaAspHisTyrGlnGlnAsnThrProIleGlyAspGly
ProValLeuLeuProAspAsnHisTyrLeuAspThrGluSerAlaLeuSerLysAspProAsnGluLysArgAspHisIle
ValLeuLeuGluGluValGluAlaAlaGlyIleThrLeuGlyMetAspGluLeuTyrLys

<SEQ ID No. 158: G1M1-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnAspIleGluLeuLysGlyIleAspPheLysGluAspGlyAsnIle
LeuGlyHisLysLeuGluTyrAsnTyrAsnSerHisAsnValTyrIleThrAlaAspLysGlnLysAsnGlyIleLysAlaAsn
PheLysIleArgHisAsnIleGluGluGluGluIleArgGluAlaPheArgValPheAspLysAspGlyAsnGlyTyrIleSer
AlaAlaGluLeuArgHisValMetThrAsnLeuAspGlySerValGlnLeuAlaAspHisTyrGlnGlnAsnThrProIle
GlyAspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys

<SEQ ID No. 159: G1M2-EGFP>
ValSerLysGlyGluGluLeuPheThrGlyValValProIleLeuValGluLeuAspGlyAspLeuAsnGlyHisLysPhe
SerValSerGlyGluGlyGluGlyAspAlaThrTyrGlyLysLeuThrLeuLysPheIleCysThrThrGlyLysLeuProVal
ProTrpProThrLeuValThrThrLeuThrTyrGlyValGlnCysPheSerArgTyrProAspHisMetLysGlnHisAsp
PhePheLysSerAlaMetProGluGlyTyrValGlnGluArgThrIlePhePheLysAspAspGlyAsnTyrLysThrArg
AlaGluValLysPheGluGlyAspThrLeuValAsnArgIleGluLeuGluGlyIlePheLysGluAspGlyAsnIle
LeuGlyHisLysLeuGluTyrAsnTyrAsnSerHisAsnValTyrIleThrAlaAspLysGlnLysAsnGlyIleLysAlaAsn
PheLysIleArgHisAsnIleGluGluGluGluIleArgGluAlaPheArgValPheAspLysAspGlyAsnGlyTyrIleSer
AlaAlaGluLeuArgHisValMetThrAsnLeuAspGlySerValGlnLeuAlaAspHisTyrGlnGlnAsnThrProIle
GlyAspGlyProValLeuLeuProAspAsnHisTyrLeuSerThrGlnSerAlaLeuSerLysAspProAsnGluLysArg
AspHisIleValLeuLeuGluPheValThrAlaAlaGlyIleThrLeuGlyMetAspGluLeuTyrLys

The invention claimed is:

1. An analyte sensor comprising an engineered fluorescent host polypeptide having a metal ion binding site comprising a plurality of negatively-charged amino acid residues providing a plurality of oxygen atoms orientated in a pentagonal bipyrimdal geometry, wherein said metal ion binding site interacts with a chromophore region of the engineered fluorescent host polypeptide such that binding of a metal ion analyte to the metal ion binding site modulates the emission of a fluorescent signal emitted by the fluorescent host polypeptide or modulates the absorbance spectrum of the engineered fluorescent host polypeptide, and wherein the negatively-charged amino acids are at positions 147, 202, 204, and 223, and optionally at positions 149 and 225, according to the amino acid sequence SEQ ID NO: 104.

2. The analyte sensor of claim 1, wherein the analyte sensor includes a targeting motif for selectively targeting an endoplasmic reticulum, a sarcoplasmic reticulum, or a mitochondrion of a cell.

3. The analyte sensor of claim 1, wherein the analyte sensor includes a targeting motif for selectively targeting an endoplasmic reticulum of a cell.

4. The analyte sensor of claim 1, wherein the analyte sensor binds to a metal ion selected from the group consisting of: calcium, lead, gadolinium, lanthanum, terbium, antimony, strontium, mercury, and cadmium.

5. The analyte sensor of claim 1, wherein the analyte sensor in the absence of a metal ion analyte emits a first fluorescent signal and in the presence of a metal ion analyte bound to the analyte sensor emits a second fluorescent signal, wherein the first and the second fluorescent signals are distinguishably detectable.

6. The analyte sensor of claim 1, wherein the negatively-charged amino acid residues are on the surface of three antiparallel beta-sheets or on three strands of the protein having a beta-can structure.

7. A method of detecting a metal ion analyte, comprising:
   (i) providing an analyte sensor according to claim 1;
   (ii) providing a test sample suspected of comprising the metal ion analyte having affinity for the metal ion binding site of the analyte sensor;
   (iii) detecting a first fluorescent signal emitted by the analyte sensor in the absence of a test sample suspected of comprising said metal ion analyte;
   (iv) contacting the analyte sensor with the test sample;
   (v) detecting a second fluorescent signal emitted by the analyte sensor in contact with the test sample; and
   (vi) comparing the first fluorescent signal and the second fluorescent signal, wherein a ratiometric change in the signal indicates a metal ion analyte in the test sample is interacting with the analyte sensor.

8. The method of claim 7, wherein if the first fluorescent signal and the second fluorescent signal differ in their wavelengths, in their intensities, or in both their wavelengths and their intensities, an interaction between said metal ion analyte and the analyte sensor is indicated.

9. The method of claim 7, further comprising the step of determining from the ratiometric change a quantitative measurement of the metal ion analyte in the test sample.

10. The method of claim 7, wherein the metal ion analyte is selected from the group consisting of: calcium, lead, gadolinium, lanthanum, terbium, antimony, strontium, mercury, and cadmium.

11. A recombinant nucleic acid encoding an analyte sensor according to claim 1.

12. The recombinant nucleic acid of claim 11, further comprising a vector nucleic acid sequence.

13. The recombinant nucleic acid of claim 11, wherein the recombinant nucleic acid is in a genetically modified cell.

14. A method for characterizing the cellular activity of a metal ion analyte comprising:
   (i) providing a genetically-modified cell expressing an analyte sensor according to claim 1;
   (ii) detecting a first fluorescent signal emitted by the analyte sensor from said cell;
   (iii) detecting a second fluorescent signal emitted by the analyte sensor after the induction of a physiological event in the cell; and
   (iv) comparing the first and the second fluorescent signals wherein, if the first and the second fluorescent signals differ in at least one of their wavelengths or their intensities, a change in the level of the analyte in the cell induced by the physiological event in said cell is indicated, and wherein the metal ion analyte is calcium, lead, gadolinium, lanthanum, terbium, antimony, strontium, mercury, or cadmium.

15. A method of detecting a metal ion analyte, comprising:
   (i) providing an analyte sensor according to claim 1;
   (ii) providing a test sample suspected of comprising a metal ion analyte having affinity for the metal ion binding site of the analyte sensor;
   (iii) detecting either (a) a first absorption signal derived from the analyte sensor in the absence of a the test sample or (b) a first fluorescent signal emitted by the analyte sensor in the absence of the test sample;
   (iv) contacting the analyte sensor with the test sample;
   (v) detecting either (a) a second absorption signal derived from the analyte sensor in contact with the test sample, or (b) a second fluorescent signal emitted by the analyte sensor in contact with the test sample; and
   (vi) comparing either (a) the first and the second absorption signals, wherein a ratiometric change in the absorption signal indicates said metal ion analyte in the test sample is interacting with the analyte sensor, or (b) the first and the second fluorescent signal, wherein a ratiometric change flouresent signal indicates said metal ion analyte in the test sample is interacting with the analyte sensor.

* * * * *

SEQUENCE LISTING

<160> NUMBER OF SEQ ID NOS: 159

<210> SEQ ID NO 1
<211> LENGTH: 251
<212> TYPE: PRT
<213> ORGANISM: Artificial sequence
<220> FEATURE:
<223> OTHER INFORMATION: Synthetic EGFP

<400> SEQUENCE: 1

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asn Gly Tyr Ile Ser Ala Ala Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 2
<211> LENGTH: 262
<212> TYPE: PRT
<213> ORGANISM: Artificial sequence
<220> FEATURE:
<223> OTHER INFORMATION: Synthetic EGFP

<400> SEQUENCE: 2

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
            260

<210> SEQ ID NO 3
<211> LENGTH: 259
<212> TYPE: PRT
<213> ORGANISM: Artificial sequence
<220> FEATURE:
<223> OTHER INFORMATION: Synthetic EGFP

<400> SEQUENCE: 3

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asn Gly Tyr Ile Ser Ala Ala Glu Leu Arg His Val Met Thr Asn
            180                 185                 190

Leu Asp Gly Ser Val Gln Leu Ala Asp His Tyr Gln Gln Asn Thr Pro
        195                 200                 205

```
Ile Gly Asp Gly Pro Val Leu Leu Pro Asp Asn His Tyr Leu Ser Thr
    210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys
```

```
<210> SEQ ID NO 4
<211> LENGTH: 270
<212> TYPE: PRT
<213> ORGANISM: Artificial sequence
<220> FEATURE:
<223> OTHER INFORMATION: Synthetic EGFP

<400> SEQUENCE: 4

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270
```

```
<210> SEQ ID NO 5
<211> LENGTH: 298
<212> TYPE: PRT
<213> ORGANISM: Artificial sequence
<220> FEATURE:
<223> OTHER INFORMATION: Synthetic EGFP
```

-continued

<400> SEQUENCE: 5

```
Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
                35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Met Ala Asp Lys Gln Lys Asn Gly Ile Lys Val Asn Phe Lys Ile
            180                 185                 190

Arg His Asn Ile Glu Glu Glu Ile Arg Glu Ala Phe Arg Val Phe
        195                 200                 205

Asp Lys Asp Gly Asn Gly Tyr Ile Ser Ala Ala Glu Leu Arg His Val
    210                 215                 220

Met Thr Asn Leu Asp Gly Ser Val Gln Leu Ala Asp His Tyr Gln Gln
225                 230                 235                 240

Asn Thr Pro Ile Gly Asp Gly Pro Val Leu Leu Pro Asp Asn His Tyr
                245                 250                 255

Leu Ser Thr Gln Ser Ala Leu Ser Lys Asp Pro Asn Glu Lys Arg Asp
            260                 265                 270

His Ile Val Leu Leu Glu Phe Val Thr Ala Ala Gly Ile Thr Leu Gly
        275                 280                 285

Met Asp Glu Leu Tyr Lys Lys Asp Glu Leu
    290                 295
```

<210> SEQ ID NO 6
<211> LENGTH: 310
<212> TYPE: PRT
<213> ORGANISM: Artificial sequence
<220> FEATURE:
<223> OTHER INFORMATION: Synthetic EGFP

<400> SEQUENCE: 6

```
Met Ser Val Leu Thr Pro Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Met Val Ser Lys Gly Glu Glu Leu
        35                  40                  45
```

Phe Thr Gly Val Val Pro Ile Leu Val Glu Leu Asp Gly Asp Leu Asn
    50                  55                  60

Gly His Lys Phe Ser Val Ser Gly Glu Gly Glu Gly Asp Ala Thr Tyr
 65                  70                  75                  80

Gly Lys Leu Thr Leu Lys Phe Ile Cys Thr Thr Gly Lys Leu Pro Val
                 85                  90                  95

Pro Trp Pro Thr Leu Val Thr Thr Leu Thr Tyr Gly Val Gln Cys Phe
             100                 105                 110

Ser Arg Tyr Pro Asp His Met Lys Gln His Asp Phe Phe Lys Ser Ala
             115                 120                 125

Met Pro Glu Gly Tyr Val Gln Glu Arg Thr Ile Phe Phe Lys Asp Asp
130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                 165                 170                 175

Ile Leu Gly His Lys Leu Glu Tyr Asn Tyr Asn Ser His Asn Val Tyr
             180                 185                 190

Ile Met Ala Asp Lys Gln Lys Asn Gly Ile Lys Val Asn Phe Lys Ile
             195                 200                 205

Arg His Asn Ile Glu Glu Glu Ile Arg Glu Ala Phe Arg Val Phe
                 210                 215                 220

Asp Lys Asp Gly Asn Gly Tyr Ile Ser Ala Ala Glu Leu Arg His Val
225                 230                 235                 240

Met Thr Asn Leu Asp Gly Ser Val Gln Leu Ala Asp His Tyr Gln Gln
                 245                 250                 255

Asn Thr Pro Ile Gly Asp Gly Pro Val Leu Leu Pro Asp Asn His Tyr
             260                 265                 270

Leu Ser Thr Gln Ser Ala Leu Ser Lys Asp Pro Asn Glu Lys Arg Asp
             275                 280                 285

His Ile Val Leu Leu Glu Phe Val Thr Ala Ala Gly Ile Thr Leu Gly
             290                 295                 300

Met Asp Glu Leu Tyr Lys
305                 310

<210> SEQ ID NO 7
<211> LENGTH: 271
<212> TYPE: PRT
<213> ORGANISM: Artificial sequence
<220> FEATURE:
<223> OTHER INFORMATION: Synthetic EGFP

<400> SEQUENCE: 7

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Glu Glu
                165                 170                 175

Glu Lys Arg Glu Ala Glu Arg Val Phe Asp Lys Asp Gly Asn Gly Tyr
        180                 185                 190

Ile Ser Ala Ala Glu Leu Arg His Ala Ala Thr Asn Leu Asp Gly Ser
    195                 200                 205

Val Gln Leu Ala Asp His Tyr Gln Gln Asn Thr Pro Ile Gly Asp Gly
210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
        260                 265                 270

<210> SEQ ID NO 8
<211> LENGTH: 270
<212> TYPE: PRT
<213> ORGANISM: Artificial sequence
<220> FEATURE:
<223> OTHER INFORMATION: Synthetic EGFP

<400> SEQUENCE: 8

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asn Lys Asp Gly Asn Gly Tyr Ile
        180                 185                 190
```

Ser Ala Ala Glu Leu Arg His Val Met Thr Asn Leu Asp Gly Ser Val
            195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 9
<211> LENGTH: 270
<212> TYPE: PRT
<213> ORGANISM: Artificial sequence
<220> FEATURE:
<223> OTHER INFORMATION: Synthetic EGFP

<400> SEQUENCE: 9

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Glu Glu
                165                 170                 175

Ile Arg Glu Ala Phe Arg Val Phe Asn Lys Asn Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 10
<211> LENGTH: 270

```
<212> TYPE: PRT
<213> ORGANISM: Artificial sequence
<220> FEATURE:
<223> OTHER INFORMATION: Synthetic EGFP

<400> SEQUENCE: 10

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Asn Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 11
<211> LENGTH: 251
<212> TYPE: PRT
<213> ORGANISM: Artificial sequence
<220> FEATURE:
<223> OTHER INFORMATION: Synthetic EGFP

<400> SEQUENCE: 11

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60
```

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Lys Asp
                165                 170                 175

Gly Asp Gly Thr Ile Thr Thr Lys Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 12
<211> LENGTH: 271
<212> TYPE: PRT
<213> ORGANISM: Artificial sequence
<220> FEATURE:
<223> OTHER INFORMATION: Synthetic EGFP

<400> SEQUENCE: 12

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Arg Asn
                165                 170                 175

```
Ile Cys Asp Ile Ser Cys Asp Lys Phe Leu Asp Asp Ile Thr Asp
            180                 185                 190

Asp Ile Met Cys Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 13
<211> LENGTH: 271
<212> TYPE: PRT
<213> ORGANISM: Artificial sequence
<220> FEATURE:
<223> OTHER INFORMATION: Synthetic EGFP

<400> SEQUENCE: 13

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Arg Asn
                165                 170                 175

Ile Cys Asp Ile Ser Ala Asp Lys Phe Leu Asp Asp Ile Thr Asp
            180                 185                 190

Asp Ile Met Cys Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270
```

<210> SEQ ID NO 14
<211> LENGTH: 271
<212> TYPE: PRT
<213> ORGANISM: Artificial sequence
<220> FEATURE:
<223> OTHER INFORMATION: Synthetic EGFP

<400> SEQUENCE: 14

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Ser Arg Asn
                165                 170                 175

Ile Cys Asp Ile Ser Cys Asp Lys Phe Leu Asp Asp Ile Thr Asp
            180                 185                 190

Asp Ile Met Ala Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270
```

<210> SEQ ID NO 15
<211> LENGTH: 271
<212> TYPE: PRT
<213> ORGANISM: Artificial sequence
<220> FEATURE:
<223> OTHER INFORMATION: Synthetic EGFP

<400> SEQUENCE: 15

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
```

```
                35                  40                  45
Cys Thr Thr Gly Lys Leu Pro Val Pro Trp Pro Thr Leu Val Thr Thr
 50                  55                  60
Leu Thr Tyr Gly Val Gln Cys Phe Ser Arg Tyr Pro Asp His Met Lys
 65                  70                  75                  80
Gln His Asp Phe Phe Lys Ser Ala Met Pro Glu Gly Tyr Val Gln Glu
                 85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
                115                 120                 125
Ile Asp Phe Lys Glu Asp Gly Asn Ile Leu Gly His Lys Leu Glu Tyr
            130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Ser Arg Asn
                165                 170                 175
Ile Cys Asp Ile Ser Ala Asp Lys Phe Leu Asp Asp Ile Thr Asp
            180                 185                 190
Asp Ile Met Ala Ala Lys Lys Ile Leu Asp Ile Lys Gly Asp Gly Ser
            195                 200                 205
Val Gln Leu Ala Asp His Tyr Gln Gln Asn Thr Pro Ile Gly Asp Gly
            210                 215                 220
Pro Val Leu Leu Pro Asp Asn His Tyr Leu Ser Thr Gln Ser Ala Leu
225                 230                 235                 240
Ser Lys Asp Pro Asn Glu Lys Arg Asp His Ile Val Leu Leu Glu Phe
                245                 250                 255
Val Thr Ala Ala Gly Ile Thr Leu Gly Met Asp Glu Leu Tyr Lys
            260                 265                 270

<210> SEQ ID NO 16
<211> LENGTH: 251
<212> TYPE: PRT
<213> ORGANISM: Artificial sequence
<220> FEATURE:
<223> OTHER INFORMATION: Synthetic EGFP

<400> SEQUENCE: 16

Met Val Ser Lys Gly Glu Glu Leu Phe Thr Gly Val Val Pro Ile Leu
 1               5                  10                  15
Val Glu Leu Asp Gly Asp Leu Asn Gly His Lys Phe Ser Val Ser Gly
                20                  25                  30
Glu Gly Glu Gly Asp Ala Thr Tyr Gly Lys Leu Thr Leu Lys Phe Ile
             35                  40                  45
Cys Thr Thr Gly Lys Leu Pro Val Pro Trp Pro Thr Leu Val Thr Thr
 50                  55                  60
Leu Thr Tyr Gly Val Gln Cys Phe Ser Arg Tyr Pro Asp His Met Lys
 65                  70                  75                  80
Gln His Asp Phe Phe Lys Ser Ala Met Pro Glu Gly Tyr Val Gln Glu
                 85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
                115                 120                 125
Ile Asp Phe Lys Glu Asp Gly Asn Ile Leu Gly His Lys Leu Glu Tyr
```

```
            130                 135                 140
Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Glu Asp Gly Ser Val Gln Leu Ala
            180                 185                 190

Asp His Tyr Gln Gln Asn Thr Pro Ile Gly Asp Gly Pro Val Leu Leu
            195                 200                 205

Pro Asp Asn His Tyr Leu Ser Thr Gln Ser Ala Leu Ser Lys Asp Pro
        210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 17
<211> LENGTH: 262
<212> TYPE: PRT
<213> ORGANISM: Artificial sequence
<220> FEATURE:
<223> OTHER INFORMATION: Synthetic EGFP

<400> SEQUENCE: 17

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
```

```
                        245                 250                 255

Met Asp Glu Leu Tyr Lys
            260

<210> SEQ ID NO 18
<211> LENGTH: 259
<212> TYPE: PRT
<213> ORGANISM: Artificial sequence
<220> FEATURE:
<223> OTHER INFORMATION: Synthetic EGFP

<400> SEQUENCE: 18

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Glu Leu Arg His Val Met Thr Asn
            180                 185                 190

Leu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
    210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 19
<211> LENGTH: 270
<212> TYPE: PRT
<213> ORGANISM: Artificial sequence
<220> FEATURE:
<223> OTHER INFORMATION: Synthetic EGFP

<400> SEQUENCE: 19

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
```

```
                    20                  25                  30
Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Gly Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 20
<211> LENGTH: 298
<212> TYPE: PRT
<213> ORGANISM: Artificial sequence
<220> FEATURE:
<223> OTHER INFORMATION: Synthetic EGFP

<400> SEQUENCE: 20

Met Leu Leu Ser Val Pro Leu Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
```

```
            115                 120                 125
Gly Asn Tyr Lys Thr Arg Ala Glu Val Lys Phe Glu Gly Asp Thr Leu
        130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Glu Glu Ile Arg Glu Ala Phe Arg Val Phe
        195                 200                 205

Asp Lys Asp Gly Asn Gly Tyr Ile Ser Ala Ala Glu Leu Arg His Val
        210                 215                 220

Met Thr Asn Leu Asp Gly Ser Val Gln Leu Ala Asp His Tyr Gln Gln
225                 230                 235                 240

Asn Thr Pro Ile Gly Asp Gly Pro Val Leu Leu Pro Asp Asn His Tyr
                245                 250                 255

Leu Ser Thr Gln Ser Ala Leu Ser Lys Asp Pro Asn Glu Lys Arg Asp
            260                 265                 270

His Ile Val Leu Leu Glu Phe Val Thr Ala Ala Gly Ile Thr Leu Gly
        275                 280                 285

Met Asp Glu Leu Tyr Lys Lys Asp Glu Leu
        290                 295

<210> SEQ ID NO 21
<211> LENGTH: 310
<212> TYPE: PRT
<213> ORGANISM: Artificial sequence
<220> FEATURE:
<223> OTHER INFORMATION: Synthetic EGFP

<400> SEQUENCE: 21

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Met Val Ser Lys Gly Glu Glu Leu
        35                  40                  45

Phe Thr Gly Val Val Pro Ile Leu Val Glu Leu Asp Gly Asp Leu Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Leu Thr Tyr Gly Val Gln Cys Phe
            100                 105                 110

Ser Arg Tyr Pro Asp His Met Lys Gln His Asp Phe Phe Lys Ser Ala
        115                 120                 125

Met Pro Glu Gly Tyr Val Gln Glu Arg Thr Ile Phe Phe Lys Asp Asp
        130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
```

```
            180             185             190
Ile Thr Ala Asp Lys Gln Lys Asn Gly Ile Lys Ala Asn Phe Lys Ile
            195             200             205
Arg His Asn Ile Glu Glu Glu Ile Arg Glu Ala Phe Arg Val Phe
210             215             220
Asp Lys Asp Gly Asn Gly Tyr Ile Ser Ala Ala Glu Leu Arg His Val
225             230             235             240
Met Thr Asn Leu Asp Gly Ser Val Gln Leu Ala Asp His Tyr Gln Gln
            245             250             255
Asn Thr Pro Ile Gly Asp Gly Pro Val Leu Leu Pro Asp Asn His Tyr
            260             265             270
Leu Ser Thr Gln Ser Ala Leu Ser Lys Asp Pro Asn Glu Lys Arg Asp
            275             280             285
His Ile Val Leu Leu Glu Phe Val Thr Ala Ala Gly Ile Thr Leu Gly
            290             295             300
Met Asp Glu Leu Tyr Lys
305             310

<210> SEQ ID NO 22
<211> LENGTH: 271
<212> TYPE: PRT
<213> ORGANISM: Artificial sequence
<220> FEATURE:
<223> OTHER INFORMATION: Synthetic EGFP

<400> SEQUENCE: 22

Met Val Ser Lys Gly Glu Glu Leu Phe Thr Gly Val Val Pro Ile Leu
1               5               10              15
Val Glu Leu Asp Gly Asp Leu Asn Gly His Lys Phe Ser Val Ser Gly
            20              25              30
Glu Gly Glu Gly Asp Ala Thr Tyr Gly Lys Leu Thr Leu Lys Phe Ile
        35              40              45
Cys Thr Thr Gly Lys Leu Pro Val Pro Trp Pro Thr Leu Val Thr Thr
    50              55              60
Leu Thr Tyr Gly Val Gln Cys Phe Ser Arg Tyr Pro Asp His Met Lys
65              70              75              80
Gln His Asp Phe Phe Lys Ser Ala Met Pro Glu Gly Tyr Val Gln Glu
            85              90              95
Arg Thr Ile Phe Phe Lys Asp Asp Gly Asn Tyr Lys Thr Arg Ala Glu
        100             105             110
Val Lys Phe Glu Gly Asp Thr Leu Val Asn Arg Ile Glu Leu Lys Gly
    115             120             125
Ile Asp Phe Lys Glu Asp Gly Asn Ile Leu Gly His Lys Leu Glu Tyr
    130             135             140
Asn Tyr Asn Ser His Asn Val Tyr Ile Thr Ala Asp Lys Gln Lys Asn
145             150             155             160
Gly Ile Lys Ala Asn Phe Lys Ile Arg His Asn Ile Glu Ser Glu Glu
            165             170             175
Glu Lys Arg Glu Ala Glu Arg Val Phe Asp Lys Asp Gly Asn Gly Tyr
            180             185             190
Ile Ser Ala Ala Glu Leu Arg His Ala Ala Thr Asn Leu Asp Gly Ser
            195             200             205
Val Gln Leu Ala Asp His Tyr Gln Gln Asn Thr Pro Ile Gly Asp Gly
            210             215             220
Pro Val Leu Leu Pro Asp Asn His Tyr Leu Ser Thr Gln Ser Ala Leu
```

```
                        225                 230                 235                 240
Ser Lys Asp Pro Asn Glu Lys Arg Asp His Ile Val Leu Leu Glu Phe
                    245                 250                 255

Val Thr Ala Ala Gly Ile Thr Leu Gly Met Asp Glu Leu Tyr Lys
                260                 265                 270

<210> SEQ ID NO 23
<211> LENGTH: 270
<212> TYPE: PRT
<213> ORGANISM: Artificial sequence
<220> FEATURE:
<223> OTHER INFORMATION: Synthetic EGFP

<400> SEQUENCE: 23

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asn Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 24
<211> LENGTH: 270
<212> TYPE: PRT
<213> ORGANISM: Artificial sequence
<220> FEATURE:
<223> OTHER INFORMATION: Synthetic EGFP

<400> SEQUENCE: 24
```

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asn Lys Asn Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 25
<211> LENGTH: 270
<212> TYPE: PRT
<213> ORGANISM: Artificial sequence
<220> FEATURE:
<223> OTHER INFORMATION: Synthetic EGFP

<400> SEQUENCE: 25

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Asn Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 26
<211> LENGTH: 251
<212> TYPE: PRT
<213> ORGANISM: Artificial sequence
<220> FEATURE:
<223> OTHER INFORMATION: Synthetic EGFP

<400> SEQUENCE: 26

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asp Gly Thr Ile Thr Thr Lys Glu Asp Gly Ser Val Gln Leu Ala
            180                 185                 190
```

Asp His Tyr Gln Gln Asn Thr Pro Ile Gly Asp Gly Pro Val Leu Leu
            195                 200                 205

Pro Asp Asn His Tyr Leu Ser Thr Gln Ser Ala Leu Ser Lys Asp Pro
210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
            245                 250

<210> SEQ ID NO 27
<211> LENGTH: 271
<212> TYPE: PRT
<213> ORGANISM: Artificial sequence
<220> FEATURE:
<223> OTHER INFORMATION: Synthetic EGFP

<400> SEQUENCE: 27

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Cys Asp Lys Phe Leu Asp Asp Ile Thr Asp
            180                 185                 190

Asp Ile Met Cys Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 28
<211> LENGTH: 271
<212> TYPE: PRT
<213> ORGANISM: Artificial sequence
<220> FEATURE:

<223> OTHER INFORMATION: Synthetic EGFP

<400> SEQUENCE: 28

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Ala Asp Lys Phe Leu Asp Asp Ile Thr Asp
            180                 185                 190

Asp Ile Met Cys Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 29
<211> LENGTH: 271
<212> TYPE: PRT
<213> ORGANISM: Artificial sequence
<220> FEATURE:
<223> OTHER INFORMATION: Synthetic EGFP

<400> SEQUENCE: 29

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Cys Asp Lys Phe Leu Asp Asp Ile Thr Asp
            180                 185                 190

Asp Ile Met Ala Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 30
<211> LENGTH: 271
<212> TYPE: PRT
<213> ORGANISM: Artificial sequence
<220> FEATURE:
<223> OTHER INFORMATION: Synthetic EGFP

<400> SEQUENCE: 30

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

```
Ile Cys Asp Ile Ser Ala Asp Lys Phe Leu Asp Asp Ile Thr Asp
            180                 185                 190

Asp Ile Met Ala Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
                260                 265                 270

<210> SEQ ID NO 31
<211> LENGTH: 251
<212> TYPE: PRT
<213> ORGANISM: Artificial sequence
<220> FEATURE:
<223> OTHER INFORMATION: Synthetic EGFP

<400> SEQUENCE: 31

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 32
```

```
<211> LENGTH: 262
<212> TYPE: PRT
<213> ORGANISM: Artificial sequence
<220> FEATURE:
<223> OTHER INFORMATION: Synthetic EGFP

<400> SEQUENCE: 32

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Asp Gly Ser Val Gln Leu Ala Asp His Tyr Gln Gln
        195                 200                 205

Asn Thr Pro Ile Gly Asp Gly Pro Val Leu Leu Pro Asp Asn His Tyr
    210                 215                 220

Leu Ser Thr Gln Ser Ala Leu Ser Lys Asp Pro Asn Glu Lys Arg Asp
225                 230                 235                 240

His Ile Val Leu Leu Glu Phe Val Thr Ala Ala Gly Ile Thr Leu Gly
                245                 250                 255

Met Asp Glu Leu Tyr Lys
            260

<210> SEQ ID NO 33
<211> LENGTH: 259
<212> TYPE: PRT
<213> ORGANISM: Artificial sequence
<220> FEATURE:
<223> OTHER INFORMATION: Synthetic EGFP

<400> SEQUENCE: 33

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
```

```
              50                  55                  60
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asn Gly Tyr Ile Ser Ala Ala Glu Leu Arg His Val Met Thr Asn
            180                 185                 190

Leu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
    210                 215                 220

Gln Ser Ala Leu Ser Lys Asp Pro Asn Glu Lys Arg Asp His Ile Val
225                 230                 235                 240

Leu Leu Glu Phe Val Thr Ala Ala Gly Ile Thr Leu Gly Met Asp Glu
                245                 250                 255

Leu Tyr Lys

<210> SEQ ID NO 34
<211> LENGTH: 270
<212> TYPE: PRT
<213> ORGANISM: Artificial sequence
<220> FEATURE:
<223> OTHER INFORMATION: Synthetic EGFP

<400> SEQUENCE: 34

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160
```

```
Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
                180                 185                 190

Ser Ala Ala Glu Leu Arg His Val Met Thr Asn Leu Asp Gly Ser Val
                195                 200                 205

Gln Leu Ala Asp His Tyr Gln Gln Asn Thr Pro Ile Gly Asp Gly Pro
210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 35
<211> LENGTH: 298
<212> TYPE: PRT
<213> ORGANISM: Artificial sequence
<220> FEATURE:
<223> OTHER INFORMATION: Synthetic EGFP

<400> SEQUENCE: 35

Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
                20                  25                  30

Phe Thr Gly Val Val Pro Ile Leu Val Glu Leu Asp Gly Asp Leu Asn
                35                  40                  45

Gly His Lys Phe Ser Val Ser Gly Glu Gly Glu Gly Asp Ala Thr Tyr
            50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
                100                 105                 110

Met Pro Glu Gly Tyr Val Gln Glu Arg Thr Ile Ser Phe Lys Asp Asp
            115                 120                 125

Gly Asn Tyr Lys Thr Arg Ala Glu Val Lys Phe Glu Gly Asp Thr Leu
        130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
                180                 185                 190

Arg His Asn Ile Glu Glu Glu Ile Arg Glu Ala Phe Arg Val Phe
                195                 200                 205

Asp Lys Asp Gly Asn Gly Tyr Ile Ser Ala Ala Glu Leu Arg His Val
        210                 215                 220

Met Thr Asn Leu Asp Gly Ser Val Gln Leu Ala Asp His Tyr Gln Gln
225                 230                 235                 240

Asn Thr Pro Ile Gly Asp Gly Pro Val Leu Leu Pro Asp Asn His Tyr
                245                 250                 255
```

Leu Ser Thr Gln Ser Ala Leu Ser Lys Asp Pro Asn Glu Lys Arg Asp
            260                 265                 270

His Ile Val Leu Leu Glu Phe Val Thr Ala Ala Gly Ile Thr Leu Gly
            275                 280                 285

Met Asp Glu Leu Tyr Lys Lys Asp Glu Leu
            290                 295

<210> SEQ ID NO 36
<211> LENGTH: 310
<212> TYPE: PRT
<213> ORGANISM: Artificial sequence
<220> FEATURE:
<223> OTHER INFORMATION: Synthetic EGFP

<400> SEQUENCE: 36

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Met Val Ser Lys Gly Glu Glu Leu
        35                  40                  45

Phe Thr Gly Val Val Pro Ile Leu Val Glu Leu Asp Gly Asp Leu Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Cys Thr Thr Gly Lys Leu Pro Val
                85                  90                  95

Pro Trp Pro Thr Leu Val Thr Thr Leu Thr Tyr Gly Val Gln Cys Phe
            100                 105                 110

Ser Arg Tyr Pro Asp His Met Lys Gln His Asp Phe Phe Lys Ser Ala
        115                 120                 125

Met Pro Glu Gly Tyr Val Gln Glu Arg Thr Ile Ser Phe Lys Asp Asp
    130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Thr Ala Asp Lys Gln Lys Asn Gly Ile Lys Ala Asn Phe Lys Ile
        195                 200                 205

Arg His Asn Ile Glu Glu Glu Ile Arg Glu Ala Phe Arg Val Phe
    210                 215                 220

Asp Lys Asp Gly Asn Gly Tyr Ile Ser Ala Ala Glu Leu Arg His Val
225                 230                 235                 240

Met Thr Asn Leu Asp Gly Ser Val Gln Leu Ala Asp His Tyr Gln Gln
                245                 250                 255

Asn Thr Pro Ile Gly Asp Gly Pro Val Leu Leu Pro Asp Asn His Tyr
            260                 265                 270

Leu Ser Thr Gln Ser Ala Leu Ser Lys Asp Pro Asn Glu Lys Arg Asp
        275                 280                 285

His Ile Val Leu Leu Glu Phe Val Thr Ala Ala Gly Ile Thr Leu Gly
    290                 295                 300

Met Asp Glu Leu Tyr Lys
305                 310

<210> SEQ ID NO 37
<211> LENGTH: 271
<212> TYPE: PRT
<213> ORGANISM: Artificial sequence
<220> FEATURE:
<223> OTHER INFORMATION: Synthetic EGFP

<400> SEQUENCE: 37

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Glu Glu
                165                 170                 175

Glu Lys Arg Glu Ala Glu Arg Val Phe Asp Lys Asp Gly Asn Gly Tyr
            180                 185                 190

Ile Ser Ala Ala Glu Leu Arg His Ala Ala Thr Asn Leu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270
```

<210> SEQ ID NO 38
<211> LENGTH: 270
<212> TYPE: PRT
<213> ORGANISM: Artificial sequence
<220> FEATURE:
<223> OTHER INFORMATION: Synthetic EGFP

<400> SEQUENCE: 38

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
```

```
                 35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asn Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 39
<211> LENGTH: 270
<212> TYPE: PRT
<213> ORGANISM: Artificial sequence
<220> FEATURE:
<223> OTHER INFORMATION: Synthetic EGFP

<400> SEQUENCE: 39

Met Val Ser Lys Gly Glu Glu Leu Phe Thr Gly Val Val Pro Ile Leu
  1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
```

```
Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asn Lys Asn Gly Asn Gly Tyr Ile
                180                 185                 190

Ser Ala Ala Glu Leu Arg His Val Met Thr Asn Leu Asp Gly Ser Val
                195                 200                 205

Gln Leu Ala Asp His Tyr Gln Gln Asn Thr Pro Ile Gly Asp Gly Pro
            210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 40
<211> LENGTH: 270
<212> TYPE: PRT
<213> ORGANISM: Artificial sequence
<220> FEATURE:
<223> OTHER INFORMATION: Synthetic EGFP

<400> SEQUENCE: 40

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
                180                 185                 190

Ser Ala Ala Glu Leu Arg His Val Met Thr Asn Leu Asp Gly Ser Val
                195                 200                 205

Gln Leu Ala Asp His Tyr Gln Gln Asn Thr Pro Ile Gly Asp Gly Pro
            210                 215                 220

Val Asn Leu Pro Asp Asn His Tyr Leu Ser Thr Gln Ser Ala Leu Ser
```

```
                225                 230                 235                 240

Lys Asp Pro Asn Glu Lys Arg Asp His Ile Val Leu Glu Phe Val
                245                 250                 255

Thr Ala Ala Gly Ile Thr Leu Gly Met Asp Glu Leu Tyr Lys
                260                 265                 270

<210> SEQ ID NO 41
<211> LENGTH: 251
<212> TYPE: PRT
<213> ORGANISM: Artificial sequence
<220> FEATURE:
<223> OTHER INFORMATION: Synthetic EGFP

<400> SEQUENCE: 41

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Lys Asp
                165                 170                 175

Gly Asp Gly Thr Ile Thr Thr Lys Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 42
<211> LENGTH: 271
<212> TYPE: PRT
<213> ORGANISM: Artificial sequence
<220> FEATURE:
<223> OTHER INFORMATION: Synthetic EGFP

<400> SEQUENCE: 42

Met Val Ser Lys Gly Glu Glu Leu Phe Thr Gly Val Val Pro Ile Leu
1               5                   10                  15
```

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Cys Asp Lys Phe Leu Asp Asp Asp Ile Thr Asp
            180                 185                 190

Asp Ile Met Cys Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 43
<211> LENGTH: 271
<212> TYPE: PRT
<213> ORGANISM: Artificial sequence
<220> FEATURE:
<223> OTHER INFORMATION: Synthetic EGFP

<400> SEQUENCE: 43

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
            165                 170                 175

Ile Cys Asp Ile Ser Ala Asp Lys Phe Leu Asp Asp Ile Thr Asp
            180                 185                 190

Asp Ile Met Cys Ala Lys Lys Ile Leu Asp Ile Lys Gly Asp Gly Ser
            195                 200                 205

Val Gln Leu Ala Asp His Tyr Gln Gln Asn Thr Pro Ile Gly Asp Gly
            210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
            245                 250                 255

Val Thr Ala Ala Gly Ile Thr Leu Gly Met Asp Glu Leu Tyr Lys
            260                 265                 270

<210> SEQ ID NO 44
<211> LENGTH: 271
<212> TYPE: PRT
<213> ORGANISM: Artificial sequence
<220> FEATURE:
<223> OTHER INFORMATION: Synthetic EGFP

<400> SEQUENCE: 44

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
            165                 170                 175

Ile Cys Asp Ile Ser Cys Asp Lys Phe Leu Asp Asp Ile Thr Asp
            180                 185                 190

Asp Ile Met Ala Ala Lys Lys Ile Leu Asp Ile Lys Gly Asp Gly Ser
            195                 200                 205
```

```
Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 45
<211> LENGTH: 271
<212> TYPE: PRT
<213> ORGANISM: Artificial sequence
<220> FEATURE:
<223> OTHER INFORMATION: Synthetic EGFP

<400> SEQUENCE: 45

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ser Arg Asn
                165                 170                 175

Ile Cys Asp Ile Ser Ala Asp Lys Phe Leu Asp Asp Ile Thr Asp
            180                 185                 190

Asp Ile Met Ala Ala Lys Lys Ile Leu Asp Ile Lys Gly Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Ile Val Leu Leu Glu Phe
                245                 250                 255

Val Thr Ala Ala Gly Ile Thr Leu Gly Met Asp Glu Leu Tyr Lys
            260                 265                 270

<210> SEQ ID NO 46
<211> LENGTH: 251
<212> TYPE: PRT
<213> ORGANISM: Artificial sequence
<220> FEATURE:
```

<223> OTHER INFORMATION: Synthetic EGFP

<400> SEQUENCE: 46

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Asp Lys
145                 150                 155                 160

Asp Gly Asn Gly Tyr Ile Ser Ala Ala Glu Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 47
<211> LENGTH: 270
<212> TYPE: PRT
<213> ORGANISM: Artificial sequence
<220> FEATURE:
<223> OTHER INFORMATION: Synthetic EGFP

<400> SEQUENCE: 47

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Glu Glu
145                 150                 155                 160

Glu Ile Arg Glu Ala Phe Arg Val Phe Asp Lys Asp Gly Asn Gly Tyr
                165                 170                 175

Ile Ser Ala Ala Glu Leu Arg His Val Met Thr Asn Leu Lys Asn Gly
            180                 185                 190

Ile Lys Val Asn Phe Lys Ile Arg His Asn Ile Glu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 48
<211> LENGTH: 251
<212> TYPE: PRT
<213> ORGANISM: Artificial sequence
<220> FEATURE:
<223> OTHER INFORMATION: Synthetic EGFP

<400> SEQUENCE: 48

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Asp Lys
145                 150                 155                 160

Asp Gly Asn Gly Tyr Ile Ser Ala Ala Glu Lys Asn Gly Ile Lys Ala
                165                 170                 175

Asn Phe Lys Ile Arg His Asn Ile Glu Asp Gly Ser Val Gln Leu Ala
            180                 185                 190
```

```
Asp His Tyr Gln Gln Asn Thr Pro Ile Gly Asp Gly Pro Val Leu Leu
            195                 200                 205

Pro Asp Asn His Tyr Leu Ser Thr Gln Ser Ala Leu Ser Lys Asp Pro
210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
            245                 250

<210> SEQ ID NO 49
<211> LENGTH: 270
<212> TYPE: PRT
<213> ORGANISM: Artificial sequence
<220> FEATURE:
<223> OTHER INFORMATION: Synthetic EGFP

<400> SEQUENCE: 49

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Glu Glu
145                 150                 155                 160

Glu Ile Arg Glu Ala Phe Arg Val Phe Asp Lys Asp Gly Asn Gly Tyr
            165                 170                 175

Ile Ser Ala Ala Glu Leu Arg His Val Met Thr Asn Leu Lys Asn Gly
        180                 185                 190

Ile Lys Ala Asn Phe Lys Ile Arg His Asn Ile Glu Asp Gly Ser Val
    195                 200                 205

Gln Leu Ala Asp His Tyr Gln Gln Asn Thr Pro Ile Gly Asp Gly Pro
210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
            245                 250                 255

Thr Ala Ala Gly Ile Thr Leu Gly Met Asp Glu Leu Tyr Lys
        260                 265                 270

<210> SEQ ID NO 50
<211> LENGTH: 251
<212> TYPE: PRT
<213> ORGANISM: Artificial sequence
```

```
<220> FEATURE:
<223> OTHER INFORMATION: Synthetic EGFP

<400> SEQUENCE: 50

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Asp Lys
145                 150                 155                 160

Asp Gly Asn Gly Tyr Ile Ser Ala Ala Glu Lys Asn Gly Ile Lys Ala
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220

Asn Glu Lys Arg Asp His Ile Val Leu Leu Glu Phe Val Thr Ala Ala
225                 230                 235                 240

Gly Ile Thr Leu Gly Met Asp Glu Leu Tyr Lys
                245                 250

<210> SEQ ID NO 51
<211> LENGTH: 270
<212> TYPE: PRT
<213> ORGANISM: Artificial sequence
<220> FEATURE:
<223> OTHER INFORMATION: Synthetic EGFP

<400> SEQUENCE: 51

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
```

```
                85                  90                  95
Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Glu Glu
145                 150                 155                 160

Glu Ile Arg Glu Ala Phe Arg Val Phe Asp Lys Asp Gly Asn Gly Tyr
            165                 170                 175

Ile Ser Ala Ala Glu Leu Arg His Val Met Thr Asn Leu Lys Asn Gly
            180                 185                 190

Ile Lys Ala Asn Phe Lys Ile Arg His Asn Ile Glu Asp Gly Ser Val
            195                 200                 205

Gln Leu Ala Asp His Tyr Gln Gln Asn Thr Pro Ile Gly Asp Gly Pro
            210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                    245                 250                 255

Thr Ala Ala Gly Ile Thr Leu Gly Met Asp Glu Leu Tyr Lys
            260                 265                 270

<210> SEQ ID NO 52
<211> LENGTH: 270
<212> TYPE: PRT
<213> ORGANISM: Artificial sequence
<220> FEATURE:
<223> OTHER INFORMATION: Synthetic EGFP

<400> SEQUENCE: 52

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Glu Glu Glu Ile Arg
            165                 170                 175

Glu Ala Phe Arg Val Phe Asp Lys Asp Gly Asn Gly Tyr Ile Ser Ala
```

```
                    180                 185                 190
Ala Glu Leu Arg His Val Met Thr Asn Leu Ile Glu Asp Gly Ser Val
            195                 200                 205

Gln Leu Ala Asp His Tyr Gln Gln Asn Thr Pro Ile Gly Asp Gly Pro
        210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
            245                 250                 255

Thr Ala Ala Gly Ile Thr Leu Gly Met Asp Glu Leu Tyr Lys
        260                 265                 270
```

<210> SEQ ID NO 53
<211> LENGTH: 273
<212> TYPE: PRT
<213> ORGANISM: Artificial sequence
<220> FEATURE:
<223> OTHER INFORMATION: Synthetic EGFP

<400> SEQUENCE: 53

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Thr Glu Glu Gln Ile
                165                 170                 175

Ala Glu Phe Lys Glu Ala Phe Ser Leu Phe Asp Lys Asp Gly Asp Gly
            180                 185                 190

Thr Ile Thr Thr Lys Glu Leu Gly Thr Val Met Arg Ser Ile Glu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys
```

<210> SEQ ID NO 54
<211> LENGTH: 270
<212> TYPE: PRT
<213> ORGANISM: Artificial sequence
<220> FEATURE:
<223> OTHER INFORMATION: Synthetic EGFP

<400> SEQUENCE: 54

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Glu Glu Glu Ile Arg
                165                 170                 175

Glu Ala Phe Arg Val Phe Asp Lys Asp Gly Asn Gly Tyr Ile Ser Ala
            180                 185                 190

Ala Glu Leu Arg His Val Met Thr Asn Leu Ile Glu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270
```

<210> SEQ ID NO 55
<211> LENGTH: 273
<212> TYPE: PRT
<213> ORGANISM: Artificial sequence
<220> FEATURE:
<223> OTHER INFORMATION: Synthetic EGFP

<400> SEQUENCE: 55

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
```

```
            35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Thr Glu Glu Gln Ile
                165                 170                 175

Ala Glu Phe Lys Glu Ala Phe Ser Leu Phe Asp Lys Asp Gly Asp Gly
            180                 185                 190

Thr Ile Thr Thr Lys Glu Leu Gly Thr Val Met Arg Ser Ile Glu Asp
        195                 200                 205

Gly Ser Val Gln Leu Ala Asp His Tyr Gln Gln Asn Thr Pro Ile Gly
210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
                245                 250                 255

Glu Phe Val Thr Ala Ala Gly Ile Thr Leu Gly Met Asp Glu Leu Tyr
            260                 265                 270

Lys

<210> SEQ ID NO 56
<211> LENGTH: 270
<212> TYPE: PRT
<213> ORGANISM: Artificial sequence
<220> FEATURE:
<223> OTHER INFORMATION: Synthetic EGFP

<400> SEQUENCE: 56

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

```
Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Glu Glu Glu Ile Arg
                165                 170                 175

Glu Ala Phe Arg Val Phe Asp Lys Asp Gly Asn Gly Tyr Ile Ser Ala
                180                 185                 190

Ala Glu Leu Arg His Val Met Thr Asn Leu Ile Glu Asp Gly Ser Val
            195                 200                 205

Gln Leu Ala Asp His Tyr Gln Gln Asn Thr Pro Ile Gly Asp Gly Pro
210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 57
<211> LENGTH: 273
<212> TYPE: PRT
<213> ORGANISM: Artificial sequence
<220> FEATURE:
<223> OTHER INFORMATION: Synthetic EGFP

<400> SEQUENCE: 57

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Thr Glu Glu Gln Ile
                165                 170                 175

Ala Glu Phe Lys Glu Ala Phe Ser Leu Phe Asp Lys Asp Gly Asp Gly
            180                 185                 190

Thr Ile Thr Thr Lys Glu Leu Gly Thr Val Met Arg Ser Ile Glu Asp
        195                 200                 205

Gly Ser Val Gln Leu Ala Asp His Tyr Gln Gln Asn Thr Pro Ile Gly
210                 215                 220
```

```
Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Ile Val Leu Leu
            245                 250                 255

Glu Phe Val Thr Ala Ala Gly Ile Thr Leu Gly Met Asp Glu Leu Tyr
        260                 265                 270

Lys

<210> SEQ ID NO 58
<211> LENGTH: 239
<212> TYPE: PRT
<213> ORGANISM: Artificial sequence
<220> FEATURE:
<223> OTHER INFORMATION: Synthetic EGFP

<400> SEQUENCE: 58

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Asp Phe Glu Gly Asp Thr Leu Asn Asn Asp Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
210                 215                 220

Val Thr Ala Ala Gly Ile Thr Leu Gly Met Asp Glu Leu Tyr Lys
225                 230                 235

<210> SEQ ID NO 59
<211> LENGTH: 239
<212> TYPE: PRT
<213> ORGANISM: Artificial sequence
<220> FEATURE:
<223> OTHER INFORMATION: Synthetic EGFP

<400> SEQUENCE: 59

Met Val Ser Lys Gly Glu Glu Leu Phe Thr Gly Val Val Pro Ile Asn
1               5                   10                  15
```

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Asn Asn Asp Ile Glu Leu Lys Gly
            115                 120                 125

Ile Asp Phe Lys Glu Asp Gly Asn Ile Leu Gly His Lys Leu Glu Tyr
 130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
210                 215                 220

Val Thr Ala Ala Gly Ile Thr Leu Gly Met Asp Glu Leu Tyr Lys
225                 230                 235

<210> SEQ ID NO 60
<211> LENGTH: 239
<212> TYPE: PRT
<213> ORGANISM: Artificial sequence
<220> FEATURE:
<223> OTHER INFORMATION: Synthetic EGFP

<400> SEQUENCE: 60

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
 130                 135                 140

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Asp Glu Asp Gly Asp
                165                 170                 175

Val Asn Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 61
<211> LENGTH: 239
<212> TYPE: PRT
<213> ORGANISM: Artificial sequence
<220> FEATURE:
<223> OTHER INFORMATION: Synthetic EGFP

<400> SEQUENCE: 61

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Asp
65                  70                  75                  80

Gln His Asp Phe Phe Asp Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 62
<211> LENGTH: 239
<212> TYPE: PRT
<213> ORGANISM: Artificial sequence
<220> FEATURE:
<223> OTHER INFORMATION: Synthetic EGFP

<400> SEQUENCE: 62

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Asp
65                  70                  75                  80

Gln His Asp Phe Phe Lys Asp Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 63
<211> LENGTH: 239
<212> TYPE: PRT
<213> ORGANISM: Artificial sequence
<220> FEATURE:
<223> OTHER INFORMATION: Synthetic EGFP

<400> SEQUENCE: 63

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Asn Lys
65                  70                  75                  80

Gln Asp Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
```

```
                    100                 105                 110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn Asp Tyr Leu Ser Thr Gln Ser Ala Leu
        195                 200                 205

Ser Lys Asp Pro Asn Glu Lys Arg Asp His Ile Val Leu Leu Glu Phe
        210                 215                 220

Val Thr Ala Ala Gly Asp Thr Leu Gly Met Asp Glu Leu Tyr Lys
225                 230                 235

<210> SEQ ID NO 64
<211> LENGTH: 239
<212> TYPE: PRT
<213> ORGANISM: Artificial sequence
<220> FEATURE:
<223> OTHER INFORMATION: Synthetic EGFP

<400> SEQUENCE: 64

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Asp Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
            195                 200                 205

Ser Lys Asp Pro Asn Glu Lys Arg Asp His Ile Val Leu Leu Glu Phe
        210                 215                 220

Val Thr Ala Ala Gly Ile Thr Leu Gly Met Asp Glu Leu Tyr Lys
```

<210> SEQ ID NO 65
<211> LENGTH: 267
<212> TYPE: PRT
<213> ORGANISM: Artificial sequence
<220> FEATURE:
<223> OTHER INFORMATION: Synthetic EGFP

<400> SEQUENCE: 65

Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Asp Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Met Ala Asp Lys Gln Lys Asn Gly Ile Lys Val Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Glu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Ile Val Leu Leu Glu Phe Val Thr Ala Ala Gly Ile Thr Leu
                245                 250                 255

Gly Met Asp Glu Leu Tyr Lys Lys Asp Glu Leu
            260                 265

<210> SEQ ID NO 66
<211> LENGTH: 274
<212> TYPE: PRT
<213> ORGANISM: Artificial sequence
<220> FEATURE:
<223> OTHER INFORMATION: Synthetic EGFP

<400> SEQUENCE: 66

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Glu Glu Leu Phe Thr Gly Val Val
            35                  40                  45

Pro Ile Leu Val Glu Leu Asp Gly Asp Leu Asn Gly His Lys Phe Ser
 50                  55                  60

Val Ser Gly Glu Gly Glu Gly Asp Ala Thr Tyr Gly Lys Leu Thr Leu
 65                  70                  75                  80

Lys Phe Ile Cys Thr Thr Gly Lys Leu Pro Val Pro Trp Pro Thr Leu
                 85                  90                  95

Val Thr Thr Leu Thr Tyr Gly Val Gln Cys Phe Ser Arg Tyr Pro Asp
            100                 105                 110

His Met Lys Gln His Asp Phe Phe Lys Asp Ala Met Pro Glu Gly Tyr
        115                 120                 125

Val Gln Glu Arg Thr Ile Phe Phe Lys Asp Asp Gly Asn Tyr Lys Thr
130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Asn Ser His Asn Val Tyr Ile Met Ala Asp Lys
            180                 185                 190

Gln Lys Asn Gly Ile Lys Val Asn Phe Lys Ile Arg His Asn Ile Glu
        195                 200                 205

Asp Gly Ser Val Gln Leu Ala Asp His Tyr Gln Gln Asn Thr Pro Ile
210                 215                 220

Gly Asp Gly Pro Val Glu Leu Pro Asp Asn His Tyr Leu Ser Thr Gln
225                 230                 235                 240

Ser Ala Leu Ser Lys Asp Pro Asn Glu Lys Arg Asp His Ile Val Leu
                245                 250                 255

Leu Glu Phe Val Thr Ala Ala Gly Ile Thr Leu Gly Met Asp Glu Leu
            260                 265                 270

Tyr Lys

<210> SEQ ID NO 67
<211> LENGTH: 239
<212> TYPE: PRT
<213> ORGANISM: Artificial sequence
<220> FEATURE:
<223> OTHER INFORMATION: Synthetic EGFP

<400> SEQUENCE: 67

Met Val Ser Lys Gly Glu Glu Leu Phe Thr Gly Val Val Pro Ile Asp
 1               5                  10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Ser Asn Glu Ile Glu Leu Lys Gly

```
                115                 120                 125
Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 68
<211> LENGTH: 239
<212> TYPE: PRT
<213> ORGANISM: Artificial sequence
<220> FEATURE:
<223> OTHER INFORMATION: Synthetic EGFP

<400> SEQUENCE: 68

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Asp Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Glu Met Asp Asp Lys Gln Lys Asn
145                 150                 155                 160

Gly Asp Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 69
<211> LENGTH: 239
<212> TYPE: PRT
<213> ORGANISM: Artificial sequence
<220> FEATURE:
<223> OTHER INFORMATION: Synthetic EGFP

<400> SEQUENCE: 69

```
Met Val Ser Lys Gly Glu Glu Leu Phe Thr Gly Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Asp Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Glu Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ser Leu Gly His Lys Asn Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Glu Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 70
<211> LENGTH: 239
<212> TYPE: PRT
<213> ORGANISM: Artificial sequence
<220> FEATURE:
<223> OTHER INFORMATION: Synthetic EGFP

<400> SEQUENCE: 70

```
Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80
```

```
Gln His Asp Phe Phe Lys Ser Ala Ser Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Asp Glu Gly Asp Thr Asp Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 71
<211> LENGTH: 239
<212> TYPE: PRT
<213> ORGANISM: Artificial sequence
<220> FEATURE:
<223> OTHER INFORMATION: Synthetic EGFP

<400> SEQUENCE: 71

```
Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Thr Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Asp Glu Gly Asp Thr Glu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205
```

```
Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 72
<211> LENGTH: 239
<212> TYPE: PRT
<213> ORGANISM: Artificial sequence
<220> FEATURE:
<223> OTHER INFORMATION: Synthetic EGFP

<400> SEQUENCE: 72

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Asp Phe Glu Gly Asp Thr Leu Asn Asn Asp Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 73
<211> LENGTH: 239
<212> TYPE: PRT
<213> ORGANISM: Artificial sequence
<220> FEATURE:
<223> OTHER INFORMATION: Synthetic EGFP

<400> SEQUENCE: 73

```
Met Val Ser Lys Gly Glu Glu Leu Phe Thr Gly Val Val Pro Ile Asn
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Asn Asn Asp Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 74
<211> LENGTH: 239
<212> TYPE: PRT
<213> ORGANISM: Artificial sequence
<220> FEATURE:
<223> OTHER INFORMATION: Synthetic EGFP

<400> SEQUENCE: 74

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Asp Glu Asp Gly Asp
                165                 170                 175

Val Asn Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 75
<211> LENGTH: 239
<212> TYPE: PRT
<213> ORGANISM: Artificial sequence
<220> FEATURE:
<223> OTHER INFORMATION: Synthetic EGFP

<400> SEQUENCE: 75

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Asp
65                  70                  75                  80

Gln His Asp Phe Phe Asp Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 76
<211> LENGTH: 239
<212> TYPE: PRT
<213> ORGANISM: Artificial sequence
<220> FEATURE:
<223> OTHER INFORMATION: Synthetic EGFP

<400> SEQUENCE: 76

Met Val Ser Lys Gly Glu Glu Leu Phe Thr Gly Val Val Pro Ile Leu

```
            1               5                  10                 15
Val Glu Leu Asp Gly Asp Leu Asn Gly His Lys Phe Ser Val Ser Gly
                20                 25                 30
Glu Gly Glu Gly Asp Ala Thr Tyr Gly Lys Leu Thr Leu Lys Phe Ile
                35                 40                 45
Cys Thr Thr Gly Lys Leu Pro Val Pro Trp Pro Thr Leu Val Thr Thr
 50                 55                 60
Leu Thr Tyr Gly Val Gln Cys Phe Ser Arg Tyr Pro Asp His Met Asp
 65                 70                 75                 80
Gln His Asp Phe Phe Lys Asp Ala Met Pro Glu Gly Tyr Val Gln Glu
                85                 90                 95
Arg Thr Ile Phe Phe Lys Asp Asp Gly Asn Tyr Lys Thr Arg Ala Glu
                100                105                110
Val Lys Phe Glu Gly Asp Thr Leu Val Asn Arg Ile Glu Leu Lys Gly
                115                120                125
Ile Asp Phe Lys Glu Asp Gly Asn Ile Leu Gly His Lys Leu Glu Tyr
                130                135                140
Asn Tyr Asn Ser His Asn Val Tyr Ile Thr Ala Asp Lys Gln Lys Asn
145                 150                155                160
Gly Ile Lys Ala Asn Phe Lys Ile Arg His Asn Ile Glu Asp Gly Ser
                165                170                175
Val Gln Leu Ala Asp His Tyr Gln Gln Asn Thr Pro Ile Gly Asp Gly
                180                185                190
Pro Val Asn Leu Pro Asp Asn His Tyr Leu Ser Thr Gln Ser Ala Leu
                195                200                205
Ser Lys Asp Pro Asn Glu Lys Arg Asp His Ile Val Leu Leu Glu Phe
                210                215                220
Val Thr Ala Ala Gly Ile Thr Leu Gly Met Asp Glu Leu Tyr Lys
225                 230                235
```

<210> SEQ ID NO 77
<211> LENGTH: 239
<212> TYPE: PRT
<213> ORGANISM: Artificial sequence
<220> FEATURE:
<223> OTHER INFORMATION: Synthetic EGFP

<400> SEQUENCE: 77

```
Met Val Ser Lys Gly Glu Glu Leu Phe Thr Gly Val Val Pro Ile Leu
 1               5                  10                 15
Val Glu Leu Asp Gly Asp Leu Asn Gly His Lys Phe Ser Val Ser Gly
                20                 25                 30
Glu Gly Glu Gly Asp Ala Thr Tyr Gly Lys Leu Thr Leu Lys Phe Ile
                35                 40                 45
Cys Thr Thr Gly Lys Leu Pro Val Pro Trp Pro Thr Leu Val Thr Thr
 50                 55                 60
Leu Thr Tyr Gly Val Gln Cys Phe Ser Arg Tyr Pro Asp His Asn Lys
 65                 70                 75                 80
Gln Asp Asp Phe Phe Lys Ser Ala Met Pro Glu Gly Tyr Val Gln Glu
                85                 90                 95
Arg Thr Ile Phe Phe Lys Asp Asp Gly Asn Tyr Lys Thr Arg Ala Glu
                100                105                110
Val Lys Phe Glu Gly Asp Thr Leu Val Asn Arg Ile Glu Leu Lys Gly
                115                120                125
Ile Asp Phe Lys Glu Asp Gly Asn Ile Leu Gly His Lys Leu Glu Tyr
```

```
                130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn Asp Tyr Leu Ser Thr Gln Ser Ala Leu
            195                 200                 205

Ser Lys Asp Pro Asn Glu Lys Arg Asp His Ile Val Leu Leu Glu Phe
            210                 215                 220

Val Thr Ala Ala Gly Asp Thr Leu Gly Met Asp Glu Leu Tyr Lys
225                 230                 235

<210> SEQ ID NO 78
<211> LENGTH: 239
<212> TYPE: PRT
<213> ORGANISM: Artificial sequence
<220> FEATURE:
<223> OTHER INFORMATION: Synthetic EGFP

<400> SEQUENCE: 78

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Asp Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
            195                 200                 205

Ser Lys Asp Pro Asn Glu Lys Arg Asp His Ile Val Leu Leu Glu Phe
            210                 215                 220

Val Thr Ala Ala Gly Ile Thr Leu Gly Met Asp Glu Leu Tyr Lys
225                 230                 235

<210> SEQ ID NO 79
<211> LENGTH: 267
<212> TYPE: PRT
```

-continued

<213> ORGANISM: Artificial sequence
<220> FEATURE:
<223> OTHER INFORMATION: Synthetic EGFP

<400> SEQUENCE: 79

```
Met Leu Leu Ser Val Pro Leu Leu Gly Leu Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Asp Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Leu Pro Asp Asn His
    210                 215                 220

Tyr Leu Ser Thr Gln Ser Ala Leu Ser Lys Asp Pro Asn Glu Lys Arg
225                 230                 235                 240

Asp His Ile Val Leu Leu Glu Phe Val Thr Ala Ala Gly Ile Thr Leu
                245                 250                 255

Gly Met Asp Glu Leu Tyr Lys Lys Asp Glu Leu
            260                 265
```

<210> SEQ ID NO 80
<211> LENGTH: 274
<212> TYPE: PRT
<213> ORGANISM: Artificial sequence
<220> FEATURE:
<223> OTHER INFORMATION: Synthetic EGFP

<400> SEQUENCE: 80

```
Met Ser Val Leu Thr Pro Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Glu Glu Leu Phe Thr Gly Val Val
        35                  40                  45

Pro Ile Leu Val Glu Leu Asp Gly Asp Leu Asn Gly His Lys Phe Ser
    50                  55                  60
```

Val Ser Gly Glu Gly Glu Gly Asp Ala Thr Tyr Gly Lys Leu Thr Leu
 65                  70                  75                  80

Lys Phe Ile Cys Thr Thr Gly Lys Leu Pro Val Pro Trp Pro Thr Leu
             85                  90                  95

Val Thr Thr Leu Thr Tyr Gly Val Gln Cys Phe Ser Arg Tyr Pro Asp
            100                 105                 110

His Met Lys Gln His Asp Phe Phe Lys Asp Ala Met Pro Glu Gly Tyr
        115                 120                 125

Val Gln Glu Arg Thr Ile Phe Phe Lys Asp Asp Gly Asn Tyr Lys Thr
    130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Asn Ser His Asn Val Tyr Ile Thr Ala Asp Lys
            180                 185                 190

Gln Lys Asn Gly Ile Lys Ala Asn Phe Lys Ile Arg His Asn Ile Glu
        195                 200                 205

Asp Gly Ser Val Gln Leu Ala Asp His Tyr Gln Gln Asn Thr Pro Ile
    210                 215                 220

Gly Asp Gly Pro Val Glu Leu Pro Asp Asn His Tyr Leu Ser Thr Gln
225                 230                 235                 240

Ser Ala Leu Ser Lys Asp Pro Asn Glu Lys Arg Asp His Ile Val Leu
                245                 250                 255

Leu Glu Phe Val Thr Ala Ala Gly Ile Thr Leu Gly Met Asp Glu Leu
            260                 265                 270

Tyr Lys

<210> SEQ ID NO 81
<211> LENGTH: 239
<212> TYPE: PRT
<213> ORGANISM: Artificial sequence
<220> FEATURE:
<223> OTHER INFORMATION: Synthetic EGFP

<400> SEQUENCE: 81

Met Val Ser Lys Gly Glu Glu Leu Phe Thr Gly Val Val Pro Ile Asp
1               5                   10                  15

Val Glu Leu Asp Gly Asp Leu Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Ser Asn Glu Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn

```
145                 150                 155                 160
Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Ile Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 82
<211> LENGTH: 239
<212> TYPE: PRT
<213> ORGANISM: Artificial sequence
<220> FEATURE:
<223> OTHER INFORMATION: Synthetic EGFP

<400> SEQUENCE: 82

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Asp Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Glu Thr Asp Lys Gln Lys Asn
145                 150                 155                 160

Gly Asp Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
            195                 200                 205

Ser Lys Asp Pro Asn Glu Lys Arg Asp His Ile Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 83
<211> LENGTH: 239
<212> TYPE: PRT
<213> ORGANISM: Artificial sequence
<220> FEATURE:
<223> OTHER INFORMATION: Synthetic EGFP

<400> SEQUENCE: 83

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Asp Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Glu Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ser Leu Gly His Lys Asn Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Glu Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
210                 215                 220

Val Thr Ala Ala Gly Ile Thr Leu Gly Met Asp Glu Leu Tyr Lys
225                 230                 235

<210> SEQ ID NO 84
<211> LENGTH: 239
<212> TYPE: PRT
<213> ORGANISM: Artificial sequence
<220> FEATURE:
<223> OTHER INFORMATION: Synthetic EGFP

<400> SEQUENCE: 84

Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Ser Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

```
Val Lys Asp Glu Gly Asp Thr Asp Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 85
<211> LENGTH: 239
<212> TYPE: PRT
<213> ORGANISM: Artificial sequence
<220> FEATURE:
<223> OTHER INFORMATION: Synthetic EGFP

<400> SEQUENCE: 85

```
Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Thr Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Asp Glu Gly Asp Thr Glu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 86
<211> LENGTH: 239
<212> TYPE: PRT
<213> ORGANISM: Artificial sequence
<220> FEATURE:
<223> OTHER INFORMATION: Synthetic EGFP

<400> SEQUENCE: 86

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Asp Phe Glu Gly Asp Thr Leu Asn Asn Asp Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 87
<211> LENGTH: 239
<212> TYPE: PRT
<213> ORGANISM: Artificial sequence
<220> FEATURE:
<223> OTHER INFORMATION: Synthetic EGFP

<400> SEQUENCE: 87

```
Met Val Ser Lys Gly Glu Glu Leu Phe Thr Gly Val Val Pro Ile Asn
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80
```

Gln His Asp Phe Phe Lys Ser Ala Met Pro Glu Gly Tyr Val Gln Glu
            85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Asn Asn Asp Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Ile Val Leu Leu Glu Phe
            210                 215                 220

Val Thr Ala Ala Gly Ile Thr Leu Gly Met Asp Glu Leu Tyr Lys
225                 230                 235

<210> SEQ ID NO 88
<211> LENGTH: 239
<212> TYPE: PRT
<213> ORGANISM: Artificial sequence
<220> FEATURE:
<223> OTHER INFORMATION: Synthetic EGFP

<400> SEQUENCE: 88

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Asp Glu Asp Gly Asp
            165                 170                 175

Val Asn Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Ile Val Leu Leu Glu Phe
            210                 215                 220

Val Thr Ala Ala Gly Ile Thr Leu Gly Met Asp Glu Leu Tyr Lys
225                 230                 235

<210> SEQ ID NO 89
<211> LENGTH: 239
<212> TYPE: PRT
<213> ORGANISM: Artificial sequence
<220> FEATURE:
<223> OTHER INFORMATION: Synthetic EGFP

<400> SEQUENCE: 89

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Asp
65                  70                  75                  80

Gln His Asp Phe Phe Asp Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Asn Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 90
<211> LENGTH: 239
<212> TYPE: PRT
<213> ORGANISM: Artificial sequence
<220> FEATURE:
<223> OTHER INFORMATION: Synthetic EGFP

<400> SEQUENCE: 90

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile 35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Asp
 65                  70                  75                  80

Gln His Asp Phe Phe Lys Asp Ala Met Pro Glu Gly Tyr Val Gln Glu
                 85                  90                  95

Arg Thr Ile Ser Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Asn Leu Pro Asp Asn His Tyr Leu Ser Thr Gln Ser Ala Leu
                195                 200                 205

Ser Lys Asp Pro Asn Glu Lys Arg Asp His Ile Val Leu Leu Glu Phe
210                 215                 220

Val Thr Ala Ala Gly Ile Thr Leu Gly Met Asp Glu Leu Tyr Lys
225                 230                 235

<210> SEQ ID NO 91
<211> LENGTH: 239
<212> TYPE: PRT
<213> ORGANISM: Artificial sequence
<220> FEATURE:
<223> OTHER INFORMATION: Synthetic EGFP

<400> SEQUENCE: 91

Met Val Ser Lys Gly Glu Glu Leu Phe Thr Gly Val Val Pro Ile Leu
 1               5                  10                  15

Val Glu Leu Asp Gly Asp Leu Asn Gly His Lys Phe Ser Val Ser Gly
                 20                  25                  30

Glu Gly Glu Gly Asp Ala Thr Tyr Gly Lys Leu Thr Leu Lys Phe Ile
                 35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Asn Lys
 65                  70                  75                  80

Gln Asp Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser

```
                165                 170                 175
Val Gln Leu Ala Asp His Tyr Gln Gln Asn Thr Pro Ile Gly Asp Gly
            180                 185                 190

Pro Val Leu Leu Pro Asp Asn Asp Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Asp Thr Leu Gly Met Asp Glu Leu Tyr Lys
225                 230                 235

<210> SEQ ID NO 92
<211> LENGTH: 239
<212> TYPE: PRT
<213> ORGANISM: Artificial sequence
<220> FEATURE:
<223> OTHER INFORMATION: Synthetic EGFP

<400> SEQUENCE: 92

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Asp Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 93
<211> LENGTH: 267
<212> TYPE: PRT
<213> ORGANISM: Artificial sequence
<220> FEATURE:
<223> OTHER INFORMATION: Synthetic EGFP

<400> SEQUENCE: 93
```

Met Leu Leu Ser Val Pro Leu Leu Leu Gly Leu Gly Leu Ala Ala
1               5                   10                  15

Ala Asp Gly Ser Gly Pro Ser Arg Met Val Ser Lys Gly Glu Glu Leu
            20                  25                  30

Phe Thr Gly Val Val Pro Ile Leu Val Glu Leu Asp Gly Asp Leu Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65              70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Asp Ala
            100                 105                 110

Met Pro Glu Gly Tyr Val Gln Glu Arg Thr Ile Ser Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Glu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Ile Val Leu Leu Glu Phe Val Thr Ala Ala Gly Ile Thr Leu
                245                 250                 255

Gly Met Asp Glu Leu Tyr Lys Lys Asp Glu Leu
        260                 265

<210> SEQ ID NO 94
<211> LENGTH: 274
<212> TYPE: PRT
<213> ORGANISM: Artificial sequence
<220> FEATURE:
<223> OTHER INFORMATION: Synthetic EGFP

<400> SEQUENCE: 94

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg Met Val Ser Lys Gly Glu Glu Leu Phe Thr Gly Val Val
        35                  40                  45

Pro Ile Leu Val Glu Leu Asp Gly Asp Leu Asn Gly His Lys Phe Ser
    50                  55                  60

Val Ser Gly Glu Gly Glu Gly Asp Ala Thr Tyr Gly Lys Leu Thr Leu
65              70                  75                  80

Lys Phe Ile Cys Thr Thr Gly Lys Leu Pro Val Pro Trp Pro Thr Leu
                85                  90                  95

Val Thr Thr Leu Thr Tyr Gly Val Gln Cys Phe Ser Arg Tyr Pro Asp
            100                 105                 110

His Met Lys Gln His Asp Phe Phe Lys Asp Ala Met Pro Glu Gly Tyr
            115                 120                 125

Val Gln Glu Arg Thr Ile Ser Phe Lys Asp Asp Gly Asn Tyr Lys Thr
130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Asn Ser His Asn Val Tyr Ile Thr Ala Asp Lys
            180                 185                 190

Gln Lys Asn Gly Ile Lys Ala Asn Phe Lys Ile Arg His Asn Ile Glu
            195                 200                 205

Asp Gly Ser Val Gln Leu Ala Asp His Tyr Gln Gln Asn Thr Pro Ile
210                 215                 220

Gly Asp Gly Pro Val Glu Leu Pro Asp Asn His Tyr Leu Ser Thr Gln
225                 230                 235                 240

Ser Ala Leu Ser Lys Asp Pro Asn Glu Lys Arg Asp His Ile Val Leu
                245                 250                 255

Leu Glu Phe Val Thr Ala Ala Gly Ile Thr Leu Gly Met Asp Glu Leu
            260                 265                 270

Tyr Lys

<210> SEQ ID NO 95
<211> LENGTH: 239
<212> TYPE: PRT
<213> ORGANISM: Artificial sequence
<220> FEATURE:
<223> OTHER INFORMATION: Synthetic EGFP

<400> SEQUENCE: 95

Met Val Ser Lys Gly Glu Glu Leu Phe Thr Gly Val Val Pro Ile Asp
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Ser Asn Glu Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly

```
                    180                 185                 190
Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
        210                 215                 220

Val Thr Ala Ala Gly Ile Thr Leu Gly Met Asp Glu Leu Tyr Lys
225                 230                 235

<210> SEQ ID NO 96
<211> LENGTH: 239
<212> TYPE: PRT
<213> ORGANISM: Artificial sequence
<220> FEATURE:
<223> OTHER INFORMATION: Synthetic EGFP

<400> SEQUENCE: 96

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Glu Thr Asp Asp Lys Gln Lys Asn
145                 150                 155                 160

Gly Asp Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Glu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235

<210> SEQ ID NO 97
<211> LENGTH: 239
<212> TYPE: PRT
<213> ORGANISM: Artificial sequence
<220> FEATURE:
<223> OTHER INFORMATION: Synthetic EGFP

<400> SEQUENCE: 97

Met Val Ser Lys Gly Glu Glu Leu Phe Thr Gly Val Val Pro Ile Leu
1               5                   10                  15
```

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Asp Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Ser Glu Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ser Leu Gly His Lys Asn Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Glu Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
 210                 215                 220

Val Thr Ala Ala Gly Ile Thr Leu Gly Met Asp Glu Leu Tyr Lys
225                 230                 235

<210> SEQ ID NO 98
<211> LENGTH: 239
<212> TYPE: PRT
<213> ORGANISM: Artificial sequence
<220> FEATURE:
<223> OTHER INFORMATION: Synthetic EGFP

<400> SEQUENCE: 98

Met Val Ser Lys Gly Glu Glu Asp Phe Thr Gly Val Asn Pro Ile Leu
 1                   5                  10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Ser Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Asp Glu Gly Asp Thr Asp Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

```
Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 99
<211> LENGTH: 239
<212> TYPE: PRT
<213> ORGANISM: Artificial sequence
<220> FEATURE:
<223> OTHER INFORMATION: Synthetic EGFP

<400> SEQUENCE: 99

```
Met Val Ser Lys Gly Glu Glu Asp Phe Thr Gly Val Asn Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Thr Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Asp Glu Gly Asp Thr Glu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Ile Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 100
<211> LENGTH: 24
<212> TYPE: PRT
<213> ORGANISM: Artificial sequence
<220> FEATURE:

<223> OTHER INFORMATION: Synthetic EGFP

<400> SEQUENCE: 100

Met Leu Leu Ser Val Pro Leu Leu Leu Gly Leu Gly Leu Ala Ala
1               5                   10                  15

Ala Asp Gly Ser Gly Pro Ser Arg
            20

<210> SEQ ID NO 101
<211> LENGTH: 4
<212> TYPE: PRT
<213> ORGANISM: Artificial sequence
<220> FEATURE:
<223> OTHER INFORMATION: Synthetic EGFP

<400> SEQUENCE: 101

Lys Asp Glu Leu
1

<210> SEQ ID NO 102
<211> LENGTH: 35
<212> TYPE: PRT
<213> ORGANISM: Artificial sequence
<220> FEATURE:
<223> OTHER INFORMATION: Synthetic EGFP

<400> SEQUENCE: 102

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Ser Gly
            20                  25                  30

Pro Ser Arg
        35

<210> SEQ ID NO 103
<211> LENGTH: 238
<212> TYPE: PRT
<213> ORGANISM: Artificial sequence
<220> FEATURE:
<223> OTHER INFORMATION: Synthetic EGFP

<400> SEQUENCE: 103

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

```
Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Ile Val Leu Leu Glu Phe Val
    210                 215                 220

Thr Ala Ala Gly Ile Thr Leu Gly Met Asp Glu Leu Tyr Lys
225                 230                 235

<210> SEQ ID NO 104
<211> LENGTH: 238
<212> TYPE: PRT
<213> ORGANISM: Artificial sequence
<220> FEATURE:
<223> OTHER INFORMATION: Synthetic EGFP

<400> SEQUENCE: 104

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
        195                 200                 205

Lys Asp Pro Asn Glu Lys Arg Asp His Ile Val Leu Leu Glu Glu Val
    210                 215                 220

Glu Ala Ala Gly Ile Thr Leu Gly Met Asp Glu Leu Tyr Lys
225                 230                 235

<210> SEQ ID NO 105
<211> LENGTH: 260
<212> TYPE: PRT
<213> ORGANISM: Artificial sequence
<220> FEATURE:
```

<223> OTHER INFORMATION: Synthetic EGFP

<400> SEQUENCE: 105

Met Leu Leu Ser Val Pro Leu Leu Leu Gly Leu Gly Leu Ala Ala
1               5                   10                  15

Ala Asp Val Ser Lys Gly Glu Glu Leu Phe Thr Gly Val Val Pro Ile
            20                  25                  30

Leu Val Glu Leu Asp Gly Asp Leu Asn Gly His Lys Phe Ser Val Ser
        35                  40                  45

Gly Glu Gly Glu Gly Asp Ala Thr Tyr Gly Lys Leu Thr Leu Lys Phe
    50                  55                  60

Ile Cys Thr Thr Gly Lys Leu Pro Val Pro Trp Pro Thr Leu Val Thr
65                  70                  75                  80

Thr Leu Thr Tyr Gly Val Gln Cys Phe Ser Arg Tyr Pro Asp His Met
                85                  90                  95

Lys Gln His Asp Phe Phe Lys Ser Ala Met Pro Glu Gly Tyr Val Gln
            100                 105                 110

Glu Arg Thr Ile Phe Phe Lys Asp Asp Gly Asn Tyr Lys Thr Arg Ala
        115                 120                 125

Glu Val Lys Phe Glu Gly Asp Thr Leu Val Asn Arg Ile Glu Leu Lys
    130                 135                 140

Gly Ile Asp Phe Lys Glu Asp Gly Asn Ile Leu Gly His Lys Leu Glu
145                 150                 155                 160

Tyr Asn Tyr Asn Glu His Asn Val Tyr Ile Thr Ala Asp Lys Gln Lys
                165                 170                 175

Asn Gly Ile Lys Ala Asn Phe Lys Ile Arg His Asn Ile Glu Asp Gly
            180                 185                 190

Ser Val Gln Leu Ala Asp His Tyr Gln Gln Asn Thr Pro Ile Gly Asp
        195                 200                 205

Gly Pro Val Leu Leu Pro Asp Asn His Tyr Leu Asp Thr Glu Ser Ala
    210                 215                 220

Leu Ser Lys Asp Pro Asn Glu Lys Arg Asp His Ile Val Leu Leu Glu
225                 230                 235                 240

Glu Val Glu Ala Ala Gly Ile Thr Leu Gly Met Asp Glu Leu Tyr Lys
                245                 250                 255

Lys Asp Glu Leu
        260

<210> SEQ ID NO 106
<211> LENGTH: 24
<212> TYPE: DNA
<213> ORGANISM: Artificial sequence
<220> FEATURE:
<223> OTHER INFORMATION: Forwrad Primer

<400> SEQUENCE: 106
acggcgacgc gaacctcgcc gacc                                          24

<210> SEQ ID NO 107
<211> LENGTH: 23
<212> TYPE: DNA
<213> ORGANISM: Artificial sequence
<220> FEATURE:
<223> OTHER INFORMATION: Reverse Primer

<400> SEQUENCE: 107
cctcgtcgtt gtggcggatc ttg                                           23

```
<210> SEQ ID NO 108
<211> LENGTH: 22
<212> TYPE: DNA
<213> ORGANISM: Artificial sequence
<220> FEATURE:
<223> OTHER INFORMATION: F99S forward primer

<400> SEQUENCE: 108
cgcaccatct ccttcaagga cg                                              22

<210> SEQ ID NO 109
<211> LENGTH: 20
<212> TYPE: DNA
<213> ORGANISM: Artificial sequence
<220> FEATURE:
<223> OTHER INFORMATION: F99S reverse primer

<400> SEQUENCE: 109
ctcctggacg tagccttccc                                                 20

<210> SEQ ID NO 110
<211> LENGTH: 24
<212> TYPE: DNA
<213> ORGANISM: Artificial sequence
<220> FEATURE:
<223> OTHER INFORMATION: Forward primer

<400> SEQUENCE: 110
gaacggcatc aaggcgaact tcaa                                            24

<210> SEQ ID NO 111
<211> LENGTH: 25
<212> TYPE: DNA
<213> ORGANISM: Artificial sequence
<220> FEATURE:
<223> OTHER INFORMATION: Reverse primer

<400> SEQUENCE: 111
ttctgcttgt cggccgtgat ataga                                           25

<210> SEQ ID NO 112
<211> LENGTH: 18
<212> TYPE: PRT
<213> ORGANISM: Artificial sequence
<220> FEATURE:
<223> OTHER INFORMATION: Synthetic EGFP

<400> SEQUENCE: 112

Met Leu Leu Ser Val Pro Leu Leu Leu Gly Leu Leu Gly Leu Ala Ala
1               5                   10                  15

Ala Asp

<210> SEQ ID NO 113
<211> LENGTH: 12
<212> TYPE: PRT
<213> ORGANISM: Artificial sequence
<220> FEATURE:
<223> OTHER INFORMATION: Synthetic EGFP

<400> SEQUENCE: 113

Asp Lys Asp Gly Asn Gly Tyr Ile Ser Ala Ala Glu
1               5                   10

<210> SEQ ID NO 114
<211> LENGTH: 31
```

<212> TYPE: PRT
<213> ORGANISM: Artificial sequence
<220> FEATURE:
<223> OTHER INFORMATION: Synthetic EGFP

<400> SEQUENCE: 114

Glu Glu Glu Ile Arg Glu Ala Phe Arg Val Phe Asp Lys Asp Gly Asn
1               5                   10                  15

Gly Tyr Ile Ser Ala Ala Glu Leu Arg His Val Met Thr Asn Leu
            20                  25                  30

<210> SEQ ID NO 115
<211> LENGTH: 2079
<212> TYPE: DNA
<213> ORGANISM: Artificial sequence
<220> FEATURE:
<223> OTHER INFORMATION: Calsequestrin-tethered CatchER

<400> SEQUENCE: 115

| | | |
|---|---|---|
| tattacgtgt tcgctggcta gcgtttaact taagcttatg ggggccagag cagtgtccga | 60 |
| gctgcggctg gcactgctgt ttgtactggt gctagggacg cccaggttag gggtccaggg | 120 |
| ggaagatggg ttggacttcc ctgagtacga cggtgtggac cgtgtgatca atgtgaatgc | 180 |
| caagaactac aagaacgtgt ttaagaagta tgaggtgctg ccctcctct accatgagcc | 240 |
| ccctgaggac gacaaggcct cgcagagaca atttgagatg gaggagctaa tcctggagtt | 300 |
| agcagcccaa gtcttagaag acaagggtgt tggctttggc ctggtggact cagagaagga | 360 |
| tgcagctgtg gccaagaaac taggactaac tgaagaagac agcgtttatg tgttcaaagg | 420 |
| agatgaagtc attgaatatg acggcgagtt ttctgcagac actctggtgg agtttctgct | 480 |
| tgatgtccta gaagaccctg tagagttgat tgaaggtgaa cgagagctgc aggcatttga | 540 |
| gaatattgaa gatgaaatca aactcattgg ctacttcaag agcaaagact cagagcatta | 600 |
| caaagcctac gaggacgcag ctgaagagtt ccatccctac atccctttct tcgctacctt | 660 |
| cgacagcaag gtggcaaaga agctgactct gaagttgaat gagattgatt tctacgaggc | 720 |
| cttcatggaa gagcctatga ccatcccaga caagcccaac agtgaagagg agattgtgag | 780 |
| cttcgtggag gagcacagga gatcaaccct gaggaaactg aagcctgaga gtatgtacga | 840 |
| gacttgggag gatgacctgg atggaatcca cactgtcgcc tttgcagagg aagcagatcc | 900 |
| tgatggctat gagttcttag agactctcaa ggctgtggcc caagacaaca ctgagaaccc | 960 |
| cgacctcagt atcatctgga ttgatcctga tgacttcccg ctgctggtcc gtactgggaa | 1020 |
| gaagaccttt gacattgacc tgtcagctcc acaaatagga gttgtcaatg ttacagacgc | 1080 |
| ggacagcata tggatggaga tggataacga ggaggacctg ccttctgctg atgagctgga | 1140 |
| ggactggctg gaggacgtgc tggagggcga gatcaacaca gaggatgacg acgacgatga | 1200 |
| cgacgatgac gatgatgacg atgatgacga cgacggatcc gggccctcta gaatggtgag | 1260 |
| caagggcgag gagctgttca ccggggtggt gcccatcctg gtcgagctgg acggcgacgt | 1320 |
| aaacggccac aagttcagcg tgtccggcga gggcgagggc gatgccacct acggcaagct | 1380 |
| gaccctgaag ttcatctgca ccaccggcaa gctgcccgtg ccctggccca ccctcgtgac | 1440 |
| caccctgacc tacggcgtgc agtgcttcag ccgctacccc gaccacatga agcagcacga | 1500 |
| cttcttcaag tccgccatgc ccgaaggcta cgtccaggag cgcaccatct tcttcaagga | 1560 |
| cgacggcaac tacaagaccc gcgccgaggt gaagttcgag ggcgacaccc tggtgaaccg | 1620 |
| catcgagctg aagggcatcg acttcaagga ggacggcaac atcctggggc acaagctgga | 1680 |

-continued

```
gtacaactac aacgagcaca acgtctatat cacggccgac aagcagaaga acggcatcaa      1740
ggcgaacttc aagatccgcc acaacatcga ggacggcagc gtgcagctcg ccgaccacta      1800
ccagcagaac accccatcg cgacggccc cgtgctgctg cccgacaacc actacctgga       1860
caccgaatcc gccctgagca agacccccaa cgagaagcgc gatcacatgg tcctgctgga     1920
ggaggtggag gccgccggga tcactctcgg catggacgag ctgtacaagt aagaattctg     1980
cagatatcca gcacagtggc ggccgctcga gtctagaggg cccgtttaaa cccgctgatc     2040
agcctcgact gtgccttcta gttgccagcc atctgttgt                            2079
```

<210> SEQ ID NO 116
<211> LENGTH: 690
<212> TYPE: PRT
<213> ORGANISM: Artificial sequence
<220> FEATURE:
<223> OTHER INFORMATION: Calsequestrin-tethered CatchER
<220> FEATURE:
<221> NAME/KEY: misc_feature
<222> LOCATION: (658)..(659)
<223> OTHER INFORMATION: Xaa can be any naturally occurring amino acid

<400> SEQUENCE: 116

```
Ile Thr Cys Ser Leu Ala Ser Val Leu Lys Leu Met Gly Ala Arg Ala
1               5                   10                  15

Val Ser Glu Leu Arg Leu Ala Leu Leu Phe Val Leu Val Leu Gly Thr
            20                  25                  30

Pro Arg Leu Gly Val Gln Gly Glu Asp Gly Leu Asp Phe Pro Glu Tyr
        35                  40                  45

Asp Gly Val Asp Arg Val Ile Asn Val Asn Ala Lys Asn Tyr Lys Asn
    50                  55                  60

Val Phe Lys Lys Tyr Glu Val Leu Ala Leu Leu Tyr His Glu Pro Pro
65                  70                  75                  80

Glu Asp Asp Lys Ala Ser Gln Arg Gln Phe Glu Met Glu Glu Leu Ile
                85                  90                  95

Leu Glu Leu Ala Ala Gln Val Leu Glu Asp Lys Gly Val Gly Phe Gly
            100                 105                 110

Leu Val Asp Ser Glu Lys Asp Ala Ala Val Ala Lys Lys Leu Gly Leu
        115                 120                 125

Thr Glu Glu Asp Ser Val Tyr Val Phe Lys Gly Asp Glu Val Ile Glu
    130                 135                 140

Tyr Asp Gly Glu Phe Ser Ala Asp Thr Leu Val Glu Phe Leu Leu Asp
145                 150                 155                 160

Val Leu Glu Asp Pro Val Glu Leu Ile Glu Gly Glu Arg Glu Leu Gln
                165                 170                 175

Ala Phe Glu Asn Ile Glu Asp Glu Ile Lys Leu Ile Gly Tyr Phe Lys
            180                 185                 190

Ser Lys Asp Ser Glu His Tyr Lys Ala Tyr Glu Asp Ala Ala Glu Glu
        195                 200                 205

Phe His Pro Tyr Ile Pro Phe Phe Ala Thr Phe Asp Ser Lys Val Ala
    210                 215                 220

Lys Lys Leu Thr Leu Lys Leu Asn Glu Ile Asp Phe Tyr Glu Ala Phe
225                 230                 235                 240

Met Glu Glu Pro Met Thr Ile Pro Asp Lys Pro Asn Ser Glu Glu Glu
                245                 250                 255

Ile Val Ser Phe Val Glu Glu His Arg Arg Ser Thr Leu Arg Lys Leu
            260                 265                 270
```

```
Lys Pro Glu Ser Met Tyr Glu Thr Trp Glu Asp Leu Asp Gly Ile
            275                 280                 285

His Thr Val Ala Phe Ala Glu Glu Ala Asp Pro Asp Gly Tyr Glu Phe
        290                 295                 300

Leu Glu Thr Leu Lys Ala Val Ala Gln Asp Asn Thr Glu Asn Pro Asp
305                 310                 315                 320

Leu Ser Ile Ile Trp Ile Asp Pro Asp Phe Pro Leu Leu Val Pro
                325                 330                 335

Tyr Trp Glu Lys Thr Phe Asp Ile Leu Ser Ala Pro Gln Ile Gly
            340                 345                 350

Val Val Asn Val Thr Asp Ala Asp Ser Ile Trp Met Glu Met Asp Asn
        355                 360                 365

Glu Glu Asp Leu Pro Ser Ala Asp Glu Leu Glu Asp Trp Leu Glu Asp
    370                 375                 380

Val Leu Glu Gly Glu Ile Asn Thr Glu Asp Asp Asp Asp Asp Asp
385                 390                 395                 400

Asp Asp Asp Asp Asp Asp Asp Asp Gly Ser Gly Pro Ser Arg
            405                 410                 415

Met Val Ser Lys Gly Glu Glu Leu Phe Thr Gly Val Val Pro Ile Leu
            420                 425                 430

Val Glu Leu Asp Gly Asp Val Asn Gly His Lys Phe Ser Val Ser Gly
        435                 440                 445

Glu Gly Glu Gly Asp Ala Thr Tyr Gly Lys Leu Thr Leu Lys Phe Ile
    450                 455                 460

Cys Thr Thr Gly Lys Leu Pro Val Pro Trp Pro Thr Leu Val Thr Thr
465                 470                 475                 480

Leu Thr Tyr Gly Val Gln Cys Phe Ser Arg Tyr Pro Asp His Met Lys
            485                 490                 495

Gln His Asp Phe Phe Lys Ser Ala Met Pro Glu Gly Tyr Val Gln Glu
        500                 505                 510

Arg Thr Ile Phe Phe Lys Asp Asp Gly Asn Tyr Lys Thr Arg Ala Glu
    515                 520                 525

Val Lys Phe Glu Gly Asp Thr Leu Val Asn Arg Ile Glu Leu Lys Gly
530                 535                 540

Ile Asp Phe Lys Glu Asp Gly Asn Ile Leu Gly His Lys Leu Glu Tyr
545                 550                 555                 560

Asn Tyr Asn Glu His Asn Val Tyr Ile Thr Ala Asp Lys Gln Lys Asn
            565                 570                 575

Gly Ile Lys Ala Asn Phe Lys Ile Arg His Asn Ile Glu Asp Gly Ser
        580                 585                 590

Val Gln Leu Ala Asp His Tyr Gln Gln Asn Thr Pro Ile Gly Asp Gly
    595                 600                 605

Pro Val Leu Leu Pro Asp Asn His Tyr Leu Asp Thr Glu Ser Ala Leu
610                 615                 620

Ser Lys Asp Pro Asn Glu Lys Arg Asp His Met Val Leu Leu Glu Glu
625                 630                 635                 640

Val Glu Ala Ala Gly Ile Thr Leu Gly Met Asp Glu Leu Tyr Lys Glu
            645                 650                 655

Phe Xaa Xaa Gln Ile Ser Ser Thr Val Ala Ala Arg Val Arg Ala
        660                 665                 670

Arg Leu Asn Pro Leu Ile Ser Leu Asp Cys Ala Phe Leu Pro Ala Ile
    675                 680                 685

Cys Cys
```

<210> SEQ ID NO 117
<211> LENGTH: 2050
<212> TYPE: DNA
<213> ORGANISM: Artificial sequence
<220> FEATURE:
<223> OTHER INFORMATION: Calsequestrin-deleted 17 Asp tethered CatchER

<400> SEQUENCE: 117

| | | | | | |
|---|---|---|---|---|---|
| tattacgtgt | tcgctggcta | gcgtttaact | taagcttatg | ggggccagag | cagtgtccga | 60 |
| gctgcggctg | gcactgctgt | ttgtactggt | gctagggacg | cccaggttag | gggtccaggg | 120 |
| ggaagatggg | ttggacttcc | ctgagtacga | cggtgtggac | cgtgtgatca | atgtgaatgc | 180 |
| caagaactac | aagaacgtgt | ttaagaagta | tgaggtgctg | cccctcctct | accatgagcc | 240 |
| ccctgaggac | gacaaggcct | cgcagagaca | atttgagatg | gaggagctaa | tcctggagtt | 300 |
| agcagcccaa | gtcttagaag | acaagggtgt | tggctttggc | ctggtggact | cagagaagga | 360 |
| tgcagctgtg | gccaagaaac | taggactaac | tgaagaagac | agcgtttatg | tgttcaaagg | 420 |
| agatgaagtc | attgaatatg | acggcgagtt | ttctgcagac | actctggtgg | agtttctgct | 480 |
| tgatgtccta | aagaccctg | tagagttgat | tgaaggtgaa | cgagagctgc | aggcatttga | 540 |
| gaatattgaa | gatgaaatca | aactcattgg | ctacttcaag | agcaaagact | cagagcatta | 600 |
| caaagcctac | gaggacgcag | ctgaagagtt | ccatccctac | atccctttct | cgctacctt | 660 |
| cgacagcaag | gtggcaaaga | agctgactct | gaagttgaat | gagattgatt | tctacgaggc | 720 |
| cttcatggaa | gagcctatga | ccatcccaga | caagcccaac | agtgaagagg | agattgtgag | 780 |
| cttcgtggag | gagcacagga | gatcaaccct | gaggaaactg | aagcctgaga | gtatgtacga | 840 |
| gacttgggag | gatgacctgg | atggaatcca | cactgtcgcc | tttgcagagg | aagcagatcc | 900 |
| tgatggctat | gagttcttag | agactctcaa | ggctgtggcc | aagacaaca | ctgagaaccc | 960 |
| cgacctcagt | atcatctgga | ttgatcctga | tgacttcccg | ctgctggtcc | cgtactggga | 1020 |
| gaagaccttt | gacattgacc | tgtcagctcc | acaaatagga | gttgtcaatg | ttacagacgc | 1080 |
| ggacagcata | tggatggaga | tggataacga | ggaggacctg | ccttctgctg | atgagctgga | 1140 |
| ggactggctg | gaggacgtgc | tggagggcga | gatcaacaca | gagtgatgac | gatgatgacg | 1200 |
| acgacggatc | cgggccctct | agaatggtga | gcaagggcga | ggagctgttc | accggggtgg | 1260 |
| tgcccatcct | ggtcgagctg | gacggcgacg | taaacggcca | caagttcagc | gtgtccggcg | 1320 |
| agggcgaggg | cgatgccacc | tacgcaagc | tgaccctgaa | gttcatctgc | accaccggca | 1380 |
| agctgcccgt | gccctggccc | accctcgtga | ccaccctgac | ctacggcgtg | cagtgcttca | 1440 |
| gccgctaccc | cgaccacatg | aagcagcacg | acttcttcaa | gtccgccatg | cccgaaggct | 1500 |
| acgtccagga | gcgcaccatc | ttcttcaagg | acgacggcaa | ctacaagacc | cgcgccgagg | 1560 |
| tgaagttcga | gggcgacacc | ctggtgaacc | gcatcgagct | gaagggcatc | gacttcaagg | 1620 |
| aggacggcaa | catcctgggg | cacaagctgg | agtacaacta | caacgagcac | aacgtctata | 1680 |
| tcacggccga | caagcagaag | aacggcatca | aggcgaactt | caagatccgc | cacaacatcg | 1740 |
| aggacggcag | cgtgcagctc | gccgaccact | accagcagaa | cacccccatc | ggcgacggcc | 1800 |
| ccgtgctgct | gcccgacaac | cactacctgg | acaccgaatc | cgccctgagc | aaagacccca | 1860 |
| acgagaagcg | cgatcacatg | gtcctgctgg | aggaggtgga | ggccgccggg | atcactctcg | 1920 |
| gcatggacga | gctgtacaag | taagaattct | gcagatatcc | agcacagtgg | cggccgctcg | 1980 |
| agtctagagg | gcccgtttaa | acccgctgat | cagcctcgac | tgtgccttct | agttgccagc | 2040 | catctgttgt 2050

<210> SEQ ID NO 118
<211> LENGTH: 673
<212> TYPE: PRT
<213> ORGANISM: Artificial sequence
<220> FEATURE:
<223> OTHER INFORMATION: Calsequestrin deleted 17 Asp tethered CartchER
<220> FEATURE:
<221> NAME/KEY: misc_feature
<222> LOCATION: (641)..(642)
<223> OTHER INFORMATION: Xaa can be any naturally occurring amino acid

<400> SEQUENCE: 118

```
Ile Thr Cys Ser Leu Ala Ser Val Leu Lys Leu Met Gly Ala Arg Ala
1               5                   10                  15

Val Ser Glu Leu Arg Leu Ala Leu Leu Phe Val Leu Val Leu Gly Thr
            20                  25                  30

Pro Arg Leu Gly Val Gln Gly Glu Asp Gly Leu Asp Phe Pro Glu Tyr
        35                  40                  45

Asp Gly Val Asp Arg Val Ile Asn Val Asn Ala Lys Asn Tyr Lys Asn
50                  55                  60

Val Phe Lys Lys Tyr Glu Val Leu Ala Leu Leu Tyr His Glu Pro Pro
65                  70                  75                  80

Glu Asp Asp Lys Ala Ser Gln Arg Gln Phe Glu Met Glu Glu Leu Ile
                85                  90                  95

Leu Glu Leu Ala Ala Gln Val Leu Glu Asp Lys Gly Val Gly Phe Gly
            100                 105                 110

Leu Val Asp Ser Glu Lys Asp Ala Ala Val Ala Lys Lys Leu Gly Leu
        115                 120                 125

Thr Glu Glu Asp Ser Val Tyr Val Phe Lys Gly Asp Glu Val Ile Glu
130                 135                 140

Tyr Asp Gly Glu Phe Ser Ala Asp Thr Leu Val Glu Phe Leu Leu Asp
145                 150                 155                 160

Val Leu Glu Asp Pro Val Glu Leu Ile Glu Gly Glu Arg Glu Leu Gln
                165                 170                 175

Ala Phe Glu Asn Ile Glu Asp Glu Ile Lys Leu Ile Gly Tyr Phe Lys
            180                 185                 190

Ser Lys Asp Ser Glu His Tyr Lys Ala Tyr Glu Asp Ala Ala Glu Glu
        195                 200                 205

Phe His Pro Tyr Ile Pro Phe Phe Ala Thr Phe Asp Ser Lys Val Ala
    210                 215                 220

Lys Lys Leu Thr Leu Lys Leu Asn Glu Ile Asp Phe Tyr Glu Ala Phe
225                 230                 235                 240

Met Glu Glu Pro Met Thr Ile Pro Asp Lys Pro Asn Ser Glu Glu Glu
                245                 250                 255

Ile Val Ser Phe Val Glu Glu His Arg Arg Ser Thr Leu Arg Lys Leu
            260                 265                 270

Lys Pro Glu Ser Met Tyr Glu Thr Trp Glu Asp Asp Leu Asp Gly Ile
        275                 280                 285

His Thr Val Ala Phe Ala Glu Glu Ala Asp Pro Asp Gly Tyr Glu Phe
    290                 295                 300

Leu Glu Thr Leu Lys Ala Val Ala Gln Asp Asn Thr Glu Asn Pro Asp
305                 310                 315                 320

Leu Ser Ile Ile Trp Ile Asp Pro Asp Asp Phe Pro Leu Leu Val Pro
                325                 330                 335
```

```
Tyr Trp Glu Lys Thr Phe Asp Ile Asp Leu Ser Ala Pro Gln Ile Gly
            340                 345                 350
Val Val Asn Val Thr Asp Ala Asp Ser Ile Trp Met Glu Met Asp Asn
            355                 360                 365
Glu Glu Asp Leu Pro Ser Ala Asp Glu Leu Gly Asp Trp Leu Glu Asp
370                 375                 380
Val Leu Glu Gly Glu Ile Asn Thr Gly Ser Gly Pro Ser Arg Met
385                 390                 395                 400
Val Ser Lys Gly Glu Glu Leu Phe Thr Gly Val Val Pro Ile Leu Val
            405                 410                 415
Glu Leu Asp Gly Asp Val Asn Gly His Lys Phe Ser Val Ser Gly Glu
            420                 425                 430
Gly Glu Gly Asp Ala Thr Tyr Gly Lys Leu Thr Leu Lys Phe Ile Cys
            435                 440                 445
Thr Thr Gly Lys Leu Pro Val Pro Trp Pro Thr Leu Val Thr Thr Leu
450                 455                 460
Thr Tyr Gly Val Gln Cys Phe Ser Arg Tyr Pro Asp His Met Lys Gln
465                 470                 475                 480
His Asp Phe Phe Lys Ser Ala Met Pro Glu Gly Tyr Val Gln Glu Arg
            485                 490                 495
Thr Ile Phe Phe Lys Asp Asp Gly Asn Tyr Lys Thr Arg Ala Glu Val
            500                 505                 510
Lys Phe Glu Gly Asp Thr Leu Val Asn Arg Ile Glu Leu Lys Gly Ile
            515                 520                 525
Asp Phe Lys Glu Asp Gly Asn Ile Leu Gly His Lys Leu Glu Tyr Asn
            530                 535                 540
Tyr Asn Glu His Asn Val Tyr Ile Thr Ala Asp Lys Gln Lys Asn Gly
545                 550                 555                 560
Ile Lys Ala Asn Phe Lys Ile Arg His Asn Ile Glu Asp Gly Ser Val
            565                 570                 575
Gln Leu Ala Asp His Tyr Gln Gln Asn Thr Pro Ile Gly Asp Gly Pro
            580                 585                 590
Val Leu Leu Pro Asp Asn His Tyr Leu Asp Thr Glu Ser Ala Leu Ser
            595                 600                 605
Lys Asp Pro Asn Glu Lys Arg Asp His Met Val Leu Leu Glu Glu Val
            610                 615                 620
Glu Ala Ala Gly Ile Thr Leu Gly Met Asp Glu Leu Tyr Lys Glu Phe
625                 630                 635                 640
Xaa Xaa Gln Ile Ser Ser Thr Val Ala Ala Arg Val Arg Ala Arg
            645                 650                 655
Leu Asn Pro Leu Ile Ser Leu Asp Cys Ala Phe Leu Pro Ala Ile Cys
            660                 665                 670
Cys

<210> SEQ ID NO 119
<211> LENGTH: 346
<212> TYPE: PRT
<213> ORGANISM: Artificial sequence
<220> FEATURE:
<223> OTHER INFORMATION: Synthetic EGFP
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
```

```
<222> LOCATION: (327)..(328)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid
<220> FEATURE:
<221> NAME/KEY: misc_feature
<222> LOCATION: (337)..(338)
<223> OTHER INFORMATION: Xaa can be any naturally occurring amino acid
<220> FEATURE:
<221> NAME/KEY: misc_feature
<222> LOCATION: (341)..(344)
<223> OTHER INFORMATION: Xaa can be any naturally occurring amino acid
<220> FEATURE:
<221> NAME/KEY: misc_feature
<222> LOCATION: (346)..(346)
<223> OTHER INFORMATION: Xaa can be any naturally occurring amino acid

<400> SEQUENCE: 119

Phe Cys Leu Thr Leu Arg Arg Arg Tyr Thr Met Gly Ser Ser His His
1               5                   10                  15

His His His His Ser Ser Gly Leu Val Pro Arg Gly Ser His Met Ala
            20                  25                  30

Ser Met Thr Gly Gly Gln Gln Met Gly Arg Gly Ser Gly Pro Ser Arg
        35                  40                  45

Met Val Ser Lys Gly Glu Glu Leu Phe Thr Gly Val Val Pro Ile Leu
50                  55                  60

Val Glu Leu Asp Gly Asp Val Asn Gly His Lys Phe Ser Val Ser Gly
65                  70                  75                  80

Glu Gly Glu Gly Asp Ala Thr Tyr Gly Lys Leu Thr Leu Lys Phe Ile
                85                  90                  95

Cys Thr Thr Gly Lys Leu Pro Val Pro Trp Pro Thr Leu Val Thr Thr
            100                 105                 110

Leu Thr Tyr Gly Val Gln Cys Phe Ser Arg Tyr Pro Asp His Met Lys
        115                 120                 125

Gln His Asp Phe Phe Lys Ser Ala Met Pro Glu Gly Tyr Val Gln Glu
    130                 135                 140

Arg Thr Ile Phe Phe Lys Asp Asp Gly Asn Tyr Lys Thr Arg Ala Glu
145                 150                 155                 160

Val Lys Phe Glu Gly Asp Thr Leu Val Asn Arg Ile Glu Leu Lys Gly
                165                 170                 175

Ile Asp Phe Lys Glu Asp Gly Asn Ile Leu Gly His Lys Leu Glu Tyr
            180                 185                 190

Asn Tyr Asn Glu His Asn Val Tyr Ile Thr Ala Asp Lys Gln Lys Asn
        195                 200                 205

Gly Ile Lys Ala Asn Phe Lys Ile Arg His Asn Ile Glu Asp Gly Ser
    210                 215                 220

Val Gln Leu Ala Asp His Tyr Gln Gln Asn Thr Pro Ile Gly Asp Gly
225                 230                 235                 240

Pro Val Leu Leu Pro Asp Asn His Tyr Leu Asp Ile Glu Ser Ala Leu
                245                 250                 255

Ser Lys Asp Pro Asn Glu Lys Arg Asp His Met Val Leu Leu Glu Glu
            260                 265                 270

Val Glu Ala Ala Gly Ile Thr Leu Gly Met Asp Glu Leu Tyr Lys Glu
        275                 280                 285

Phe Glu Leu Arg Arg Gln Ala Cys Gly Arg Thr Arg Val Pro Pro Pro
    290                 295                 300

Pro Pro Leu Arg Ser Gly Cys Gln Ser Pro Lys Gly Ser Xaa Gly Cys
```

```
                  305                 310                 315                 320
Cys Pro Thr Pro Leu Pro Xaa Xaa Arg Ile Arg Pro Xaa Gln Arg Pro
                        325                 330                 335

Xaa Xaa Ser Ala Xaa Xaa Xaa Cys Xaa
                340                 345

<210> SEQ ID NO 120
<211> LENGTH: 319
<212> TYPE: PRT
<213> ORGANISM: Artificial sequence
<220> FEATURE:
<223> OTHER INFORMATION: Synthetic EGFP
<220> FEATURE:
<221> NAME/KEY: misc_feature
<222> LOCATION: (1)..(1)
<223> OTHER INFORMATION: Xaa can be any naturally occurring amino acid

<400> SEQUENCE: 120

Xaa Ile Thr Cys Ser Leu Ala Ser Val Leu Lys Leu Gly Thr Glu Leu
1               5                  10                  15

Gly Ser Gly Pro Ser Arg Met Val Ser Lys Gly Glu Glu Leu Phe Thr
                20                  25                  30

Gly Val Val Pro Ile Leu Val Glu Leu Asp Gly Asp Val Asn Gly His
            35                  40                  45

Lys Phe Ser Val Ser Gly Glu Gly Glu Gly Asp Ala Thr Tyr Gly Lys
    50                  55                  60

Leu Thr Leu Lys Phe Ile Cys Thr Thr Gly Lys Leu Pro Val Pro Trp
65                  70                  75                  80

Pro Thr Leu Val Thr Thr Leu Thr Tyr Gly Val Gln Cys Phe Ser Arg
                85                  90                  95

Tyr Pro Asp His Met Lys Gln His Asp Phe Phe Lys Ser Ala Met Pro
            100                 105                 110

Glu Gly Tyr Val Gln Glu Arg Thr Ile Phe Phe Lys Asp Asp Gly Asn
        115                 120                 125

Tyr Lys Thr Arg Ala Glu Val Lys Phe Glu Gly Asp Thr Leu Val Asn
130                 135                 140

Arg Ile Glu Leu Lys Gly Ile Asp Phe Lys Glu Asp Gly Asn Ile Leu
145                 150                 155                 160

Gly His Lys Leu Glu Tyr Asn Tyr Asn Glu His Asn Val Tyr Ile Thr
                165                 170                 175

Ala Asp Lys Gln Lys Asn Gly Ile Lys Ala Asn Phe Lys Ile Arg His
            180                 185                 190

Asn Ile Glu Asp Gly Ser Val Gln Leu Ala Asp His Tyr Gln Gln Asn
        195                 200                 205

Thr Pro Ile Gly Asp Gly Pro Val Leu Leu Pro Asp Asn His Tyr Leu
    210                 215                 220

Asp Thr Glu Ser Ala Leu Ser Lys Asp Pro Asn Glu Lys Arg Asp His
225                 230                 235                 240

Met Val Leu Leu Glu Glu Val Glu Ala Ala Gly Ile Thr Leu Gly Met
                245                 250                 255

Asp Glu Leu Tyr Lys Phe Tyr Thr Leu Arg Phe Leu Ala Leu Phe Leu
            260                 265                 270

Ala Phe Ala Ile Asn Phe Ile Leu Leu Phe Tyr Lys Val Ser Glu Phe
        275                 280                 285

Cys Arg Tyr Pro Ala Gln Trp Arg Pro Leu Glu Ser Arg Gly Pro Val
    290                 295                 300
```

```
Thr Arg Ser Ala Ser Thr Val Pro Ser Ser Cys Gln Pro Ser Val
305                 310                 315
```

<210> SEQ ID NO 121
<211> LENGTH: 238
<212> TYPE: PRT
<213> ORGANISM: Artificial sequence
<220> FEATURE:
<223> OTHER INFORMATION: D8-EGFP

<400> SEQUENCE: 121

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Gln Ser Ala Leu Ser
        195                 200                 205

Lys Asp Pro Asn Glu Lys Arg Asp His Ile Val Leu Leu Glu Glu Val
    210                 215                 220

Thr Ala Ala Gly Ile Thr Leu Gly Met Asp Glu Leu Tyr Lys
225                 230                 235
```

<210> SEQ ID NO 122
<211> LENGTH: 238
<212> TYPE: PRT
<213> ORGANISM: Artificial sequence
<220> FEATURE:
<223> OTHER INFORMATION: D9-EGFP

<400> SEQUENCE: 122

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60
```

```
Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Gln Ser Ala Leu Ser
        195                 200                 205

Lys Asp Pro Asn Glu Lys Arg Asp His Ile Val Leu Leu Glu Glu Val
210                 215                 220

Thr Ala Ala Gly Ile Thr Leu Gly Met Asp Glu Leu Tyr Lys
225                 230                 235

<210> SEQ ID NO 123
<211> LENGTH: 238
<212> TYPE: PRT
<213> ORGANISM: Artificial sequence
<220> FEATURE:
<223> OTHER INFORMATION: D10-EGFP

<400> SEQUENCE: 123

Val Ser Lys Gly Glu Glu Leu Phe Thr Gly Val Val Pro Ile Leu Val
 1               5                  10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190
```

Val Leu Leu Pro Asp Asn His Tyr Leu Asp Thr Gln Ser Ala Leu Ser
        195                 200                 205

Lys Asp Pro Asn Glu Lys Arg Asp His Ile Val Leu Glu Glu Val
    210                 215                 220

Glu Ala Ala Gly Ile Thr Leu Gly Met Asp Glu Leu Tyr Lys
225                 230                 235

<210> SEQ ID NO 124
<211> LENGTH: 238
<212> TYPE: PRT
<213> ORGANISM: Artificial sequence
<220> FEATURE:
<223> OTHER INFORMATION: D11-EGFP, CatchER without ER tag

<400> SEQUENCE: 124

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
        195                 200                 205

Lys Asp Pro Asn Glu Lys Arg Asp His Ile Val Leu Glu Glu Val
    210                 215                 220

Glu Ala Ala Gly Ile Thr Leu Gly Met Asp Glu Leu Tyr Lys
225                 230                 235

<210> SEQ ID NO 125
<211> LENGTH: 260
<212> TYPE: PRT
<213> ORGANISM: Artificial sequence
<220> FEATURE:
<223> OTHER INFORMATION: D11-EGFP, CatchER with ER tag

<400> SEQUENCE: 125

Met Leu Leu Ser Val Pro Leu Leu Leu Gly Leu Leu Gly Leu Ala Ala
1               5                   10                  15

Ala Asp Val Ser Lys Gly Glu Glu Leu Phe Thr Gly Val Val Pro Ile

```
                20                  25                  30
Leu Val Glu Leu Asp Gly Asp Leu Asn Gly His Lys Phe Ser Val Ser
            35                  40                  45
Gly Glu Gly Glu Gly Asp Ala Thr Tyr Gly Lys Leu Thr Leu Lys Phe
        50                  55                  60
Ile Cys Thr Thr Gly Lys Leu Pro Val Pro Trp Pro Thr Leu Val Thr
65                  70                  75                  80
Thr Leu Thr Tyr Gly Val Gln Cys Phe Ser Arg Tyr Pro Asp His Met
                85                  90                  95
Lys Gln His Asp Phe Phe Lys Ser Ala Met Pro Glu Gly Tyr Val Gln
            100                 105                 110
Glu Arg Thr Ile Phe Phe Lys Asp Asp Gly Asn Tyr Lys Thr Arg Ala
        115                 120                 125
Glu Val Lys Phe Glu Gly Asp Thr Leu Val Asn Arg Ile Glu Leu Lys
    130                 135                 140
Gly Ile Asp Phe Lys Glu Asp Gly Asn Ile Leu Gly His Lys Leu Glu
145                 150                 155                 160
Tyr Asn Tyr Asn Glu His Asn Val Tyr Ile Thr Ala Asp Lys Gln Lys
                165                 170                 175
Asn Gly Ile Lys Ala Asn Phe Lys Ile Arg His Asn Ile Glu Asp Gly
            180                 185                 190
Ser Val Gln Leu Ala Asp His Tyr Gln Gln Asn Thr Pro Ile Gly Asp
        195                 200                 205
Gly Pro Val Leu Leu Pro Asp Asn His Tyr Leu Asp Thr Glu Ser Ala
    210                 215                 220
Leu Ser Lys Asp Pro Asn Glu Lys Arg Asp His Ile Val Leu Leu Glu
225                 230                 235                 240
Glu Val Glu Ala Ala Gly Ile Thr Leu Gly Met Asp Glu Leu Tyr Lys
                245                 250                 255
Lys Asp Glu Leu
            260

<210> SEQ ID NO 126
<211> LENGTH: 238
<212> TYPE: PRT
<213> ORGANISM: Artificial sequence
<220> FEATURE:
<223> OTHER INFORMATION: D12-EGFP

<400> SEQUENCE: 126

Val Ser Lys Gly Glu Glu Leu Phe Thr Gly Val Val Pro Ile Leu Val
1               5                   10                  15
Glu Leu Asp Gly Asp Leu Asn Gly His Lys Phe Ser Val Ser Gly Glu
            20                  25                  30
Gly Glu Gly Asp Ala Thr Tyr Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Thr Tyr Gly Val Gln Cys Phe Ser Arg Tyr Pro Asp His Met Lys Gln
65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
```

```
                115                 120                 125
Asp Phe Lys Glu Asp Gly Asn Ile Leu Gly His Lys Leu Glu Tyr Asn
        130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
                195                 200                 205

Lys Asp Pro Asn Glu Lys Arg Asp His Ile Val Leu Leu Glu Asp Val
            210                 215                 220

Glu Ala Ala Gly Ile Thr Leu Gly Met Asp Glu Leu Tyr Lys
225                 230                 235

<210> SEQ ID NO 127
<211> LENGTH: 238
<212> TYPE: PRT
<213> ORGANISM: Artificial sequence
<220> FEATURE:
<223> OTHER INFORMATION: D13-EGFP

<400> SEQUENCE: 127

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Asn Ser Ala Leu Ser
                195                 200                 205

Lys Asp Pro Asn Glu Lys Arg Asp His Ile Val Leu Leu Glu Asp Val
            210                 215                 220

Glu Ala Ala Gly Ile Thr Leu Gly Met Asp Glu Leu Tyr Lys
225                 230                 235
```

<210> SEQ ID NO 128
<211> LENGTH: 238
<212> TYPE: PRT
<213> ORGANISM: Artificial sequence
<220> FEATURE:
<223> OTHER INFORMATION: D14-EGFP

<400> SEQUENCE: 128

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Glu Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Gln Ser Ala Leu Ser
        195                 200                 205

Lys Asp Pro Asn Glu Lys Arg Asp His Ile Val Leu Leu Glu Glu Val
    210                 215                 220

Thr Ala Ala Gly Ile Thr Leu Gly Met Asp Glu Leu Tyr Lys
225                 230                 235
```

<210> SEQ ID NO 129
<211> LENGTH: 238
<212> TYPE: PRT
<213> ORGANISM: Artificial sequence
<220> FEATURE:
<223> OTHER INFORMATION: D15-EGFP

<400> SEQUENCE: 129

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80
```

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Glu Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
        195                 200                 205

Lys Asp Pro Asn Glu Lys Arg Asp His Ile Val Leu Leu Glu Glu Val
    210                 215                 220

Thr Ala Ala Gly Ile Thr Leu Gly Met Asp Glu Leu Tyr Lys
225                 230                 235

<210> SEQ ID NO 130
<211> LENGTH: 238
<212> TYPE: PRT
<213> ORGANISM: Artificial sequence
<220> FEATURE:
<223> OTHER INFORMATION: D16-EGFP

<400> SEQUENCE: 130

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Glu Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
        195                 200                 205

```
Lys Asp Pro Asn Glu Lys Arg Asp His Ile Val Leu Glu Glu Val
    210                 215                 220

Glu Ala Ala Gly Ile Thr Leu Gly Met Asp Glu Leu Tyr Lys
225                 230                 235

<210> SEQ ID NO 131
<211> LENGTH: 238
<212> TYPE: PRT
<213> ORGANISM: Artificial sequence
<220> FEATURE:
<223> OTHER INFORMATION: D11-EGFP-203I, CatchER-203I

<400> SEQUENCE: 131

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Ile Glu Ser Ala Leu Ser
        195                 200                 205

Lys Asp Pro Asn Glu Lys Arg Asp His Ile Val Leu Glu Glu Val
    210                 215                 220

Glu Ala Ala Gly Ile Thr Leu Gly Met Asp Glu Leu Tyr Lys
225                 230                 235

<210> SEQ ID NO 132
<211> LENGTH: 238
<212> TYPE: PRT
<213> ORGANISM: Artificial sequence
<220> FEATURE:
<223> OTHER INFORMATION: D11-EGFP-203V, CatchER-203V

<400> SEQUENCE: 132

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

```
Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Val Glu Ser Ala Leu Ser
            195                 200                 205

Lys Asp Pro Asn Glu Lys Arg Asp His Ile Val Leu Leu Glu Glu Val
        210                 215                 220

Glu Ala Ala Gly Ile Thr Leu Gly Met Asp Glu Leu Tyr Lys
225                 230                 235
```

<210> SEQ ID NO 133
<211> LENGTH: 238
<212> TYPE: PRT
<213> ORGANISM: Artificial sequence
<220> FEATURE:
<223> OTHER INFORMATION: D11-EGFP-203D, CatchER-203D

<400> SEQUENCE: 133

```
Val Ser Lys Gly Glu Glu Leu Phe Thr Gly Val Val Pro Ile Leu Val
 1               5                  10                  15

Glu Leu Asp Gly Asp Leu Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175
```

Gln Leu Ala Asp His Tyr Gln Gln Asn Thr Pro Ile Gly Asp Gly Pro
              180                 185                 190

Val Leu Leu Pro Asp Asn His Tyr Leu Asp Asp Glu Ser Ala Leu Ser
          195                 200                 205

Lys Asp Pro Asn Glu Lys Arg Asp His Ile Val Leu Leu Glu Glu Val
210                 215                 220

Glu Ala Ala Gly Ile Thr Leu Gly Met Asp Glu Leu Tyr Lys
225                 230                 235

<210> SEQ ID NO 134
<211> LENGTH: 238
<212> TYPE: PRT
<213> ORGANISM: Artificial sequence
<220> FEATURE:
<223> OTHER INFORMATION: D11-EGFP-203F, CatchER-203F

<400> SEQUENCE: 134

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Phe Glu Ser Ala Leu Ser
        195                 200                 205

Lys Asp Pro Asn Glu Lys Arg Asp His Ile Val Leu Leu Glu Glu Val
    210                 215                 220

Glu Ala Ala Gly Ile Thr Leu Gly Met Asp Glu Leu Tyr Lys
225                 230                 235

<210> SEQ ID NO 135
<211> LENGTH: 238
<212> TYPE: PRT
<213> ORGANISM: Artificial sequence
<220> FEATURE:
<223> OTHER INFORMATION: D11-EGFP-203E, CatchER-203E

<400> SEQUENCE: 135

Val Ser Lys Gly Glu Glu Leu Phe Thr Gly Val Val Pro Ile Leu Val

```
  1               5                  10                 15
Glu Leu Asp Gly Asp Leu Asn Gly His Lys Phe Ser Val Ser Gly Glu
            20                  25                 30

Gly Glu Gly Asp Ala Thr Tyr Gly Lys Leu Thr Leu Lys Phe Ile Cys
            35                  40                 45

Thr Thr Gly Lys Leu Pro Val Pro Trp Pro Thr Leu Val Thr Thr Leu
 50                      55                  60

Thr Tyr Gly Val Gln Cys Phe Ser Arg Tyr Pro Asp His Met Lys Gln
 65                      70                  75                 80

His Asp Phe Phe Lys Ser Ala Met Pro Glu Gly Tyr Val Gln Glu Arg
                 85                  90                 95

Thr Ile Phe Phe Lys Asp Asp Gly Asn Tyr Lys Thr Arg Ala Glu Val
                100                 105                110

Lys Phe Glu Gly Asp Thr Leu Val Asn Arg Ile Glu Leu Lys Gly Ile
                115                 120                125

Asp Phe Lys Glu Asp Gly Asn Ile Leu Gly His Lys Leu Glu Tyr Asn
130                     135                 140

Tyr Asn Glu His Asn Val Tyr Ile Thr Ala Asp Lys Gln Lys Asn Gly
145                     150                 155                160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Asp Glu Glu Ser Ala Leu Ser
                195                 200                 205

Lys Asp Pro Asn Glu Lys Arg Asp His Ile Val Leu Leu Glu Glu Val
    210                 215                 220

Glu Ala Ala Gly Ile Thr Leu Gly Met Asp Glu Leu Tyr Lys
225                     230                 235
```

<210> SEQ ID NO 136
<211> LENGTH: 238
<212> TYPE: PRT
<213> ORGANISM: Artificial sequence
<220> FEATURE:
<223> OTHER INFORMATION: D11-EGFP-175G, CatchER-175G

<400> SEQUENCE: 136

```
Val Ser Lys Gly Glu Glu Leu Phe Thr Gly Val Val Pro Ile Leu Val
 1               5                  10                 15

Glu Leu Asp Gly Asp Leu Asn Gly His Lys Phe Ser Val Ser Gly Glu
            20                  25                 30

Gly Glu Gly Asp Ala Thr Tyr Gly Lys Leu Thr Leu Lys Phe Ile Cys
            35                  40                 45

Thr Thr Gly Lys Leu Pro Val Pro Trp Pro Thr Leu Val Thr Thr Leu
 50                      55                  60

Thr Tyr Gly Val Gln Cys Phe Ser Arg Tyr Pro Asp His Met Lys Gln
 65                      70                  75                 80

His Asp Phe Phe Lys Ser Ala Met Pro Glu Gly Tyr Val Gln Glu Arg
                 85                  90                 95

Thr Ile Phe Phe Lys Asp Asp Gly Asn Tyr Lys Thr Arg Ala Glu Val
                100                 105                110

Lys Phe Glu Gly Asp Thr Leu Val Asn Arg Ile Glu Leu Lys Gly Ile
                115                 120                125

Asp Phe Lys Glu Asp Gly Asn Ile Leu Gly His Lys Leu Glu Tyr Asn
```

```
                130             135             140
Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
            195                 200                 205

Lys Asp Pro Asn Glu Lys Arg Asp His Ile Val Leu Leu Glu Glu Val
        210                 215                 220

Glu Ala Ala Gly Ile Thr Leu Gly Met Asp Glu Leu Tyr Lys
225                 230                 235

<210> SEQ ID NO 137
<211> LENGTH: 238
<212> TYPE: PRT
<213> ORGANISM: Artificial sequence
<220> FEATURE:
<223> OTHER INFORMATION: D11-EGFP-148D, CatchER-148D

<400> SEQUENCE: 137

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu Asp Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
            195                 200                 205

Lys Asp Pro Asn Glu Lys Arg Asp His Ile Val Leu Leu Glu Glu Val
        210                 215                 220

Glu Ala Ala Gly Ile Thr Leu Gly Met Asp Glu Leu Tyr Lys
225                 230                 235

<210> SEQ ID NO 138
<211> LENGTH: 269
<212> TYPE: PRT
```

<213> ORGANISM: Artificial sequence
<220> FEATURE:
<223> OTHER INFORMATION: G1M1-EGFP

<400> SEQUENCE: 138

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Asp Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Glu Glu Glu Ile
                165                 170                 175

Arg Glu Ala Phe Arg Val Phe Asp Lys Asp Gly Asn Gly Tyr Ile Ser
            180                 185                 190

Ala Ala Glu Leu Arg His Val Met Thr Asn Leu Asp Gly Ser Val Gln
        195                 200                 205

Leu Ala Asp His Tyr Gln Gln Asn Thr Pro Ile Gly Asp Gly Pro Val
210                 215                 220

Leu Leu Pro Asp Asn His Tyr Leu Ser Thr Gln Ser Ala Leu Ser Lys
225                 230                 235                 240

Asp Pro Asn Glu Lys Arg Asp His Ile Val Leu Leu Glu Phe Val Thr
                245                 250                 255

Ala Ala Gly Ile Thr Leu Gly Met Asp Glu Leu Tyr Lys
            260                 265
```

<210> SEQ ID NO 139
<211> LENGTH: 269
<212> TYPE: PRT
<213> ORGANISM: Artificial sequence
<220> FEATURE:
<223> OTHER INFORMATION: G1M2-EGFP

<400> SEQUENCE: 139

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60
```

```
Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Glu Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Glu Glu Glu Ile
                165                 170                 175

Arg Glu Ala Phe Arg Val Phe Asp Lys Asp Gly Asn Gly Tyr Ile Ser
            180                 185                 190

Ala Ala Glu Leu Arg His Val Met Thr Asn Leu Asp Gly Ser Val Gln
        195                 200                 205

Leu Ala Asp His Tyr Gln Gln Asn Thr Pro Ile Gly Asp Gly Pro Val
210                 215                 220

Leu Leu Pro Asp Asn His Tyr Leu Ser Thr Gln Ser Ala Leu Ser Lys
225                 230                 235                 240

Asp Pro Asn Glu Lys Arg Asp His Ile Val Leu Leu Glu Phe Val Thr
                245                 250                 255

Ala Ala Gly Ile Thr Leu Gly Met Asp Glu Leu Tyr Lys
            260                 265
```

<210> SEQ ID NO 140
<211> LENGTH: 690
<212> TYPE: PRT
<213> ORGANISM: Artificial sequence
<220> FEATURE:
<223> OTHER INFORMATION: calsequestrin tethered CatchER
<220> FEATURE:
<221> NAME/KEY: misc_feature
<222> LOCATION: (658)..(659)
<223> OTHER INFORMATION: Xaa can be any naturally occurring amino acid

<400> SEQUENCE: 140

```
Ile Thr Cys Ser Leu Ala Ser Val Leu Lys Leu Met Gly Ala Arg Ala
  1               5                  10                  15

Val Ser Glu Leu Arg Leu Ala Leu Leu Phe Val Leu Val Leu Gly Thr
             20                  25                  30

Pro Arg Leu Gly Val Gln Gly Glu Asp Gly Leu Asp Phe Pro Glu Tyr
         35                  40                  45

Asp Gly Val Asp Arg Val Ile Asn Val Asn Ala Lys Asn Tyr Lys Asn
     50                  55                  60

Val Phe Lys Lys Tyr Glu Val Leu Ala Leu Leu Tyr His Glu Pro Pro
 65                  70                  75                  80

Glu Asp Asp Lys Ala Ser Gln Arg Gln Phe Glu Met Glu Glu Leu Ile
                 85                  90                  95

Leu Glu Leu Ala Ala Gln Val Leu Glu Asp Lys Gly Val Gly Phe Gly
            100                 105                 110

Leu Val Asp Ser Glu Lys Asp Ala Ala Val Ala Lys Lys Leu Gly Leu
        115                 120                 125

Thr Glu Glu Asp Ser Val Tyr Val Phe Lys Gly Asp Glu Val Ile Glu
    130                 135                 140
```

```
Tyr Asp Gly Glu Phe Ser Ala Asp Thr Leu Val Glu Phe Leu Leu Asp
145                 150                 155                 160

Val Leu Glu Asp Pro Val Glu Leu Ile Glu Gly Arg Glu Leu Gln
            165                 170                 175

Ala Phe Glu Asn Ile Glu Asp Glu Ile Lys Leu Ile Gly Tyr Phe Lys
            180                 185                 190

Ser Lys Asp Ser Glu His Tyr Lys Ala Tyr Glu Asp Ala Ala Glu Glu
            195                 200                 205

Phe His Pro Tyr Ile Pro Phe Phe Ala Thr Phe Asp Ser Lys Val Ala
            210                 215                 220

Lys Lys Leu Thr Leu Lys Leu Asn Glu Ile Asp Phe Tyr Glu Ala Phe
225                 230                 235                 240

Met Glu Glu Pro Met Thr Ile Pro Asp Lys Pro Asn Ser Glu Glu Glu
                245                 250                 255

Ile Val Ser Phe Val Glu Glu His Arg Arg Ser Thr Leu Arg Lys Leu
            260                 265                 270

Lys Pro Glu Ser Met Tyr Glu Thr Trp Glu Asp Leu Asp Gly Ile
            275                 280                 285

His Thr Val Ala Phe Ala Glu Glu Ala Asp Pro Asp Gly Tyr Glu Phe
290                 295                 300

Leu Glu Thr Leu Lys Ala Val Ala Gln Asp Asn Thr Glu Asn Pro Asp
305                 310                 315                 320

Leu Ser Ile Ile Trp Ile Asp Pro Asp Phe Pro Leu Leu Val Pro
                325                 330                 335

Tyr Trp Glu Lys Thr Phe Asp Ile Asp Leu Ser Ala Pro Gln Ile Gly
            340                 345                 350

Val Val Asn Val Thr Asp Ala Asp Ser Ile Trp Met Glu Met Asp Asn
            355                 360                 365

Glu Glu Asp Leu Pro Ser Ala Asp Glu Leu Glu Asp Trp Leu Glu Asp
370                 375                 380

Val Leu Glu Gly Glu Ile Asn Thr Glu Asp Asp Asp Asp Asp Asp
385                 390                 395                 400

Asp Asp Asp Asp Asp Asp Asp Asp Asp Gly Ser Gly Pro Ser Arg
            405                 410                 415

Met Val Ser Lys Gly Glu Glu Leu Phe Thr Gly Val Val Pro Ile Leu
            420                 425                 430

Val Glu Leu Asp Gly Asp Val Asn Gly His Lys Phe Ser Val Ser Gly
            435                 440                 445

Glu Gly Glu Gly Asp Ala Thr Tyr Gly Lys Leu Thr Leu Lys Phe Ile
            450                 455                 460

Cys Thr Thr Gly Lys Leu Pro Val Pro Trp Pro Thr Leu Val Thr Thr
465                 470                 475                 480

Leu Thr Tyr Gly Val Gln Cys Phe Ser Arg Tyr Pro Asp His Met Lys
            485                 490                 495

Gln His Asp Phe Phe Lys Ser Ala Met Pro Glu Gly Tyr Val Gln Glu
            500                 505                 510

Arg Thr Ile Phe Phe Lys Asp Asp Gly Asn Tyr Lys Thr Arg Ala Glu
            515                 520                 525

Val Lys Phe Glu Gly Asp Thr Leu Val Asn Arg Ile Glu Leu Lys Gly
            530                 535                 540

Ile Asp Phe Lys Glu Asp Gly Asn Ile Leu Gly His Lys Leu Glu Tyr
545                 550                 555                 560
```

```
Asn Tyr Asn Glu His Asn Val Tyr Ile Thr Ala Asp Lys Gln Lys Asn
                565                 570                 575

Gly Ile Lys Ala Asn Phe Lys Ile Arg His Asn Ile Glu Asp Gly Ser
            580                 585                 590

Val Gln Leu Ala Asp His Tyr Gln Gln Asn Thr Pro Ile Gly Asp Gly
        595                 600                 605

Pro Val Leu Leu Pro Asp Asn His Tyr Leu Asp Thr Glu Ser Ala Leu
    610                 615                 620

Ser Lys Asp Pro Asn Glu Lys Arg Asp His Met Val Leu Leu Glu Glu
625                 630                 635                 640

Val Glu Ala Ala Gly Ile Thr Leu Gly Met Asp Glu Leu Tyr Lys Glu
                645                 650                 655

Phe Xaa Xaa Gln Ile Ser Ser Thr Val Ala Ala Ala Arg Val Arg Ala
            660                 665                 670

Arg Leu Asn Pro Leu Ile Ser Leu Asp Cys Ala Phe Leu Pro Ala Ile
                675                 680                 685

Cys Cys
    690
```

<210> SEQ ID NO 141
<211> LENGTH: 673
<212> TYPE: PRT
<213> ORGANISM: Artificial sequence
<220> FEATURE:
<223> OTHER INFORMATION: calsequestrin 17 Asp deleted tethered CatchER
<220> FEATURE:
<221> NAME/KEY: misc_feature
<222> LOCATION: (641)..(642)
<223> OTHER INFORMATION: Xaa can be any naturally occurring amino acid

<400> SEQUENCE: 141

```
Ile Thr Cys Ser Leu Ala Ser Val Leu Lys Leu Met Gly Ala Arg Ala
1               5                   10                  15

Val Ser Glu Leu Arg Leu Ala Leu Leu Phe Val Leu Val Leu Gly Thr
            20                  25                  30

Pro Arg Leu Gly Val Gln Gly Glu Asp Gly Leu Asp Phe Pro Glu Tyr
        35                  40                  45

Asp Gly Val Asp Arg Val Ile Asn Val Asn Ala Lys Asn Tyr Lys Asn
    50                  55                  60

Val Phe Lys Lys Tyr Glu Val Leu Ala Leu Leu Tyr His Glu Pro Pro
65                  70                  75                  80

Glu Asp Asp Lys Ala Ser Gln Arg Gln Phe Glu Met Glu Glu Leu Ile
                85                  90                  95

Leu Glu Leu Ala Ala Gln Val Leu Glu Asp Lys Gly Val Gly Phe Gly
            100                 105                 110

Leu Val Asp Ser Glu Lys Asp Ala Ala Val Ala Lys Lys Leu Gly Leu
        115                 120                 125

Thr Glu Glu Asp Ser Val Tyr Val Phe Lys Gly Asp Glu Val Ile Glu
    130                 135                 140

Tyr Asp Gly Glu Phe Ser Ala Asp Thr Leu Val Glu Phe Leu Leu Asp
145                 150                 155                 160

Val Leu Glu Asp Pro Val Glu Leu Ile Glu Gly Glu Arg Glu Leu Gln
                165                 170                 175

Ala Phe Glu Asn Ile Glu Asp Glu Ile Lys Leu Ile Gly Tyr Phe Lys
            180                 185                 190

Ser Lys Asp Ser Glu His Tyr Lys Ala Tyr Glu Asp Ala Ala Glu Glu
        195                 200                 205
```

-continued

Phe His Pro Tyr Ile Pro Phe Phe Ala Thr Phe Asp Ser Lys Val Ala
    210                 215                 220

Lys Lys Leu Thr Leu Lys Leu Asn Glu Ile Asp Phe Tyr Glu Ala Phe
225                 230                 235                 240

Met Glu Glu Pro Met Thr Ile Pro Asp Lys Pro Asn Ser Glu Glu Glu
                    245                 250                 255

Ile Val Ser Phe Val Glu Glu His Arg Arg Ser Thr Leu Arg Lys Leu
                260                 265                 270

Lys Pro Glu Ser Met Tyr Glu Thr Trp Glu Asp Asp Leu Asp Gly Ile
                275                 280                 285

His Thr Val Ala Phe Ala Glu Glu Ala Asp Pro Asp Gly Tyr Glu Phe
    290                 295                 300

Leu Glu Thr Leu Lys Ala Val Ala Gln Asp Asn Thr Glu Asn Pro Asp
305                 310                 315                 320

Leu Ser Ile Ile Trp Ile Asp Pro Asp Asp Phe Pro Leu Leu Val Pro
                    325                 330                 335

Tyr Trp Glu Lys Thr Phe Asp Ile Asp Leu Ser Ala Pro Gln Ile Gly
                340                 345                 350

Val Val Asn Val Thr Asp Ala Asp Ser Ile Trp Met Glu Met Asp Asn
                355                 360                 365

Glu Glu Asp Leu Pro Ser Ala Asp Glu Leu Glu Asp Trp Leu Glu Asp
370                 375                 380

Val Leu Glu Gly Glu Ile Asn Thr Glu Gly Ser Gly Pro Ser Arg Met
385                 390                 395                 400

Val Ser Lys Gly Glu Glu Leu Phe Thr Gly Val Val Pro Ile Leu Val
                405                 410                 415

Glu Leu Asp Gly Asp Val Asn Gly His Lys Phe Ser Val Ser Gly Glu
                420                 425                 430

Gly Glu Gly Asp Ala Thr Tyr Gly Lys Leu Thr Leu Lys Phe Ile Cys
                435                 440                 445

Thr Thr Gly Lys Leu Pro Val Pro Trp Pro Thr Leu Val Thr Thr Leu
                450                 455                 460

Thr Tyr Gly Val Gln Cys Phe Ser Arg Tyr Pro Asp His Met Lys Gln
465                 470                 475                 480

His Asp Phe Phe Lys Ser Ala Met Pro Glu Gly Tyr Val Gln Glu Arg
                485                 490                 495

Thr Ile Phe Phe Lys Asp Asp Gly Asn Tyr Lys Thr Arg Ala Glu Val
                500                 505                 510

Lys Phe Glu Gly Asp Thr Leu Val Asn Arg Ile Glu Leu Lys Gly Ile
                515                 520                 525

Asp Phe Lys Glu Asp Gly Asn Ile Leu Gly His Lys Leu Glu Tyr Asn
530                 535                 540

Tyr Asn Glu His Asn Val Tyr Ile Thr Ala Asp Lys Gln Lys Asn Gly
545                 550                 555                 560

Ile Lys Ala Asn Phe Lys Ile Arg His Asn Ile Glu Asp Gly Ser Val
                565                 570                 575

Gln Leu Ala Asp His Tyr Gln Gln Asn Thr Pro Ile Gly Asp Gly Pro
                580                 585                 590

Val Leu Leu Pro Asp Asn His Tyr Leu Asp Thr Glu Ser Ala Leu Ser
                595                 600                 605

Lys Asp Pro Asn Glu Lys Arg Asp His Met Val Leu Leu Glu Glu Val
                610                 615                 620

```
Glu Ala Ala Gly Ile Thr Leu Gly Met Asp Glu Leu Tyr Lys Glu Phe
625                 630                 635                 640

Xaa Xaa Gln Ile Ser Ser Thr Val Ala Ala Arg Val Arg Ala Arg
            645                 650                 655

Leu Asn Pro Leu Ile Ser Leu Asp Cys Ala Phe Leu Pro Ala Ile Cys
            660                 665                 670

Cys
```

```
<210> SEQ ID NO 142
<211> LENGTH: 238
<212> TYPE: PRT
<213> ORGANISM: Artificial sequence
<220> FEATURE:
<223> OTHER INFORMATION: D8-EGFP

<400> SEQUENCE: 142

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Gln Ser Ala Leu Ser
        195                 200                 205

Lys Asp Pro Asn Glu Lys Arg Asp His Ile Val Leu Leu Glu Glu Val
    210                 215                 220

Thr Ala Ala Gly Ile Thr Leu Gly Met Asp Glu Leu Tyr Lys
225                 230                 235
```

```
<210> SEQ ID NO 143
<211> LENGTH: 238
<212> TYPE: PRT
<213> ORGANISM: Artificial sequence
<220> FEATURE:
<223> OTHER INFORMATION: D9-EGFP

<400> SEQUENCE: 143

Val Ser Lys Gly Glu Glu Leu Phe Thr Gly Val Val Pro Ile Leu Val
1               5                   10                  15
```

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Gln Ser Ala Leu Ser
        195                 200                 205

Lys Asp Pro Asn Glu Lys Arg Asp His Ile Val Leu Leu Glu Glu Val
    210                 215                 220

Thr Ala Ala Gly Ile Thr Leu Gly Met Asp Glu Leu Tyr Lys
225                 230                 235

<210> SEQ ID NO 144
<211> LENGTH: 238
<212> TYPE: PRT
<213> ORGANISM: Artificial sequence
<220> FEATURE:
<223> OTHER INFORMATION: D10-EGFP

<400> SEQUENCE: 144

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

```
Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Gln Ser Ala Leu Ser
        195                 200                 205

Lys Asp Pro Asn Glu Lys Arg Asp His Ile Val Leu Leu Glu Glu Val
    210                 215                 220

Glu Ala Ala Gly Ile Thr Leu Gly Met Asp Glu Leu Tyr Lys
225                 230                 235
```

<210> SEQ ID NO 145
<211> LENGTH: 238
<212> TYPE: PRT
<213> ORGANISM: Artificial sequence
<220> FEATURE:
<223> OTHER INFORMATION: D11-EGFP

<400> SEQUENCE: 145

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
        195                 200                 205

Lys Asp Pro Asn Glu Lys Arg Asp His Ile Val Leu Leu Glu Glu Val
    210                 215                 220

Glu Ala Ala Gly Ile Thr Leu Gly Met Asp Glu Leu Tyr Lys
225                 230                 235
```

<210> SEQ ID NO 146
<211> LENGTH: 238
<212> TYPE: PRT
<213> ORGANISM: Artificial sequence
<220> FEATURE:

<223> OTHER INFORMATION: D12-EGFP

<400> SEQUENCE: 146

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
        195                 200                 205

Lys Asp Pro Asn Glu Lys Arg Asp His Ile Val Leu Leu Glu Asp Val
    210                 215                 220

Glu Ala Ala Gly Ile Thr Leu Gly Met Asp Glu Leu Tyr Lys
225                 230                 235

<210> SEQ ID NO 147
<211> LENGTH: 238
<212> TYPE: PRT
<213> ORGANISM: Artificial sequence
<220> FEATURE:
<223> OTHER INFORMATION: D13-EGFP

<400> SEQUENCE: 147

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Asn Ser Ala Leu Ser
        195                 200                 205

Lys Asp Pro Asn Glu Lys Arg Asp His Ile Val Leu Leu Glu Asp Val
    210                 215                 220

Glu Ala Ala Gly Ile Thr Leu Gly Met Asp Glu Leu Tyr Lys
225                 230                 235

<210> SEQ ID NO 148
<211> LENGTH: 238
<212> TYPE: PRT
<213> ORGANISM: Artificial sequence
<220> FEATURE:
<223> OTHER INFORMATION: D14-EGFP

<400> SEQUENCE: 148

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Glu Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Gln Ser Ala Leu Ser
        195                 200                 205

Lys Asp Pro Asn Glu Lys Arg Asp His Ile Val Leu Leu Glu Glu Val
    210                 215                 220

Thr Ala Ala Gly Ile Thr Leu Gly Met Asp Glu Leu Tyr Lys
225                 230                 235
```

<210> SEQ ID NO 149
<211> LENGTH: 238
<212> TYPE: PRT
<213> ORGANISM: Artificial sequence
<220> FEATURE:
<223> OTHER INFORMATION: D15-EGFP

<400> SEQUENCE: 149

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Glu Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
        195                 200                 205

Lys Asp Pro Asn Glu Lys Arg Asp His Ile Val Leu Leu Glu Glu Val
    210                 215                 220

Thr Ala Ala Gly Ile Thr Leu Gly Met Asp Glu Leu Tyr Lys
225                 230                 235

<210> SEQ ID NO 150
<211> LENGTH: 238
<212> TYPE: PRT
<213> ORGANISM: Artificial sequence
<220> FEATURE:
<223> OTHER INFORMATION: D16-EGFP

<400> SEQUENCE: 150

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln

His Asp Phe Phe Lys Ser Ala Met Pro Glu Gly Tyr Val Gln Glu Arg
65                  70                  75                  80

Thr Ile Phe Phe Lys Asp Asp Gly Asn Tyr Lys Thr Arg Ala Glu Val
            85                  90                  95

Lys Phe Glu Gly Asp Thr Leu Val Asn Arg Ile Glu Leu Lys Gly Ile
        100                 105                 110

Asp Phe Lys Glu Asp Gly Asn Ile Leu Gly His Lys Leu Glu Tyr Asn
    115                 120                 125

Tyr Asn Glu His Glu Val Tyr Ile Thr Ala Asp Lys Gln Lys Asn Gly
130                 135                 140

Ile Lys Ala Asn Phe Lys Ile Arg His Asn Ile Glu Asp Gly Ser Val
145                 150                 155                 160

Gln Leu Ala Asp His Tyr Gln Gln Asn Thr Pro Ile Gly Asp Gly Pro
        165                 170                 175

Val Leu Leu Pro Asp Asn His Tyr Leu Asp Thr Glu Ser Ala Leu Ser
    180                 185                 190

Lys Asp Pro Asn Glu Lys Arg Asp His Ile Val Leu Leu Glu Glu Val
195                 200                 205

Glu Ala Ala Gly Ile Thr Leu Gly Met Asp Glu Leu Tyr Lys
210                 215                 220

225                 230                 235

<210> SEQ ID NO 151
<211> LENGTH: 238
<212> TYPE: PRT
<213> ORGANISM: Artificial sequence
<220> FEATURE:
<223> OTHER INFORMATION: D11-EGFP-203I

<400> SEQUENCE: 151

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
            85                  90                  95

Thr Ile Phe Phe Lys Asp Asp Gly Asn Tyr Lys Thr Arg Ala Glu Val
        100                 105                 110

Lys Phe Glu Gly Asp Thr Leu Val Asn Arg Ile Glu Leu Lys Gly Ile
    115                 120                 125

Asp Phe Lys Glu Asp Gly Asn Ile Leu Gly His Lys Leu Glu Tyr Asn
130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
        180                 185                 190

Val Leu Leu Pro Asp Asn His Tyr Leu Asp Ile Glu Ser Ala Leu Ser

```
              195                 200                 205
Lys Asp Pro Asn Glu Lys Arg Asp His Ile Val Leu Glu Glu Val
        210                 215                 220

Glu Ala Ala Gly Ile Thr Leu Gly Met Asp Glu Leu Tyr Lys
225                 230                 235
```

<210> SEQ ID NO 152
<211> LENGTH: 238
<212> TYPE: PRT
<213> ORGANISM: Artificial sequence
<220> FEATURE:
<223> OTHER INFORMATION: D11-EGFP-203V

<400> SEQUENCE: 152

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Val Glu Ser Ala Leu Ser
        195                 200                 205

Lys Asp Pro Asn Glu Lys Arg Asp His Ile Val Leu Leu Glu Glu Val
    210                 215                 220

Glu Ala Ala Gly Ile Thr Leu Gly Met Asp Glu Leu Tyr Lys
225                 230                 235
```

<210> SEQ ID NO 153
<211> LENGTH: 238
<212> TYPE: PRT
<213> ORGANISM: Artificial sequence
<220> FEATURE:
<223> OTHER INFORMATION: D11-EGFP-203D

<400> SEQUENCE: 153

```
Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30
```

Gly Glu Gly Asp Ala Thr Tyr Gly Lys Leu Thr Leu Lys Phe Ile Cys
                35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
                115                 120                 125

Asp Phe Lys Glu Asp Gly Asn Ile Leu Gly His Lys Leu Glu Tyr Asn
                130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Asp Asp Glu Ser Ala Leu Ser
                195                 200                 205

Lys Asp Pro Asn Glu Lys Arg Asp His Ile Val Leu Leu Glu Glu Val
                210                 215                 220

Glu Ala Ala Gly Ile Thr Leu Gly Met Asp Glu Leu Tyr Lys
225                 230                 235

<210> SEQ ID NO 154
<211> LENGTH: 238
<212> TYPE: PRT
<213> ORGANISM: Artificial sequence
<220> FEATURE:
<223> OTHER INFORMATION: D11-EGFP-203F

<400> SEQUENCE: 154

Val Ser Lys Gly Glu Glu Leu Phe Thr Gly Val Val Pro Ile Leu Val
 1               5                  10                  15

Glu Leu Asp Gly Asp Leu Asn Gly His Lys Phe Ser Val Ser Gly Glu
                20                  25                  30

Gly Glu Gly Asp Ala Thr Tyr Gly Lys Leu Thr Leu Lys Phe Ile Cys
                35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
                115                 120                 125

Asp Phe Lys Glu Asp Gly Asn Ile Leu Gly His Lys Leu Glu Tyr Asn
                130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Phe Glu Ser Ala Leu Ser
            195                 200                 205

Lys Asp Pro Asn Glu Lys Arg Asp His Ile Val Leu Leu Glu Glu Val
            210                 215                 220

Glu Ala Ala Gly Ile Thr Leu Gly Met Asp Glu Leu Tyr Lys
225                 230                 235

<210> SEQ ID NO 155
<211> LENGTH: 238
<212> TYPE: PRT
<213> ORGANISM: Artificial sequence
<220> FEATURE:
<223> OTHER INFORMATION: D11-EGFP-203E

<400> SEQUENCE: 155

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Glu Glu Ser Ala Leu Ser
        195                 200                 205

Lys Asp Pro Asn Glu Lys Arg Asp His Ile Val Leu Leu Glu Glu Val
    210                 215                 220

Glu Ala Ala Gly Ile Thr Leu Gly Met Asp Glu Leu Tyr Lys
225                 230                 235

<210> SEQ ID NO 156
<211> LENGTH: 238
<212> TYPE: PRT
<213> ORGANISM: Artificial sequence
<220> FEATURE:
<223> OTHER INFORMATION: D11-EGFP-175G

<400> SEQUENCE: 156

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                          60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Glu His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
        195                 200                 205

Lys Asp Pro Asn Glu Lys Arg Asp His Ile Val Leu Leu Glu Glu Val
    210                 215                 220

Glu Ala Ala Gly Ile Thr Leu Gly Met Asp Glu Leu Tyr Lys
225                 230                 235

<210> SEQ ID NO 157
<211> LENGTH: 238
<212> TYPE: PRT
<213> ORGANISM: Artificial sequence
<220> FEATURE:
<223> OTHER INFORMATION: D11-EGFP-148D

<400> SEQUENCE: 157

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                          60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

```
Asp Phe Lys Glu Asp Gly Asn Ile Leu Gly His Lys Leu Glu Tyr Asn
            130                 135                 140

Tyr Asn Glu Asp Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Asp Thr Glu Ser Ala Leu Ser
            195                 200                 205

Lys Asp Pro Asn Glu Lys Arg Asp His Ile Val Leu Leu Glu Glu Val
            210                 215                 220

Glu Ala Ala Gly Ile Thr Leu Gly Met Asp Glu Leu Tyr Lys
225                 230                 235

<210> SEQ ID NO 158
<211> LENGTH: 269
<212> TYPE: PRT
<213> ORGANISM: Artificial sequence
<220> FEATURE:
<223> OTHER INFORMATION: G1M1-EGFP

<400> SEQUENCE: 158

Val Ser Lys Gly Glu Glu Leu Phe Thr Gly Val Val Pro Ile Leu Val
1               5                   10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Asp Ile Glu Leu Lys Gly Ile
        115                 120                 125

Asp Phe Lys Glu Asp Gly Asn Ile Leu Gly His Lys Leu Glu Tyr Asn
            130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Glu Glu Glu Ile
                165                 170                 175

Arg Glu Ala Phe Arg Val Phe Asp Lys Asp Gly Asn Gly Tyr Ile Ser
            180                 185                 190

Ala Ala Glu Leu Arg His Val Met Thr Asn Leu Asp Gly Ser Val Gln
        195                 200                 205

Leu Ala Asp His Tyr Gln Gln Asn Thr Pro Ile Gly Asp Gly Pro Val
    210                 215                 220

Leu Leu Pro Asp Asn His Tyr Leu Ser Thr Gln Ser Ala Leu Ser Lys
225                 230                 235                 240

Asp Pro Asn Glu Lys Arg Asp His Ile Val Leu Leu Glu Phe Val Thr
                245                 250                 255
```

```
Ala Ala Gly Ile Thr Leu Gly Met Asp Glu Leu Tyr Lys
            260                 265

<210> SEQ ID NO 159
<211> LENGTH: 269
<212> TYPE: PRT
<213> ORGANISM: Artificial sequence
<220> FEATURE:
<223> OTHER INFORMATION: G1M2-EGFP

<400> SEQUENCE: 159

Val Ser Lys Gly Glu Glu Leu Phe Thr Gly Val Val Pro Ile Leu Val
1               5                  10                  15

Glu Leu Asp Gly Asp Leu Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Glu Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Glu Glu Glu Ile
                165                 170                 175

Arg Glu Ala Phe Arg Val Phe Asp Lys Asp Gly Asn Gly Tyr Ile Ser
            180                 185                 190

Ala Ala Glu Leu Arg His Val Met Thr Asn Leu Asp Gly Ser Val Gln
        195                 200                 205

Leu Ala Asp His Tyr Gln Gln Asn Thr Pro Ile Gly Asp Gly Pro Val
    210                 215                 220

Leu Leu Pro Asp Asn His Tyr Leu Ser Thr Gln Ser Ala Leu Ser Lys
225                 230                 235                 240

Asp Pro Asn Glu Lys Arg Asp His Ile Val Leu Leu Glu Phe Val Thr
                245                 250                 255

Ala Ala Gly Ile Thr Leu Gly Met Asp Glu Leu Tyr Lys
            260                 265
```